(12) United States Patent
Rajguru et al.

(10) Patent No.: US 11,628,300 B2
(45) Date of Patent: *Apr. 18, 2023

(54) METHOD AND APPARATUS FOR TRANSDERMAL STIMULATION OVER THE PALMAR AND PLANTAR SURFACES

(71) Applicant: EMKinetics, Inc., San Francisco, CA (US)

(72) Inventors: Amit Rajguru, Lafayette, CA (US); Daniel R. Burnett, San Francisco, CA (US); Alexander Vergara, San Francisco, CA (US); Michael Hemati, San Francisco, CA (US)

(73) Assignee: EMKinetics, Inc., San Francisco, CA (US)

( * ) Notice: Subject to any disclaimer, the term of this patent is extended or adjusted under 35 U.S.C. 154(b) by 155 days.

This patent is subject to a terminal disclaimer.

(21) Appl. No.: 17/346,084

(22) Filed: Jun. 11, 2021

(65) Prior Publication Data

US 2021/0299445 A1   Sep. 30, 2021

Related U.S. Application Data

(63) Continuation of application No. 16/732,706, filed on Jan. 2, 2020, now Pat. No. 11,247,053, which is a
(Continued)

(51) Int. Cl.
*A61N 1/34* (2006.01)
*A61N 1/04* (2006.01)
(Continued)

(52) U.S. Cl.
CPC ....... *A61N 1/36021* (2013.01); *A61N 1/0456* (2013.01); *A61N 1/36007* (2013.01);
(Continued)

(58) Field of Classification Search
CPC ....... A61B 5/4047; A61B 5/24; A61B 5/4848; A61B 5/6825; A61B 5/6829; A61B 5/685;
(Continued)

(56) References Cited

U.S. PATENT DOCUMENTS 2,003,392 A    6/1935  Rucker
2,893,392 A    7/1959  Wagner et al.
(Continued)

FOREIGN PATENT DOCUMENTS

CN    1083402    3/1994
EP    2456512    5/2012
(Continued)

OTHER PUBLICATIONS

"Bioflex® RX754P, Single Coated Medical Pressure Sensitive Adhesive Tape," *Technical Data*, 2 pages, Dec. 2005.
(Continued)

*Primary Examiner* — Jon Eric C Morales
(74) *Attorney, Agent, or Firm* — Levine Bagade Han LLP

(57) ABSTRACT

The disclosure describes devices and methods for providing transdermal electrical stimulation therapy to a subject including positioning a stimulator electrode over a glabrous skin surface overlying a palm of the subject and delivering electrical stimulation via a pulse generator transdermally through the glabrous skin surface and to a target nerve or tissue within the hand to stimulate the target nerve or tissue within the hand so that pain felt by the subject is mitigated. The pulses generated during the electrical stimulation therapy may include pulses of two different magnitudes.

17 Claims, 72 Drawing Sheets

Related U.S. Application Data continuation of application No. 15/474,875, filed on Mar. 30, 2017, now Pat. No. 10,786,669, which is a continuation-in-part of application No. 15/084,356, filed on Mar. 29, 2016, now Pat. No. 9,630,004, which is a continuation of application No. 13/840,936, filed on Mar. 15, 2013, now Pat. No. 9,339,641, which is a continuation-in-part of application No. PCT/US2011/052415, filed on Sep. 20, 2011, said application No. 15/474,875 is a continuation-in-part of application No. 12/508,529, filed on Jul. 23, 2009, now abandoned, which is a continuation-in-part of application No. 11/866,329, filed on Oct. 2, 2007, now abandoned.

(60) Provisional application No. 62/350,610, filed on Jun. 15, 2016, provisional application No. 61/403,680, filed on Sep. 20, 2010, provisional application No. 60/848,720, filed on Oct. 2, 2006.

(51) Int. Cl.
  *A61N 1/36* (2006.01)
  *A61N 2/02* (2006.01)
  *A61N 1/378* (2006.01)
  *A61N 2/00* (2006.01)
  *A61B 5/00* (2006.01)
  *A61N 1/05* (2006.01)

(52) U.S. Cl.
  CPC ........... *A61N 1/36057* (2013.01); *A61N 2/02* (2013.01); *A61B 5/4047* (2013.01); *A61N 1/0551* (2013.01); *A61N 1/36017* (2013.01); *A61N 1/3787* (2013.01); *A61N 2/004* (2013.01)

(58) Field of Classification Search
  CPC ................ A61N 1/0456; A61N 1/0551; A61N 1/36007; A61N 1/36017; A61N 1/36021; A61N 1/36057; A61N 1/3787; A61N 2/004; A61N 2/02; A61N 1/36031; A61N 1/36034; A61N 2/006
  See application file for complete search history.

(56) References Cited

U.S. PATENT DOCUMENTS

| | | |
|---|---|---|
| 3,034,507 A | 5/1962 | McConnell et al. |
| 3,817,254 A | 6/1974 | Maurer |
| 3,841,305 A | 10/1974 | Hallgren |
| 4,233,965 A | 11/1980 | Fairbanks |
| 4,266,533 A | 5/1981 | Ryaby et al. |
| 4,428,366 A | 1/1984 | Findl et al. |
| 4,456,012 A | 6/1984 | Lattin |
| 4,548,208 A | 10/1985 | Niemi |
| 4,574,809 A | 3/1986 | Talish et al. |
| 4,784,737 A | 11/1988 | Ray et al. |
| 4,804,054 A | 2/1989 | Howson et al. |
| 4,837,049 A | 6/1989 | Byers et al. |
| 4,915,110 A | 4/1990 | Kitov |
| 4,926,878 A | 5/1990 | Snedeker |
| 4,940,453 A | 7/1990 | Cadwell |
| 4,969,468 A | 11/1990 | Byers et al. |
| 4,994,015 A | 2/1991 | Cadwell |
| 5,000,178 A | 3/1991 | Griffith |
| 5,014,699 A | 5/1991 | Pollack et al. |
| 5,067,478 A | 11/1991 | Berlant |
| 5,092,835 A | 3/1992 | Schurig et al. |
| 5,158,080 A | 10/1992 | Kallok |
| 5,181,902 A | 1/1993 | Erickson et al. |
| 5,299,572 A | 4/1994 | Chen et al. |
| 5,309,909 A | 5/1994 | Gadsby et al. |
| 5,314,401 A | 5/1994 | Tepper |
| 5,314,453 A | 5/1994 | Jeutter |
| 5,374,283 A | 12/1994 | Flick |
| 5,401,233 A | 3/1995 | Erickson et al. |
| 5,449,378 A | 9/1995 | Schouenborg |
| 5,518,495 A | 5/1996 | Kolt |
| 5,540,735 A | 7/1996 | Wingrove |
| 5,562,707 A | 10/1996 | Prochazka et al. |
| 5,690,693 A | 11/1997 | Wang et al. |
| 5,715,837 A | 2/1998 | Chen |
| 5,725,471 A | 3/1998 | Davey et al. |
| 5,749,909 A | 5/1998 | Schroeppel et al. |
| 5,766,124 A | 6/1998 | Polson |
| 5,792,187 A | 8/1998 | Adams |
| 5,792,209 A | 8/1998 | Varner |
| 5,833,600 A | 11/1998 | Young |
| 5,857,957 A | 1/1999 | Lin |
| 5,978,712 A | 11/1999 | Suda et al. |
| 5,984,854 A | 11/1999 | Ishikawa et al. |
| 5,995,873 A | 11/1999 | Rhodes |
| 6,009,878 A | 1/2000 | Weijand et al. |
| 6,024,691 A | 2/2000 | Tepper et al. |
| 6,029,090 A | 2/2000 | Herbst |
| 6,032,677 A | 3/2000 | Blechman et al. |
| 6,066,084 A | 5/2000 | Edrich et al. |
| 6,086,525 A | 7/2000 | Davey et al. |
| 6,088,619 A | 7/2000 | Hein et al. |
| 6,123,658 A | 9/2000 | Schweighofer et al. |
| 6,132,386 A | 10/2000 | Gozani et al. |
| 6,143,035 A | 11/2000 | McDowell |
| 6,155,966 A | 12/2000 | Parker |
| 6,179,770 B1 | 1/2001 | Mould |
| 6,190,893 B1 | 2/2001 | Shastri et al. |
| 6,200,259 B1 | 3/2001 | March |
| 6,213,933 B1 | 4/2001 | Lin |
| 6,219,575 B1 | 4/2001 | Nemati |
| 6,256,533 B1 | 7/2001 | Yuzhakov et al. |
| 6,261,221 B1 | 7/2001 | Tepper et al. |
| 6,312,612 B1 | 11/2001 | Sherman et al. |
| 6,319,241 B1 | 11/2001 | King et al. |
| 6,334,856 B1 | 1/2002 | Allen et al. |
| 6,349,233 B1 | 2/2002 | Adams |
| 6,366,795 B1 | 4/2002 | Bremer et al. |
| 6,379,313 B1 | 4/2002 | Gozani et al. |
| 6,379,324 B1 | 4/2002 | Gartstein et al. |
| 6,432,037 B1 | 8/2002 | Eini et al. |
| 6,440,096 B1 | 8/2002 | Lastovich et al. |
| 6,443,883 B1 | 9/2002 | Ostrow et al. |
| 6,451,240 B1 | 9/2002 | Sherman et al. |
| 6,471,903 B2 | 10/2002 | Sherman et al. |
| 6,473,652 B1 | 10/2002 | Sarwal et al. |
| 6,491,620 B1 | 12/2002 | Davey |
| 6,493,588 B1 | 12/2002 | Malaney et al. |
| 6,500,110 B1 | 12/2002 | Davey et al. |
| 6,503,231 B1 | 1/2003 | Prausnitz et al. |
| 6,511,463 B1 | 1/2003 | Wood et al. |
| 6,527,694 B1 | 3/2003 | Ishikawa et al. |
| 6,533,949 B1 | 3/2003 | Yeshurun et al. |
| 6,537,242 B1 | 3/2003 | Palmer |
| 6,553,263 B1 | 4/2003 | Meadows et al. |
| 6,558,361 B1 | 5/2003 | Yeshurun |
| 6,565,532 B1 | 5/2003 | Yuzhakov et al. |
| 6,582,393 B2 | 6/2003 | Sage, Jr. |
| 6,591,124 B2 | 7/2003 | Sherman et al. |
| 6,595,947 B1 | 7/2003 | Mikszta et al. |
| 6,603,987 B2 | 8/2003 | Whitson |
| 6,611,707 B1 | 8/2003 | Prausnitz et al. |
| 6,615,080 B1 | 9/2003 | Unsworth et al. |
| 6,622,035 B1 | 9/2003 | Merilainen et al. |
| 6,623,457 B1 | 9/2003 | Rosenberg |
| 6,652,443 B1 | 11/2003 | Struppler et al. |
| 6,652,478 B1 | 11/2003 | Gartstein et al. |
| 6,654,636 B1 | 11/2003 | Dev et al. |
| 6,656,147 B1 | 12/2003 | Gertsek et al. |
| 6,663,556 B2 | 12/2003 | Barker |
| 6,663,820 B2 | 12/2003 | Arias et al. |
| 6,671,527 B2 | 12/2003 | Petersson et al. |
| 6,678,556 B1 | 1/2004 | Nolan et al. |
| 6,684,106 B2 | 1/2004 | Herbst |

(56) References Cited

U.S. PATENT DOCUMENTS

| | | |
|---|---|---|
| 6,689,100 B2 | 2/2004 | Connelly et al. |
| 6,690,959 B2 | 2/2004 | Thompson |
| 6,692,444 B2 | 2/2004 | Gozani et al. |
| 6,697,669 B2 | 2/2004 | Dev et al. |
| 6,701,185 B2 | 3/2004 | Burnett et al. |
| 6,735,474 B1 | 5/2004 | Loeb et al. |
| 6,743,211 B1 | 6/2004 | Prausnitz et al. |
| 6,767,341 B2 | 7/2004 | Cho |
| 6,770,022 B2 | 8/2004 | Mechlenburg et al. |
| 6,770,480 B1 | 8/2004 | Canham |
| 6,782,283 B2 | 8/2004 | Schmidt et al. |
| 6,790,372 B2 | 9/2004 | Roy et al. |
| 6,808,506 B2 | 10/2004 | Lastovich et al. |
| 6,835,184 B1 | 12/2004 | Sage et al. |
| 6,866,659 B2 | 3/2005 | Nemati |
| 6,881,203 B2 | 4/2005 | Delmore et al. |
| 6,899,838 B2 | 5/2005 | Lastovich |
| 6,904,614 B2 | 6/2005 | Yamazaki et al. |
| 6,908,453 B2 | 6/2005 | Fleming et al. |
| 6,926,660 B2 | 8/2005 | Miller |
| 6,931,277 B1 | 8/2005 | Yuzhakov et al. |
| 6,939,311 B2 | 9/2005 | Geiger |
| 6,941,171 B2 | 9/2005 | Mann et al. |
| 6,960,193 B2 | 11/2005 | Rosenberg |
| 6,962,772 B2 | 11/2005 | Liu et al. |
| 6,972,013 B1 | 12/2005 | Zhang et al. |
| 6,980,855 B2 | 12/2005 | Cho |
| 7,013,179 B2 | 3/2006 | Carter et al. |
| 7,027,478 B2 | 4/2006 | Ackley |
| 7,032,302 B1 | 4/2006 | Schmidt et al. |
| 7,045,069 B2 | 5/2006 | Ozeryansky |
| 7,047,070 B2 | 5/2006 | Wilkinson et al. |
| 7,048,723 B1 | 5/2006 | Frazier et al. |
| 7,079,355 B2 | 7/2006 | Hsiao et al. |
| 7,083,592 B2 | 8/2006 | Lastovich et al. |
| 7,104,947 B2 | 9/2006 | Riehl |
| 7,115,108 B2 | 10/2006 | Wilkinson et al. |
| 7,117,034 B2 | 10/2006 | Kronberg |
| 7,130,696 B2 | 10/2006 | Carter et al. |
| 7,132,054 B1 | 11/2006 | Kravitz et al. |
| 7,153,256 B2 | 12/2006 | Riehl et al. |
| 7,187,976 B2 | 3/2007 | Duncan et al. |
| 7,226,439 B2 | 6/2007 | Prausnitz et al. |
| 7,262,068 B2 | 8/2007 | Roy et al. |
| 7,273,474 B2 | 9/2007 | Chang et al. |
| 7,285,113 B2 | 10/2007 | Yeshurun |
| 7,315,758 B2 | 1/2008 | Kwiatkowski et al. |
| 7,316,665 B2 | 1/2008 | Laurent et al. |
| 7,320,664 B2 | 1/2008 | Riehl et al. |
| 7,332,197 B2 | 2/2008 | Wood et al. |
| 7,332,339 B2 | 2/2008 | Canham |
| 7,344,499 B1 | 3/2008 | Prausnitz et al. |
| 7,367,936 B2 | 5/2008 | Myers et al. |
| D571,920 S | 6/2008 | Juliana et al. |
| 7,396,326 B2 | 7/2008 | Ghiron et al. |
| 7,410,476 B2 | 8/2008 | Wilkinson et al. |
| 7,415,299 B2 | 8/2008 | Zimmermann et al. |
| 7,416,541 B2 | 8/2008 | Yuzhakov et al. |
| 7,429,333 B2 | 9/2008 | Chiou et al. |
| 7,473,244 B2 | 1/2009 | Frazier et al. |
| 7,481,337 B2 | 1/2009 | Luharuka et al. |
| 7,497,980 B2 | 3/2009 | Xu et al. |
| 7,500,911 B2 | 3/2009 | Johnson et al. |
| 7,520,848 B2 | 4/2009 | Schneider et al. |
| 7,522,061 B2 | 4/2009 | Rondoni et al. |
| 7,530,968 B2 | 5/2009 | Gonnelli |
| 7,536,226 B2 | 5/2009 | Williams et al. |
| 7,556,615 B2 | 7/2009 | Pettis et al. |
| 7,556,821 B2 | 7/2009 | Ameri et al. |
| 7,560,036 B2 | 7/2009 | Golubovic-Liakopoulos et al. |
| 7,570,992 B2 | 8/2009 | Nolan et al. |
| 7,572,405 B2 | 8/2009 | Sherman et al. |
| 7,574,256 B2 | 8/2009 | Carter |
| 7,578,954 B2 | 8/2009 | Gartstein et al. |
| 7,582,069 B2 | 9/2009 | Laurent et al. |
| 7,588,552 B2 | 9/2009 | Yeshurun et al. |
| 7,591,806 B2 | 9/2009 | Xu |
| 7,627,938 B2 | 12/2009 | Kim et al. |
| 7,628,761 B2 | 12/2009 | Gozani et al. |
| 7,647,112 B2 | 1/2010 | Tracey et al. |
| 7,648,484 B2 | 1/2010 | Yeshurun et al. |
| 7,651,946 B2 | 1/2010 | Wilke et al. |
| 7,658,728 B2 | 2/2010 | Yuzhakov |
| 7,941,201 B2 | 5/2011 | Chiou et al. |
| 8,308,665 B2 | 11/2012 | Harry et al. |
| 8,430,805 B2 | 4/2013 | Burnett et al. |
| 8,435,166 B2 | 5/2013 | Burnett et al. |
| 8,588,884 B2 | 11/2013 | Hegde et al. |
| 8,660,646 B2 | 2/2014 | Laing et al. |
| 8,805,510 B2 | 8/2014 | Chancellor et al. |
| 8,812,114 B2 | 8/2014 | Van den biggelaar et al. |
| 8,818,520 B2 | 8/2014 | Laing et al. |
| 8,954,153 B2 | 2/2015 | Boggs |
| 9,002,477 B2 | 4/2015 | Burnett |
| 9,005,102 B2 | 4/2015 | Burnett et al. |
| 9,056,194 B2 | 6/2015 | Van den biggelaar et al. |
| 9,076,187 B1 | 7/2015 | Laing et al. |
| 9,245,265 B2 | 1/2016 | Laing et al. |
| 9,265,941 B2 | 2/2016 | Van den biggelaar et al. |
| 9,339,641 B2 | 5/2016 | Rajguru et al. |
| 9,387,338 B2 | 7/2016 | Burnett |
| 9,610,459 B2 | 4/2017 | Burnett et al. |
| 9,630,004 B2 | 4/2017 | Rajguru et al. |
| 9,757,584 B2 | 9/2017 | Burnett |
| 10,786,669 B2 * | 9/2020 | Rajguru ............ A61N 1/36007 |
| 11,224,742 B2 | 1/2022 | Burnett |
| 11,247,053 B2 | 2/2022 | Rajguru et al. |
| 2002/0007128 A1 | 1/2002 | Ives et al. |
| 2002/0028991 A1 | 3/2002 | Thompson |
| 2002/0040233 A1 | 4/2002 | George et al. |
| 2002/0055761 A1 | 5/2002 | Mann et al. |
| 2002/0082465 A1 | 6/2002 | Bashford et al. |
| 2002/0099323 A1 | 7/2002 | Dev et al. |
| 2002/0111777 A1 | 8/2002 | David |
| 2002/0133129 A1 | 9/2002 | Arias et al. |
| 2002/0138116 A1 | 9/2002 | Bertolucci |
| 2002/0183647 A1 | 12/2002 | Gozani et al. |
| 2002/0183804 A1 | 12/2002 | Malaney et al. |
| 2003/0003968 A1 | 1/2003 | Muraki |
| 2003/0004392 A1 | 1/2003 | Tanner et al. |
| 2003/0028072 A1 | 2/2003 | Fischell et al. |
| 2003/0144625 A1 | 7/2003 | Sherman et al. |
| 2003/0158583 A1 | 8/2003 | Burnett et al. |
| 2003/0158585 A1 | 8/2003 | Burnett |
| 2003/0216729 A1 | 11/2003 | Marchitto et al. |
| 2003/0217754 A1 | 11/2003 | Thomas et al. |
| 2004/0010276 A1 | 1/2004 | Jacobs et al. |
| 2004/0015188 A1 | 1/2004 | Coulter |
| 2004/0054393 A1 | 3/2004 | Stemme et al. |
| 2004/0082875 A1 | 4/2004 | Donoghue et al. |
| 2004/0092860 A1 | 5/2004 | Dev et al. |
| 2004/0102819 A1 | 5/2004 | Zou et al. |
| 2004/0111139 A1 | 6/2004 | McCreery |
| 2004/0122787 A1 | 6/2004 | Avanash et al. |
| 2004/0127939 A1 | 7/2004 | Grey |
| 2004/0138517 A1 | 7/2004 | Osorio et al. |
| 2004/0146611 A1 | 7/2004 | Arias et al. |
| 2004/0147964 A1 | 7/2004 | Nolan et al. |
| 2004/0173220 A1 | 9/2004 | Harry et al. |
| 2004/0210254 A1 | 10/2004 | Burnett et al. |
| 2004/0210282 A1 | 10/2004 | Flock et al. |
| 2004/0237170 A1 | 12/2004 | Yamazaki et al. |
| 2005/0021104 A1 | 1/2005 | Dilorenzo |
| 2005/0029223 A1 | 2/2005 | Yeshurun |
| 2005/0033380 A1 | 2/2005 | Tanner et al. |
| 2005/0099290 A1 | 5/2005 | Govari |
| 2005/0107654 A1 | 5/2005 | Riehl |
| 2005/0143783 A1 | 6/2005 | Boveja et al. |
| 2005/0143789 A1 | 6/2005 | Whitehurst et al. |
| 2005/0171576 A1 | 8/2005 | Williams et al. |
| 2005/0203602 A1 | 9/2005 | Wallace et al. |
| 2005/0240230 A1 | 10/2005 | Preston et al. |
| 2005/0277998 A1 | 12/2005 | Tracey et al. |
| 2005/0283202 A1 | 12/2005 | Gellman |

(56) References Cited

U.S. PATENT DOCUMENTS

| | | |
|---|---|---|
| 2005/0283204 A1 | 12/2005 | Buhlmann et al. |
| 2006/0004244 A1 | 1/2006 | Phillips et al. |
| 2006/0015153 A1 | 1/2006 | Gliner et al. |
| 2006/0016452 A1 | 1/2006 | Goetz et al. |
| 2006/0030845 A1 | 2/2006 | Leung et al. |
| 2006/0047316 A1 | 3/2006 | Fischeii et al. |
| 2006/0047326 A1 | 3/2006 | Wheeler |
| 2006/0049957 A1 | 3/2006 | Surgenor et al. |
| 2006/0052839 A1 | 3/2006 | Kim et al. |
| 2006/0069415 A1 | 3/2006 | Cameron et al. |
| 2006/0084938 A1 | 4/2006 | Zhang et al. |
| 2006/0115130 A1 | 6/2006 | Kozlay |
| 2006/0122454 A1 | 6/2006 | Riehl et al. |
| 2006/0122660 A1 | 6/2006 | Boveja et al. |
| 2006/0135844 A1 | 6/2006 | Alekseyenko |
| 2006/0155345 A1 | 7/2006 | Williams et al. |
| 2006/0161039 A1 | 7/2006 | Juliana et al. |
| 2006/0173261 A1 | 8/2006 | Kall et al. |
| 2006/0178576 A1 | 8/2006 | Weber et al. |
| 2006/0184211 A1 | 8/2006 | Gaunt et al. |
| 2006/0199159 A1 | 9/2006 | Ghiron et al. |
| 2006/0276702 A1 | 12/2006 | Mcginnis |
| 2007/0021712 A1 | 1/2007 | Bernard et al. |
| 2007/0021803 A1 | 1/2007 | Deem et al. |
| 2007/0027353 A1 | 2/2007 | Ghiron et al. |
| 2007/0027354 A1 | 2/2007 | Riehl et al. |
| 2007/0027355 A1 | 2/2007 | Riehl et al. |
| 2007/0142885 A1 | 6/2007 | Hantash et al. |
| 2007/0208212 A1 | 9/2007 | Dilorenzo |
| 2007/0250162 A1 | 10/2007 | Royalty |
| 2007/0265489 A1 | 11/2007 | Fowler et al. |
| 2007/0265675 A1 | 11/2007 | Lund et al. |
| 2007/0276318 A1 | 11/2007 | Henley |
| 2007/0282246 A1 | 12/2007 | Henley |
| 2008/0004484 A1 | 1/2008 | Wieraszko et al. |
| 2008/0033510 A1 | 2/2008 | Herregraven et al. |
| 2008/0058874 A1 | 3/2008 | Westlund et al. |
| 2008/0063866 A1 | 3/2008 | Allen et al. |
| 2008/0065167 A1 | 3/2008 | Boggs et al. |
| 2008/0097142 A1 | 4/2008 | Savage |
| 2008/0114199 A1 | 5/2008 | Riehl et al. |
| 2008/0177128 A1 | 7/2008 | Riehl et al. |
| 2008/0177347 A1 | 7/2008 | Tehran et al. |
| 2008/0183070 A1 | 7/2008 | Unal et al. |
| 2008/0200748 A1 | 8/2008 | Testani et al. |
| 2008/0224808 A1 | 9/2008 | Ghiron et al. |
| 2008/0262287 A1 | 10/2008 | Dussau |
| 2008/0288035 A1 | 11/2008 | Gill et al. |
| 2008/0300655 A1 | 12/2008 | Cholette |
| 2008/0306325 A1 | 12/2008 | Burnett et al. |
| 2008/0312725 A1 | 12/2008 | Penner |
| 2009/0030337 A1 | 1/2009 | Gozani et al. |
| 2009/0054950 A1 | 2/2009 | Stephens |
| 2009/0073991 A1 | 3/2009 | Landrum et al. |
| 2009/0076336 A1 | 3/2009 | Mazar et al. |
| 2009/0076340 A1 | 3/2009 | Libbus et al. |
| 2009/0076344 A1 | 3/2009 | Libbus et al. |
| 2009/0076345 A1 | 3/2009 | Manicka et al. |
| 2009/0076363 A1 | 3/2009 | Bly et al. |
| 2009/0076364 A1 | 3/2009 | Libbus et al. |
| 2009/0076397 A1 | 3/2009 | Libbus et al. |
| 2009/0076410 A1 | 3/2009 | Libbus et al. |
| 2009/0076559 A1 | 3/2009 | Libbus et al. |
| 2009/0076565 A1 | 3/2009 | Surwit |
| 2009/0099623 A1 | 4/2009 | Bentwich |
| 2009/0118777 A1 | 5/2009 | Iki et al. |
| 2009/0132018 A1 | 5/2009 | DiUbaldi et al. |
| 2009/0162570 A1 | 6/2009 | Swenberg et al. |
| 2009/0171236 A1 | 7/2009 | Davies |
| 2009/0198305 A1 | 8/2009 | Naroditsky et al. |
| 2009/0227829 A1 | 9/2009 | Burnett et al. |
| 2009/0227831 A1 | 9/2009 | Burnett et al. |
| 2009/0234179 A1 | 9/2009 | Burnett et al. |
| 2009/0234410 A1 | 9/2009 | Libbus et al. |
| 2009/0264792 A1 | 10/2009 | Mazar |
| 2009/0292194 A1 | 11/2009 | Libbus et al. |
| 2010/0016929 A1 | 1/2010 | Prochazka |
| 2010/0022864 A1 | 1/2010 | Cordero et al. |
| 2010/0049021 A1 | 2/2010 | Jina et al. |
| 2010/0056881 A1 | 3/2010 | Libbus et al. |
| 2010/0057147 A1 | 3/2010 | Fassih et al. |
| 2010/0057149 A1 | 3/2010 | Fahey |
| 2010/0114259 A1 | 5/2010 | Herregraven et al. |
| 2010/0119482 A1 | 5/2010 | Yun et al. |
| 2010/0160712 A1 | 6/2010 | Burnett et al. |
| 2010/0161005 A1 | 6/2010 | Wahlgren et al. |
| 2010/0168501 A1 | 7/2010 | Burnett et al. |
| 2010/0204538 A1 | 8/2010 | Burnett et al. |
| 2010/0222629 A1 | 9/2010 | Burnett et al. |
| 2010/0222630 A1 | 9/2010 | Mangrum et al. |
| 2010/0318009 A1 | 12/2010 | Stanley |
| 2011/0021863 A1 | 1/2011 | Burnett et al. |
| 2011/0144468 A1 | 6/2011 | Boggs et al. |
| 2011/0264163 A1 | 10/2011 | Tracey et al. |
| 2011/0270140 A1 | 11/2011 | Israeli |
| 2011/0295100 A1 | 12/2011 | Hedge et al. |
| 2012/0059432 A1 | 3/2012 | Emborg et al. |
| 2012/0101326 A1 | 4/2012 | Simon et al. |
| 2012/0302821 A1 | 11/2012 | Burnett |
| 2013/0006322 A1 | 1/2013 | Tai |
| 2013/0072746 A1 | 3/2013 | Burnett et al. |
| 2013/0072835 A1 | 3/2013 | Harry et al. |
| 2014/0046423 A1 | 2/2014 | Rajguru et al. |
| 2014/0148870 A1 | 5/2014 | Burnett |
| 2014/0213842 A1 | 7/2014 | Simon et al. |
| 2013/0310909 A1 | 9/2014 | Simon et al. |
| 2014/0249595 A1 | 9/2014 | Chancellor et al. |
| 2014/0288613 A1 | 9/2014 | Laing et al. |
| 2015/0190648 A1 | 7/2015 | Fischell et al. |
| 2015/0202454 A1 | 7/2015 | Burnett |
| 2015/0227909 A1 | 8/2015 | Laing et al. |
| 2015/0260471 A1 | 9/2015 | Azhocar |
| 2016/0067515 A1 | 3/2016 | Burnett et al. |
| 2016/0067517 A1 | 3/2016 | Burnett |
| 2016/0074671 A1 | 3/2016 | Burnett et al. |
| 2016/0193466 A1 | 7/2016 | Burnett |
| 2017/0354831 A1 | 12/2017 | Burnett |
| 2018/0050216 A9 | 2/2018 | Burnett |
| 2018/0133472 A1 | 5/2018 | Tai |
| 2020/0139120 A1 | 5/2020 | Rajguru et al. |
| 2022/0088373 A1 | 3/2022 | Burnett |
| 2022/0126095 A1 | 4/2022 | Rajguru et al. |
| 2022/0021007 A1 | 7/2022 | Rajguru et al. |

FOREIGN PATENT DOCUMENTS

| | | |
|---|---|---|
| EP | 2456519 | 5/2012 |
| EP | 2493551 | 9/2012 |
| EP | 2493552 | 9/2012 |
| EP | 2618890 | 7/2013 |
| GB | 0637560 | 5/1950 |
| GB | 2298370 | 9/1996 |
| GB | 2336544 | 10/1999 |
| JP | 2000-254239 | 9/2000 |
| JP | 2009-153904 | 7/2009 |
| WO | WO 2003/070317 | 8/2003 |
| WO | WO 2006/061688 | 6/2006 |
| WO | WO 2006/092007 | 9/2006 |
| WO | WO 2008/032279 | 3/2008 |
| WO | WO 2008/042902 | 4/2008 |
| WO | WO 2008/115426 | 9/2008 |
| WO | WO 2010/047599 | 4/2010 |
| WO | WO 2010/084482 | 7/2010 |
| WO | WO 2011/011748 | 1/2011 |
| WO | WO 2011/011749 | 1/2011 |
| WO | WO 2011/053607 | 5/2011 |
| WO | WO 2011/053661 | 5/2011 |
| WO | WO 2011/150332 | 12/2011 |
| WO | WO 2011/150502 | 12/2011 |

(56) References Cited

FOREIGN PATENT DOCUMENTS

| WO | WO 2012/040243 | 3/2012 |
|----|----|----|
| WO | WO 2014/151431 | 9/2014 |

OTHER PUBLICATIONS

"Tibial Nerve." Wikipedia, accessed Oct. 5, 2020, https://en.wikipedia.org/wiki/Tibial_nerve. (Year: 2020).

3M Corporation, 3M™ XYZ/Isotropic Electrically Conductive Adhesive Transfer Tape 9707, *3M Electronics Markets Materials Division*, 60-5002-0350-4, 8 pages, 2004, 3M.

Aaron, Roy K. et al., "Therapeutic Effects of Electromagnetic Fields in the Stimulation of Connective Tissue Repair," *Journal of Cellular Biography*, 52(1):42-6, May 1993, Wiley-Liss, Inc.

Amarenco et al., "Urodynamic effect of acute transcutaneous posterior tibial nerve stimulation in overactive bladder," Journal of Urology, vol. 169, 2210-2215. (Jun. 2003).

AmGel Technologies, "AG603 Sensing Gel, Sensing Gel Designed for ECG Applications," AG603-3/10, 1 page, 2010.

AmGel Technologies, "AG702 Stimulating Gel, Stimulating Gel Designed for carbon film," AG702-02/06, 1 page, 2006.

AmGel Technologies, "AG902-184/229 Grounding Gel, Grounding Gel Designed for Electrosurgical Pads," AG902 Series, 1 page, 2010.

AmGel Technologies, "Release Films," 1 Page, Jul. 25, 2006, Revision 1.

Balmaseda, Marion T. Jr., et al., "Burns in Functional Electric Stimulation: Two Case Reports," *Archives of Physical Medicine and Rehabilitation*, vol. 38., pp. 452-453, Jul. 1987.

Biowave Corporation, "510(k) Summary for the Biowave Deepwave Neuromodulation Pain Therapy Device," 6 pages, Appendix B, Dec. 13, 2005.

Biowave Corporation, "510(k) Summary for the Biowave Deepwave Neuromodulation Pain Therapy Device," 7 pages, Appendix E, Aug. 15, 2006.

Biowave Corporation, "Percutaneous Neuromodulation Pain Therapy System," *deepwave*, RevB/080926, 2008.

BlueCross BlueShield of Kansas City, "Percutaneous Electrical Nerve Stimulation (PENS) and Percutaneous Neuromodulation Therapy (PNT)," 7 pages, 1988.

Bodhale, D.W. et al., "Design, fabrication and analysis of silicon microneedles for transdermal drug delivery applications," *Proceedings of the 3rd International Conference on the Development of BME in Vietnam*, pp. 84-88, Jan. 11-14, 2010.

Bruce, C.J. et al., "Intracardiac Echocardiography," *European Journal Echocardiography*, vol. 2, pp. 234-244, 2001, The European Society of Cardiology.

Cabodevila, G. et al., "An overview on drug delivery using microneedles", *Institute FEMTO-ST, Dept LPMO*, 24 pages, Oct. 2005, Workshop Micro Dosing Systems.

Certified Pulsed Signal Therapy Centers, http://www.certifiedpst.com, 10 pages.

Choi, S. et al., "Microneedle Electrode Array for Electroporation of Skin for Gene Therapy," 2 pages, 2005, Controlled Release Society 32nd Annual Meeting and Exposition Transactions.

Curley, S. et al., "Radiofrequency Ablation of Unresectable Primary and Metastatic Hepatic Malignancies," *Annals of Surgery*, vol. 230(1):1-8, 1999 Lippincott Williams & Wilkins, Inc.

Cystomedix, Inc., "Percutaneous Tibial Nerve Stimulation via Urgent® PC Neuromodulation System—An Emerging Technology for managing Overactive Bladder," *Business Briefing: Global Surgery*, 6 pages, 2004.

Ebi, L.P., Ebi Bone Healing System, http://www.ebimedical.com/products/fracture/bonehealing.html, 5 pages.

Fallon Community Health Plan, "Spinal Cord Stimulation," 4 pages, 2006.

Grundfest H. et al., "Stainless Steel Micro-Needle Electrodes Made by Electrolytic Pointing," *Review of Scientific Instruments*, vol. 21(4):2 pages, 1950, American Institute of Physics.

Harvinder S. Gill et al., "Effect of microneedle design on pain in human subjects," *NIH Public Access Author Manuscript*, 24(7): 585-594, Sep. 2008, Clinical Journal of Pain.

Huber, D.E. et al., "Popliteal Vein Compression Under General Anaesthesia," *European Journal of Vascular and Endovascular Surgery*, vol. 37, pp. 464-469, 2009, Elsevier Ltd.

Isseroff, Roslyn R. et al., "Beta Adrenergic Receptor ($\beta$AR) Signaling as a novel target for optimizing skin wound healing", 5 pages.

Jacobson, Jerry I. et al., "Low-Amplitude, Extremely Low Frequency Magnetic Fields for the Treatment of Osteoarthritic Knees: A Double-Blind Clinical Study," *Electromagnetic Fields and Human Health. Fundamental and Applied Research*, pp. 363-364, Sep. 17-24, 2002, Proceedings of the Third International Conference.

Jasper, H. et al., "Unipolar Electromyograms of Normal and Denervated Human Muscle," pp. 231-244, Oct. 12, 1948, Department of Neurology and Neurosurgery, McGill University, and Montreal Neurological Institute.

Kravitz, S. et al., Microneedles for In-Situ/In-vivo Electrochemical Sensor Applications, 1 page, Sandia National Laboratories.

Kurtzke, John F., "Epidemiology of Spinal Cord Injury," *IV Panamerican Congress of Neurology*, 18(2-3): 157-90, 93, 1975.

Lin et al., "Magnetic Stimulation of the Bladder in Dogs," AAEM Annual Meeting 1993, *Muscle & Nerve*, Oct. 1993 (Abstract).

Luttge, R. "Microneedle array electrode for human EEG recording," IFMBE Proceedings 22, pp. 1246-1249, 2008, Springer-Verlag Berlin Heidelberg 2009.

Maass et al., "Contactless Nerve Stimulation and Signal Detection by Inductive Transducer," *Symposium on Application of Magnetism in Bioengineering*, 1969.

McFarlane, J.P. et al., "Acute Suppression of Idiopathic Detrusor Instability with Magnetic Stimulation of the Sacral Nerve Roots," *British Journal of Urology*, 80(5): 734-41, Nov. 1997.

Morrison, P.R. et al., "Radiofrequency Ablation of Thoracic Lesions: Part I, Experiments in the Normal Porcine Thorax," *American Journal of Roentgenology*, 2005;184:375-380, Feb. 2005, American Roentgen Ray Society.

NeuroStar TMS Therapy, NeuroStar TMS Therapy® Recipient of Medical Design Excellence Award, *PRNewswire*, 3 pages, Apr. 2009.

Newmark, Inc., "Standard Products, Highest Quality Components, Designed & Produced Exclusively for Electrode Manufacturers," *Innovation by Design Newmark*, 2 pages, www.newmarkine.com/std_prods.htm, printed on May 3, 2010.

Noble, J.H. et al., "Automatic segmentation of the facial nerve and chorda tympani in CT images using spatially dependent features values", Medical Phsysics, vol. 35(12), pp. 5375-5384, Dec. 2008, American Association Physical Medicine.

Patel, G. et al., "Microneedles: The option for painless delivery," www.pharmainfo.net/reviews/microneedles-option-painless-delivery, 6 pages, printed on Sep. 9, 2008.

PubMed, *U.S. National Library of Medicine National Institutes of Health*, microneedle array electrode—Pub Med results, www.ncbi.nlm.nig.gov/sites/entrez, 2 pages, Search performed on Apr. 22, 2010.

PubMed, *U.S. National Library of Medicine National Institutes of Health*, microneedle electrode—Pub Med results, www.ncbi.nlm.nig.gov/sites/entrez, 7 pages, Search performed on Apr. 22, 2010.

Schaefer, O. et al., "CT-guided radiofrequency ablation of a bronchogenic carcinoma," *The British Journal of Radiology*, 76 (2003), pp. 268-270, 2003, The British Institute of Radiology.

Shafik, Ahmed, "Magnetic Stimulation: A Novel Method for Inducing Evacuation of the Neuropathic Rectum and Urinary Bladder in a Canine Model," *Urology* 54(2): 368-372, Aug. 1999.

Sheridan, MT. et al., "Pretreatment apoptosis in carcinoma of the cervix correlates with changes in tumour oxygenation during radiotherapy," *British Journal of Cancer*, 82(6):1177-1182, 2000 Cancer Research Campaign.

Sivagangabalan, G. et al., "Comparison of Electroanatomic Contact and Noncontact Mapping of Ventricular Scar in a Postinfarct Ovine Model With Intramural Needle Electrode Recording and Histologi-

(56) References Cited

OTHER PUBLICATIONS cal Validation," *Circulation: Arrhythmia and Electrophysiology, Journal of the American Heart Association*, vol. 1:363-369, 2008, American Heart Association.

Solbiati, L. et al., "Percutaneous US-guided Radio-Frequency Tissue Ablation of Liver Metastases: Treatment and Follow-up in 16 Patients," *Radiology*, 202(1):195-203, 1997 L.S. RSNA.

The Magstim Company Ltd, "Air Film Coil," *Magstim*, 4 pages, 2007.

Thon, W.F. et al., "Neuromodulation of voiding dysfunction and pelvic pain," *World Journal of Urology*, vol. 9: pp. 138-141, 1991, Springer-Verlag.

Trock, David H., "Electromagnetic Fields and Magnets Investigational Treatment for Musculoskeletal Disorders," *Rheumatic Diseases Clinics of North America*, vol. 26, No. 1., Feb. 2000.

Trock, David H., et al., "The Effect of Pulsed Electromagnetic Fields in the Treatment of Osteoarthritis of the Knee and Cervical Spine. Report of Randomized, Double Blind, Placebo Controlled Trials," *The Journal of Rheumatology*, 1903-1911, 1994.

Tyco Adhesives, "2932 Designed Adhesives," *Specialty Tape Group*, 1 page.

VanSonnenberg, E. et al., "Radiofrequency Ablation of Thoracic Lesions: Part 2, Initial Clinical Experience—Technical and Multidisciplinary Considerations in 30 Patients," *American Journal of Roentgenology*, 2005;184:381-390, Feb. 2005, American Roentgen Ray Society.

Wanich, T. et al., "A Randomized Placebo-Controlled Study to Determine Safety and Efficacy in Terms of Pain Reduction, Increased Range of Motion, and Reduced Pain Medications, for a Novel Percutaneous Neuromodulation Pain Therapy Device ("Deepwave®") Following Post-Operative Treatments for Total Knee Replacement Procedures, American Academy of Orthopaedic Surgeons 2009 Annual Meeting", 6 pages, Feb. 25-28, 2008, Biowave Corporation.

Warwick, K. et al., "The Application of Implant Technology for Cybernetic Systems," *Archives of Neurology*, vol. 60:1369-1373, Oct. 2003, American Medical Association.

Wijkstrda et al., "Selective Stimulation and Blocking of Sacral Nerves: Research Setup and Preliminary Results," *Annual International Conference of the IEEE Engineering in Medicine and Biology Society*, vol. 13, No. 2, 1991.

Wilke, N. et al., "Fabrication and Characterisation of Microneedle Electrode Arrays using Wet Etch Technologies," 5 pages, Oct. 20-21, 2004, EMN04, NMRC, University College.

Zhao, M., "Genetic Analysis of Electric Signal-directed Cell Movement," 33 pages, Apr. 8, 2008, Modelling Complex Biological Systems in the Context of Genomics.

Zoll Lifecor Corporation, "What is the LifeVest Wearable Defibrillator," http://www.lifecor.com/about_lifevest/about.asp#, 1 page, printed on Jan. 7, 2011.

\* cited by examiner

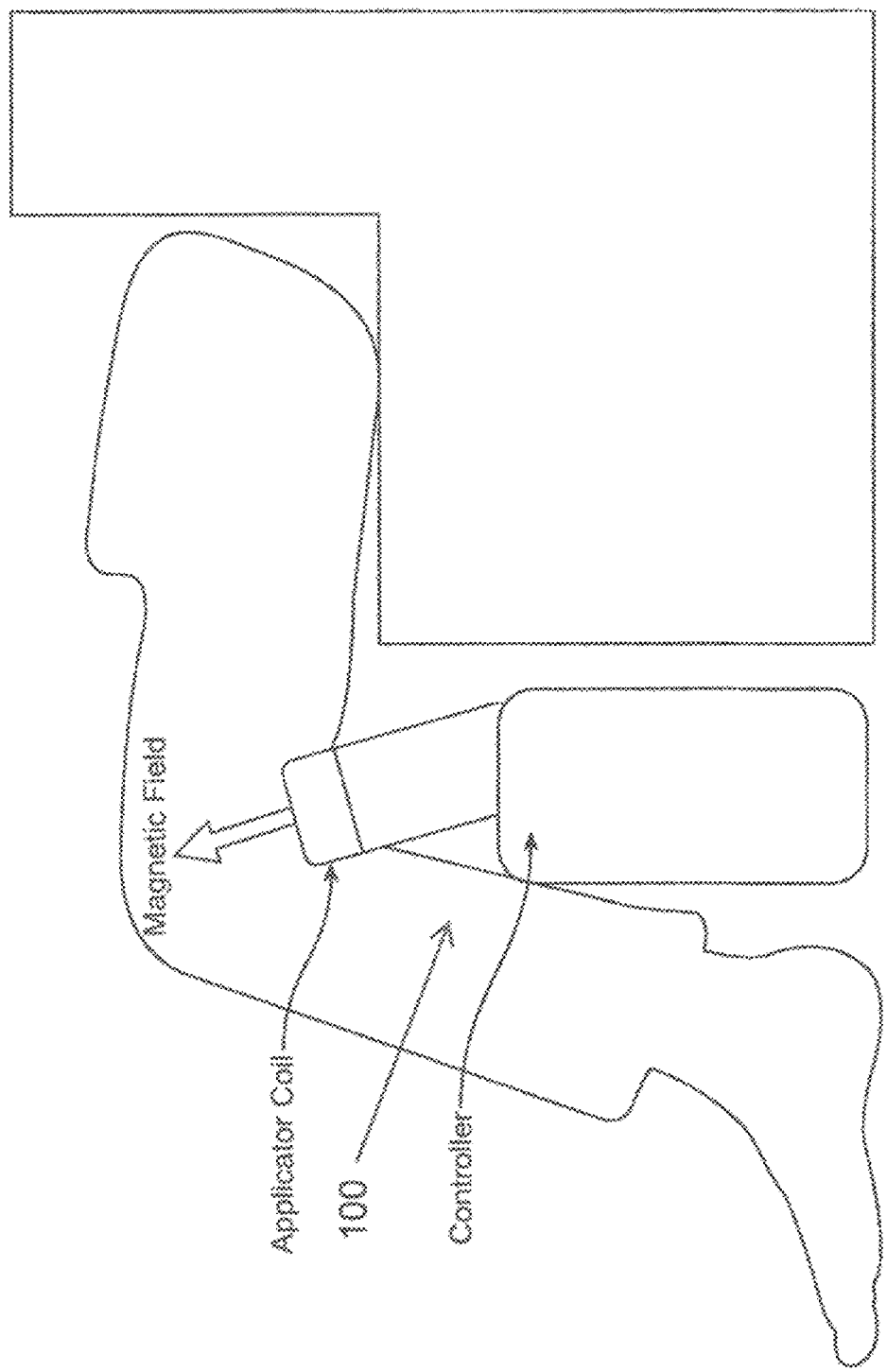

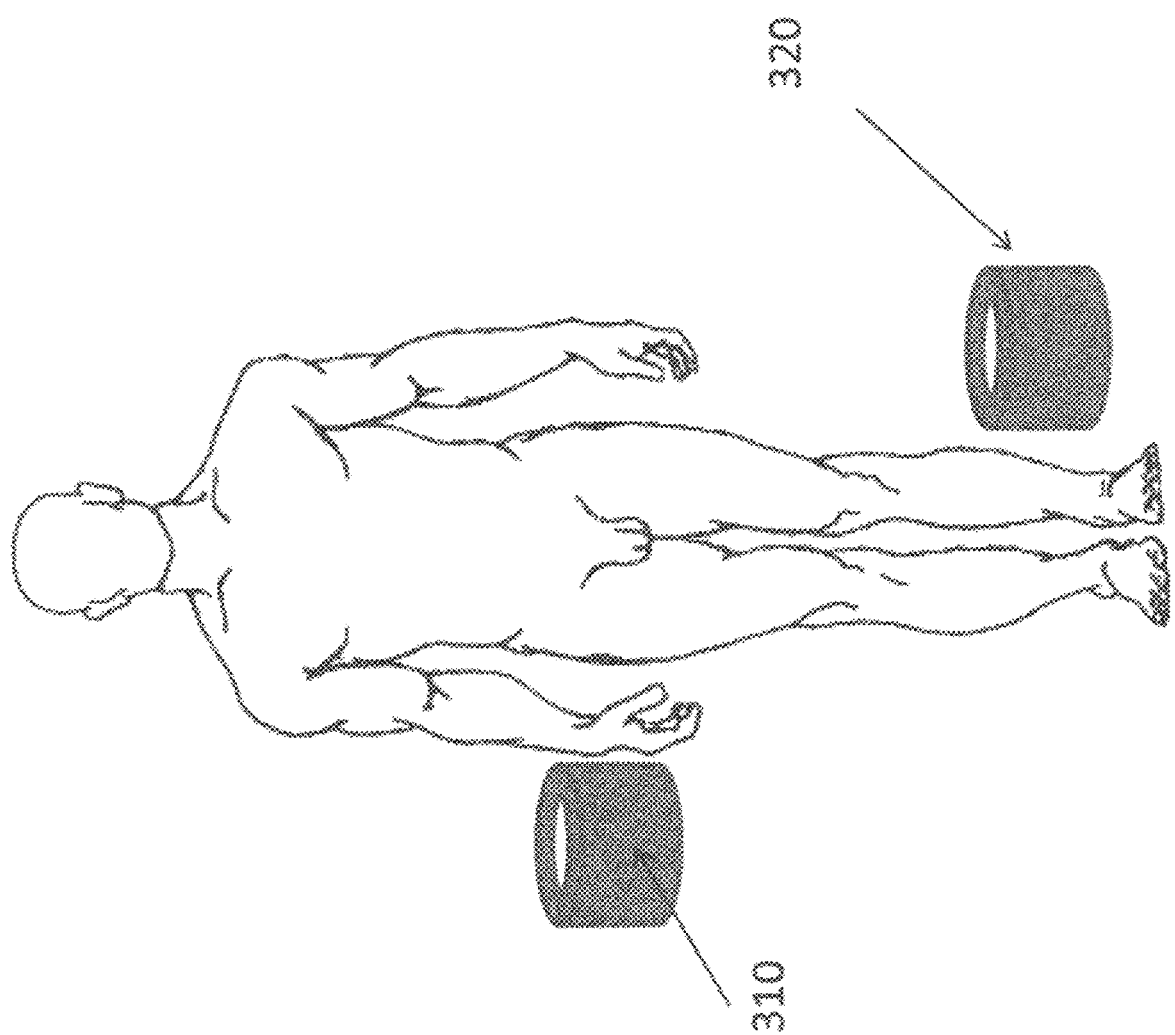

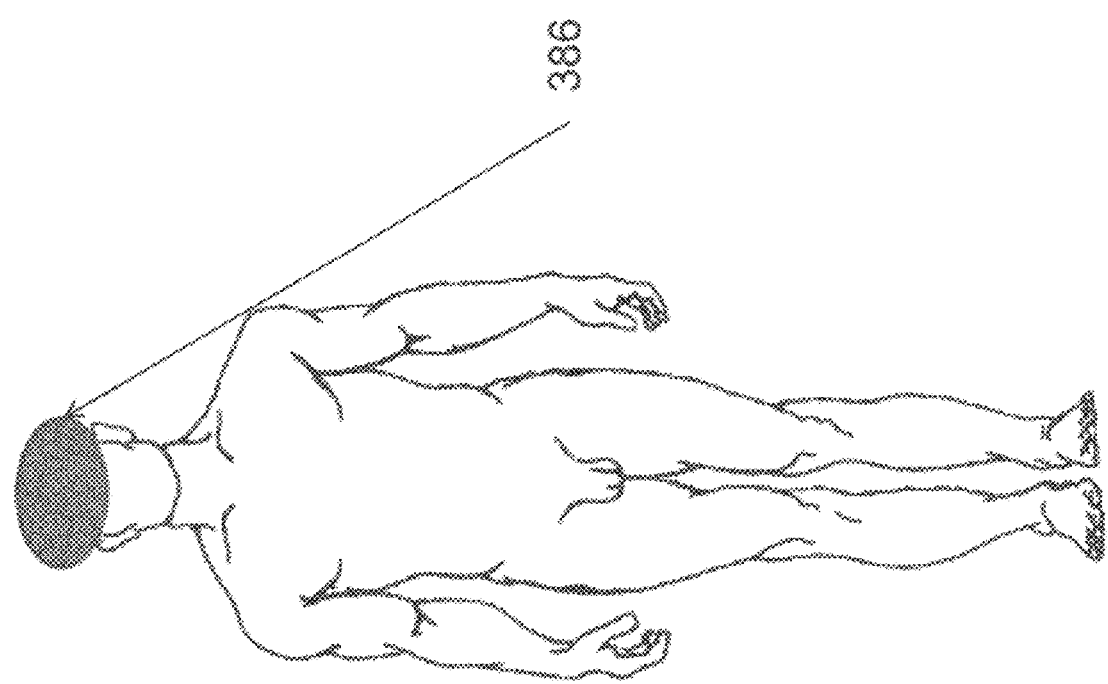

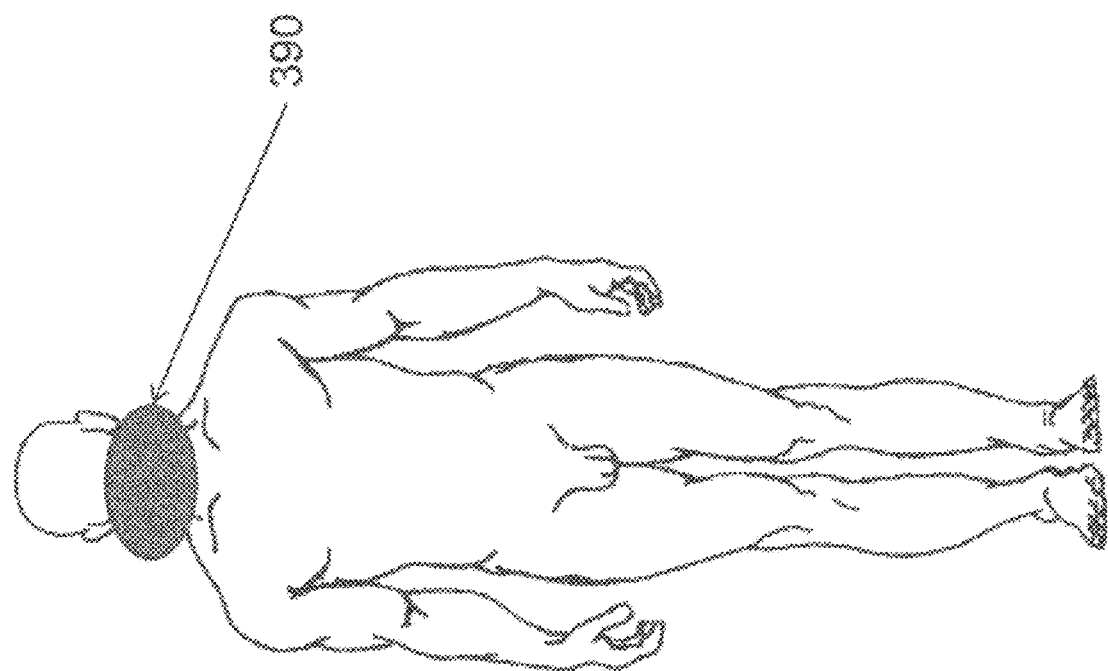

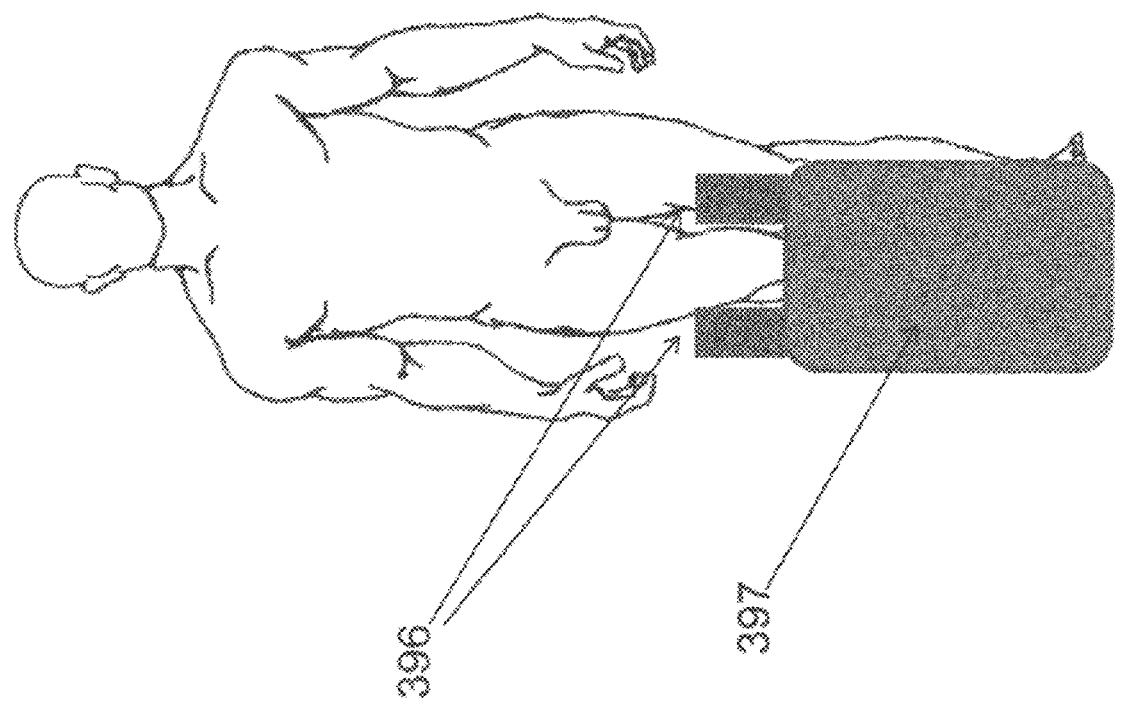

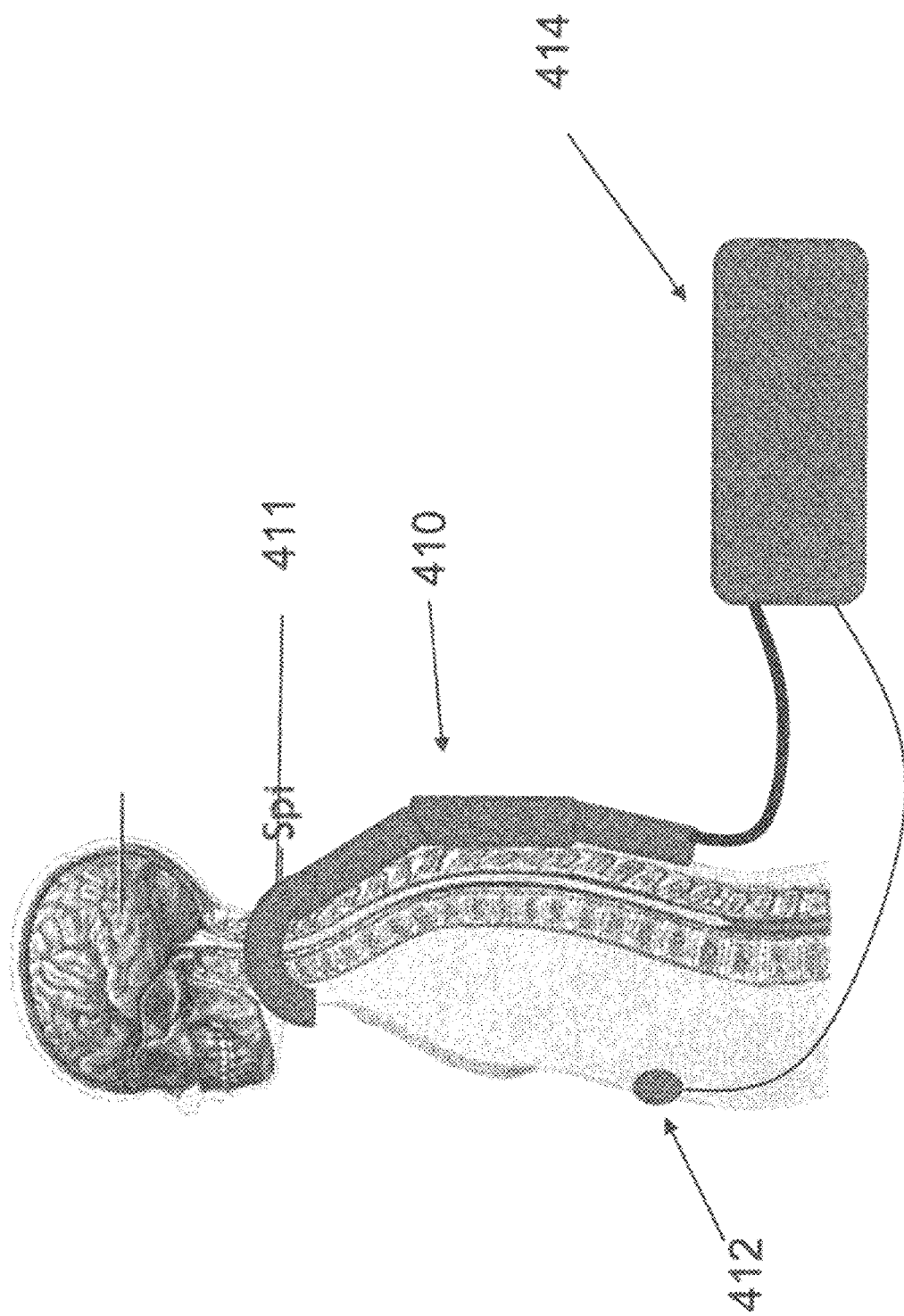

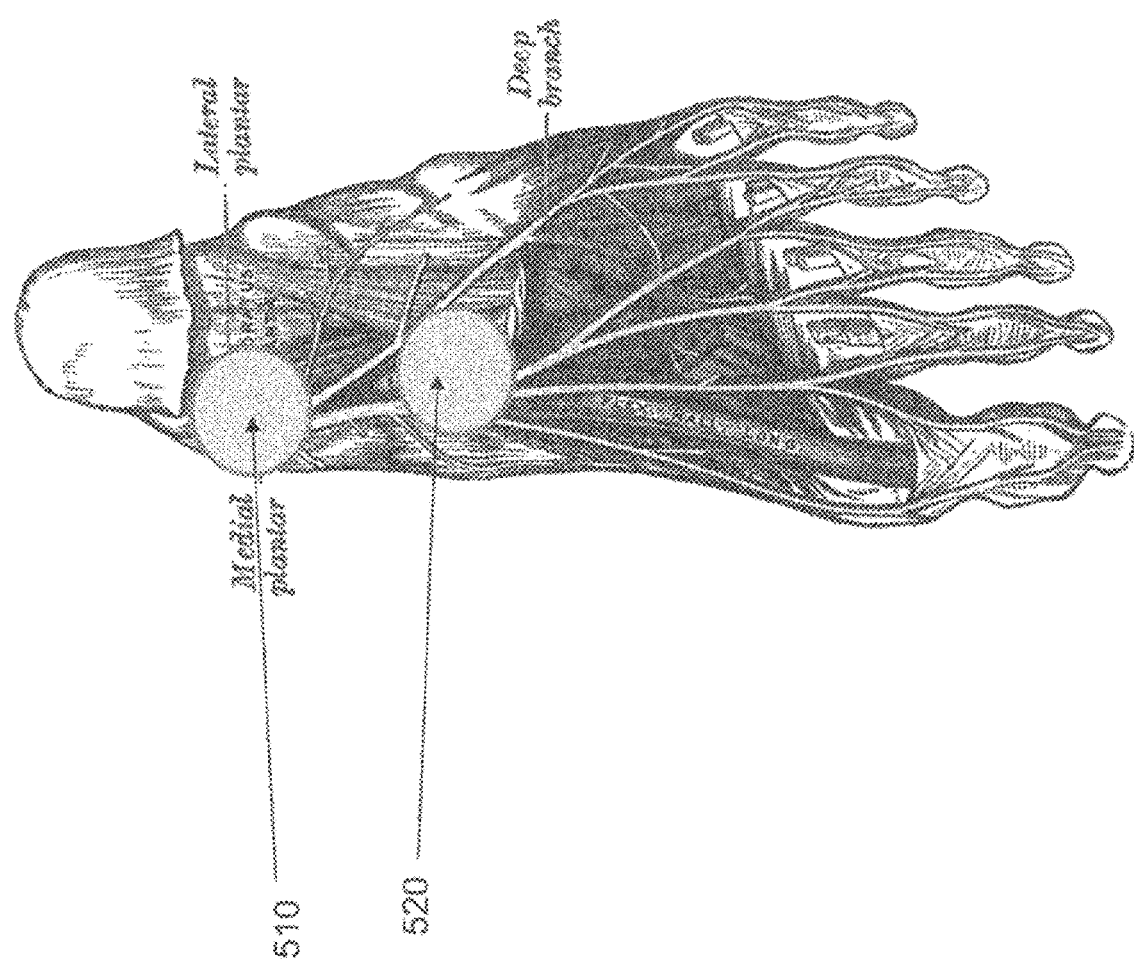

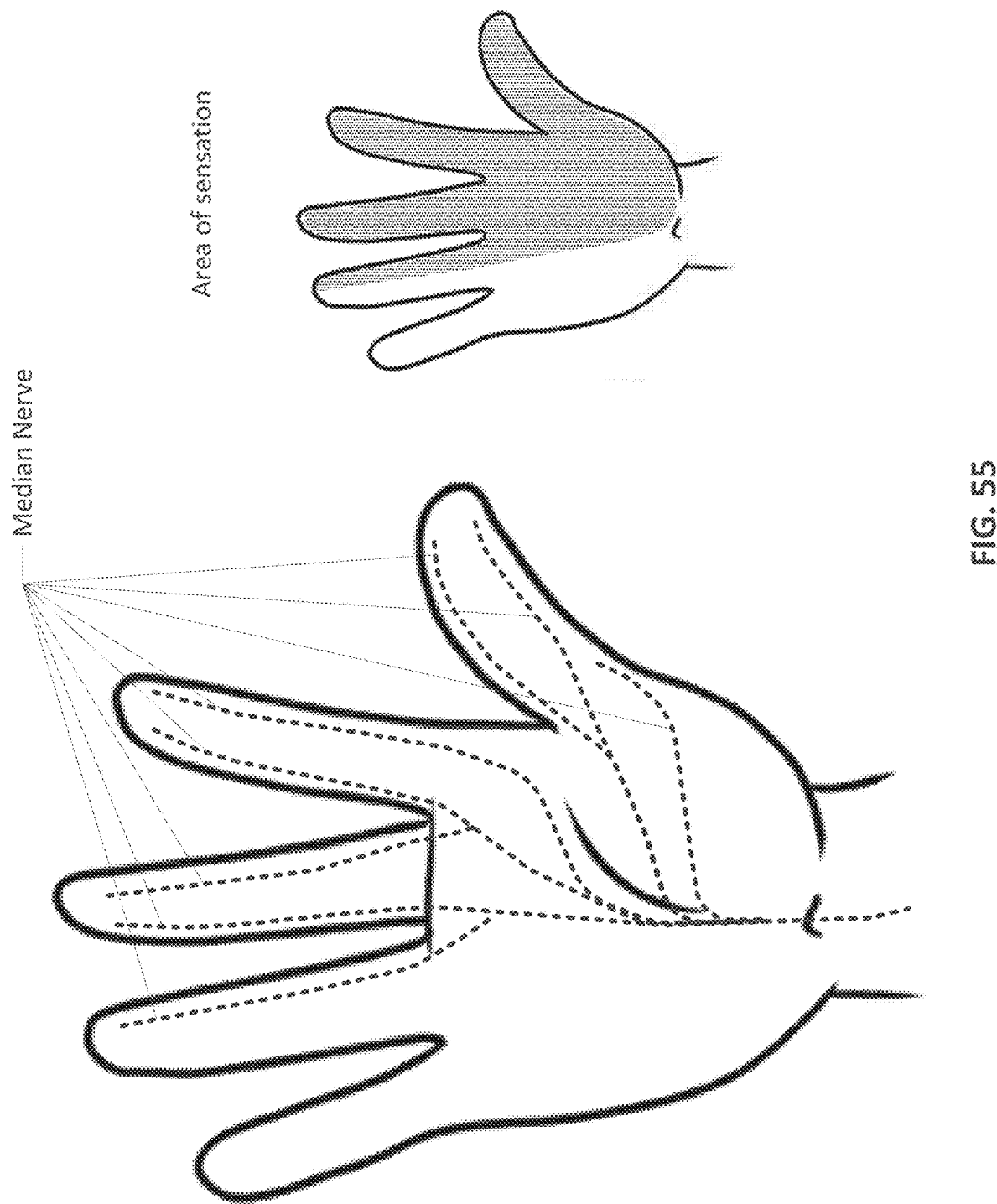

Schematic Representation of Output (one 10 pulse period)

5/6 met clinical endpoint with some degree of relief and 2/3 improved by two categories on the index

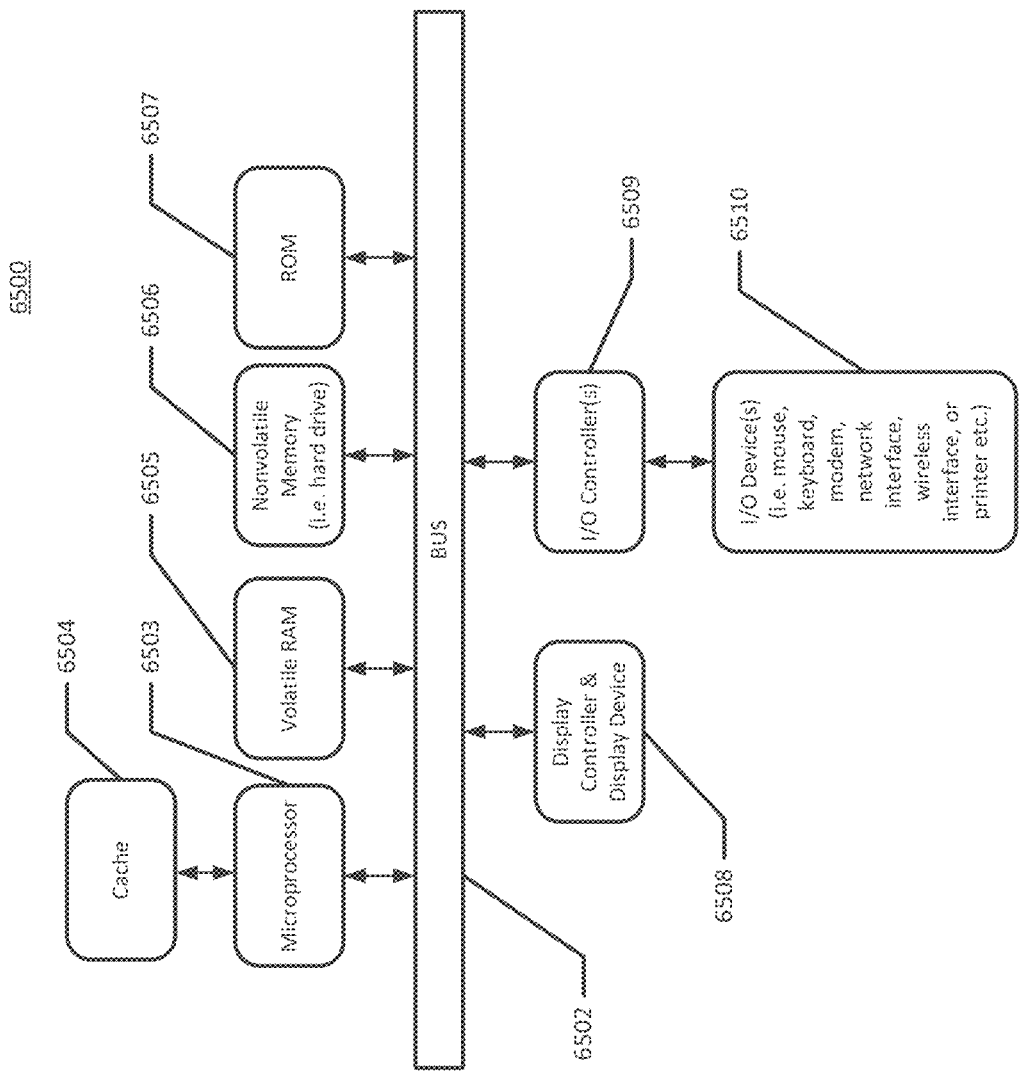

METHOD AND APPARATUS FOR TRANSDERMAL STIMULATION OVER THE PALMAR AND PLANTAR SURFACES

CROSS-REFERENCE TO RELATED APPLICATIONS

This application is a continuation of U.S. patent application Ser. No. 16/732,706 filed Jan. 2, 2020, which is a continuation of U.S. patent application Ser. No. 15/474,875 filed Mar. 30, 2017 (now U.S. Pat. No. 10,786,669), which is a continuation-in-part of U.S. patent application Ser. No. 15/084,356 filed Mar. 29, 2016 (now U.S. Pat. No. 9,630,004), which is a continuation of U.S. patent application Ser. No. 13/840,936 filed Mar. 15, 2013 (now U.S. Pat. No. 9,339,641), which is a continuation in part of PCT International Patent Application Number PCT/US2011/052415 filed Sep. 20, 2011, which claims benefit of priority to U.S. Provisional Patent Application No. 61/403,680 filed Sep. 20, 2010. U.S. patent application Ser. No. 15/474,875 is also a continuation-in part of U.S. patent application Ser. No. 12/508,529 filed Jul. 23, 2009 (now abandoned), which is a continuation-in-part of U.S. patent application Ser. No. 11/866,329 filed Oct. 2, 2007 (now abandoned), which claims priority to U.S. Provisional Patent Application No. 60/848,720 filed Oct. 2, 2006. U.S. patent application Ser. No. 15/474,875 also claims priority to U.S. Provisional Patent Application No. 62/350,610 filed Jun. 15, 2016. Each of the above referenced applications is incorporated herein by reference in their entirety.

The following applications are also incorporated herein by reference in their entirety for all purposes: PCT Application Serial No. PCT/US10/54167 filed Oct. 26, 2010; PCT Application Serial No. PCT/US10/054353 filed Oct. 27, 2010; U.S. patent application Ser. No. 12/508,529 filed Jul. 23, 2009 (now abandoned), which is a continuation in part of U.S. patent application Ser. No. 11/866,329 filed Oct. 2, 2007 (now abandoned), which claims priority to U.S. Provisional Patent Application Ser. No. 60/848,720 filed Oct. 2, 2006; U.S. patent application Ser. No. 12/695,087 filed Jan. 27, 2010 (now abandoned), which is a continuation of U.S. patent application Ser. No. 11/332,797 filed Jan. 17, 2006 (now abandoned); U.S. patent application Ser. No. 12/509,362 filed Jul. 24, 2009 (now U.S. Pat. No. 9,610,459); Ser. No. 12/469,365 filed May 20, 2009 (now abandoned), which is a continuation of U.S. patent application Ser. No. 11/866,329 filed Oct. 2, 2007 (now abandoned), which claims priority to U.S. Provisional Patent Application Ser. No. 60/848,720 filed Oct. 2, 2006, and Ser. No. 12/469,625 filed May 20, 2009 (now U.S. Pat. No. 8,430,805), which is a continuation of U.S. patent application Ser. No. 11/866,329 filed Oct. 2, 2007 (now abandoned), which claims priority to U.S. Provisional Patent Application Ser. No. 60/848,720 filed Oct. 2, 2006; and Ser. No. 12/509,304 filed Jul. 24, 2009 (now abandoned), which is a continuation of U.S. patent application Ser. No. 12/508,529 filed Jul. 23, 2009 (now abandoned), which is a continuation-in-part of U.S. patent application Ser. No. 11/866,329 filed Oct. 2, 2007 (now abandoned), which claims priority to U.S. Provisional Patent Application Ser. No. 60/848,720 filed Oct. 2, 2006; and Ser. No. 12/509,345 filed Jul. 24, 2009 (now abandoned), which is a continuation of U.S. patent application Ser. No. 12/508,529 filed Jul. 23, 2009 (now abandoned), which is a continuation-in-part of U.S. patent application Ser. No. 11/866,329 filed Oct. 2, 2007 (now abandoned), which claims priority to U.S. Provisional Patent Application Ser. No. 60/848,720 filed Oct. 2, 2006.

FIELD OF THE INVENTION

The present apparatus and methods relate generally to energy emitting apparatus and methods for providing a medical therapy. The apparatus and methods may provide for central and peripheral nerve and other tissue modulation or stimulation therapies

BACKGROUND OF THE INVENTION

The OAB and UI market in the United States is well over a $12 billion a year industry. It affects over 16% of all Americans, for a total U.S. market of approximately 34 million men and women each year. Due to social stigmas attached to OAB and UI, as well as misunderstanding of the signs and symptoms associated with OAB and UI, only 40% of those affected (13.6M) seek treatment. Of those 13.6 million individuals, nearly 30% are unsatisfied with their current therapy.

The use of pulsed electromagnetic stimulation (PES) has been well established as a beneficial therapy in a variety of medical applications. The scientific principle behind this technology is that an electric current passed through a coil will generate an electromagnetic field. These fields, in turn, have been shown to induce current within conductive materials placed within the field. When applied to the human body, pulsed electromagnetic stimulation has been found to be an effective method of stimulating nerves resting within the electromagnetic field. Recent data highlights the beneficial effects of invasive, needle-based electrostimulation (ES) of the posterior tibial nerve in individuals with OAB and UI. ES has been found to modulate bladder dysfunction through its action on the pudendal nerve and the sacral plexus which provides the major excitatory input to the bladder.

Current treatment options for OAB and UI are exercise and behavioral modifications, pharmacological therapies, surgical intervention, and neuromodulation. Although each of these treatment options targets the UI and OAB populations, each has severe limitations.

Exercise and behavioral modifications often require patients to adhere to stringent routines, including scheduled voiding, maintenance of a bladder diary, and intense exercise regiments. While this may be a viable option for a small group of highly dedicated individuals, its daily impact on one's life makes it an unattractive option for most individuals.

Pharmacological intervention is the most widely prescribed therapy for OAB and UI. Unfortunately, as with the ingestion of any chemical, patients are often subject to side effects from their drug therapy. This is especially detrimental in older and elderly patient populations where interaction with other prescribed medications can have adverse effects. Further, there is a high rate of dissatisfaction, approximately 30%, amongst individuals using pharmacological treatment.

Surgical intervention is an extremely invasive treatment and often results in the long-term, and in some cases permanent, requirement for catheterization. The high expense of these procedures, coupled with the negative impact the procedures have on the patients quality of life, make this an option only when all other treatment options have been exhausted.

Neuromodulation is another treatment alternative for OAB and UI patients. Sacral nerve stimulation (SNS) has shown itself to be an effective treatment option for those with OAB or UI. However, the procedure requires the permanent implantation of an electrical stimulation device in the patient. One estimate puts the cost at nearly $14,000 with additional routine care costs of $593 per patient per year. Additionally, SNS's risk of battery failure, implant infection, and electrode migration, lead to a high reoperation rate and make this procedure unattractive.

More recently, the introduction of a posterior tibial nerve stimulator, often referred to as SANS, has shown itself to be another neuromodulation alternative. Yet as is the case with other forms of neuromodulation, this system is invasive in its nature. It requires the insertion of a needle two inches into the patient's ankle region in order to stimulate the posterior tibial nerve. As well, it requires a minimum of 12 sessions for initial treatment, with the possibility of additional sessions needed for maintenance. Despite its high cost and invasive nature, though, an abundance of published peer-reviewed clinical trials demonstrate the safety and efficacy of the SANS therapy.

SUMMARY

In certain variations, a method for providing transdermal electrical stimulation therapy to a patient is provided. The method may include positioning a stimulator electrode over a glabrous skin surface overlying a target nerve of a subject. Electrical stimulation may be delivered through or across the glabrous skin surface to the target nerve to stimulate the target nerve, while remaining safe and tolerable to the patient. Electrical stimulation may be delivered at frequencies that may be painful or intolerable when applied over non-glabrous surfaces of the body. The electrical stimulation may be utilized to treat various conditions, e.g., urinary incontinence and overactive bladder.

In certain variations, an applicator, e.g., an ergonomic applicator, for providing transdermal electrical stimulation therapy to a patient is provided. The applicator may be configured to position a stimulator electrode over a glabrous skin surface of the subject to deliver transdermal electrical stimulation through or across the glabrous skin surface to an underlying target nerve, resulting in stimulation of the target nerve.

In certain variations, a method for providing an energy based stimulation therapy to a subject is provided. The method may include positioning an energy emitting device in proximity to a glabrous surface overlying a target tissue. Energy may be delivered through the glabrous skin surface to the target tissue to stimulate the target tissue.

In certain variations, another method for providing an energy based stimulation therapy to a subject is proved. The method may include positioning an energy emitting device in proximity to a skin surface overlying a target nerve. Energy may be delivered at a frequency of about 1 Hz to about 30 Hz through the skin surface to the target nerve, thereby generating motor and/or sensory nerve conduction of the target nerve while remaining safe and tolerable to the subject. Optionally, energy may be delivered at less than 10 Hz to generate nerve conduction.

In certain variations, systems for electromagnetic induction therapy may include one or more conductive coils disposed within or along an applicator. The coils may be configured to generate a magnetic field focused on a target nerve, muscle or other body tissues in proximity to the coil. One or more sensors may be utilized to detect electrical conduction in the target nerve, to detect a muscular response caused by an electrical conduction in the target nerve, or to detect stimulation of a nerve, muscle or other body tissues and to provide feedback about the efficacy of the applied electromagnetic induction therapy. A controller in communication with the sensor may be adjustable to vary a current through the at least one coil so as to adjust the magnetic field focused upon the target nerve, muscle or other body tissues. Optionally, a user or patient may detect stimulation of a nerve, muscle or body tissue and the therapy may be adjusted based on feedback from the user or patient.

In certain variations, the applicator may be configured to intermittently apply or deliver pulsed magnetic fields to a target nerve, muscle or tissue without causing habituation of the target nerve, muscle or tissue.

In certain variations, methods of electromagnetic induction therapy may include one or more of the following steps. A first portion of a patient's body may be positioned relative to or in proximity to an applicator or an applicator may be positioned relative to or in proximity to a first portion of a patient's body, such that a target nerve, muscle or tissue within the first portion of the body is in proximity to one or more conductive coils disposed within or along the applicator. A current may be passed through a coil to generate a magnetic field focused on the target nerve, muscle or tissue. An electrical conduction through the target nerve, a muscular response caused by an electrical conduction through the target nerve or stimulation of a nerve, muscle, or body tissue may be detected by a sensor positioned along a second portion of the body. A signal from the sensor indicative of the electrical conduction or stimulation may be received, which provides feedback about the efficacy of the applied electromagnetic induction therapy. The current may be adjusted by a controller in communication with the conductive coils based on the feedback.

Optionally, a user may detect stimulation of a nerve, muscle or body tissue and the therapy may be adjusted based on feedback from the user. In certain variations, pulsed magnetic fields may be intermittently applied or delivered a target nerve, muscle or tissue without causing habituation of the target nerve, muscle or tissue. Such intermittent magnetic fields may be used to treat chronic conditions, e.g., chronic pain, without causing habituation.

In certain variations, applicators may be ergonomic or may be designed or configured to accommodate, approximate or be positioned relative to or in proximity to specific regions of the body or anatomy. The specific regions of the body or anatomy may be positioned relative to the applicators, or the applicators may be positioned relative to the specific regions of the body or anatomy to treat various conditions, for example, osteoarthritis, arthritis, back or neck pain, atrophy or paralysis, chronic pain, phantom or neuropathic pain, neuralgia, migraines, orthopedic conditions.

In one embodiment, the invention provides a method or device for providing transdermal electrical stimulation therapy to a subject including positioning a stimulator electrode over a glabrous skin surface overlying a palm of the subject and delivering electrical stimulation via a pulse generator transdermally through the glabrous skin surface and to a target nerve or tissue within the hand to stimulate the target nerve or tissue within the hand so that pain felt by the subject is mitigated. The pulses generated during the electrical stimulation therapy may include pulses of one or two or more different magnitudes.

In some embodiments, the electrical stimulation is delivered at a frequency of about 5 Hz to about 60 Hz, while remaining safe and tolerable to the subject. In some embodiments, the stimulator electrode is a surface electrode. The electrical stimulation may be delivered intermittently or on a chronic basis.

In some embodiments, the device includes a sensor (which may be a surface electrode, or other type of electrode) for detecting nerve stimulation which receives a signal from the sensor indicative of the detected electrical stimulation thereby providing a feedback about the efficacy of the applied electrical stimulation therapy such that the therapy is adjusted or optimized. An M-wave and/or F-wave may be detected by the sensor. A parameter of the M-wave and/or F-wave may be displayed to the subject.

In some embodiments, the feedback is queried by a controller such that the electrical stimulation therapy is adjusted to ensure that a minimum amount of energy is being applied to stimulate the target nerve within the hand while reducing the risk of burns or intolerance. Alternatively, the feedback may be queried such that the positioning of the stimulator electrode is adjusted to optimize the electrical stimulation therapy.

In some embodiments, a return electrode may be positioned on the subject to facilitate penetration of an electrical current through the glabrous surface to stimulate the target nerve within the hand. The stimulator electrode may be attached to the glabrous skin surface with an adhesive. The stimulator electrode may be positioned over the glabrous skin surface with an ergonomic applicator. The applicator may be a glove or brace configured to be positioned against the palmar surface of a hand such that the electrode delivers electrical stimulation to a target nerve within the hand.

In some embodiments, the electrical stimulation is automatically paused for a preset amount of time every 10 minutes to overcome habituation. In some embodiments, the electrical stimulation is automatically paused for a preset amount of time every 10 minutes based on feedback provided by a sensor regarding target nerve stimulation or habituation.

In some embodiments, once tetany is detected in a patient, indicating that a threshold frequency of the applied stimulation has been reached, the strength of the applied stimulation is automatically or manually decreased.

In some embodiments, electrical stimulation is provided by delivering a cycle comprising a preset number of pulses followed by a pause in stimulation, followed by a preset number of pulses, and repeating the cycle as necessary.

In some embodiments, the device is used to treat migraine pain.

Other features and advantages will appear hereinafter. The features and elements described herein can be used separately or together, or in various combinations of one or more of them.

BRIEF DESCRIPTION OF THE DRAWINGS

The drawings constitute a part of this specification and include exemplary embodiments of the invention, which may be embodied in various forms. It is to be understood that in some instances various aspects of the embodiments may be shown exaggerated or enlarged to facilitate an understanding of the embodiments.

FIGS. 30a-30b show schematic views of an energy emitting device in the form of a knee support.

FIGS. 31a-31b shows a schematic view of a variation of an arm applicator and a foot, knee or leg applicator.

FIG. 38 shows a schematic view of a variation of an applicator which may be placed over the occipital nerve for the treatment of migraines.

FIG. 39 shows a schematic view of a variation of an applicator which may be placed over the frontal cortex for the treatment of depression.

FIG. 40 shows a schematic view of a variation an applicator in the form of a stimulator coil platform for positioning one or more coils in proximity to a knee or popliteal nerve.

FIG. 41 shows a schematic view of a system including a variation of a back applicator held on a patient's body by an ergonomic positioning element in the form of a shoulder harness, a sensor, and a logic controller.

FIG. 44 shows a view of the underside or glabrous surface of the foot and exemplary sites for delivering electrical stimulation.

FIG. 55 shows a close up anterior or palmar view of the Median nerve's palmar branch in the hand and its area of sensation.

FIG. 65 is a block diagram of a data processing system.

DETAILED DESCRIPTION

Figure 1:
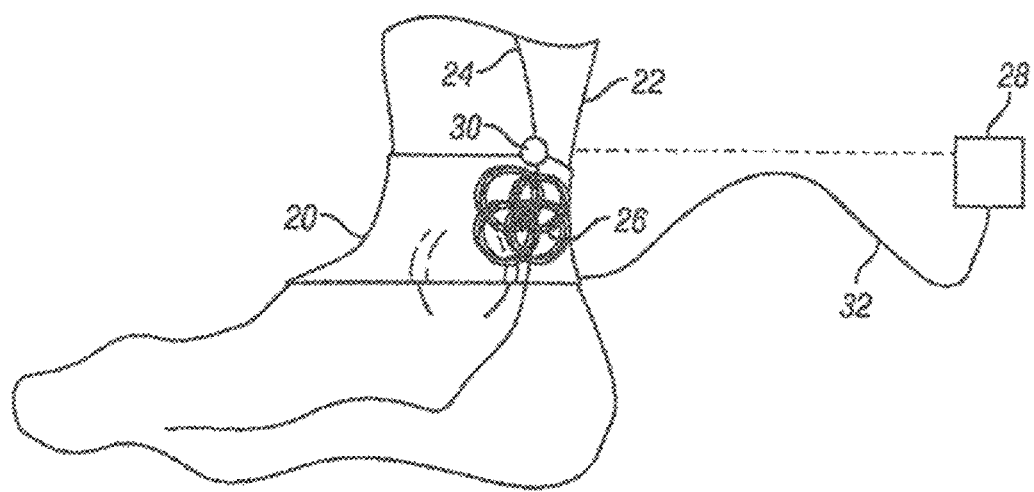
FIG. 1 is a schematic view of an apparatus for magnetic induction therapy according to a first variation.

In certain variations, various apparatus and methods for providing magnetic induction therapy or electrical stimulation therapy are provided. In certain variations, various apparatus and methods may provide for central and peripheral nerve and other tissue modulation or stimulation therapies, including both excitation and blocking of nerve impulses. In certain variations, a low frequency induction therapy may be performed. In certain variations, these apparatus and methods may be useful in the treatment and prevention of urinary incontinence (UI), overactive bladder (OAB) and other conditions.

In certain variations, apparatus and methods for magnetic induction therapy, in which dosage of magnetic energy can be regulated according to conduction in a target nerve exposed to the magnetic field are provided.

In certain variations, apparatus and methods for magnetic induction therapy, in which the flow of magnetic energy can be adjusted directionally by the patient or a healthcare provider without altering the position of a housing containing conductive coils that produce the magnetic field are provided.

In certain variations, apparatus and methods for treating a variety of ailments by providing energy to a target nerve, for example magnetic energy, electrical energy or ultrasound energy, at a location and in an amount optimized by detecting conduction in the target nerve are provided.

In certain variations, an energy emitting apparatus for delivering a medical therapy that includes one or more energy generators, a logic controller electrically connected to the one or more energy generators, and one or more sensors for detecting electric conduction in a target nerve, which are connected to the logic controller is provided. The one or more energy generators produce energy focused on the target nerve upon receiving a signal from the logic controller, and the applied energy is varied by the logic controller according to an input provided by the one or more sensors based on electric conduction in the target nerve. The feedback provided by the sensors to the logic controller about the efficacy of the applied treatment causes the logic controller to modulate the current transmitted to the coils.

The applied energy may be a magnetic field, an electrical field, an ultrasound, a visible light, or an infrared or an ultraviolet energy. When a magnetic field is applied, the energy-emitting device is an apparatus that provides a magnetic induction therapy and that includes one or more conductive coils disposed in an ergonomic housing. A logic controller is electrically connected to the one or more coils, and one or more sensors detect electric conduction in the target nerve and are connected to the logic controller so to provide a feedback to the logic controller. The conductive coils receive an electric current from the logic controller and produce a magnetic field focused on a target nerve, and the electric current fed by the logic controller is varied by the logic controller according to an input provided by the sensors, thereby causing amplitude, frequency or direction of the magnetic field, or the firing sequence of the one or more coils, to be varied according to the efficiency of the treatment provided to the target nerve. In certain variations, the housing containing the conductive coils may be a flexible wrap, a cradle or a garment, and the coils may be overlapping and/or be disposed in different positions within the housing, so to generate a magnetic field on different body parts with the desired direction and amplitude.

The one or more coils may be stationary or movable within the housing, making it possible to optimize the direction of magnetic flow to the target nerve by disposing the coils in the most effective direction. In different variations, the coils may be movable manually by acting on a knob, lever, or similar type of actuator, or may be translated automatically by the logic controller in response to the input provided by the sensors. When a preferred position for the coils has been established, the coils may be locked in position and maintain that position during successive therapy sessions. In other variations, the sensors may be incorporated within the housing, or instead may be disposed on a body part of interest independently of the housing.

In still other variations, the inductive coils are disposed in a housing that is situated externally to a patient's body, and additional inductive coils are implanted into the body of the patient and are magnetically coupled to the external inductive coils. With this coil arrangement, energy may be transmitted from the external coils to the internal coils either to recharge or to activate an implantable device. In yet other variations, the electric current may varied by the logic controller both on the basis of an input provided by the one or more sensors and also an input provided by the patient according to a muscular response she has perceived, for example, the twitching of a toe after application of the magnetic field.

In yet other variations, the source of energy for nerve stimulation may be electrical energy and nerve conduction may be detected at a site sufficiently distant from the site of stimulation, so to enable detection of nerve conduction despite any interference from the direct electrical stimuli. In these variations, direct electrical stimulation of nerve and muscle may be tailored to provide optimal therapy and, in the case of electrode migration or other electrode malfunction, to report lack of stimulation of the bodily tissues. Furthermore, these variations enable a reduction in power requirement, because control of the signal is provided by the sensor to the signal generator loop.

In other variations, an energy emitting system for providing a medical therapy is provided. The system may include one or more conductive coils disposed within or along a housing and configured to generate a magnetic field focused on a target nerve in proximity to coils; one or more sensors in the form of microneedle patch configured to detect electrical conduction in the target nerve; and a controller coupled to the conductive coils and optionally in communication with the sensor.

In other variations, an energy emitting system for providing a medical therapy is provided. The system may include one or more microneedle patches having one or more microneedle arrays deposited on a surface of one or more electrodes and configured to generate or deliver an electrical or magnetic stimulus or field focused on a target nerve in proximity to the microneedle patch; one or more sensors configured to detect electrical conduction in the target nerve; and a controller coupled to the conductive coils and optionally in communication with the sensor. Optionally, the above variations may incorporate an electrode needle. Optionally, the above variations or systems may be utilized without a sensor or mechanism for detecting conduction or stimulation.

Methods of use of the above apparatus, systems and variations thereof for treating various conditions are also described herein.

Referring first to FIG. 1, a first variation includes a coil wrap 20, which is depicted as disposed over ankle 22 circumferentially to surround a portion of tibial nerve 24. Because tibial nerve 24 is targeted, this variation is particularly suited for the treatment of OAB and VI. In other variations, coil wrap 20 may be configured to surround other body parts that contain a portion of tibial nerve 24 or of other nerves branching from or connected to tibial nerve 24, still making these variations suitable for treating OAB and VI. In still other variations, coil wrap 20 may be configured for surrounding body parts that contain other nerves when treatments of other ailments are intended.

Coil wrap 20 may be manufactured from a variety of materials suitable for wearing over ankle 22. Preferably, coil wrap is produced from a soft, body-compatible material, natural or synthetic, for example, cotton, wool, polyester, rayon, Gore-Tex®, or other fibers or materials known to a person skilled in the art as non-irritating and preferably breathable when tailored into a garment. Coil wrap 22 may even be manufactured from a molded or cast synthetic material, such as a urethane gel, to add extra comfort to the patient by providing a soft and drapable feel. Additionally, coil wrap 20 may be produced from a single layer of material or from multiple material layers and may include padding or other filling between the layers.

Coil wrap 20 contains one or more conductive coils 26 arranged to produce a pulsed magnetic field that will flow across tibial nerve 24 and generate a current that will flow along tibial nerve 24 and spread along the length of tibial nerve 24 all the way to its sacral or pudendal nerve root origins. Coils 26 may be a single coil shaped in a simple helical pattern or as a FIG. eight coil, a four leaf clover coil, a Helmholtz coil, a modified Helmholtz coil, or may be shaped as a combination of the aforementioned coils patterns. Additionally, other coil designs beyond those mentioned hereinabove might be utilized as long as a magnetic field is developed that will encompass tibial nerve 24 or any other target nerve. When a plurality of coils is utilized, such coils may be disposed on a single side of ankle 22, or may be disposed on more than one side, for example, on opposing sides, strengthening and directionalizing the flow of the magnetic field through tibial nerve 24 or other peripheral nerves of interest.

Coil wrap 20 is preferably configured as an ergonomic wrap, for example, as an essentially cylindrical band that can be pulled over ankle 22, or as an open band that can be wrapped around ankle 22 and have its ends connected with a buckle, a hoop and loop system, or any other closing system known to a person skilled in the art. By properly adjusting the position of coil wrap 20 over ankle 22, a patient or a health care provider may optimize the flow of the magnetic field through tibial nerve 24, based on system feedback or on sensory perceptions of the patient, as described in greater detail below.

The electric current that produces the magnetic field by flowing through coils 26 is supplied by a programmable logic controller 28, which is connected to coils 26, for example, with a power cord 32. A sensor 30 that feeds information to logic controller 28 is also provided, in order to tailor the strength of the magnetic field and control activation of coils 26 based on nerve conduction. The purpose of sensor 30 is to detect and record the firing of the target nerve and to provide related information to logic controller 28, so to render the intended therapy most effective. For example, sensor input may cause logic controller 28 to alter the strength or pulse amplitude of the magnetic field based on sensor input, or fire the coils in a certain sequence.

In this variation, as well as in the other variations described hereinafter, sensor 30 may include one or more sensor patches and may be placed at different distances from the region of direct exposure to the magnetic field. For example, sensor 30 may be configured as a voltage or current detector in the form of an EKG patch and may be placed anywhere in the vicinity of the target nerve to detect its activation. For ease of description, the term "coils" will be used hereinafter to indicate "one or more coils" and "sensor" to indicate "one or more sensors," unless specified otherwise.

By virtue of the above described arrangement, coil wrap 20 provides a reproducibly correct level of stimulation during an initial therapy session and during successive therapy sessions, because the presence or absence of nerve conduction is detected and, in some variations, measured when coil wrap 20 is first fitted and fine-tuned on the patient. In addition to properly modulating the applied magnetic field, the positioning of coils 26 over ankle 22 may also be tailored according to the input provided by sensor 30, so to fine-tune the direction of the magnetic field. Such an adjustment of the direction, amplitude, and level of the stimulation provided to the target nerve through the above described automated feedback loop, to ensure that peripheral nerve conduction is being achieved, is one of the key features.

If the magnetic pulse does not substantially interfere with sensor 30, sensor 30 may be placed directly within the field of stimulation, so that power supplied to the system may be conserved. This is particularly important for battery-powered systems. Alternatively, sensor 30 may also be placed at a distance from the magnetic field and still properly detect neural stimulation.

In a method of use of coil wrap 20, the amplitude and/or firing sequence of coils 26 may be ramped up progressively, so that the magnetic field is increased in strength and/or breadth until nerve conduction is detected, after which the applied stimulus is adjusted or maintained at its current level for the remainder of the therapy. The level of stimulation may be also controlled through a combination of feedback from sensor 30 and feedback based on perceptions of the patient. For example, the patient may activate a switch once she perceives an excessive stimulation, in particular, an excessive level of muscular stimulation. In one instance, the patient may be asked to push a button or turn a knob when she feels her toe twitching or when she experiences paresthesia over the sole of her foot. The patient will then continue pressing the button or keep the knob in the rotated position until she can no longer feel her toe twitching or paresthesia in her foot, indicating that that level of applied stimulation corresponds to an optimal therapy level. From that point on, the patient may be instructed to simply retain her foot, knee, or other limb within coil wrap 20 until therapy has been terminated while the system is kept at the optimal level. Adding patient input enables control of coil wrap 20 during outpatient treatments, because the patient is now able to adjust the intensity of the magnetic field herself beyond the signals provided to logic controller 28 by sensor 30.

Detecting and, if the case, measuring conduction in one or more nerves along the conduction pathways of the stimulated nerve confirms that the target nerve has been stimulated, providing an accurate assessment of the efficiency of the applied therapy on the patient. A concomitant detection of muscle contraction may also confirm that the target nerve is being stimulated and provide an indication to the patient or to a healthcare provider as to whether stimulation has been applied at an excessive level in view of the anatomical and physiological characteristics of the patient.

Based on the foregoing, coil wrap 20 allows for a consistent, user-friendly targeting and modulation of the peripheral nerves via the posterior tibial nerve on an outpatient basis, in particular, the targeting and modulation of the pudendal nerve and of the sacral plexus. When multiple coils 26 are present, coils 26 may be activated simultaneously or differentially to generate the desired magnetic field. The direction and location of each of coils 26 may be reversibly or irreversibly adjusted by the healthcare provider or by the patient, customizing the location of the applied stimulation to the anatomy and therapy needs of each patient. After a healthcare provider has optimized position and firing sequence for each of coils 26, the patient may be sent home with coil wrap 20 adjusted to consistently target the desired nerve. In one variant of the present variation, an automatic feedback system adjusts one or more of firing sequence, firing strength or position of coils 26 within coil wrap 20 during the initial setup and also during successive therapy sessions.

In summary, certain variations include the creation of a loop consisting of feeding information on nerve conduction to logic controller 28 and on logic controller 28 tailoring the electrical current sent to coil wrap 20 according to the information received from sensor 26 based on whether or not the nerve is receiving the desired stimulation and, in some variations, the desired amount of stimulation. This arrangement offers an unparalleled level of therapy control and flexibility within a home care setting, because a consistent, repeatable stimulation of the target nerve can be attained. Aside from adjusting the position of coils 26 in accordance with the patient's anatomy and physiological variations, controlling pulse amplitude is also of great importance even during different therapy sessions with the same patient. For example, a patient with leg edema will encounter difficulties in properly adjusting coil wrap 20 based on whether her legs and ankles are swollen or not swollen, and the power required to penetrate to posterior tibial nerve 24 (in the case of a VI therapy) will vary greatly due to the variable depth of the nerve. Thus, having feedback provided by sensor 26 becomes a necessity for achieving an accurate dosage of the treatment rather than an option. Benchtop testing has demonstrated that a system constructed as described herein is capable of non-invasively generating electrical currents similar to those found in therapeutic electrostimulation and to do so in different settings.

Figure 2:
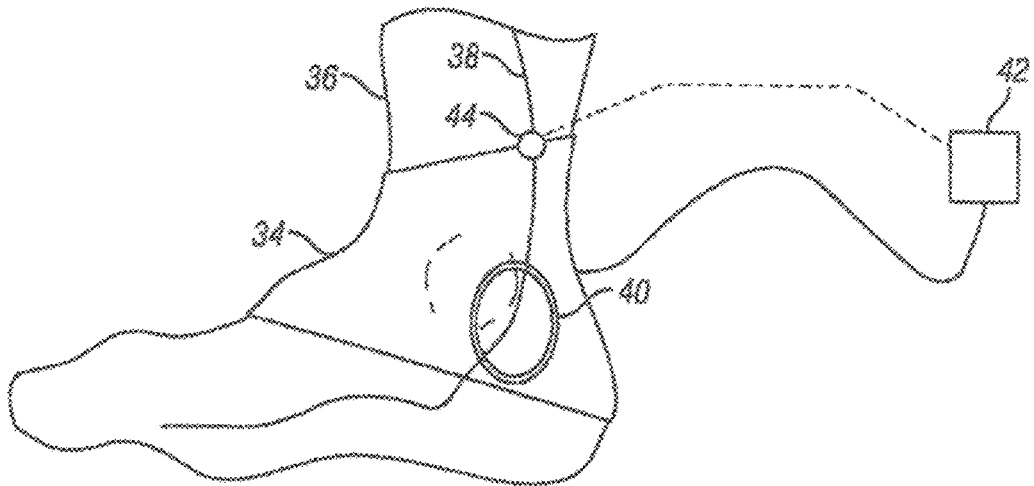
FIG. 2 is a schematic view of an apparatus for magnetic induction therapy according to a second variation.

Referring now to FIG. 2, a second variation will be described with reference to a coil wrap 34 disposed over ankle 36 for the purpose of treating VI by targeting tibial nerve 38. In this second variation, one or more Helmholtz coils 40 are disposed within coil wrap 34 to create a more narrowly directed magnetic field over tibial nerve 38. Like in the all other variations described herein, more than one coil (in the present variation, more than one Helmholtz coil 40) may be placed within coil wrap 34 and be disposed in different positions within coil wrap 34, in order to optimize magnetic flux over tibial nerve. For example, two Helmholtz coils may be disposed one opposite to the other within coil wrap 34.

Having coil windings arranged along a common longitudinal axis, as required in a Helmholtz coil configuration, generates a more focused magnetic field and a more accurate targeting of tibial nerve 38 or of any other nerve. Like in the previous variation, the operation of coils 40 is controlled by a logic controller 42, which is in turn connected to sensor 44 that monitors conduction in tibial nerve 44 and that generates a feedback to logic controller 42 about the efficiency of the therapy in progress. Therefore, like in the previous variation, the coupling of sensor 44 with logic controller 42 optimizes operation of coil wrap 34 according to results measured at the level of tibial nerve 38. Also like in the previous variation, manual adjustments to the parameters of electric current provided by logic controller 42 to Helmholtz coil 40 may also be made manually by the patient or by a healthcare provider, and coil wrap 34 may be structured so that the position of Helmholtz coil 40 within coil wrap 34 is adjusted as desired either manually by the patient or by a healthcare provider, or automatically by logic controller 42.

Figure 3:
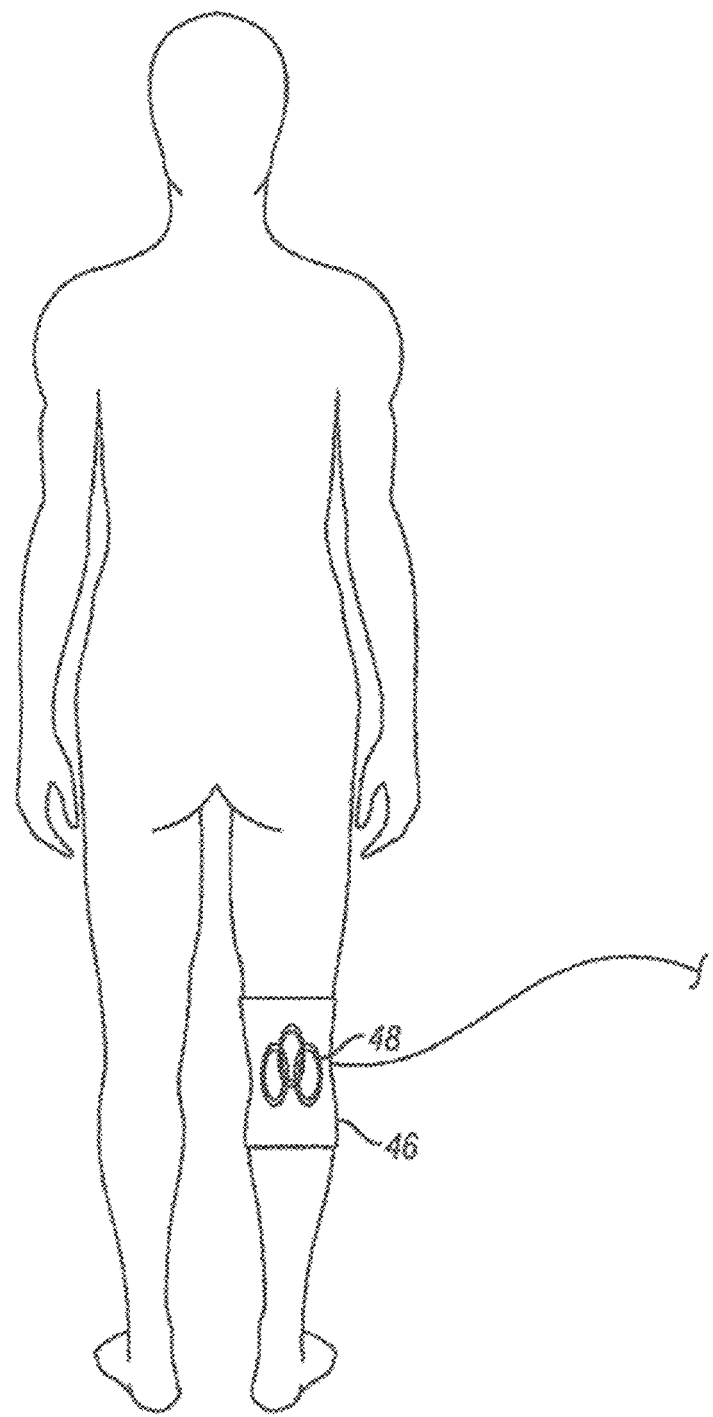
FIG. 3 is a schematic view of an apparatus for magnetic induction therapy according to a third variation.

Referring now to FIG. 3, a third variation includes a coil wrap 46 configured for wrapping over the popliteal fossa of a patient, in the region of the knee, to stimulate the posterior tibial nerve (not shown). The configuration and structure of coil wrap 46 reflect the body portion covered by coil wrap 46, but the key system components of coil wrap 46, such as the type, number and disposition of the coils (for example, the use of overlapping coils); the connections of the coils with a logic controller; and the use of one or more sensors (also not shown) to detect nerve conduction are all comparable to those in the previously described variations.

Figure 4:
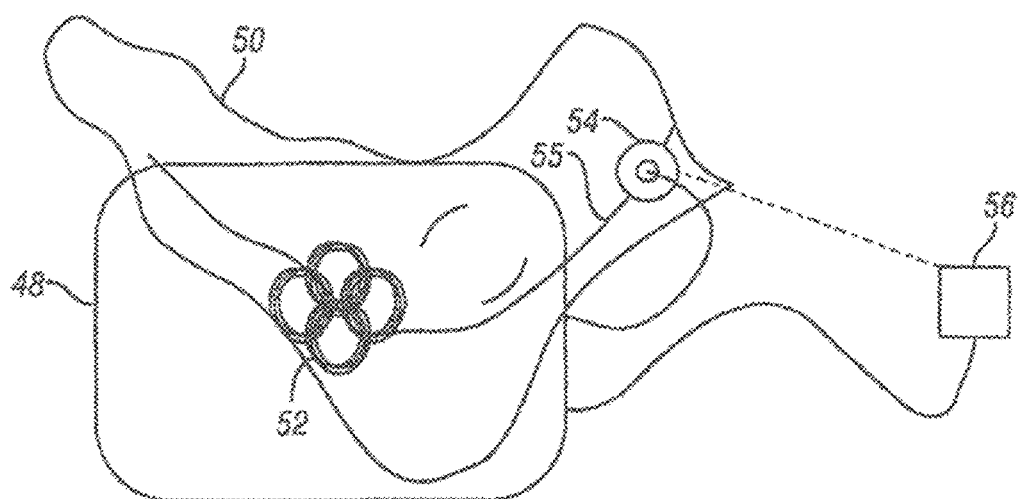
FIG. 4 is a schematic view of an apparatus for magnetic induction therapy according to a fourth variation.

Referring now to FIG. 4, a fourth variation includes a footrest or foot cradle 48, which is structured to contain at least a portion of a foot 50. One or more coils 52 are enclosed within cradle 48, and a sensor 54 is disposed along the pathway of tibial nerve 55, sensing conduction in tibial nerve 55, and is also connected to a logic controller 56. Coils 52, sensor 54 and logic controller 56 may be arranged in different configurations, in the same manner as in the preceding variations.

Cradle 48 may be made from a variety of materials and may be monolithic, or have a hollow or semi-hollow structure to enable the movement of coils 52 within cradle 48, as described in greater detail below. Preferably, cradle 48 has an ergonomically design allowing the ankle and heel of the patient to be retained within cradle 48, in a position that matches the positions of stimulating coils 52 to the area of stimulation. The design of cradle 48 provides for a particularly comfortable delivery of therapy to patients that prefer to remain seated during their therapy, and enables the patient to perform the required therapy within a health care facility, or to take cradle 48 home, typically after an initial session and appropriate training in a health care facility. In that event, the patient will be trained to apply sensor 54 autonomously and to adjust stimulation to a comfortable level.

FIG. 4 shows coils 52 disposed as overlapping and the use of a single sensor patch 54 positioned proximally to the stimulation site. However, coil 52 may be configured as a single coil, a FIG. eight coil, a four leaf clover coil, a Helmholtz coil, a modified Helmholtz coil or a any combination of the aforementioned coils, or as any other coil design providing an effective stimulation to the target nerve. In addition, coils 52 may be fired individually, sequentially or simultaneously according to the feedback provided by sensor 54.

In one variant of this variation, sensor 54 may include a conductive electrode patch that provides a feedback to logic controller 56 for adjusting, if necessary, the stimulation parameters of coils 52. Alternatively, sensor 54 may be a sensor patch that is either applied to the skin of the patient or is incorporated within the structure of cradle 48.

Figure 5:
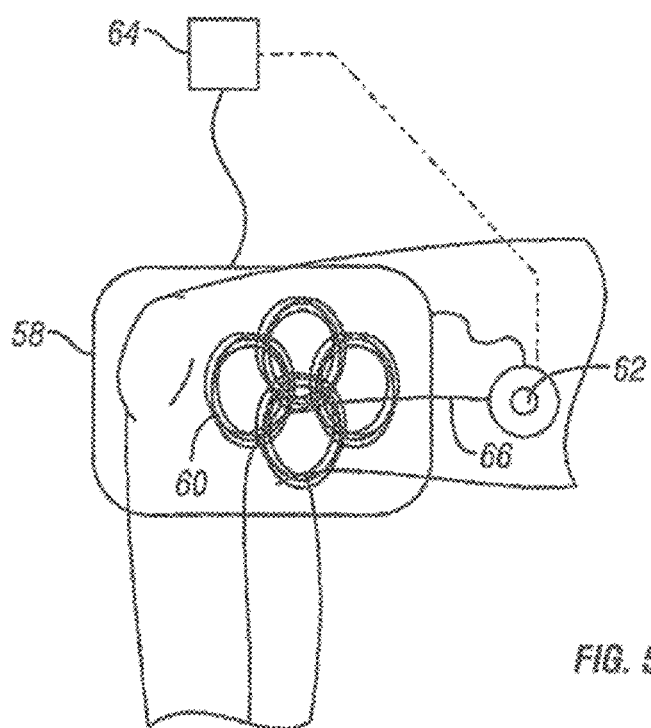
FIG. 5 is a schematic view of an apparatus for magnetic induction therapy according to a fifth variation.

Referring now to FIG. 5, a fifth variation includes a knee rest or knee cradle 58 that contains one or more conductive coils 60, one or more sensors 62 and a logic controller 64. The components of this variation are similar to those described with reference to the preceding variations, as regards the structure and materials of cradle 58, the nature and disposition of coils 60, the type and operation of sensor 62, and the function and operation of logic controller 64. Cradle 58 is configured to target the popliteal fossa of the patient, thus to target tibial nerve 66. In that respect, the present variation is similar to the variation illustrated in FIG. 3, but while the variation of FIG. 3 is configured as a wrap that may be worn while the patient is standing, the present variation is configured as a cradle that is more suited for treatment while the patient is sitting or laying down.

A method of use of the foot cradle depicted in FIG. 4 is described with reference to FIGS. 6A-6D. During a first step illustrated in FIG. 6A, foot 68 is disposed in cradle 70 that contains one or more conductive coils 72, which are connected to a logic controller (not shown) that manages the flow of electric power to coils 72.

Figure 6A:
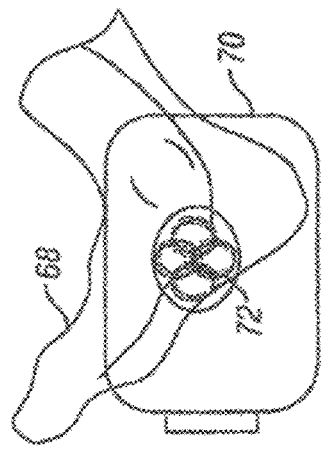
FIGS. 6A-6D are schematic illustrations depicting a first method of use of an apparatus for magnetic induction therapy. This method is based on adjusting the position of the conductive coils so to optimize a magnetic flow applied to a target nerve.
Figure 6B:
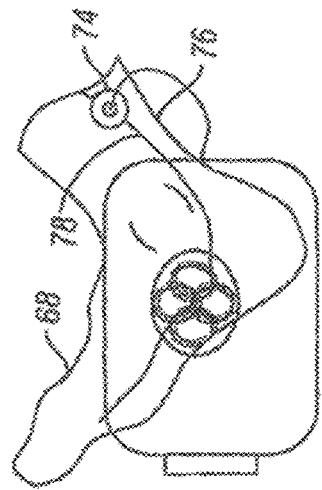

During a second step illustrated in FIG. 6B, a sensor 74 is disposed on foot 68 or on ankle 76 or on another appropriate portion of the patient's body, in order to detect conductivity in tibial nerve 78 or in another target nerve.

Figure 6C:
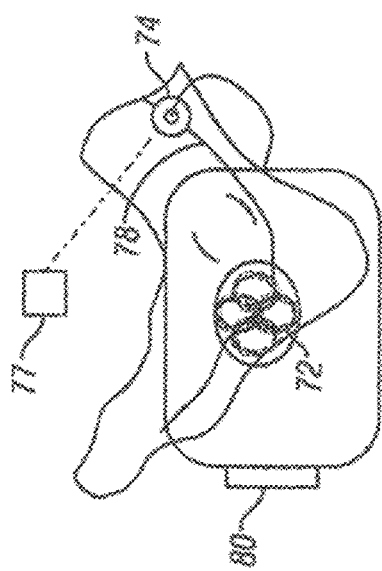

During a third step illustrated in FIG. 6C, a healthcare provider analyzes conductivity measurements provided by sensor 74 (for example, by reading gauge 77) and first adjusts the positioning of coils 72 until conduction in nerve 78 is detected. For example, the healthcare provider may rotate a knob 80, slide a lever or actuate any other displacement system for coils 72 that is known in the art, so that coils 72 are translated until a magnetic field of the proper amplitude and intensity is applied to cause conduction in nerve 78. The position of coils 72 is then fine-tuned manually until an optimal level of conduction in nerve 78 is attained, and the therapy is continued for a length of time as prescribed by the attending healthcare provider.

Figure 6D:
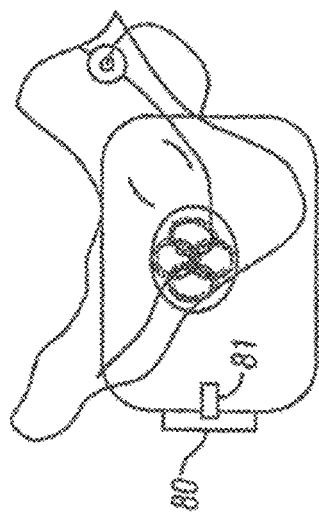

During a fourth, optional step illustrated in FIG. 6D, settings for successive therapy sessions are set, for example by locking knob 80 (in one variation, with a pin 81) so that the healthcare provider or the patient repeat the therapy using the predetermined settings. Alternatively, the patient may be trained to adjust the amplitude and/or strength of the applied magnetic field, as each therapy session requires.

While the present method has been described with regard to foot cradle 70, the same method steps may be envisioned for coil wraps or cradles of different configurations, for example, for the coil wraps and cradles described with reference to the previous FIGS.

In an alternative variation, the logic controller (not shown) may automatically adjust coil positioning to optimize therapy during the initial and successive sessions. While this setup may be more difficult to implement, it also provides for an accurate targeting of the target nerve during each therapy session, regardless of alterations in patient positioning or changes to the anatomy of the patient (for example, when a foot is swollen). In this variation, the device simply varies the orientation of coils 84 until stimulation has been sensed.

Further, coils 84 may be translated along a single direction (for example, horizontally) or along a plurality of directions, to provide for the most accurate positioning of coils 84 with respect to the target nerve.

A second method of use of the foot cradle depicted in FIG. 4 is described now with reference to FIG. 7. While this second method is also described with reference to a foot cradle 82 employing one or more coils 84 that have a reversibly lockable, adjustable orientation, the present method may be equally implemented with a body-worn coil wrap, such as those described with reference to the previous FIGS., or to other variations. In this method, the patient or the healthcare provider adjusts the positioning of coils 84 to detect conductivity in target nerve 89.

The position of coils 84 may be translated in different directions (in the illustrated variation, may be translated horizontally) and may be locked in an initial position once conduction in nerve 89 is detected by a sensor (for example, sensing patch 86).

Figure 7A:
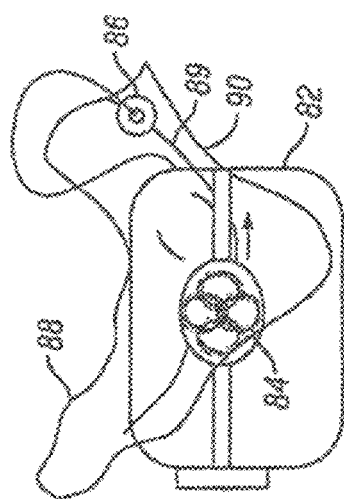
FIGS. 7A-7D are schematic illustrations of a second method of use of an apparatus for magnetic induction therapy. This method is based on locking the conductive coils in position once electrical conduction in a target nerve has been detected.
Figure 7B:
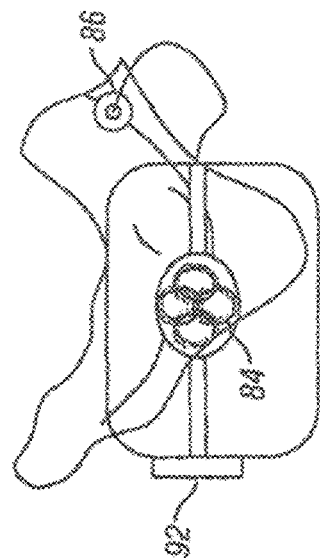

More particularly, FIG. 7A illustrates the initial positioning of foot 88 into cradle 82 and of sensor patch 86 on ankle 90 or other appropriate body part of the patient. After proper positioning of foot 88 is attained, a knob 92 (or other equivalent device) may be employed to adjust the position of coils 84, based on the signals (for example, nerve conduction signals) provided by sensor patch 86, as shown in FIG. 7B.

Figure 7C:
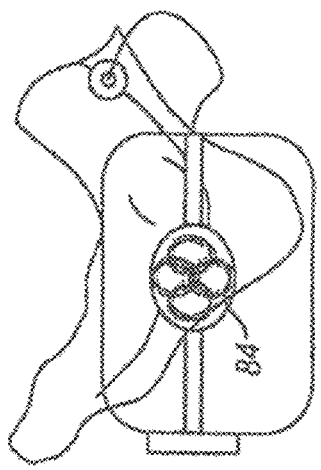
Figure 7D:
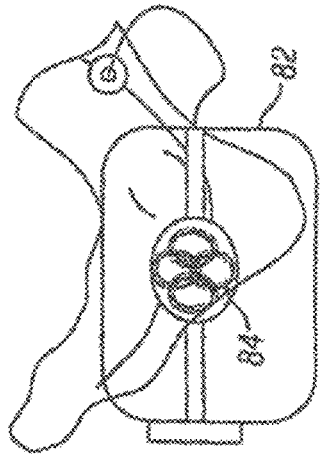

With reference to FIG. 7C, after neural conduction is detected, coils 84 are locked in place, and, with further reference to FIG. 7D, foot cradle 82 retains coils 84 locked in position for further use in a home or healthcare office environment. Therefore, in the present method, the patient or a healthcare provider simply adjusts coil position by sliding coils 84 back and along one axis until electric conduction in the target nerve is detected, although adjustments along all three axes may be possible in different variants of the present variation.

Figure 8:
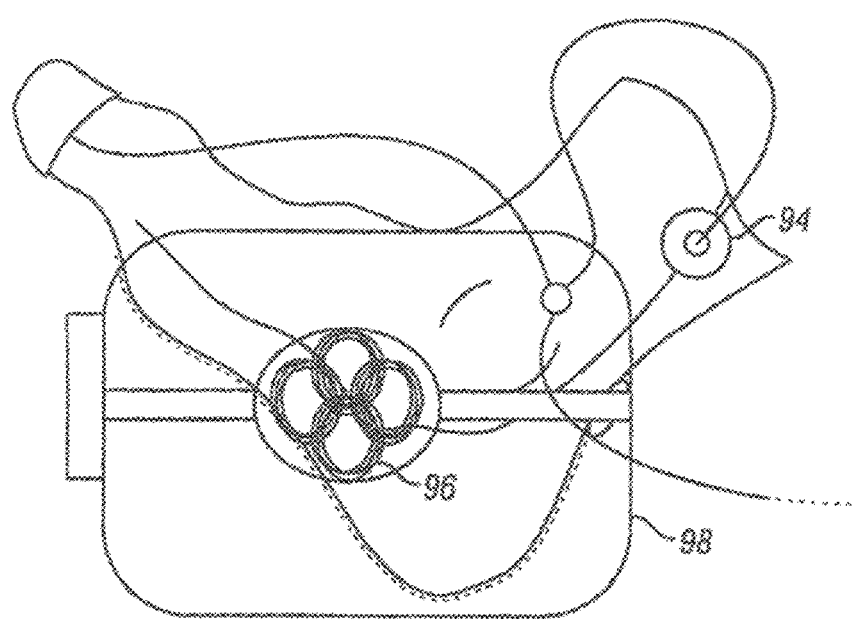
FIG. 8 is a schematic view of a variation that includes a plurality of sensors.

Referring now to FIG. 8, a sixth variation relates to the use of multiple sensors. While FIG. 8 depicts a variation shaped as a foot cradle 98, it should be understood that the following description also relates to any other design, whether shaped as a cradle or a wrap or otherwise. The plurality of sensors 94 described herein may detect a variety of physiologic changes, including neural impulses, muscular contraction, twitching, etc. that may occur with neural or muscular stimulation.

One or more of the illustrated sensors 94 may be employed over body regions being stimulated (for example, back, leg, arm, neck, head, torso, etc.) and may be either incorporated within an actual cradle or wrap or, otherwise, be applied separately from the cradle or the wrap.

Sensors 94 may be structured as disposable, single-use, EKG-type patches that are attached to the body outside of cradle 98 along the nerve conduction pathway and are then connected to the logic controller (not shown) before beginning therapy. This arrangement provides for an intimate body contact of sensors 94 without the risk of infection or other detrimental side effects that may be present with transcutaneous devices. Sensors 94 may be employed both for beginning and for monitoring the stimulation therapy; more specifically, sensors 94 may be employed during the beginning of the therapy to optimize the strength of the magnetic field and/or to adjust the positioning of coils 96 within the cradle 98. Once therapy has begun, sensors 94 continue to monitor nerve conduction to ensure that the correct level of stimulation is being provided. In the event that for some reason nerve conduction decays during therapy, the logic controller can automatically adjust the magnetic field, ensuring that the appropriate therapy is delivered for the appropriate amount of time.

One or more of sensors 94 in this variation, or any of the variations described herein, may take the form of an inductive coil designed to receive impulses from the underlying nerves, so that inductive technologies may be used to both stimulate the nerve or tissues as well as to record the effect of the stimulation on nerves or tissues. Any of sensors 94 may be connected to the logic controller through one or more connection modes, including, but not limited to, wireless signals, wired signals, radio frequencies, Bluetooth® (Bluetooth Sig, Inc., Kirkland, Wash.), infrared, ultrasound, direct switching of the current circuit, etc., so long as communication between the sensor and the device is effective.

During implementation of the present method, a healthcare provider may simply elect to use sensors 94 to adjust the device, for example, to lock coils 96 into position, during the first therapy session and not require the use of sensors 94 during each successive therapy session.

Referring now to FIGS. 9A-9D, there are shown different, non-limiting variations shaped as body worn ergonomic applicator garments. Each of these variations is shown with overlapping coils, although coils of any configurations may be used. Each of the wraps of FIGS. 9A-9D corresponds to a coil wrap, into which a body part may be placed. These garments contain one or more sensors (not shown) that provide feedback to a logic controller (also not shown), or sensors may be applied separately from those garments. Systems may also be included for reversibly or irreversibly locking the coils within the applicator.

Figure 9B:
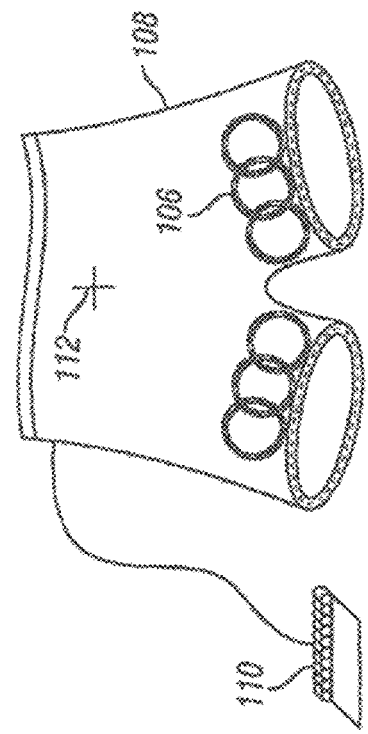
FIGS. 9A-9D are schematic representations of different garments adapted to operate as apparatus for magnetic induction therapy.
Figure 9D:
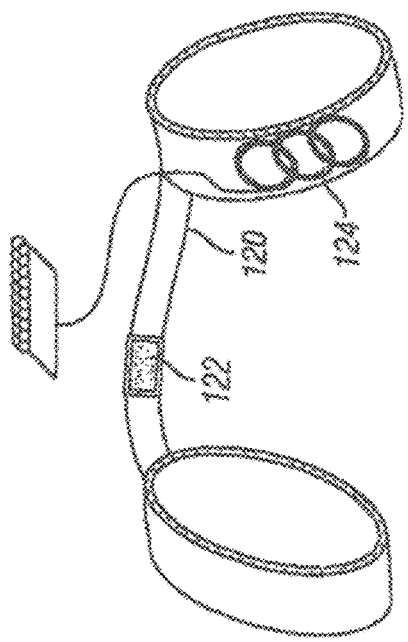
Figure 9A:
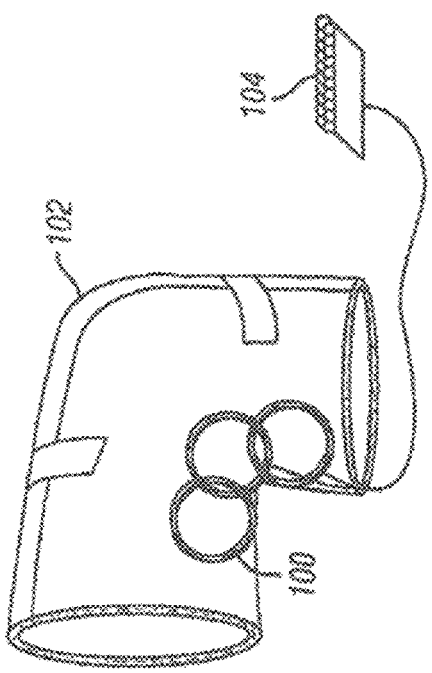
Figure 9C:
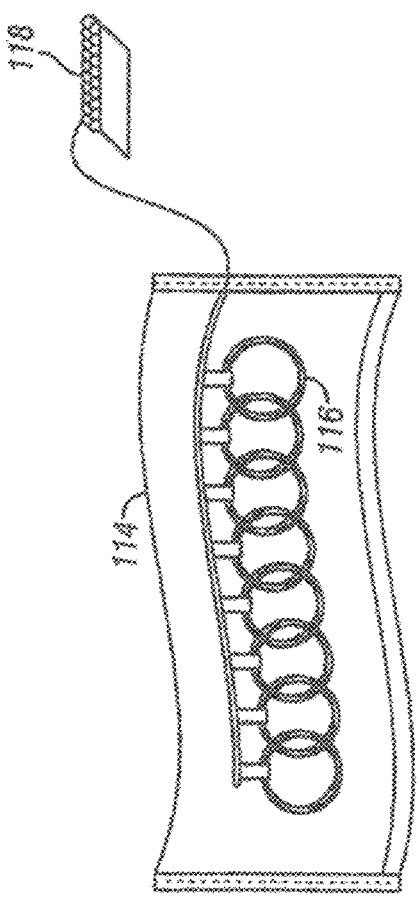

More particularly, FIG. 9A illustrates a variation, in which coils 100 are embedded in a knee wrap 102 and are connected to a logic controller (not shown) by a connector 104. FIG. 9B instead illustrates a variation, in which coils 106 are disposed within an abdominal garment, for example shorts 108 and in which coils 106 are also connected to a logic controller (not shown) by a connector 110. A marking 112 may be added on one side of shorts 108 to indicate wrap orientation. FIG. 9C illustrates a coil wrap shaped like a band 114, in which coils 116 are connected to a logic controller (not shown) by a connector 118. When this variation is employed, band 114 may be wrapped around a body portion (for example, an arm) and be retained in place by a system known in the art, for example, a hook and loop system, a strap and buckle system, or simply a hook disposed at one end of band 114 for engaging fabric or other material in another portion of band 114. FIG. 9D illustrates a variation shaped as a shoulder strap 120, the length of which may be adjusted by a buckle 122 and which has coils 124 disposed in one or more points, for example, at the joint between an arm and a shoulder as shown. Each of these variations includes one or ore sensors (not shown) that may be coupled to the garment, or that may be applied separately from the garment.

Other variations that are not illustrated include, bur are not limited to: a head worn garment, such as a cap; a neck worn garment, such as a neck brace; and a lower-back garment. Each garment and applicator may also utilize the locking, targeting coil feature described previously, without requiring the use of the any sensing components after a proper positioning of the coils in relation to the target nerve or nerves has been established.

Figure 10:
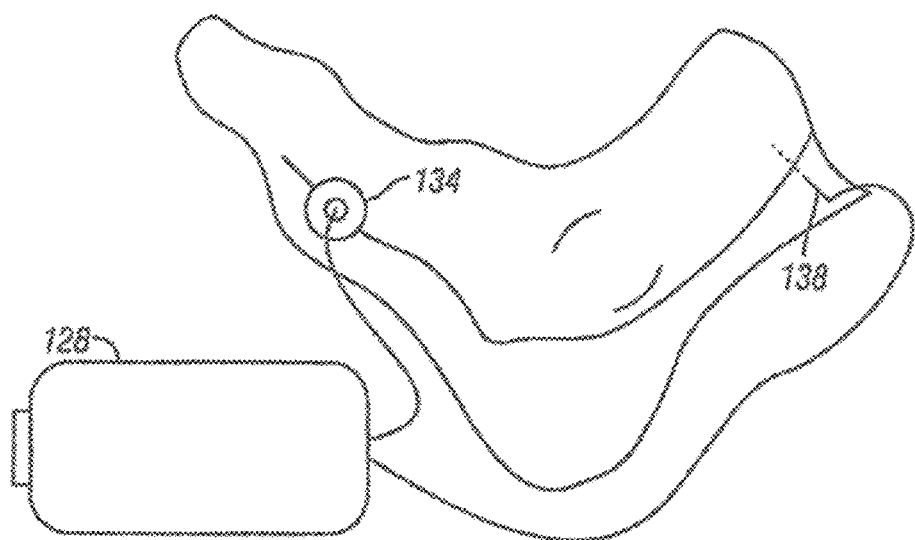
FIG. 10 is a schematic view of an apparatus for providing electrical stimulation.
Figure 11:
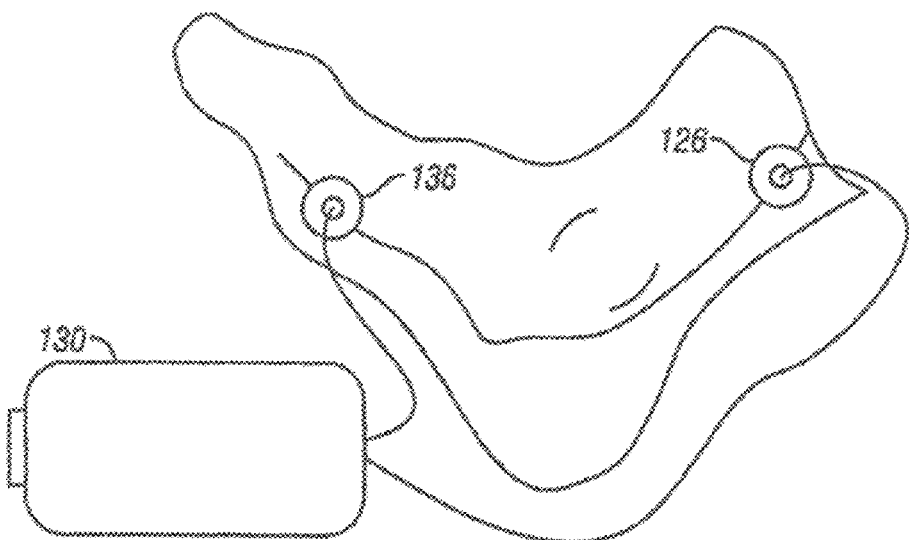
FIG. 11 is a schematic view of another variation of an apparatus for providing electrical stimulation.

Still other variations are depicted in FIGS. 10 and 11. In these variations, the source of energy for nerve stimulation is electrical energy that is dispensed through a percutaneous stimulator, such as a percutaneous needle 124, or a transcutaneous stimulator, such as an electrode 126. As shown in FIG. 10, an electrical pulse controller 128 is electrically connected both to percutaneous needle 124 and to sensor 134, to provide the desired feedback and modulate the power to percutaneous needle 134. In the variation of FIG. 11, electrical pulse controller 130 is connected both to electrode 126 and to sensor 136, and performs a function similar to that of electrical pulse controller 128. With these variations, nerve conduction may be detected at a site sufficiently distant from the site of stimulation, so to enable detection of nerve conduction despite the confounding interference from the direct electrical stimuli. Further, direct electrical stimulation of nerve and muscle may be tailored to provide optimal therapy and, in the case of electrode migration or other electrode malfunction, to report lack of stimulation of the bodily tissues. Still further, these variations enable a reduction in power requirement, because control of the signal is provided by the sensor to the signal generator loop.

As shown, a device constructed according to the principles described herein provides a targeted and precise stimulation of the posterior tibial nerve, or of other peripheral nerves, in a non-invasive manner by employing an ergonomic wrap or cradle that specifically targets the posterior tibial nerve in a consistent and repeatable manner. For example, in patients with OAB or VI, the novel, reversibly lockable movement of the coils and the use of a logic controller-sensor loop enables the application of a magnetic field that can be varied in location, amplitude and strength according to the amount of stimulation actually induced in one or more target nerves and of the response of the patient to the therapy. An apparatus according to the variations described herein may deliver any frequency of stimulation, including low frequencies, high frequencies, mid frequencies and ultrahigh frequencies, and overlapping and non-overlapping coils may be used to generate the desired field, although overlapping or Helmholtz coils are preferred due to their ability to target a broader region and achieve more thorough stimulation.

Ailments that may be treated through the use of apparatus and methods as described herein include not only OAB and VI, but also obesity, depression, urinary incontinence, fecal incontinence, hypertension, pain, back pain, restless leg syndrome, Guillain Barre syndrome, quadriplegia, paraplegia, diabetic polyneuropthy, dyskinesias, paresthesias, dental procedure pain, knee osteoarthritis, anesthesia (pain relief during surgery), Alzheimer's disease, angina (chest pain from heart disease), ankylosing spondylitis, back pain, burn pain, cancer pain, chronic pain, dysmenorrhea (painful menstruation), headache, hemiplegia, hemiparesis (paralysis on one side of the body), labor pain, local anesthesia during gallstone lithotripsy, facial pain, trigeminal neuralgia, bruxism (tooth grinding) pain, myofascial pain, pregnancy-related nausea or vomiting, neck and shoulder pain, pain from broken bones, rib fracture or acute trauma, diabetic peripheral neuropathy, phantom limb pain, post-herpetic neuralgia (pain after shingles), postoperative ileus (bowel obstruction), irritable bowel syndrome, postoperative nausea or vomiting, postoperative pain, post-stroke rehabilitation, rheumatoid arthritis, skin ulcers, spinal cord injury, temporomandibular joint pain, detrusor instability, spinal muscular atrophy (in children), pain during hysteroscopy, gastroparesis, chronic obstructive pulmonary disease rehabilitation, carpal tunnel syndrome, soft tissue injury, multiple sclerosis, intermittent claudication, attention-deficit hyperactivity disorder (ADHD), cognitive impairment, knee replacement pain, achalasia, atopic eczema, bursitis, carpal tunnel syndrome, dementia, depression, dry mouth, dystonia, enhanced blood flow in the brain, enhanced blood perfusion of the uterus and placenta, esophageal spasm, fibromyalgia, fracture pain, Guillain-Barre syndrome, hemophilia, herpes, hip pain, interstitial cystitis, irritable bowel syndrome, pruritis, joint pain, labor induction, local anesthesia, menstrual cramps, muscle cramps, muscle spasticity, muscle strain or pain, musculoskeletal trauma, myofascial pain dysfunction syndrome, nerve damage, osteoarthritis, pain medication adjunct, pancreatitis, Raynaud's phenomenon, repetitive strain injuries, sacral pain, schizophrenia, shingles, shoulder subluxation, sickle cell anemia pain, Skin flap ischemia (during plastic surgery), sphincter of Oddi disorders, sports injuries, thrombophlebitis, tinnitus (ringing in the ear), restless legs, tremor, whiplash and neuralgias. In contrast to implantable nerve stimulators, this therapy is completely non-invasive and does not require a major surgery to implant a permanent nerve stimulation device. Moreover, this therapy can be controlled to optimize the level of therapy delivered according to power consumption and nerve stimulation requirements and need not be delivered by a professional healthcare provider.

In other variations, neural stimulation may be applied as electrical transcutaneous stimulation, for example, by inserting an invasive electrical needle into a target body part and by modulating stimulation is modulated on the basis of information sent back to the logic controller from the one or more sensors that are used to detect and/or maintain the correct level of stimulation. The transcutaneous electrical stimulation sensor may be placed in the body independently or be incorporated within the wrap and may provide, among other things, feedback as to the quality of the electrical connection to the skin, which is directly related to the burn risk inherently associated with this type of therapy. In fact, these methods of stimulation may not be optimal due to the resulting skin irritation and risk of potential burns, a very serious issue in the large percentage of patients that have neuropathies. Even when patches are applied to monitor transcutaneous stimulation very closely, the patches may still become displaced and allow a burn to occur. Moreover, potentially interfering electrical impulses may develop at the treatment site, creating a noisy environment for the detection of nerve conduction.

In still other variations, an external coil or coils may be inductively connected to an implanted coil or coils may be utilized. In these variations, an ergonomic applicator may be adjusted by the user or by a healthcare provider such to optimize inductive power transmission between the external and implanted coils. One or more sensors may be utilized to provide a feedback that the relative coil positions have been optimized, and the external coil may then be reversibly locked into position within the ergonomic applicator. Two applications of this variation relate to the transfer of power to recharge an implantable device, and to the transfer of power to activate an implantable device.

In the first application, when an implantable rechargeable device is utilized, the external coils may be used for recharging the implanted device by means of inductive fields generated by the external coils. The external coils may include circuitry that determines the amount of resistance encountered by the magnetic field or other electrical properties related to the quality and degree of the magnetic coupling that is being established. Based on this feedback, the position of the external coils may be adjusted manually or automatically to optimize the coupling achieved with during each recharging session. Alternatively, a sensor may be incorporated into the implantable device and may communicate the degree and quality of the magnetic coupling to the external coils and/or the connected circuitry via wireless communication, providing a feedback for the automatic or manual adjustment of the external recharging coils.

The coils within the ergonomic applicator may be reversibly locked into place for the duration of the recharge session, and the implantable device may also communicate to the external recharging unit that the implantable device has been fully recharged, terminating the recharging session has been completed. By providing for an intermittent recharging of an implanted device, an apparatus according as described herein enables the implantable device to devote more power to performing its intended function optimally and with a lesser concern about protecting or extending battery life.

In the second application, the powering coils may contain circuitry to determine the amount of resistance encountered by the applied magnetic field, or other electrical properties that may reflect the quality and degree of the magnetic coupling that is being achieved. Based on this feedback, the powering coils in the applicator may be adjusted manually or automatically to activate and optimize the coil coupling at the beginning of each therapy session. Alternatively, a sensor may be incorporated into the implantable device and communicate the degree and quality of the magnetic coupling externally via wireless communication, which may in turn provide feedback for the automatic or manual adjustment of the powering coil. In one variant of the present variation, the inductive coils may be magnetically coupled to a needle targeting the posterior tibial nerve.

An exemplary method of use of an apparatus as described herein on a patient suffering from VI and/or OAB includes the following steps:

The patient places a conductive wrap contained within a flexible material over a region of the ankle (or alternatively over the knee) to provide the required pulsed magnetic field. Alternatively, the patient may use an ergonomic foot/leg rest or cradle having embedded coils.

A sensor (for example, a sensor patch) is placed on the patient's body along the path of the nerve, ideally proximal to the stimulation site to ensure afferent nerve stimulation, and is connected to a logic controller.

A physician or healthcare provider adjusts the coils in the wrap or cradle until nerve conduction is achieved based on patient and sensor feedback. An optimal position is sought, and the coils may be reversibly locked into position within the conductive wrap or ergonomic cradle and remain in this position during subsequent use.

During the therapy session, the logic controller provides an electric current to the coils, generating an inductive magnetic field. In one variation, this field begins at low amplitude and slowly ramps up until nerve conduction exceeds a threshold level, as signaled by the sensor and possibly by the patient, who may feel motor conduction. Alternatively, one or more coils may also be activated to increase the covered area of stimulation in the event that stimulation does not occur with the initial coil configuration or is inadequate The optimal stimulation may be determined in a variety of manners, for example, by measuring exposure to electromagnetic fields capable of generating a square wave electric signal at a frequency of 10-30 Hz at the targeted tissue depth. The square wave configuration of the signal may be generated via Fourier transformation or may be a ramped current generated in any manner.

The inductive magnetic pulses continue for an appropriate duration of use, for example, for 15-30 minutes. The sensor may remain in place during the entire therapy session to ensure that stimulation occurs consistently and to provide for appropriate corrections if nerve conduction deteriorated. The logic controller may be powered either by a portable power source such as a battery, or by or a fixed power source such as a traditional wall outlet.

The conductive wrap and/or ergonomic cradle is removed from the body when therapeutic stimulation is not being delivered, typically at the end of the therapy session.

The conductive wrap and/or ergonomic cradle is reapplied along with the sensor patch (ideally disposable) from time to time as indicated, for example, on a daily basis, and steps 4-8 are repeated.

The devices and methods described herein may be applied to any body tissues, including nerve, muscle, skin, vasculature, or any other organ or tissue within the human body. Further, the devices and methods described herein may be used to treat any conditions suited for neuromodulation regardless of whether the stimulation source is an electromagnetic field, a direct electric current, a RF field, infrared energy, visible light, ultraviolet light, ultrasound, or other energy dispensing device.

Figure 12:
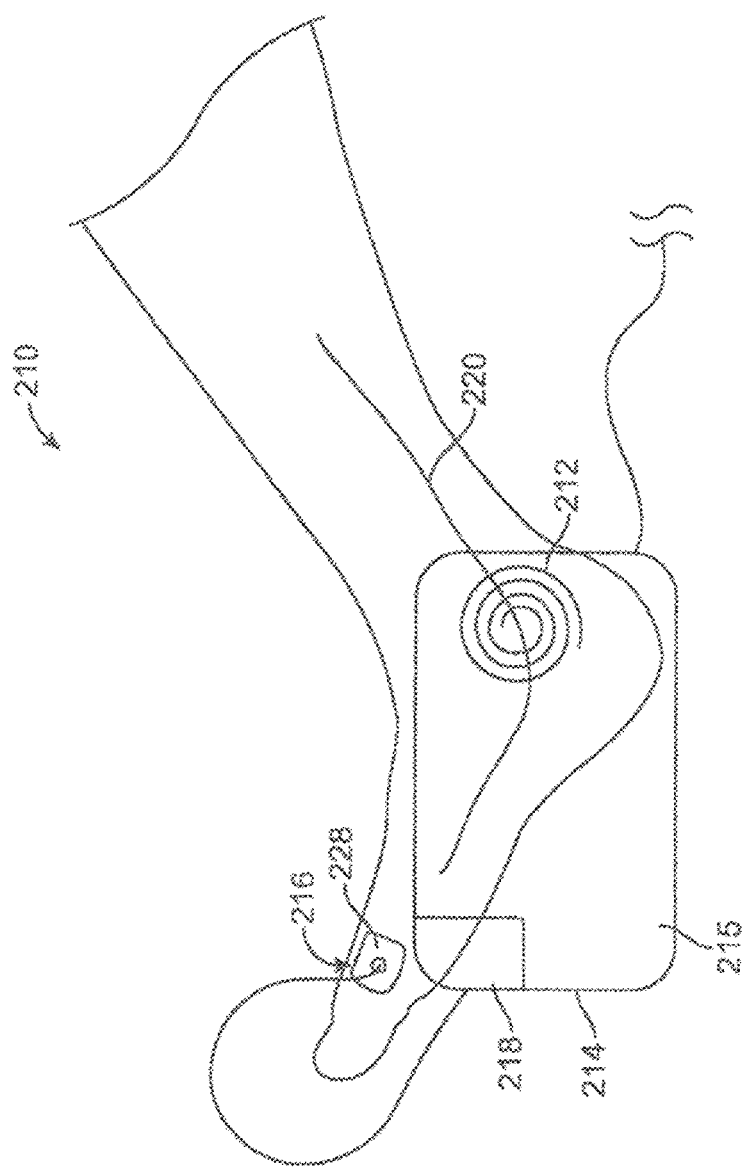
FIG. 12 shows a schematic view of an energy emitting system including a microneedle patch sensor.

In other variations, as shown in FIG. 12, an energy emitting system 210 for providing a medical therapy includes one or more conductive coils 212 disposed within or along a housing 214, one or more sensors 216 configured to detect electrical conduction in a target nerve or to detect muscle stimulation, and a controller 218 connected or coupled to the conductive coils 212 and optionally in communication with the sensor 216. In certain variations (as shown in FIG. 12), the controller 218 can be integral with the housing 214). The coils 212 are configured such that an electrical current generated by the controller 218 is passed through the coils 212 generating a magnetic field which will stimulate a target nerve, e.g., the tibial nerve 220, a muscle or other body part containing a portion of a target nerve, or any nerves branching off of a target nerve, located in proximity to the coils 212. In this particular variation, the housing 214 is in the form of a foot cradle, as shown in FIG. 4, however, the housing could also be in the form of a flexible wrap, garment or other design suitable for use with a subject. In various variations described herein, sensors may detect voltage or current and may be connected, coupled, wirelessly connected or coupled or otherwise in communication with the housing and/or controller using a variety of methods or techniques known in the art. The sensor may be placed over a muscle to detect muscle stimulation resulting from stimulating the target nerve (as shown in FIG. 12) or over any other portion of the subject's body suitable for detecting conduction of the target nerve.

Figure 13:
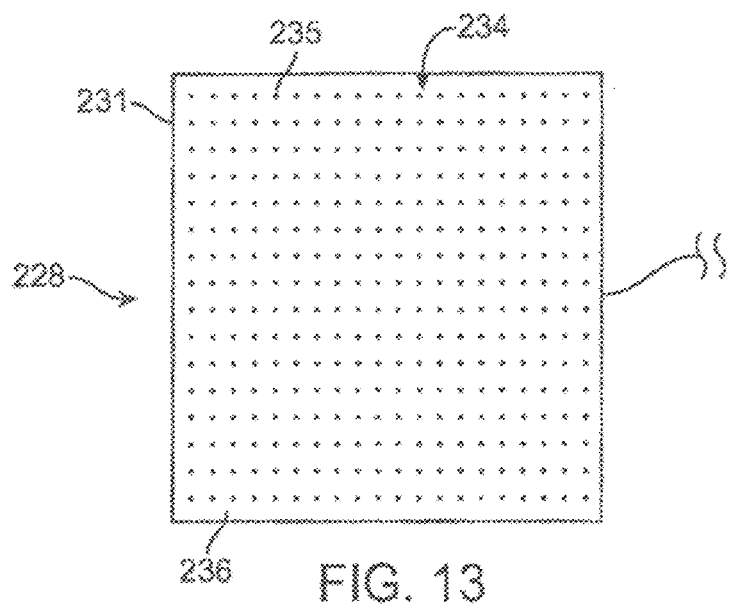
FIG. 13-15 shows magnified bottom views of variations of microneedle patches.
Figure 14:
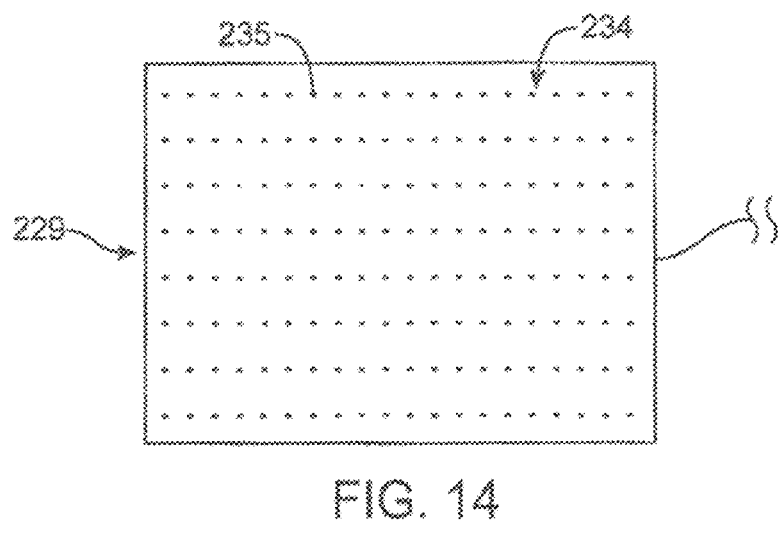
Figure 15:
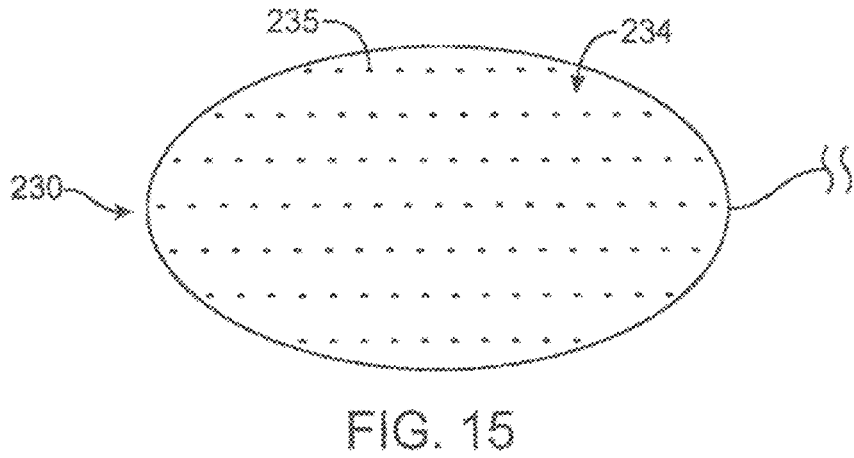
Figure 16:
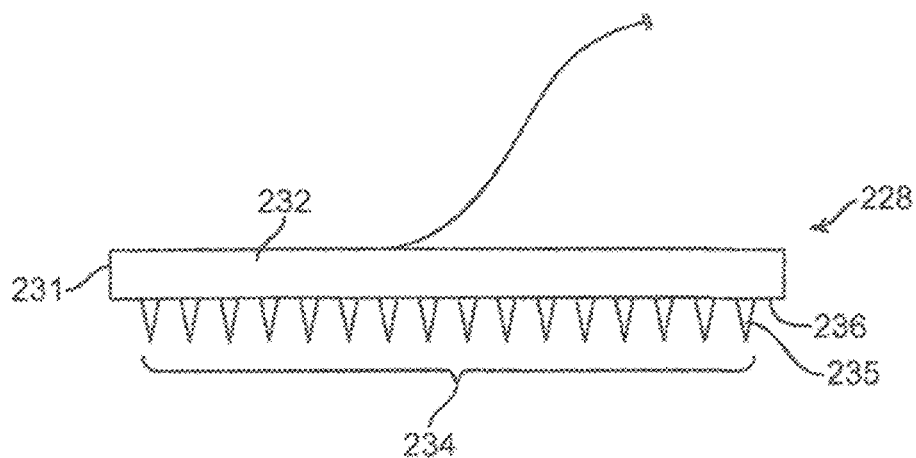
FIGS. 16-17 shows magnified side views of variations of a microneedle patch.

Referring to FIGS. 13 and 16, the sensor may be in the form of a microneedle patch 228, which can be removably attached to the skin surface of a subject. The microneedle patch 228 may include a housing 231, having one or more electrodes 232 and one or more microneedles 235 deposited or arrayed on a surface of the electrode 232, forming one or more microneedle arrays 234. In FIG. 13, microneedle patch 228 has the shape of a square, and the microneedles 235 are arrayed on the bottom surface 236 of the electrode 232 in a 16.times.16 configuration. However, as shown in FIGS. 14-15, microneedle patches may be designed in a variety of shapes, e.g., round, oval 229, rectangular 230, hexagonal, and a variety of sizes. The microneedles may be arrayed in a variety of arrangements and patterns (e.g., 14.times.14, 12.times.12, etc.) depending on the particular use and needles.

Additionally, microneedles may be attached, deposited, or arrayed on an electrode surface or patch in a variety of configurations and arrangements, depending on where the particular microneedle patch will be utilized and the treatment to be delivered. The number of microneedles included in an array can vary. For example, the number of microneedles may range from about 5 to 500 or 100 to 400 or about 200 to 300 or about 256. In certain variations where microneedles are composed of strong, highly conductive material, the number of microneedles necessary may be less and may range from about 5 to 100 or 10 to 50 or 5 to 50. However, where microneedles are composed of higher resistance metal, a greater number of needles may be needed, e.g., about 100 to 500 or about 200 to 300 or greater than 500.

Figure 17:
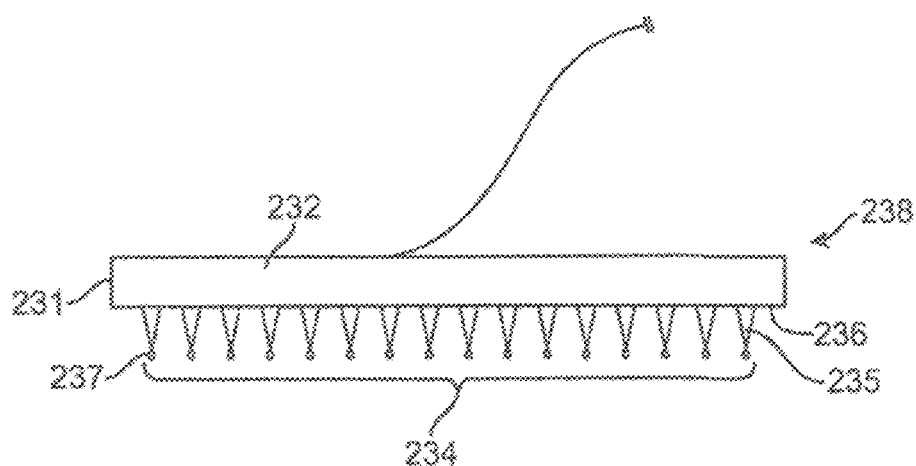
Figure 18:
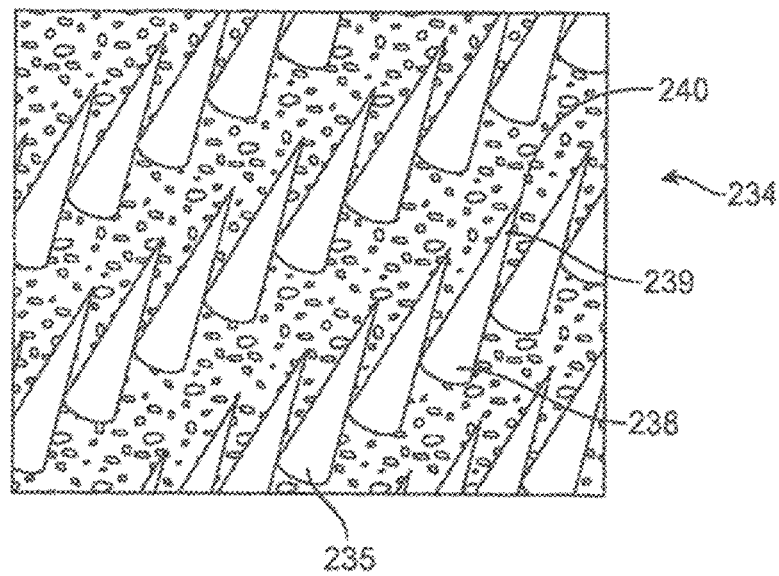
FIG. 18 shows a magnified bottom perspective view of a microneedle patch.

Referring to FIG. 18, a magnified view of a microneedle array 234 composed of one or more microneedles 235 is shown. Microneedles 235 may include a base portion 238 and an upper portion 239. Microneedles 235 may have lengths in the range of about 1 to 400 microns or 10 to 400 microns or preferably about 100 to 150 microns, and a diameter in the range of about 1 to 100 microns. A microneedle 235 may be tapered in diameter, going from a larger to smaller diameter from the base portion 238 to the upper portion 239 where the distal tip 240 of the microneedle is preferably pointed or sharp. The upper portion 239 of the microneedle 235 may have a diameter in the range of about 10-30 microns or about 15 to 25 microns. Optionally, for ease of production, the base portion 238 of the microneedle 235 may be thicker than the distal tip 240 or upper portion 239 of the microneedle 235. In certain variations, as shown in FIG. 17, a bulb 237 may be provided at the distal tip 240 of a microneedle 235 to provide for effective anchoring of the microneedle 235 in the skin of a patient or subject. Microneedles 335 can include any number of friction or grip increasing features. For example, they may include projections, barbs, bulbs or a roughened surface or tip. Microneedles 235 may take on various configurations, e.g., straight, bent, filtered, hollow or a combination of the above.

In other variations, microneedles may have lengths that range from about 480 to 1450 microns, widths from about 160 to 470 microns, thicknesses from about 30 to 100 microns and tip angles from about 20 to 90 degrees, and arrays can contain from 5 to 50 microneedles. For example, microneedles having these dimensions have been shown to be less painful than hypodermic needles. Length and number of microneedles can affect the level of pain experienced. Decreasing microneedle length and/or the number of microneedles may be beneficial and act to further reduce pain and provide comfort.

In certain variations, the one or more microneedles may include an electrically conductive material such that the microneedles may transmit an electrical signal to an overlying electrode or other surface. Microneedles may be constructed of an electrically conductive material and/or coated with an electrically conductive material. Optionally, microneedles may be coated with an electrically conductive material and constructed of a non-conductive material. Microneedles may be fabricated using a variety of materials, e.g., metals, stainless steel, solid or coat of gold over NI, Pd or Pd—Co, Pt, silicon, silicon dioxide, polymers, glass, biocompatible polymers, titanium, silver, or suture materials. Biodegradable polymers may also be used such that if a tip of a microneedle were to snap or break off during insertion, it would easily biodegrade.

A microneedle array 234 may be constructed or fabricated using any variety of manufacturing methods known to persons of ordinary skill in the art. Microneedles may be arrayed, attached, etched or deposited onto a surface of an electrode. In another variation, microneedles may be etched from or deposited onto a silicon electrode, such that the microneedle patch, including electrode and microneedles, are made from one material creating a durable and stable microneedle patch.

As shown in FIG. 18, microneedles may be fabricated by creating micron sized holes on a silicon substrate and by using a KOH solution to create the needle shape. In other variations, the microneedles may be made of non-conductive material but may still be utilized to provide superior anchoring properties such that a microneedle patch may effectively adhere or attached to a subject's skin.

In certain variations, microneedle arrays are fabricated by patterning SU-8 onto glass substrates and defining needle shapes by lithography. The tips of the needles can be sharpened using reactive ion etching. Optionally, holes may be drilled, e.g., by laser, through the microneedles and base substrate. Holes may be drilled off-center, but parallel to the microneedle axis, terminating in side-opening holes along the needle shaft below the needle tip. If desired, the holes can serve as micro fluidic needle bores for injection or infusion of drugs, medicines, insulin, proteins, nanoparticles that would encapsulate a drug or demonstrate the ability to deliver a virus for vaccinations, etc. to be used separately or in combination with electrical or magnetic therapy. The microneedles may also be coated with nickel by electroplating, which can increase their mechanical strength.

In certain variations, microneedle patches or microneedle electrode arrays are made by fabricating master structures from which replicates are molded and then made electrically active. For example, SU-8 may be spun on a glass substrate bearing an array mask pattern, baked, and then exposed from the backside to from a tapered needle structure. Microneedles may be sharpened by RIE etching. A PDMS (polydimethylsiloxane) or similar material mold can then be copied from the master. A PMMA (polymethylmethacrylate) microneedle array is formed by solvent-casting and then released from the mold.

To provide the arrays with electrical functionality, a Ti/Cu seed layer may be deposited on the PMMA array and patterned by excimer laser to electrically isolate adjacent rows. A Ni layer (e.g., about 15 to 30 microns or 20 to 25 microns thick) may be electroplated on the patterned seed layer to enhance structural rigidity. A backside electrical connection to the array may be formed by backside etching of a hole and forming an electrical connection through the hole.

In another variation, the microneedle array is arranged in a 16.times.16 array (i.e., 256 needles). Each needle has a height of about 400 microns and the base diameter is about 100 microns. The pitch between microneedles can be about 250 microns. The microneedle arrays are then coated with metal and laser-etched to provide electrical functionality.

Optionally, rows of microneedles can be electrically isolated from each other so that alternating rows can provide alternating electrical polarity. The arrays are also interfaced with a power source. Microneedles may be made of polymer, coated with a metal, and etched to act as alternating electrodes. In certain variations, the firing sequence of the microneedles by rows or groups may be varied or configured to alternate.

In certain variations, a microneedle array may include one or more microneedles having multiple channels. For example, a multichannel silicon microneedle may be constructed to deliver bioactive compounds into neural or other tissue while simultaneously monitoring and stimulating neurons and nerves.

Figure 19:
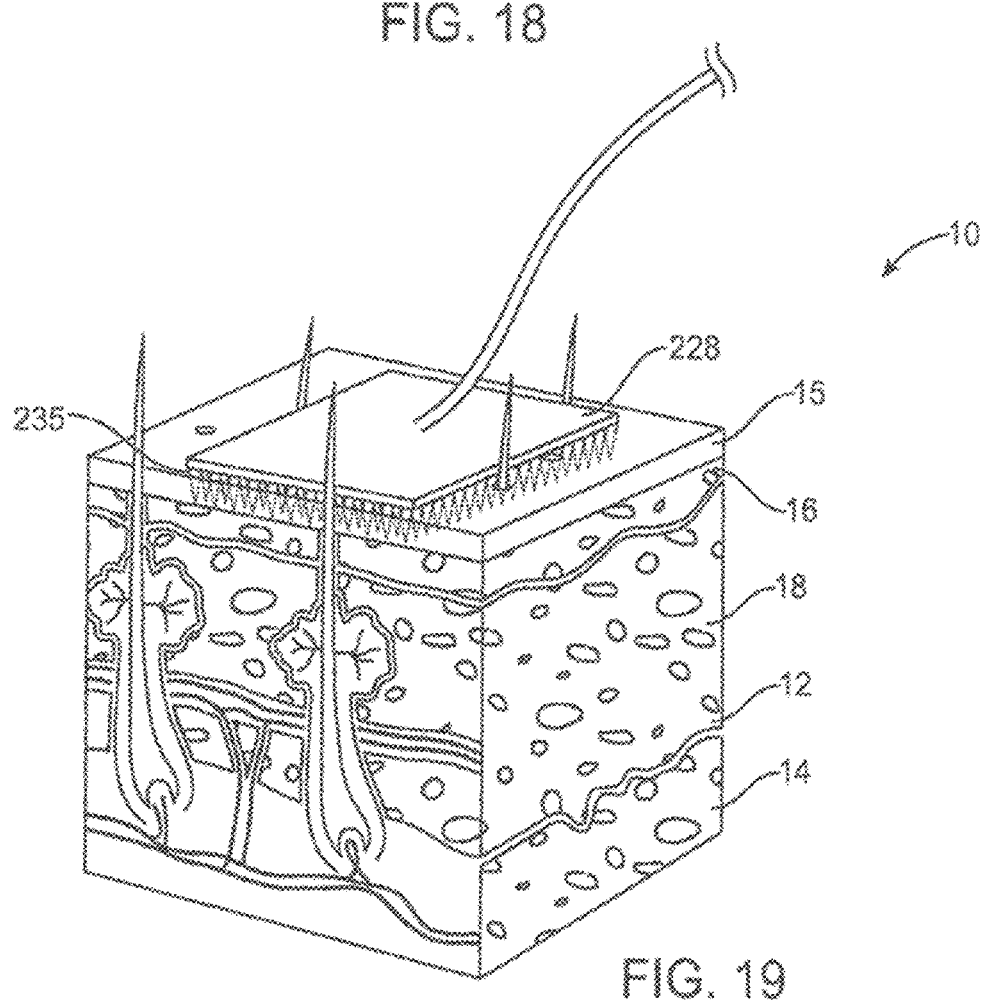
FIG. 19 shows a representative cross sectional view of the skin composed of an outer stratum corneum covering the epidermal and dermal layers of skin and the underlying subcutaneous tissue, with a variation of a microneedle patch attached thereto.

FIG. 19 shows a cross sectional view of the skin 10 composed of an outer stratum corneum 15 covering the epidermis 16. The skin also includes the dermis 18, subcutaneous tissue/fat 12, and these layers cover muscle tissue 14. As shown in FIG. 19, when a microneedle patch 228 is attached to a subject's skin, the microneedles 235 pierce the outer insulating stratum corneum layer 15. The microneedle patch 228 can detect current passing through a stimulated nerve, and provide a superior signal as the current detected is conducted through the microneedles 235, thereby bypassing the poorly conductive stratum corneum layer 15 which generally encompasses the outer 10 to 15 microns of skin. In other variations, microneedles 235 may be fabricated to be long enough to penetrate the stratum corneum 15, but short enough not to puncture nerve endings, thus reducing the risk of pain, infection or injury.

In certain variations, microneedles are formed such that they are in direct contact with their corresponding or overlying electrodes. For example, a microneedle patch may include an adhesive electrode pad and may utilize a conductive gel to help hold the microneedles in place to prevent shear forces from breaking or bending the microneedles.

Figure 20A:
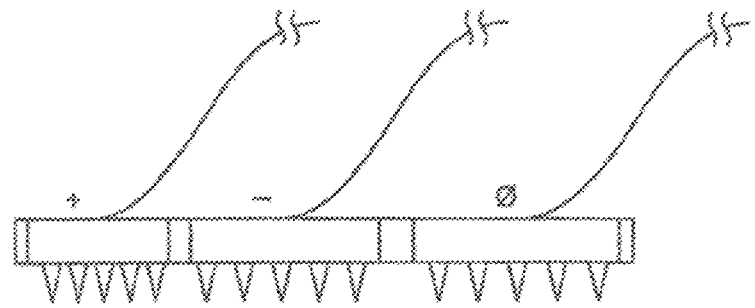
FIG. 20a shows a magnified side view of a variation of a microneedle patch including multiple electrodes.
Figure 20B:
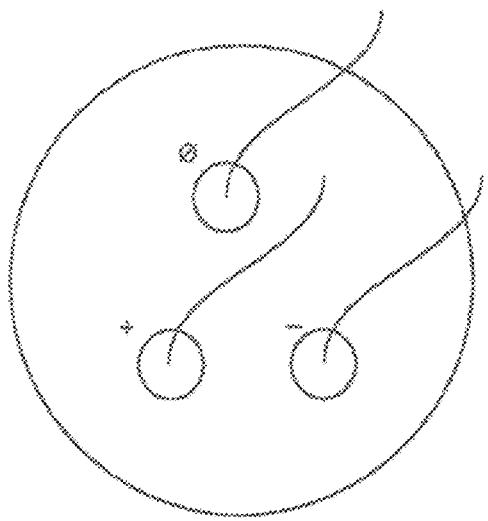
FIG. 20b-20d show variations of a microneedle patches including multiple electrodes.
Figure 20C:
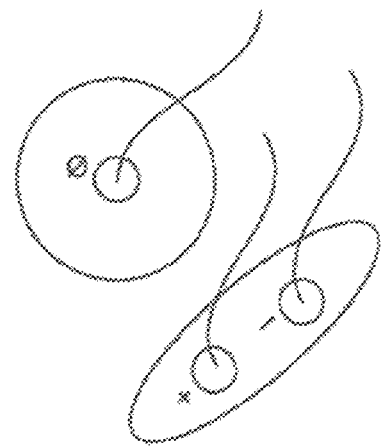
Figure 20D:
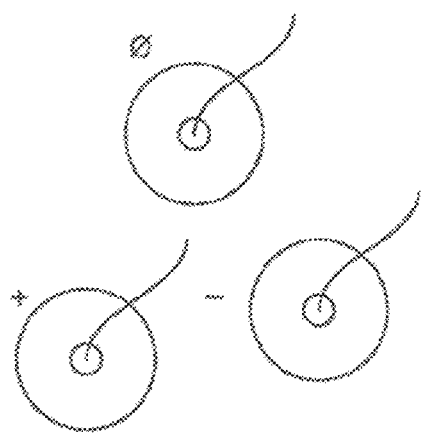

In certain variation, as shown in FIGS. 20a-20d, a microneedle patch or applicator may include multiple electrodes on a single patch or applicator, e.g., positive, negative, and/or control or ground electrodes, where the microneedles will be grouped in multiple arrays such that they conduct to the appropriate electrode. For example, FIGS. 20a and 20b show a single patch having positive, negative and control electrodes where a separate array of electrodes is in contact with each respective electrode. This arrangement can be created using a single patch. Alternatively, as shown in FIG. 20c, two patches may be implemented, one including the control electrode with corresponding microneedle array and the other including the positive and negative electrodes with corresponding microneedle arrays. The various electrodes could be interchanged. Alternatively, as shown in FIG. 20d, three patches may be implemented, each having a separate electrode (control, positive, or negative) with a corresponding microneedle array. In use, in certain variations, the control may be attached above or near bone, while the positive and/or negative electrodes may be attached above nerve or muscle.

Referring again to FIG. 12, the energy emitting system 210 can be used to treat or prevent various conditions, e.g., urinary incontinence, restless leg syndrome and fecal incontinence, among others. Energy emitting system 210 includes one or more conductive coils 212 disposed within or along a housing 214, one or more sensors 216 configured to detect electrical conduction in the target nerve or to detect muscle stimulation, and a controller 218 coupled to the conductive coils 212 and optionally in communication with the sensor 216. The coils 212 are configured such that an electrical current generated by the controller 218 is passed through the coils 212 generating a magnetic field which will stimulate a target nerve, e.g., the tibial nerve 220, a muscle or other body part containing a portion of a target nerve, or any nerves branching off of a target nerve, located in proximity to the coils 212. In this particular variation, the housing 214 is in the form of a foot cradle, as shown in FIG. 4, however, the housing could also be in the form of a flexible wrap, garment or other design suitable for use with a subject.

Referring again to FIG. 12, energy emitting system 210 may be used to treat or prevent various conditions, e.g., urinary incontinence, restless leg syndrome or fecal incontinence. In certain variations, a method of using the energy emitting system 210 includes positioning a first portion of a patient's body, for example a foot, ankle, or leg, relative to housing 214 such that a posterior tibial nerve 220 within the first portion of the patient's body is in proximity to one or more conductive coils 212 disposed within or along the housing. In this particular variation, a patient's foot is positioned in a housing which is in the form of a foot cradle 215. A sensor in the form of a microneedle patch 228 may optionally be positioned along a second portion of the patient's body in proximity to the posterior tibial nerve 220. In this particular variation, microneedle patch 228 is attached to the patient's foot over a muscle to detect muscle stimulation. Alternatively, a patch could be placed elsewhere on the patient, for example, on the leg in proximity to the posterior tibial nerve 220, proximal to and up-stream from coils 212. Microneedle patch 228 may be composed of one or more microneedle arrays and one or more electrodes, as described supra.

Once the patient's foot is in position and the microneedle patch 228 (e.g., conductive microneedle patch) is in place, a current is passed from controller 218 through coils 212, and as a result, the coils 212 generate a magnetic field which is focused on the posterior tibial nerve 220. The magnetic field stimulates tibial nerve 220, generating a current that will flow along the tibial nerve 220 and spread along its length, to its sacral or pudendal nerve roots. Microneedle patch 228 detects corresponding muscle stimulation or twitching or electrical conduction through the stimulated posterior tibial nerve. Upon detection, the microneedle array may conduct and transmit an electrical signal to the overlying electrode of microneedle patch 228. The signal may be transmitted to controller 218, which can be integral or a separate controller or device, or a separate controller coupled to controller 218. The controller can then be varied or adjusted (to adjust the current or magnetic field) based on the signal received from microneedle patch 228 to ensure that adequate conduction of the posterior tibial nerve 220 occurs and an adequate and accurate dosage of treatment is being received. Although shown utilizing a sensor, it is also contemplated that the system could be used without a sensor.

Figure 21:
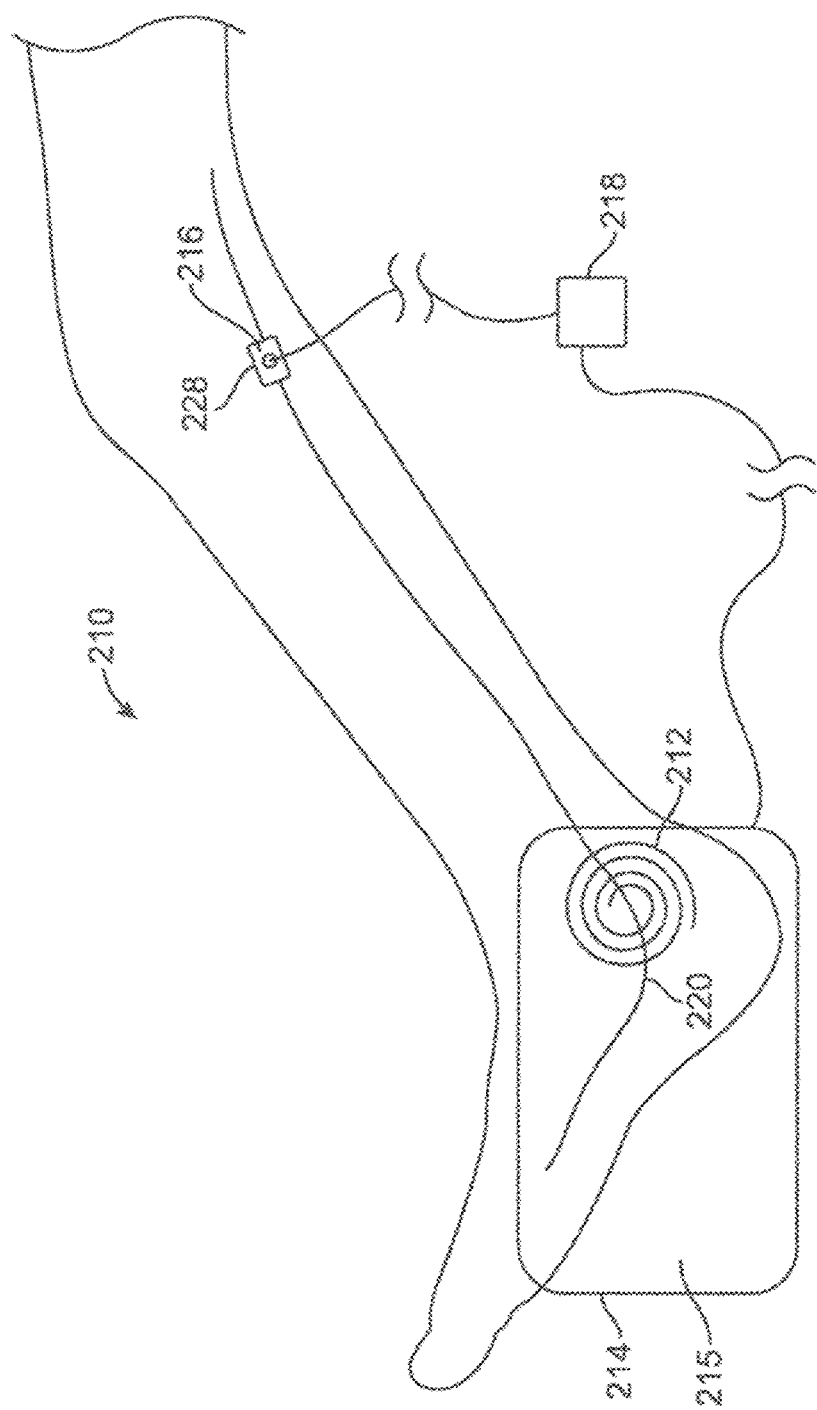
FIG. 21 shows a schematic view of an energy emitting system including a microneedle patch sensor placed behind a subject's knee.

Referring to FIG. 21, the method of using energy emitting system 210 described above with respect to FIG. 12 may be varied such that a conductive microneedle patch 228 is placed in proximity to or proximally over the afferent posterior tibial nerve 220, i.e., behind the patient's knee. In this position, a conductive microneedle patch 228 detects electrical conduction through the afferent posterior tibial nerve, i.e., it detects the electrical signal traveling through the posterior tibial nerve back up to the brain and spinal cord or it may detect corresponding muscle stimulation. The microneedle patch 228 sends the signal to controller 218 or to a separate controller coupled to controller 218. The controller can then be varied or adjusted based on the signal received from microneedle patch 228 to ensure that adequate conduction or stimulation of the posterior tibial nerve 220 occurs and an adequate and accurate dosage of treatment is being received.

A sensor utilized in the energy emitting system 210 may be a microneedle patch 228 as described above or optionally the sensor may a sensor type known in the art (e.g., EKG sensor) or as described in any of the variations herein. It is also contemplated that energy emitting system 250 can be utilized without a sensor. Optionally, the sensor may be positioned within or along the housing, e.g., the foot cradle, along with the one or more conductive coils, or positioned at a site distant from the housing or conductive coils.

In certain variations, energy emitting system 210 may optionally include one or more conductive microneedle patches which can be positioned in proximity to the target nerve or muscle and provide an additional or supplemental electrical or magnetic stimulus to the target nerve or muscle.

Figure 22:
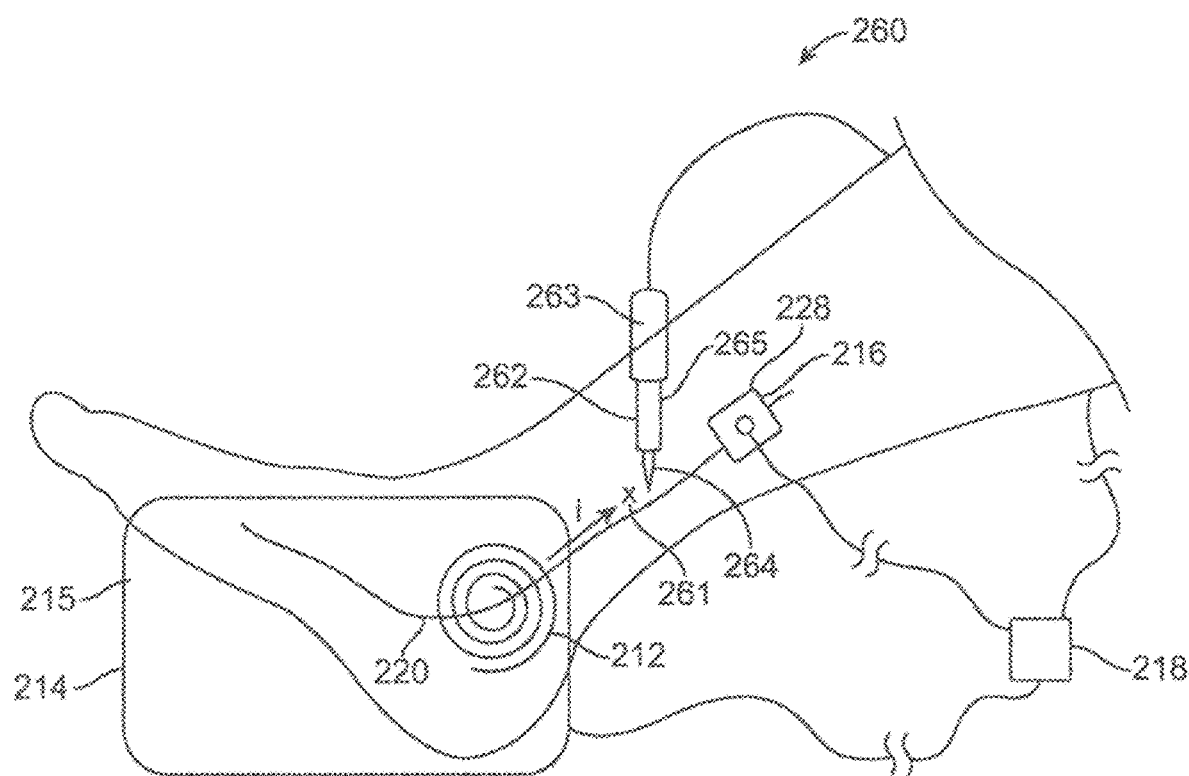
FIGS. 22-23 show schematic views of energy emitting systems including an electrode needle and sensor.

Referring to FIG. 22, the energy emitting system 210 described above with respect to FIG. 12 may be varied to create energy emitting system 260. Energy emitting system 260 further includes one or more percutaneous electrode needles 262 or other needles or other percutaneous electrodes coupled to a controller 218 and having an end insertable into a subject's body in proximity to said target nerve or stimulation site. The percutaneous electrode needle 262 is inductively coupled to one or more conductive coils 212. In use, a first portion of a patient's body, for example a foot, ankle, or leg, is positioned relative to housing 214, e.g., foot cradle 215, such that a target nerve, e.g., posterior tibial nerve 220, located within the first portion of the patient's body is in proximity to one or more conductive coils 212 disposed within or along the housing 214. Conductive coils 212 are positioned proximate, optionally down-stream or distal to, a selected stimulation site 261. The percutaneous electrode needle 262 is inserted through the skin at a location and to a depth that brings the tip in close proximity to the stimulation site or target nerve to be stimulated. The controller 218 is activated and a current passes through conductive coils 212. The resulting magnetic field generates a current that traverses the internal stimulation site 261 by passing from conductive coils 212 to the internal percutaneous electrode needle 262, as indicated by arrow i. Also, the percutaneous electrode needle may be positioned within the generated magnetic field, whereby the magnetic field itself generates a current in the percutaneous electrode which stimulates a target nerve or traverses an internal stimulation site. Optionally, a current may be passed from the controller 218 through conductive coils 212 and/or from the controller 218 through percutaneous electrode needle 262, traversing the internal stimulation site as the current passes between the coils and needle.

In energy emitting system 260, current density and subsequent electric field intensity generated between conductive coils 212 and percutaneous electrode needle 262 is greater than that generated by traditional percutaneous stimulators. A greater electric field intensity makes site location for conductive coils 212 and percutaneous electrode needle 262 easier. Furthermore, the load impedance through the surface of the skin is much higher than the internal impedance, and as such, the relatively high load impedance lessens the likelihood of damage to tissue and nerves due to high current pulses.

Referring again to FIG. 22, a percutaneous electrode needle for use in any of the energy emitting systems described herein may include a variety of designs. For example, percutaneous electrode needle 262 may include a metal or plastic handle 263 to provide a secure grip for the user, while minimizing the risk of shock to the user. The needle tip can have a terminal portion 264 which may extend between about 0.5 and 10 mm or about 2.0 mm from the needle tip and may be constructed out of medical grade stainless steel or other biocompatible metals. The diameter of the needle can be small (less than about 0.25 mm) which minimizes trauma during insertion. Optionally, needle 262 can be coated with Teflon or similar insulative material 265 except for an exposed tip area 264. This allows for a higher field density at the tip for more precise operation. The exposed needle tip area 264 should have a sufficiently large surface area so as not to create too high a local current field that may cause irritation or pain.

Figure 23:
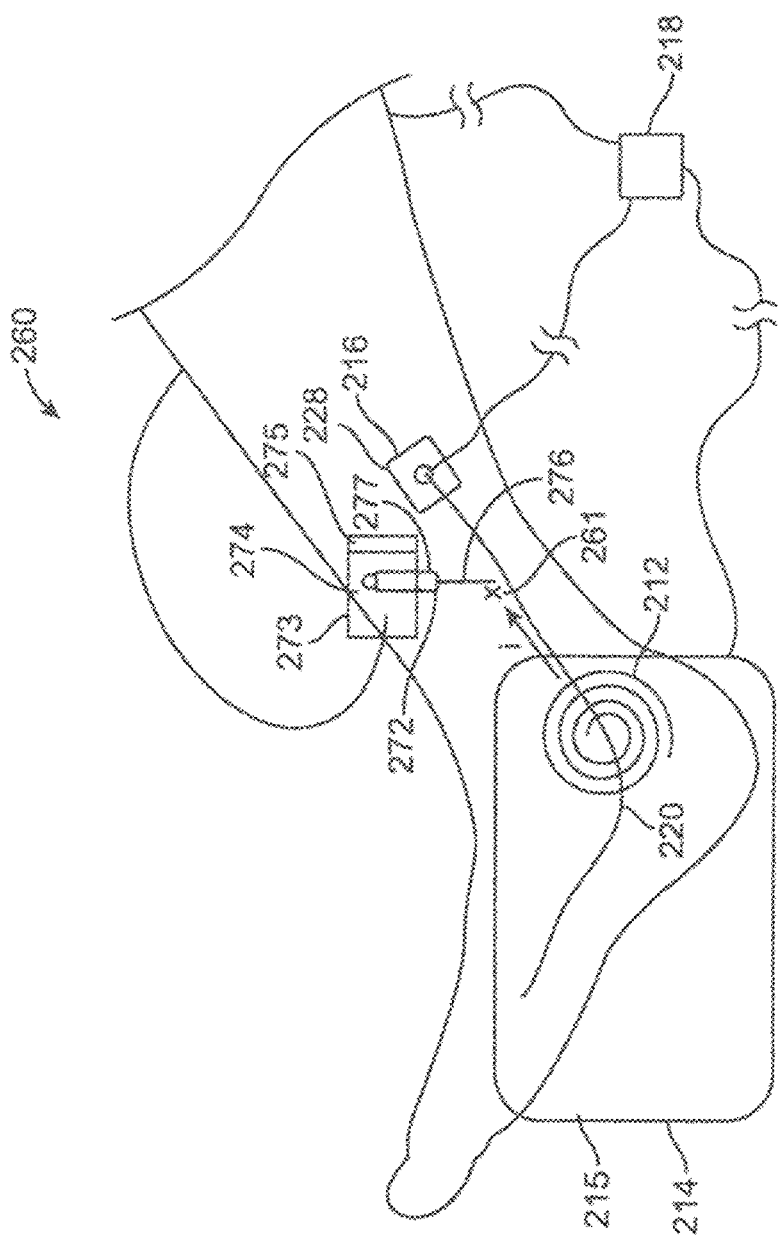

In another variation, as shown in FIG. 23, percutaneous electrode needle 272 may be used in energy emitting system 260. Percutaneous electrode needle 272 may be constructed out of medical grade stainless steel or other biocompatible electrically conductive metal. Percutaneous electrode needle 272 includes a first end 276 for insertion into the patient's body in proximity to the preselected internal stimulation site or target nerve to be stimulated, and a second end 277. The size of the needle electrode 272 is preferably small, for example 34 G needle electrode (0.22.times.10 mm), to minimize trauma during insertion. Percutaneous electrode needle 272 may also include an electrically conductive adaptor, e.g., an electrically conductive tape member 273. The tape member 273 includes an electrically conductive adhesive portion 274 and an electrically conductive non-adhesive portion 275. Alternatively, the adaptor may include an electrically conductive clip. The second end 277 of the needle electrode 272 preferably includes an enlarged portion to enable the electrically conductive tape member 273 to be more easily adhered thereto. Once it is determined that the percutaneous needle electrode 272 is properly positioned, the needle is fixedly adhered to the electrically conductive tape member 273 by folding the ends of the adhesive portion 274 of the electrically conductive tape member 272 over the second end 277 of the needle electrode thereby forming an electrical connection there between. The percutaneous needle electrode 272 is electrically coupled to controller 218 via electrically conductive tape member 273. Various other implantable or insertable electrode needles known to persons of skill in the art may also be utilized in the above described systems.

Figure 24:
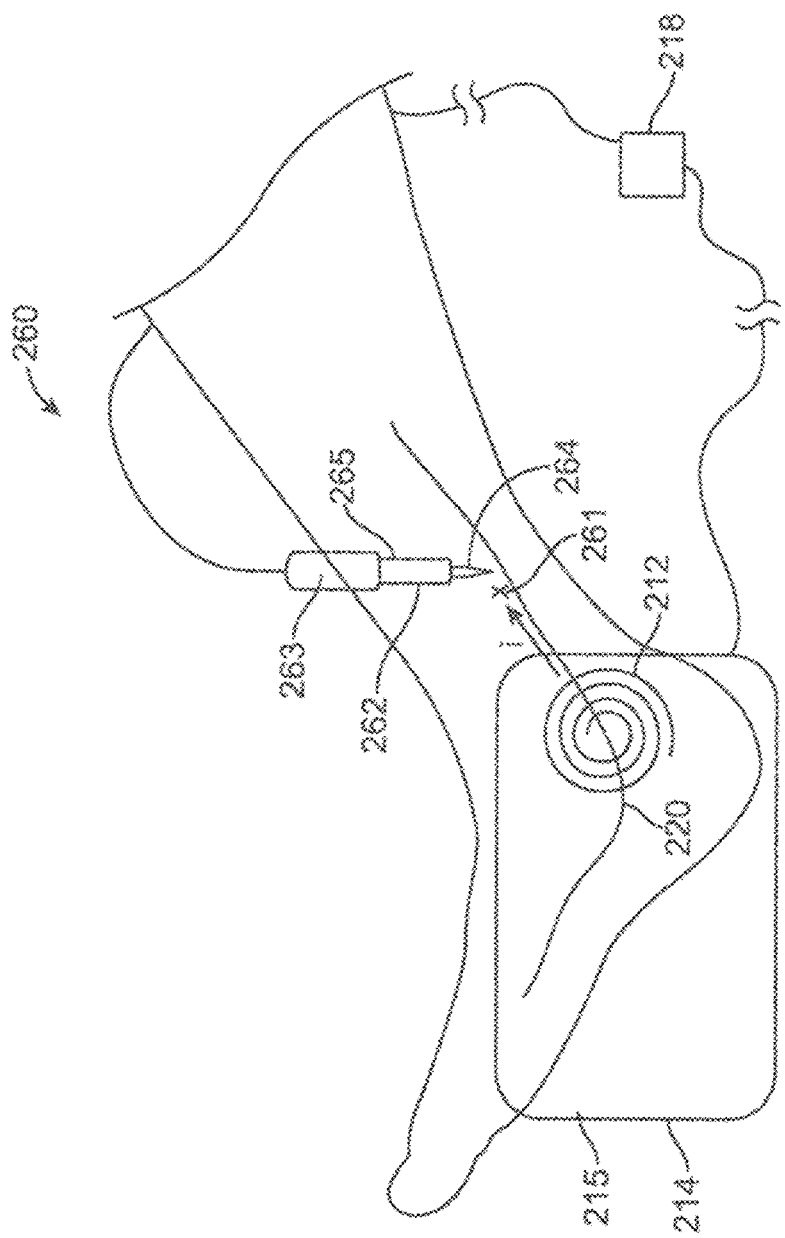
FIGS. 24-25 show schematic views of energy emitting systems including an electrode needle without a sensor.
Figure 25:
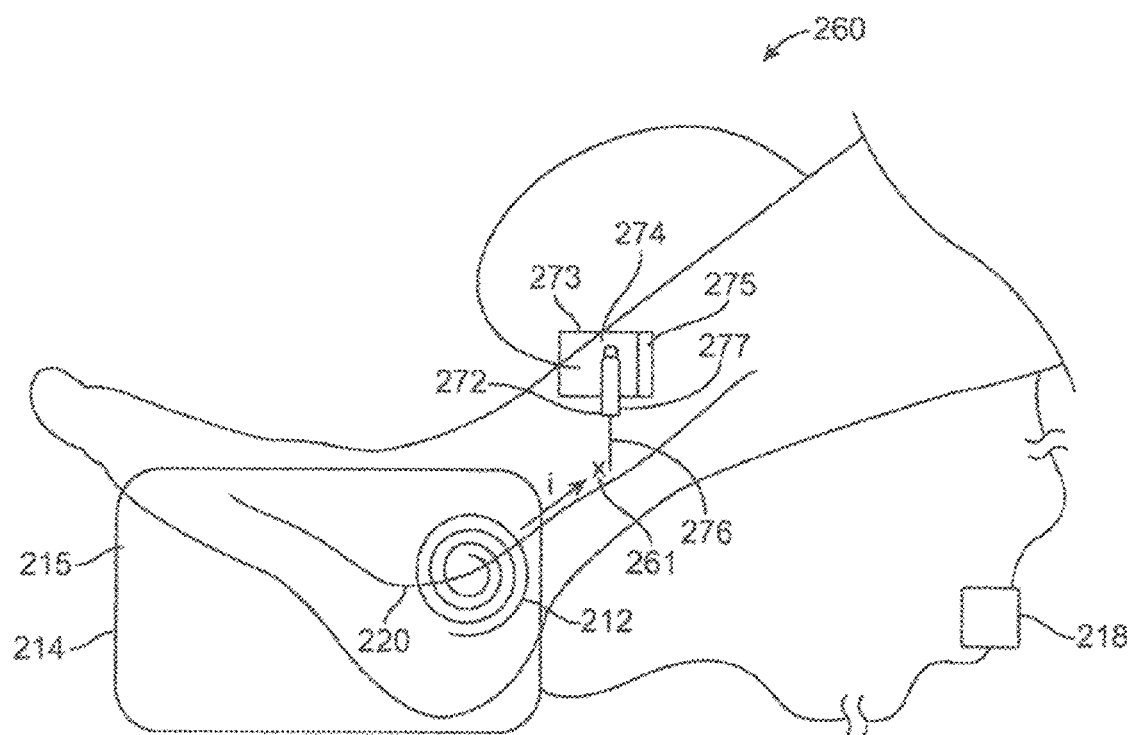

In certain variations of energy emitting system 260 as described above and shown in FIGS. 22-23, a sensor 216, such as a conductive microneedle patch 228, may be utilized to detect electrical conduction through the stimulated posterior tibial nerve 220 or to detect muscle stimulation, and transmit the signal to controller 218. The signal may be transmitted to controller 218, a separate controller or device, or a separate controller coupled to controller 218. The controller can then be varied or adjusted based on the signal from microneedle patch 228 to ensure that adequate conduction of the posterior tibial nerve 220 occurs and an adequate and accurate dosage of treatment is being received. It is also contemplated that energy system 260 may be utilized without a sensor 216, see for example FIGS. 24-25. Optionally, other types of sensors may be used in place of a microneedle patch sensor, such as other sensors described herein and sensors known to persons of ordinary skill in the art. The sensor may be placed over a portion of the subject's body suitable for detecting conduction of the target nerve (e.g., on the leg as shown) or over a muscle to detect muscle stimulation resulting from stimulating the target nerve.

Figure 26:
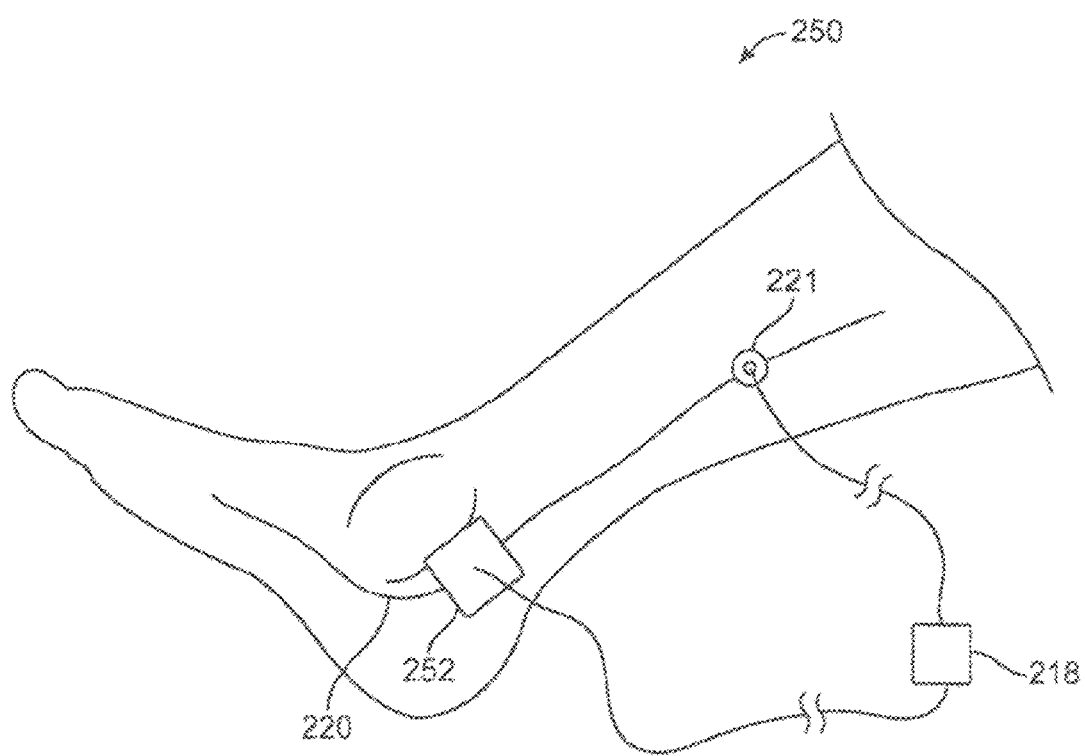
FIG. 26 shows a schematic view of an energy emitting system including a microneedle patch for providing stimulation.

In certain variations, as shown in FIG. 26, an energy emitting system 250 for providing a medical therapy includes a microneedle patch 252 (e.g., conductive microneedle patch) having one or more microneedle arrays deposited on a surface of one or more electrodes; one or more sensors 221 configured to detect electrical conduction in the target nerve or to detect muscle stimulation; and a controller 218 coupled to microneedle patch 252 and in communication with sensor 221. The microneedle patch 252 is configured such that an electrical current generated by the controller 218 is passed through the microneedle patch 252, generating a magnetic field or delivering or generating an electrical or magnetic stimulus to a target nerve, e.g., the tibial nerve 220, a muscle or other body part containing a portion of a target nerve, or any nerves branching off of a target nerve, located in proximity to microneedle patch 252.

Referring to FIG. 26, a method of using the energy emitting system 250 may include placing a conductive microneedle patch 252 on a first portion of a patient's body, for example a foot, ankle, or leg, in proximity to posterior tibial nerve 220 within the first portion of the patient's body. Sensor 221 is positioned along a second portion of the patient's body in proximity to the posterior tibial nerve 220. In this particular variation, sensor 216 is attached to the patient's leg in proximity to the posterior tibial nerve 220, proximal to and up-stream from conductive microneedle patch 252. Conductive microneedle patch 252 is composed of one or more microneedle arrays and one or more electrodes, as described in the variations above.

Once conductive microneedle patch 252 and sensor 221 are in position, a current is passed from controller 218 through conductive microneedle patch 252, resulting in an electrical stimulus of the posterior tibial nerve 220. Alternatively, the microneedle array may be insulated or constructed of non conductive material such that the microneedle patch 252 generates a magnetic field that stimulates tibial nerve 220 in a manner similar to the one or more coils described in the variations above, without an electrical stimulus. Whether the stimulus is electrical or magnetic, either stimulus will generate a current that will flow along the tibial nerve 220 and spread along its length, to its sacral or pudendal nerve roots. Sensor 221 detects electrical conduction through the stimulated posterior tibial nerve 220, and then transmits the signal to controller 218. In certain variations, the sensor may be in the form of a microneedle patch sensor. The signal may be transmitted to controller 218, a separate controller or device, or a separate controller coupled to controller 218. The controller can then be varied or adjusted based on the signal from sensor 221 to ensure that adequate conduction of the posterior tibial nerve 220 occurs and an adequate and accurate dosage of treatment is being received.

The sensor utilized in the energy emitting system 250 may be a sensor of the type described above, with respect to other variations. Optionally, for example, the sensor may be a microneedle patch. It is also contemplated that energy emitting system 250 can be utilized without a sensor. The sensor may be placed over a portion of the subject's body suitable for detecting conduction of the target nerve (e.g., on the leg as shown) or over a muscle to detect muscle stimulation resulting from stimulating the target nerve.

In certain variations, energy emitting system 250 may optionally include one or more conductive coils disposed within or along a housing which can be positioned in proximity to the target nerve or muscle and provide an additional or supplemental stimulation of the target nerve or muscle.

Figure 27:
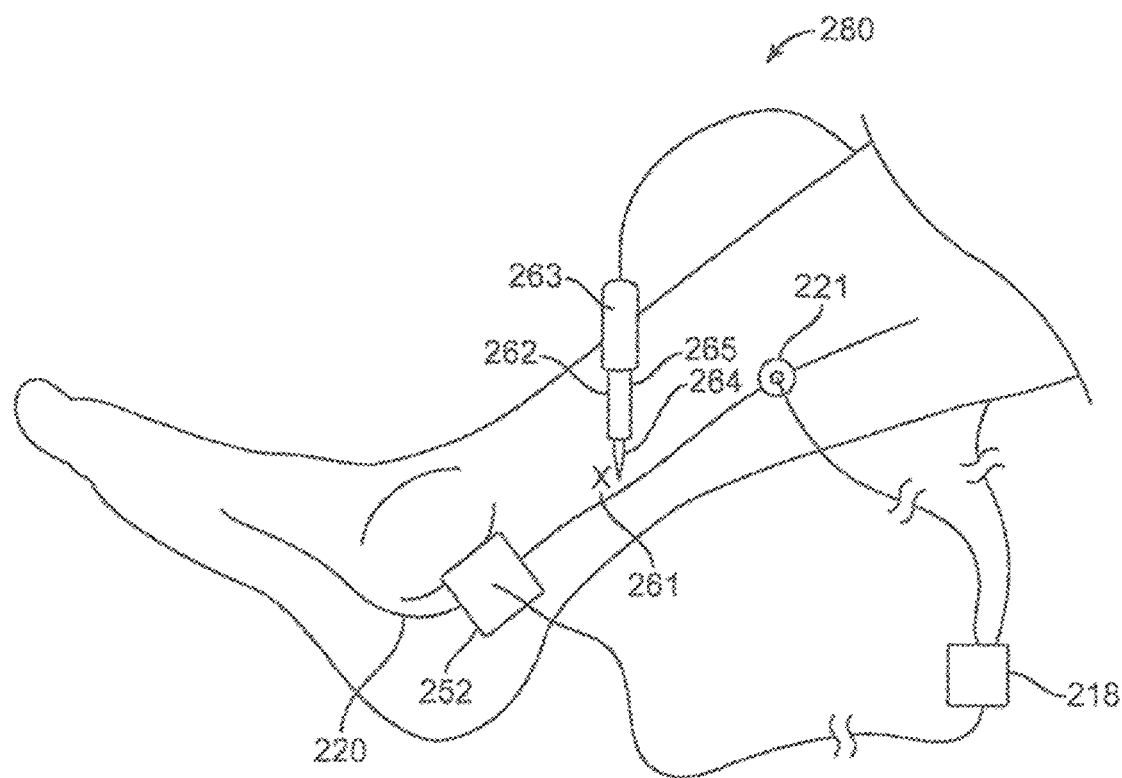
FIGS. 27-28 show schematic views of energy emitting systems including an electrode needle and microneedle patch for providing stimulation.

Referring to FIG. 27, the energy emitting system 250 described above with respect to FIG. 26 may be varied to create energy emitting system 280. Energy emitting system 280 further includes one or more percutaneous electrode needles 262 coupled to a controller 218 and having an end insertable into a subject's body in proximity to said target nerve.

Optionally, the electrode needle may be non-percutaneous, such that it is insertable in an orifice or opening in the subject, such as a natural orifice. The percutaneous electrode needle 262 is inductively coupled to conductive microneedle patch 252. In use, a microneedle patch 252 is placed on a first portion of a patient's body, for example a foot, ankle, or leg, in proximity to posterior tibial nerve 220 within the first portion of the patient's body and down-stream or distal to a selected stimulation site 261. The percutaneous electrode needle 262 is inserted through the skin at a location and to a depth that brings the tip in close proximity to the target nerve to be stimulated.

The controller 218 is activated and a current passes through microneedle patch 252 and traverses the internal stimulation site 261 by passing from microneedle patch 252 to the internal percutaneous electrode needle 262, as indicated by arrow i. The current passing through microneedle patch 252 may also generate a magnetic field which can generate a current that traverses the internal stimulation site 261 by passing from microneedle patch 252 to the internal percutaneous electrode needle 262. Also, the percutaneous electrode needle may be positioned within the generated magnetic field, whereby the magnetic field generates a current in the percutaneous electrode which stimulates a target nerve and traverses an internal stimulation site. Optionally, a current may be passed from the controller 218 through microneedle patch 252 and/or from the controller 218 through percutaneous electrode needle 262, traversing the internal stimulation site as the current passes between the patch and needle.

Figure 28:
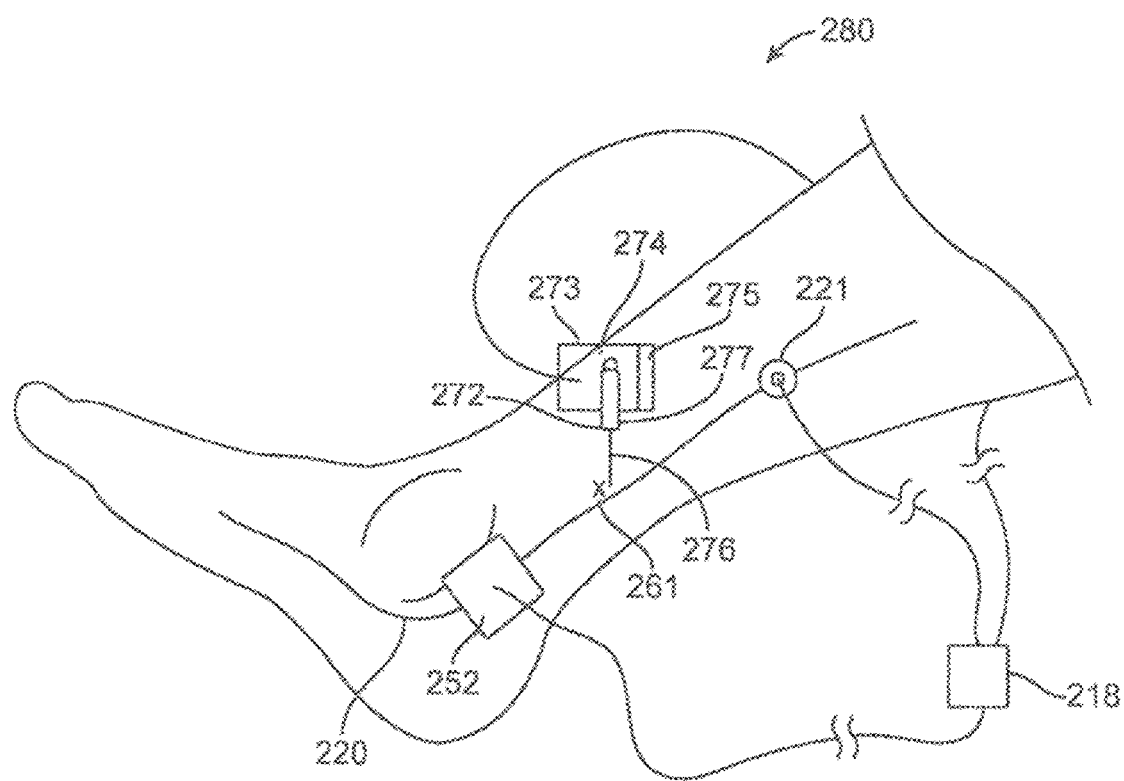
Figure 29A:
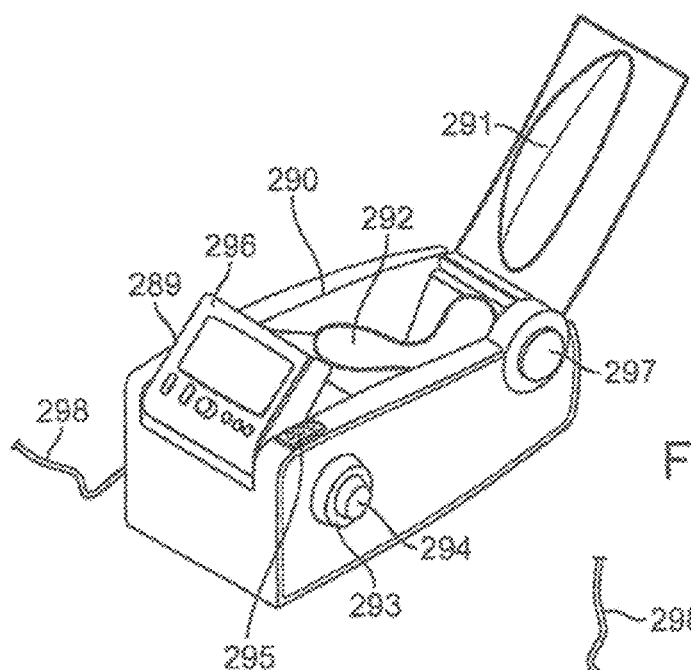
FIG. 29a-29d show a prospective, side, top and rear views of an energy emitting device in the form of a foot cradle.
Figure 29B:
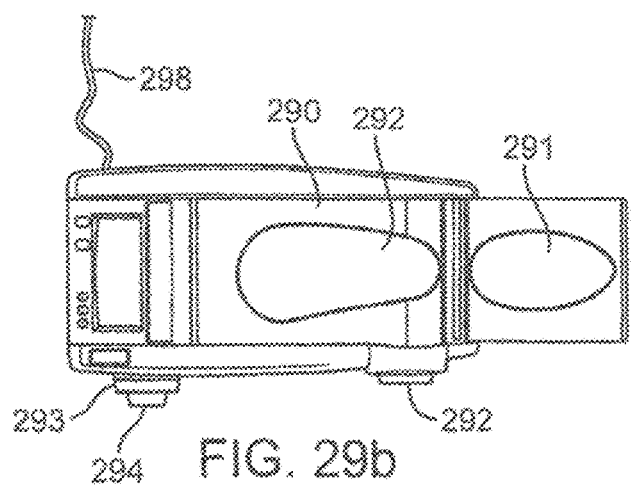
Figure 29C:
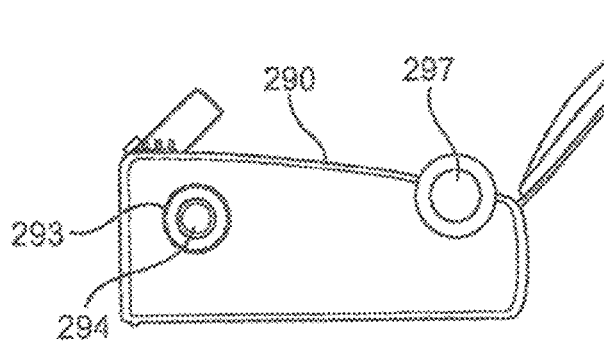
Figure 29D:
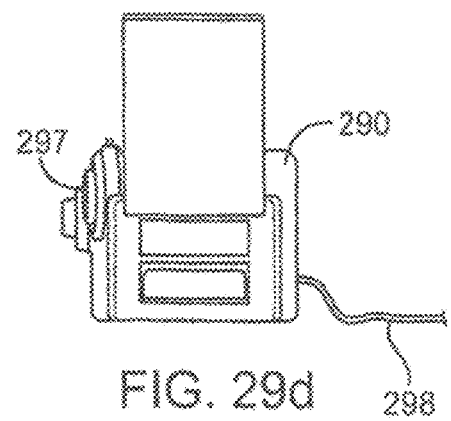

Referring to FIG. 28, energy emitting system 280 may be modified by using percutaneous electrode needle 272 in place of percutaneous electrode needle 262. Percutaneous electrode needle 272 would be constructed and function as described above with respect to FIG. 23. Various other implantable or insertable electrode needles known to persons of skill in the art may also be utilized in the above described systems. Additionally, energy emitting system 280 may utilize a sensor to detect electrical conduction through the stimulated posterior tibial nerve 220 and send a corresponding signal indicative of the detected conduction to controller 218 or other device such that the electrical or magnetic stimulus can be adjusted as necessary. The sensor may be a sensor 221, or optionally the sensor may be a microneedle patch. It is also contemplated that energy emitting system 280 can be utilized without a sensor. The sensor may be placed over a portion of the subject's body suitable for detecting conduction of the target nerve (e.g., on the leg as shown) or over a muscle to detect muscle stimulation resulting from stimulating the target nerve.

In any of the above systems, variations are contemplated where the sensors are also coupled or connected to or otherwise in communication with energy emitting devices, e.g., the conductive coils or conductive microneedle patches.

In certain variations, the one or more microneedles of the microneedle patch may include an electrically conductive material such that the microneedles may transmit an electrical signal to an overlying electrode or other surface. Microneedles may be constructed of an electrically conductive material and/or coated with an electrically conductive material. Optionally, microneedles may be coated with an electrically conductive material and constructed of a non-conductive material. Microneedles may be fabricated using a variety of materials, e.g., metals, stainless steel, solid or coat of gold over NI, Pd or Pd—Co, Pt, silicon, silicon dioxide, polymers, glass, biocompatible polymers, titanium, silver, or suture materials. Biodegradable polymers may also be used such that if a tip of a microneedle were to snap or break off during insertion, it would easily biodegrade. Optionally, the microneedle patch may be non-conductive.

In certain variations, an electrode patch for improved conductance or conduction is provided. The patch can include at least one electrode having a first surface and/or a second surface. The electrode may optionally be attached to various other materials or adhesive materials. An array of microneedles may be deposited on a surface of the electrode, or attached to a patch or other material and indirectly or directly connected to the electrode. The array of microneedles may include a conductive material. Such patches may be used as a sensor to detect muscle stimulation or electrical conduction, or to provide or deliver an electrical stimulus or magnetic field, e.g., to a target nerve, and may optionally be used in any of the variations described herein or in any application where improved conductance or conduction is desired. Microneedles yield improved reduction in impedance compared to simple abrasion and other techniques, and are less painful and more comfortable for the patient.

In certain variations, typical voltage sensed at the skin and detectable or conductible by a microneedle patch or microneedle array may range from about 1 to 400 microvolts or about 10 to 300 microvolts.

In certain variations, methods of treating a subject with urinary incontinence or various pelvic floor disorders utilizing the energy emitting systems described herein are contemplated. Symptoms associated with urinary incontinence may be observed, detected, or diagnosed. An energy emitting device having one or more energy generators, e.g., one or more conductive coils or one or more microneedle patches, may be positioned in proximity to a target nerve, e.g., the tibial or posterior tibial nerve or popliteal or sacral nerve or branches thereof of a subject or patient along a first portion of a subject's or patient's body. The subject may or may not be exhibiting symptoms associated with urinary incontinence. In the case of the conductive coils, the coils may be positioned within or along a housing, such as a foot or knee cradle, and a foot or leg may be positioned therein. In the case of a microneedle patch, the patch may be attached to a subject's skin. Optionally, the method involves positioning a first portion of a subject's body, the subject exhibiting symptoms associated with urinary incontinence, relative to an energy emitting device such that a target nerve within the first portion of the body is in proximity to at least one energy generator disposed within or along the energy emitting device.

A current is then passed through the energy generator to produce, generate or deliver energy, e.g., a magnetic or electromagnetic field or electrical or magnetic energy or stimulus, focused on the tibial or posterior tibial nerve or branches thereof. This in turn may cause the stimulation of a pudendal nerve, sacral plexus, or other nerves in the pelvic floor. Various nerves innervating the various muscles, sphincters, nerves, organs and conduits of the urinary tract and bladder may be stimulated directly or indirectly. In certain variations, a current is passed through one more coils, which generate a magnetic or electromagnetic field which stimulates the posterior tibial nerve. In certain variations, the positioning of the coils relative to the first portion of the subject's body may be adjusted to re-focus the magnetic field on the posterior tibial nerve as needed. In certain variations, a current is passed through a microneedle patch generating or delivering an electrical or magnetic stimulus or field. The positioning of the microneedle patch relative to the first portion of the subject's body may be adjusted to re-focus the electrical or magnetic stimulus or field on the posterior tibial nerve as needed.

Optionally, electrical conduction through the target nerve, e.g., the posterior tibial nerve, or muscle stimulation can be detected via at least one sensor. A conductive sensor may be positioned in proximity to the posterior tibial nerve along a second portion of the subject's body. Optionally, a sensor may be positioned over a corresponding muscle to detect muscle stimulation or twitching resulting from nerve stimulation. Optionally, the electrical conduction is detected along a second portion of the subject's body which is different from the first portion of the body. Optionally, the sensor in the form of a microneedle patch. In certain variations, the sensor may be positioned behind a subject's knee to detect the electrical conduction along the afferent posterior tibial nerve or on another portion of a patient's leg or foot. In other variations, the sensor may be positioned within or along a housing along with the one or more conductive coils.

Where a sensor is used, a signal is received from the sensors and the signal is indicative of the electrical conduction of the target nerve, e.g., posterior tibial nerve. The current may be adjusted or varied using a controller which is in communication with the energy generator. Adjustments may be made in response to the nerve or muscle stimulation detected by the conductive sensor, in order to optimize or ensure adequate treatment of urinary incontinence by achieving the appropriate level of conductance and appropriate level of nerve or muscle stimulation. Appropriate levels or parameters for current, frequency, magnetic field, treatment duration, etc., are those that result in an observed or detected reduction or prevention of symptoms associated with urinary incontinence. Treatment could also be administered and the appropriate levels and parameters achieved through observing or detecting reduction or prevention of symptoms where a sensor is not used. Examples of these symptoms include but are not limited to the inability to control urinary function, urinary leakage, and loss of bladder control.

In certain variations, the amplitude, frequency, direction of a generated magnetic field, electrical or magnetic stimulus, or firing sequence of the coils or microneedles making up the microneedle array may be adjusted. Optionally, the current may be varied according to a muscular response in the patient. Thus, to treat urinary incontinence, the magnetic field or electrical stimulus is applied to a subject or patient until the desired effects (e.g., reduction of symptoms) are achieved.

In certain variations, methods of treating a subject with fecal incontinence utilizing the energy emitting systems described herein are contemplated. Symptoms associated with fecal incontinence may be observed, detected, or diagnosed. An energy emitting device having one or more energy generators, e.g., one or more conductive coils or one or more microneedle patches, may be positioned in proximity to a target nerve, e.g., the tibial or posterior tibial nerve, or popliteal or sacral nerve or branches thereof, of a subject along a first portion of a subject's body. The subject may or may not be exhibiting symptoms associated with fecal incontinence. In the case of the conductive coils, the coils may be positioned within or along a housing, such as a foot or knee cradle, and a foot or leg may be positioned therein. In the case of a microneedle patch, the patch may be attached to a subject's skin. Optionally, the method involves positioning a first portion of a subject's body, the subject exhibiting symptoms associated with fecal incontinence, relative to an energy emitting device such that a target nerve within the first portion of the body is in proximity to at least one energy generator disposed within or along the energy emitting device.

A current is then passed through the energy generator to produce, generate or deliver energy, e.g., a magnetic or electromagnetic field or electrical or magnetic energy or stimulus, focused on the tibial or posterior tibial nerve or branches thereof. This in turn causes the stimulation of a pudendal nerve, sacral plexus, or nerves in the pelvic floor. Various nerves innervating the various muscles, sphincters, rectum, nerves, organs and conduits associated with bowel movements, fecal control, and the intestines may be stimulated directly or indirectly. Optionally, a current is passed through one more coils, which generate a magnetic or electromagnetic field which stimulates the posterior tibial nerve. In certain variations, the positioning of the coils relative to the first portion of the subject's body may be adjusted to re-focus the magnetic field on the posterior tibial nerve as needed. In certain variations, a current is passed through a microneedle patch generating or delivering an electrical or magnetic stimulus or field. The positioning of the microneedle patch relative to the first portion of the subject's body may be adjusted to re-focus the electrical or magnetic stimulus or field on the posterior tibial nerve as needed.

Optionally, electrical conduction through the target nerve, e.g., the posterior tibial nerve, or muscle stimulation can be detected via at least one sensor. A conductive sensor may be positioned in proximity to the posterior tibial nerve along a second portion of the subject's body. Optionally, a sensor may be positioned over a corresponding muscle to detect muscle stimulation or twitching resulting from nerve stimulation. Optionally, the electrical conduction is detected along a second portion of the subject's body which is different from the first portion of the body. Optionally, the sensor is in the form a of a microneedle patch. In certain variations, the sensor may be positioned behind a subject's knee to detect the electrical conduction along the afferent posterior tibial nerve or on another portion of a patient's leg or foot. In other variations, the sensor may be positioned within or along a housing along with the one or more conductive coils.

Where a sensor is used, a signal is received from the sensors and the signal is indicative of the electrical conduction of the target nerve, e.g., posterior tibial nerve. The current may be adjusted or varied using a controller which is in communication with the energy generator. Adjustments may be made in response to the nerve or muscle stimulation detected by the conductive sensor, in order to optimize or ensure adequate treatment of fecal incontinence by achieving the appropriate level of conductance and appropriate level of nerve or muscle stimulation. Appropriate levels or parameters for current, frequency, magnetic field, treatment duration, etc., are those that result in an observed or detected reduction or prevention of symptoms associated with fecal incontinence. Treatment could also be administered and the appropriate levels and parameters achieved through observing or detecting reduction or prevention of symptoms where a sensor is not used. Examples of these symptoms include but are not limited: the loss of voluntary control to retain stool in the rectum; loss of fecal control; inability to control bowel movements, and fecal leaking;

In certain variations, the amplitude, frequency, direction of a generated magnetic field, electrical or magnetic stimulus, or firing sequence of the coils or microneedles making up the microneedle array may be adjusted. Optionally, the current may be varied according to a muscular response in the patient. Thus, to treat fecal incontinence, the magnetic field or electrical stimulus is applied to a subject or patient until the desired effects (e.g., reduction of symptoms) are achieved.

In certain variations, methods of treating a subject with restless leg syndrome utilizing the energy emitting systems described herein are contemplated. Victims afflicted with Restless Leg Syndrome (RLS or Ekbom's syndrome), are unable to remain seated or to stand still. Activities that require maintaining motor rest and limited cognitive stimulation, such as transportation, e.g., in a car, plane, train, etc., or attending longer meetings, lectures, movies or other performances, become difficult if not impossible. These sensations become more severe at night and RLS patients find sleep to be virtually impossible, adding to the diminishing quality of their lives. The urge to move, which increases over periods of rest, can be completely dissipated by movement, such as walking. However, once movement ceases, symptoms return with increased intensity. If an RLS patient is forced to lie still, symptoms will continue to build like a loaded spring and, eventually, the legs will involuntary move, relieving symptoms immediately.

Thus, symptoms associated with restless leg syndrome may be observed, detected, or diagnosed. An energy emitting device having one or more energy generators, e.g., one or more conductive coils or one or more microneedle patches, may be positioned in proximity to a target nerve, e.g., the tibial or posterior tibial nerve, or popliteal or sacral nerve or branches thereof or other nerves associated with restless leg syndrome, of a subject along a first portion of a subject's body. The subject may or may not be exhibiting symptoms associated with restless leg syndrome. In the case of the conductive coils, the coils may be positioned within or along a housing, such as a foot or knee cradle, and a foot or leg may be positioned therein. In the case of a microneedle patch, the patch may be attached to a subject's skin. Optionally, the method involves positioning a first portion of a subject's body, the subject exhibiting symptoms associated with restless leg syndrome, relative to an energy emitting device such that a target nerve within the first portion of the body is in proximity to at least one energy generator disposed within or along the energy emitting device.

A current is then passed through the energy generator to produce, generate or deliver energy, e.g., a magnetic field or electrical or magnetic energy or stimulus, focused on the tibial or posterior tibial nerve or branches thereof or other nerves associated with restless leg syndrome. This in turn causes the stimulation of a pudendal nerve, sacral plexus or other nerves innervating the pelvic floor or various muscles, nerves, or organs associated with restless leg syndrome. The various nerves may stimulated directly or indirectly. Optionally, a current is passed through one more coils, which generates a magnetic or electromagnetic field which stimulates the posterior tibial nerve. In certain variations, the positioning of the coils relative to the first portion of the subject's body may be adjusted to re-focus the magnetic field on the posterior tibial nerve as needed. In certain variations, a current is passed through a microneedle patch generating or delivering an electrical or magnetic stimulus or field. The positioning of the microneedle patch relative to the first portion of the subject's body may be adjusted to re-focus the electrical or magnetic stimulus or field on the posterior tibial nerve as needed.

Optionally, electrical conduction through the target nerve, e.g., the posterior tibial nerve, or muscle stimulation can be detected via at least one sensor. A conductive sensor may be positioned in proximity to the posterior tibial nerve along a second portion of the subject's body. Optionally, a sensor may be positioned over a corresponding muscle to detect muscle stimulation or twitching resulting from nerve stimulation. Optionally, the electrical conduction is detected along a second portion of the subject's body which is different from the first portion of the body. Optionally, the sensor in the form a of a microneedle patch. In certain variations, the sensor may be positioned behind a subject's knee to detect the electrical conduction along the afferent posterior tibial nerve or on another portion of a patient's leg or foot. In other variations, the sensor may be positioned within or along a housing along with the one or more conductive coils.

Where a sensor is used, a signal is received from the sensors and the signal is indicative of the electrical conduction of the target nerve, e.g., posterior tibial nerve. The current may be adjusted or varied using a controller which is in communication with the energy generator. Adjustments may be made in response to the nerve or muscle stimulation detected by the conductive sensor, in order to optimize or ensure adequate treatment of restless leg syndrome by achieving the appropriate level of conductance and appropriate level of nerve or muscle stimulation. Appropriate levels or parameters for current, frequency, magnetic field, treatment duration, etc., are those that result in an observed or detected reduction or prevention of symptoms associated with restless leg syndrome. Treatment could also be administered and the appropriate levels and parameters achieved through observing or detecting reduction or prevention of symptoms where a sensor is not used. Examples of these symptoms include but are not limited to: uncomfortable sensations in the limbs, irresistible urges to move, usually the legs; motor restlessness; when at rest, symptoms return or worsen; and symptoms worsen in the evening and at night.

In certain variations, the amplitude, frequency, direction of a generated magnetic field, electrical or magnetic stimulus, or firing sequence of the coils or microneedles making up the microneedle array may be adjusted. Optionally, the current may be varied according to a muscular response in the patient. Thus, to treat restless leg syndrome, the magnetic field or electrical stimulus is applied to a subject or patient until the desired effects (e.g., reduction of symptoms) are achieved.

In certain variations, methods of treating a subject suffering from premature ejaculation or various pelvic floor disorders utilizing the energy emitting systems described herein are contemplated. Symptoms associated with premature ejaculation may be observed, detected, or diagnosed. An energy emitting device having one or more energy generators, e.g., one or more conductive coils or one or more microneedle patches, may be positioned in proximity to a target nerve, e.g., the tibial or posterior tibial nerve or popliteal or sacral nerve or branches thereof of a subject along a first portion of a subject's body. The subject may or may not be exhibiting symptoms associated with premature ejaculation. In the case of the conductive coils, the coils may be positioned within or along a housing, such as a foot or knee cradle, and a foot or leg may be positioned therein. In the case of a microneedle patch, the patch may be attached to a subject's skin. Optionally, the method involves positioning a first portion of a subject's body, the subject exhibiting symptoms associated with premature ejaculation, relative to an energy emitting device such that a target nerve within the first portion of the body is in proximity to at least one energy generator disposed within or along the energy emitting device.

A current is then passed through the energy generator to produce, generate or deliver energy, e.g., a magnetic or electromagnetic field or electrical or magnetic energy or stimulus, focused on the tibial or posterior tibial nerve or branches thereof. This in turn may cause the stimulation of a pudendal nerve, sacral plexus, or other nerves in the pelvic floor or nerves associated with the control of ejaculation. Various nerves innervating the various muscles, sphincters, nerves, organs and conduits of the urinary tract, bladder or reproductive system, or pelvic floor may be stimulated directly or indirectly. Optionally, a current is passed through one more coils, which generates a magnetic or electromagnetic field which stimulates the posterior tibial nerve. In certain variations, the positioning of the coils relative to the first portion of the subject's body may be adjusted to re-focus the magnetic field on the posterior tibial nerve as needed. In certain variations, a current is passed through a microneedle patch generating or delivering an electrical or magnetic stimulus or field. The positioning of the microneedle patch relative to the first portion of the subject's body may be adjusted to re-focus the electrical or magnetic stimulus or field on the posterior tibial nerve as needed.

Optionally, electrical conduction through the target nerve, e.g., the posterior tibial nerve, or muscle stimulation can be detected via at least one sensor. A conductive sensor may be positioned in proximity to the posterior tibial nerve along a second portion of the subject's body. Optionally, a sensor may be positioned over a corresponding muscle to detect muscle stimulation or twitching resulting from nerve stimulation. Optionally, the electrical conduction is detected along a second portion of the subject's body which is different from the first portion of the body. Optionally, the sensor in the form of a microneedle patch. In certain variations, the sensor may be positioned behind a subject's knee to detect the electrical conduction along the afferent posterior tibial nerve or on another portion of a patient's leg or foot. In other variations, the sensor may be positioned within or along a housing along with the one or more conductive coils.

Where a sensor is used, a signal is received from the sensors and the signal is indicative of the electrical conduction of the posterior tibial nerve. The current may be adjusted or varied using a controller which is in communication with the energy generator. Adjustments may be made in response to the nerve or muscle stimulation detected by the conductive sensor, in order to optimize or ensure adequate treatment of premature ejaculation by achieving the appropriate level of conductance and appropriate level of nerve or muscle stimulation. Appropriate levels for current, frequency, magnetic field, treatment duration, etc., are levels that result in an observed or detected reduction or prevention of symptoms associated with premature ejaculation. Treatment could also be administered and the appropriate levels and parameters achieved through observing or detecting reduction or prevention of symptoms where a sensor is not used. Examples of these symptoms include but are not limited to: ejaculation that frequently occurs within one minute or less of penetration, the inability to delay ejaculation on penetrations; or persistent or recurrent ejaculation with minimal stimulation before, on or shortly after penetration.

In certain variations, the amplitude, frequency, direction of a generated magnetic field, electrical or magnetic stimulus, or firing sequence of the coils or microneedles making up the microneedle array may be adjusted. Optionally, the current may be varied according to a muscular response in the patient. Thus, to treat premature ejaculation, the magnetic field or electrical stimulus is applied to a subject or patient until the desired effects (e.g., reduction of symptoms) are achieved.

Exemplary treatment parameters for treating various conditions, e.g., urinary incontinence, using the systems and methods described herein may include the following. Operation of a conductive coil at about 10 to 20 hertz generating a magnetic field of about 0.25 to 1.5 tesla, where the coil is administered to a patient for a duration of about 30 minutes/day or 30 minutes per week, depending on the severity of the symptoms, until the symptoms subside. The above treatment parameters or variations on the parameters may be used for treatment of urinary incontinence, fecal incontinence, restless leg syndrome, or premature ejaculation or other conditions. For example, the coil may be operated at various parameter ranges falling with the following ranges: about 5 to 100 hertz, about 1 to 10 tesla, for about 15 minutes to 2 hours per day or week. In treating premature ejaculation, a patient may receive treatment about 4 to 10 hours prior to intercourse. A maintenance phase of treatment, after the initial treatment, may vary for various conditions. For example, the maintenance phase may require application of the systems and methods described herein at the parameters described herein for 30 minutes/week or 30 minutes/month. Any treatment parameter may be varied or modified based on the effect on the patient or sensor or patient feedback regarding stimulation, until the desired result of treating or preventing a condition is achieved.

In certain variations, as shown in FIGS. 29a-29d, energy emitting device may include a controller 289 and a foot cradle 290. Foot cradle 290 may include vertical foot plate 291, and horizontal foot plate 292, where each plate can be adjusted using vertical foot plate knob 293 and horizontal foot plate knob 294. One or more EMG plugs 295 are provided. An air core coil 297 or other type of coil is provided. A display screen 296 may also be provided along with power cord 298. The display screen 296 can display a variety of information to the user and/or practitioner such as the level of power or current applied, treatment time, temperature of the cradle device, detected current levels and/or physiological parameters, etc., to facilitate effective and efficient therapeutic treatment. The information can be used to vary or adjust the controller to ensure that adequate conduction of a target nerve, e.g., posterior tibial nerve 220 or muscle stimulation occurs and an adequate and accurate dosage of treatment is being received. Controls may also be included to affect the following: power, field strength, frequency, pulse, start/pause and cancellation of therapy (as shown) or other parameters one of skill in the art would find necessary or useful to control or monitor. In certain variations, a sensor may be connected, connected or in communication with the foot cradle or other energy emitting apparatus, controller, housing, conductive coils, or microneedle patch.

Figure 30B:
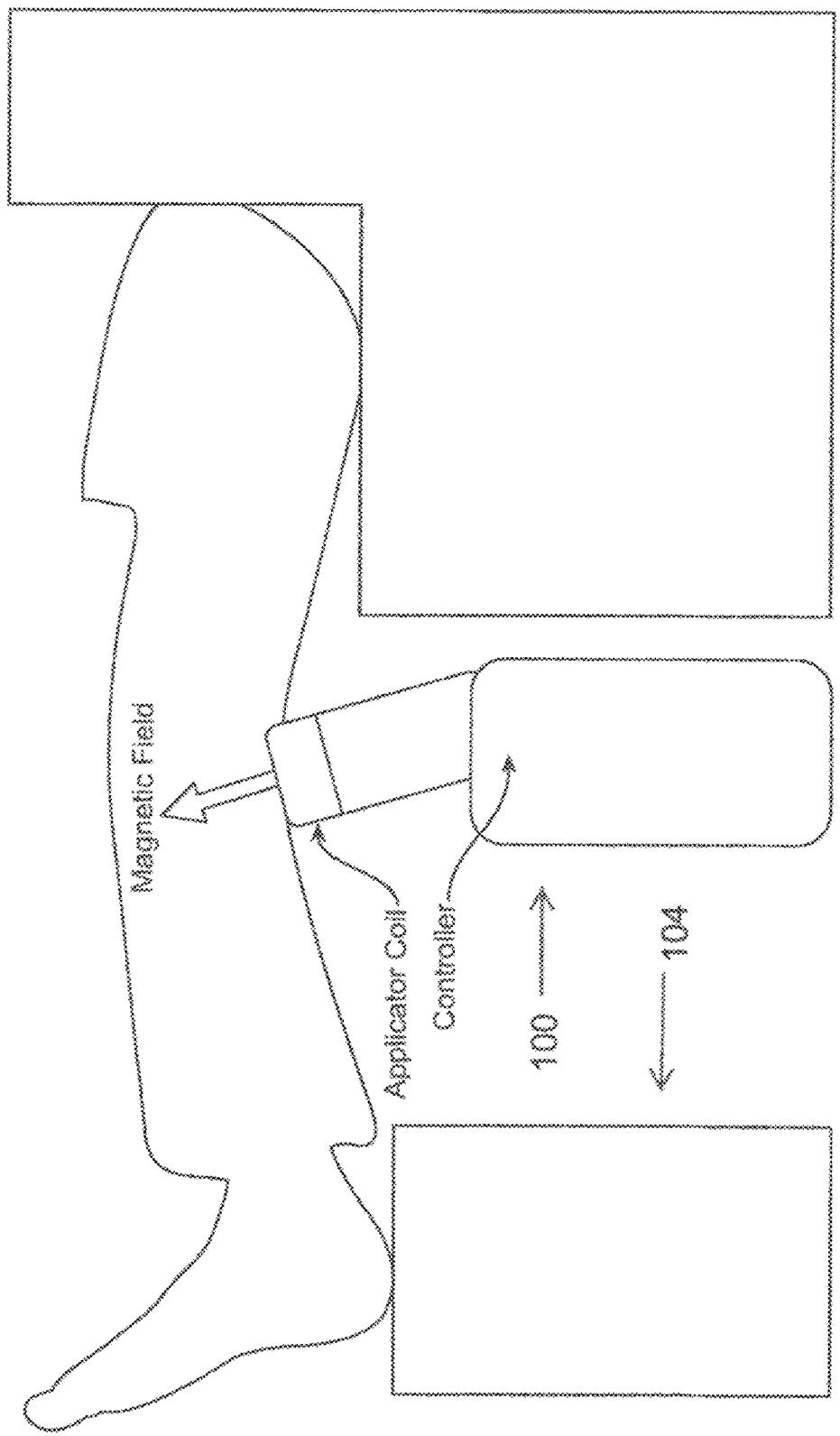

In certain variations, as shown in FIGS. 30A-30B, an energy emitting device may include a controller and a knee support or knee cradle. The cradle may be configured to provide the conductive coil in proximity to the popliteal fossa or area directly behind the knee. In certain variations, the knee cradle may be configured to cradle or surround at least a portion of the knee or substantially the entire knee without placing direct pressure on the popliteal fossa, thereby minimizing or avoiding venous thrombosis. In one variation, the device may be utilized while the knee is in the flexed position (FIG. 30A). In another variation, the device may be utilized while the knee is in a non-flexed position (FIG. 30B).

In certain variations, the energy emitting device, e.g., foot support or cradle, knee support or cradle, etc., includes a conductive coil positioned such that a target nerve is automatically targeted. The conductive coil is configured, sized and positioned within the device such that the generated magnetic field may encompass and stimulate the target nerve in any patient based on the target nerve's anatomical location, thus providing automatic targeting of the nerve in any patient once the patient positions a particular body portion in the device.

In certain variations described herein, sensors may detect voltage or current and may be connected, coupled, wirelessly connected or coupled or otherwise in communication with housing, conductive coils, microneedle patch, energy emitting apparatus, energy generators, or electrode needles and/or controller using a variety of methods or techniques known in the art. In various variations described herein, housings, conductive coils, microneedle patches, energy emitting apparatus, energy generators, or electrode needles may be connected, coupled, wirelessly connected or coupled or otherwise in communication with each other, controllers or sensors, using a variety of methods or techniques known in the art.

Coils used in any of the variations described herein and illustrated in the corresponding FIGS. may take on a variety of shapes, sizes, and configurations. For example, a coil may be shaped as a spiral (as shown) or have a simple helical pattern or be a FIG. eight coil, a four leaf clover coil, a Helmholtz coil, a modified Helmholtz coil, or may be shaped as a combination of the aforementioned coil patterns. Additionally, other coil designs beyond those mentioned hereinabove might be utilized as long as a magnetic field is developed that will encompass a target nerve.

The coils may have a variety of dimensions and configurations. In certain variations, a coil may have a central aperture. The diameter of the aperture may range from about 0.5 inch to 2 inches or 1 inch to 1.5 inches or the aperture may have a diameter of about 1 inch. The diameter of the coil body may vary. For example, the diameter may range from about 3.0 to about 7 inches or from about 4 to about 5 inches or the diameter may about 4.5 inches. The coil body may include any suitable number of turns. For example, the coil body may include from about 2 to about 25 turns or from about 10 to about 20 turns or 14 to 17 turns. The adjacent turns may be spaced apart from each other, providing a gap there between. An end or cross section of a turn may have various dimensions. For example, the end or cross section may have a height that is greater than its width. An end or cross section of a turn may have a height ranging from about 1 to 5 cm or from about 10 mm to 51 mm (about 0.3 inches to 2 inches) or about 25 mm to 40 mm (about 1 inch to 1.5 inches) or about 12 mm to 40 mm (about 0.5 inch to 1.5 inch) or about 0.5 inch to 2 inch. The end or cross section of the turn may have a width ranging from about 0.5 mm to about 5 mm (about 0.019 inch to 0.19 inch) or from about 1 mm to about 2 mm (about 0.03 inch to 0.07 inch) or about 0.2 mm to about 1.6 mm (about 0.01 inch to 0.06 inch). The above are all exemplary dimensions, where other dimensions are also contemplated depending on the use and configuration of a device.

In certain variations, a system or device for electromagnetic or magnetic induction therapy may include one or more conductive coils disposed within or along an applicator. The coil may be configured to generate an electromagnetic or magnetic field focused on a target nerve, muscle or other body tissue positioned in proximity to the coil. The system may also include one or more sensors. The sensor may be configured to detect electrical conduction in the target nerve or to detect stimulation of a muscle or other body tissue. The sensor may also detect a muscular response caused by an electrical conduction in a target nerve. The sensor provides feedback about the efficacy of the applied electromagnetic or magnetic induction therapy. Optionally, a user may provide such feedback based on detection by the user, with or without the use of a sensor. The system may also include a controller which is in communication with the sensor. The controller may be adjustable to vary a current through the coil in order to adjust the magnetic field focused upon the target nerve based on feedback from the sensor or user. The various systems or devices described herein may be utilized with or without a sensor.

A variety of electromagnetic or magnetic induction applicators designed or configured to stimulate various portions of a patient's body for treating various conditions are contemplated herein.

FIG. 31A illustrates a variation of a hand or arm applicator 310. The hand or arm applicator 310 may be ergonomic or contoured to a hand or arm to be positioned relative to or in proximity to a hand or arm to generate an electromagnetic or magnetic field focused on a target nerve, muscle or other tissue within the hand or arm. Optionally, a hand or arm applicator 310 may be designed to stimulate the entire hand or arm of a patient, for example, where the patient has limited or reduced nerve innervation to those portions of the body.

FIG. 31B also illustrates a variation of a foot, knee or leg applicator 320. The foot, knee or leg applicator 320 may be ergonomic or contoured to a foot, knee or leg to be positioned relative to or in proximity to a foot, knee or leg to generate an electromagnetic or magnetic field focused on a target nerve, muscle or other tissue within the foot, knee or leg. Optionally, a foot, knee or leg applicator 320 may be designed to stimulate the entire foot, knee or leg of a patient, for example, where the patient has limited or reduced nerve innervation to those portions of the body.

Figure 32:
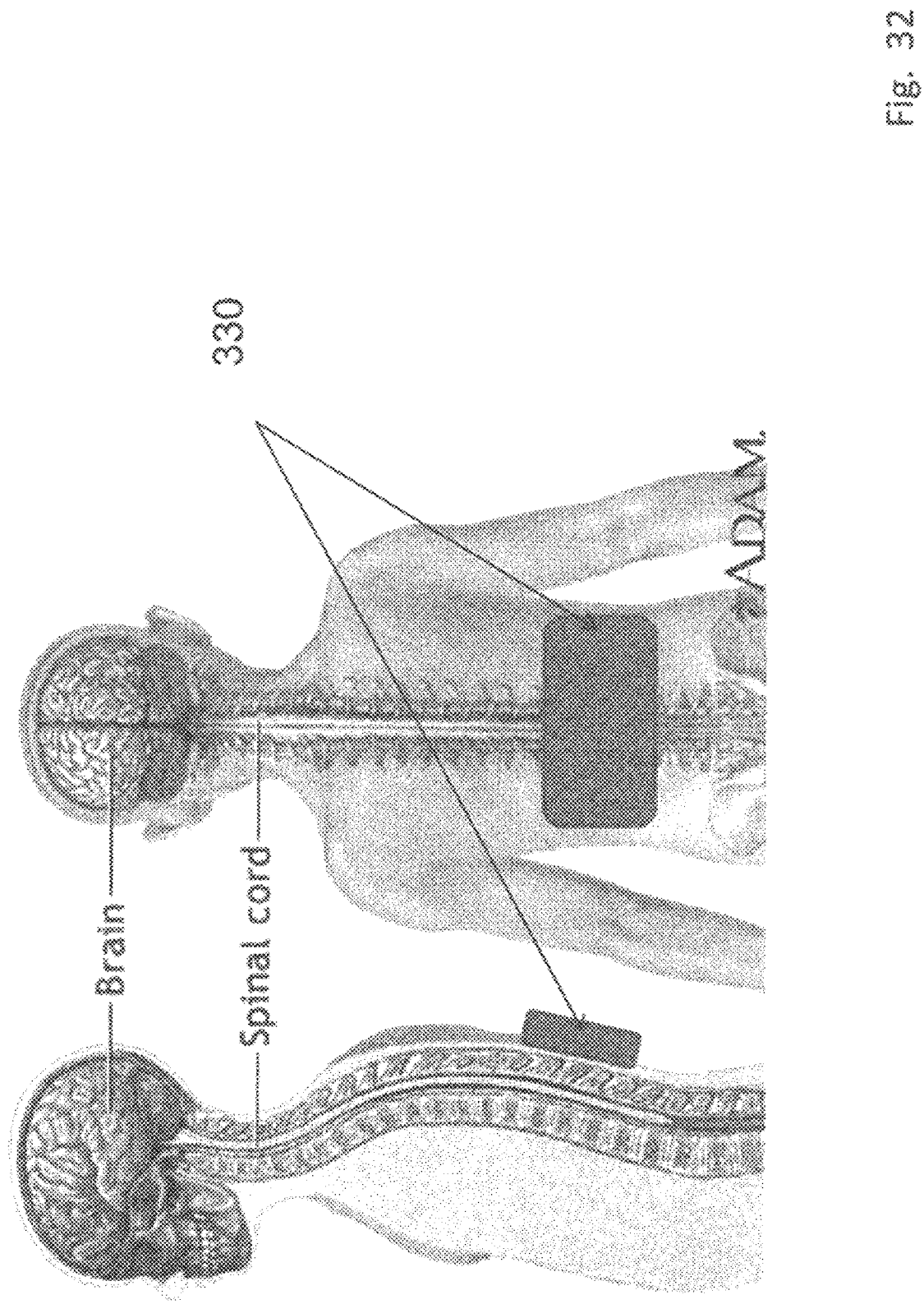
FIG. 32 shows a schematic view of a variation of a back applicator.

FIG. 32 illustrates a variation of a stand alone back applicator 330. The back applicator 330 may be ergonomic or contoured to the back or to a specific area of the back to be positioned relative to or in proximity to the back to generate an electromagnetic or magnetic field focused on a target nerve, muscle or other tissue within the back. A back applicator 330 may be aligned along the spine or positionable in proximity to the spine. The back applicator 330 may be utilized to stimulate nerve offshoots, dorsal ganglion, the spinal cord itself or any other nerve in the body, to treat various conditions, for example, to treat atrophy or paralysis.

The back applicator 330 may include several coils, which may be pulsed intermittently. In certain variations, a sensor may be placed on muscle in dermatome to provide feedback to ensure stimulation of the proper dorsal root ganglion or vertebral body. The sensor may provide feedback to channel energy or current to the proper or effective coil in an applicator, e.g., in an applicator having multiple coils.

Figure 33:
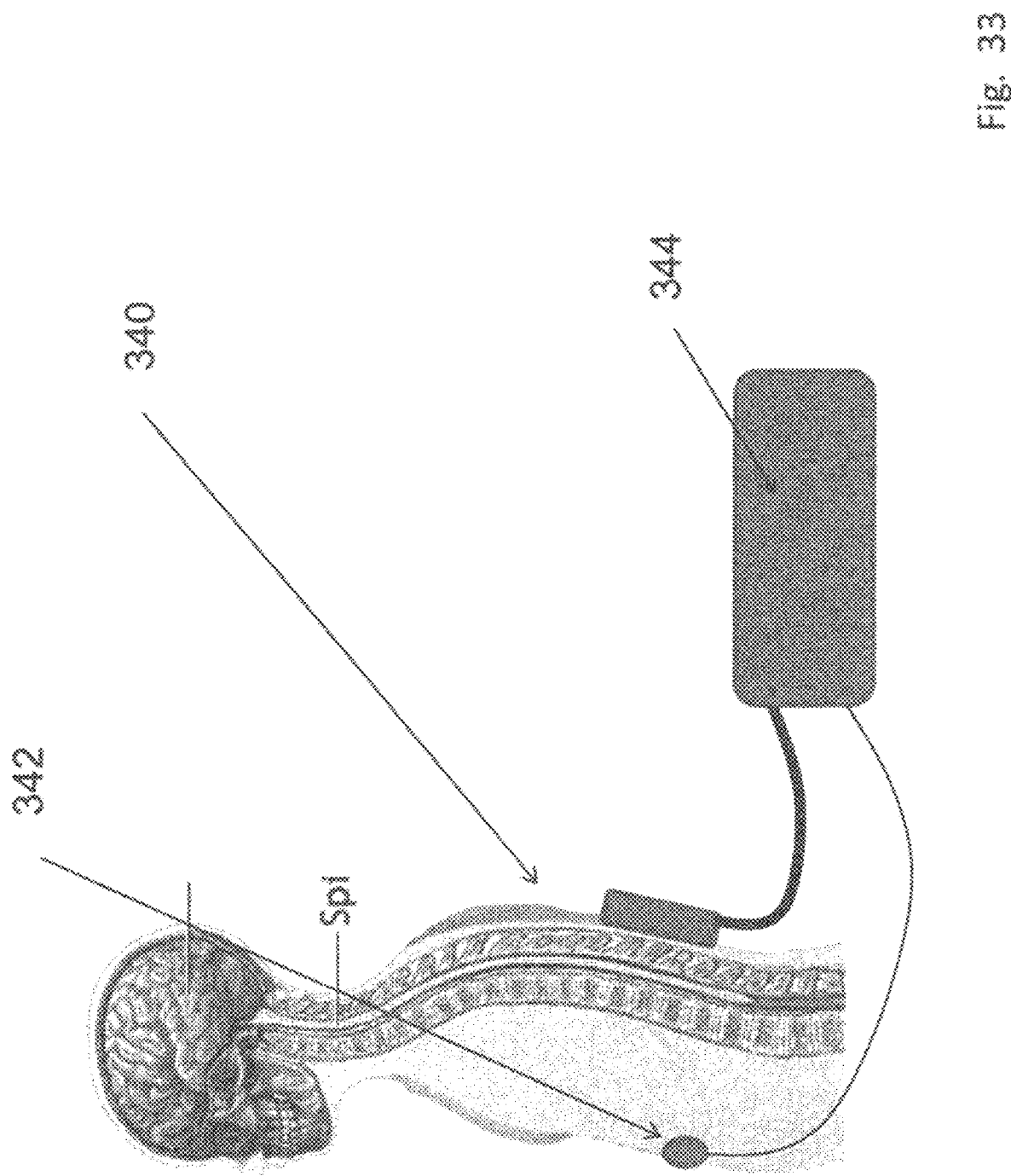
FIG. 33 shows a schematic view of a variation of a system including a back applicator, a sensor and logic controller.

FIG. 33 shows a system including a corded back applicator 340, a sensor 342 and a logic controller 344. Various sensors may be utilized, e.g., a three lead EMG, other EMG electrode, a microneedle electrode, or any sensor for detecting physiologic changes associated with nerve firing and/or muscle contraction. The sensor 342 provides feedback which may be used to monitor and/or control therapy. The sensor 342 may be used to position or optimize therapy in a clinic or home healthcare setting. The applicator 340 may or may not contain a pulse generator and/or logic controller circuitry. FIG. 33 shows the logic controller 344 and pulse generator as a separate unit. The logic controller may optimize therapy and minimize energy usage or overheating based on feedback from sensor 342. Optionally, the logic controller 344 may be incorporated into an applicator. The logic controller 344, whether separate from the applicator or incorporated in the applicator, may be controlled based on feedback from the sensor.

Figure 34:
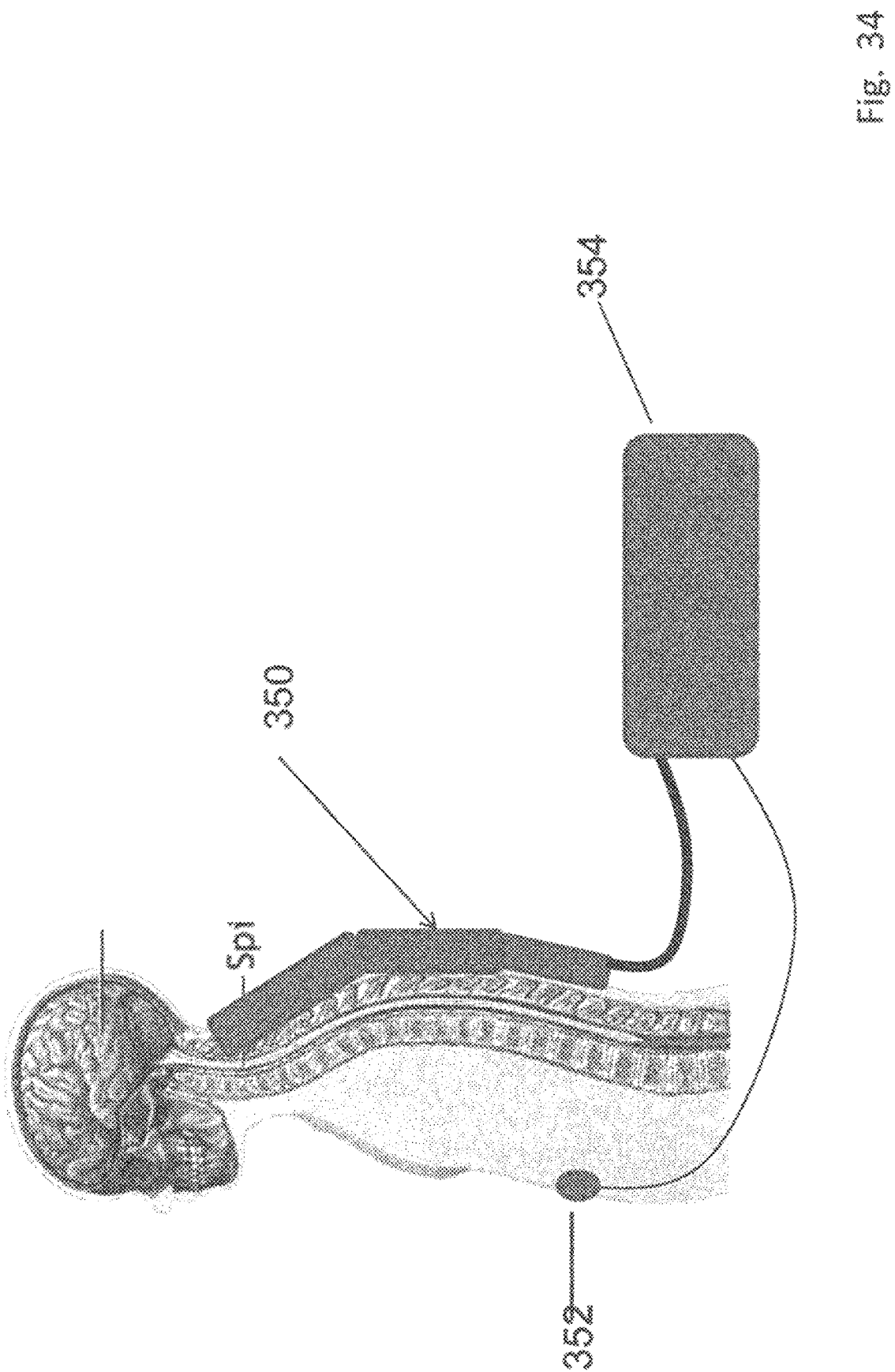
FIG. 34 shows a schematic view of system including multiple back applicators, a sensor and logic controller.

FIG. 34 shows a system including a whole back applicator 350, a sensor 352 and a logic controller 354. One or more back applicators 350 may be provided. One or more applicators 350 may include automated therapy targeting. The applicators 350 may include multiple coils, which can be fired sequentially to stimulate the entire spine or chain of dorsal root ganglion (with or without user or sensor feedback) for osteoarthritis therapy, back or neck pain therapy, prevention of muscular atrophy and/or nerve recovery after paralysis, stroke, or after suffering other nerve damaging conditions. In one variation, one or more applicators 350 may include multiple coils fired sequentially in order to determine the optimal coil for stimulation based on user or sensor feedback. Once the optimal coil is determined, that coil may be selected and used for the remainder of the therapy. In another variation, one or more applicators may include one or more coils that are slidable, adjustable or movable within the applicator housing. The coils may be moved within the applicator housing to treat a large area and/or to be focused on the optimal treatment zone based on feedback from the user and/or feedback from the sensor.

Figure 35:
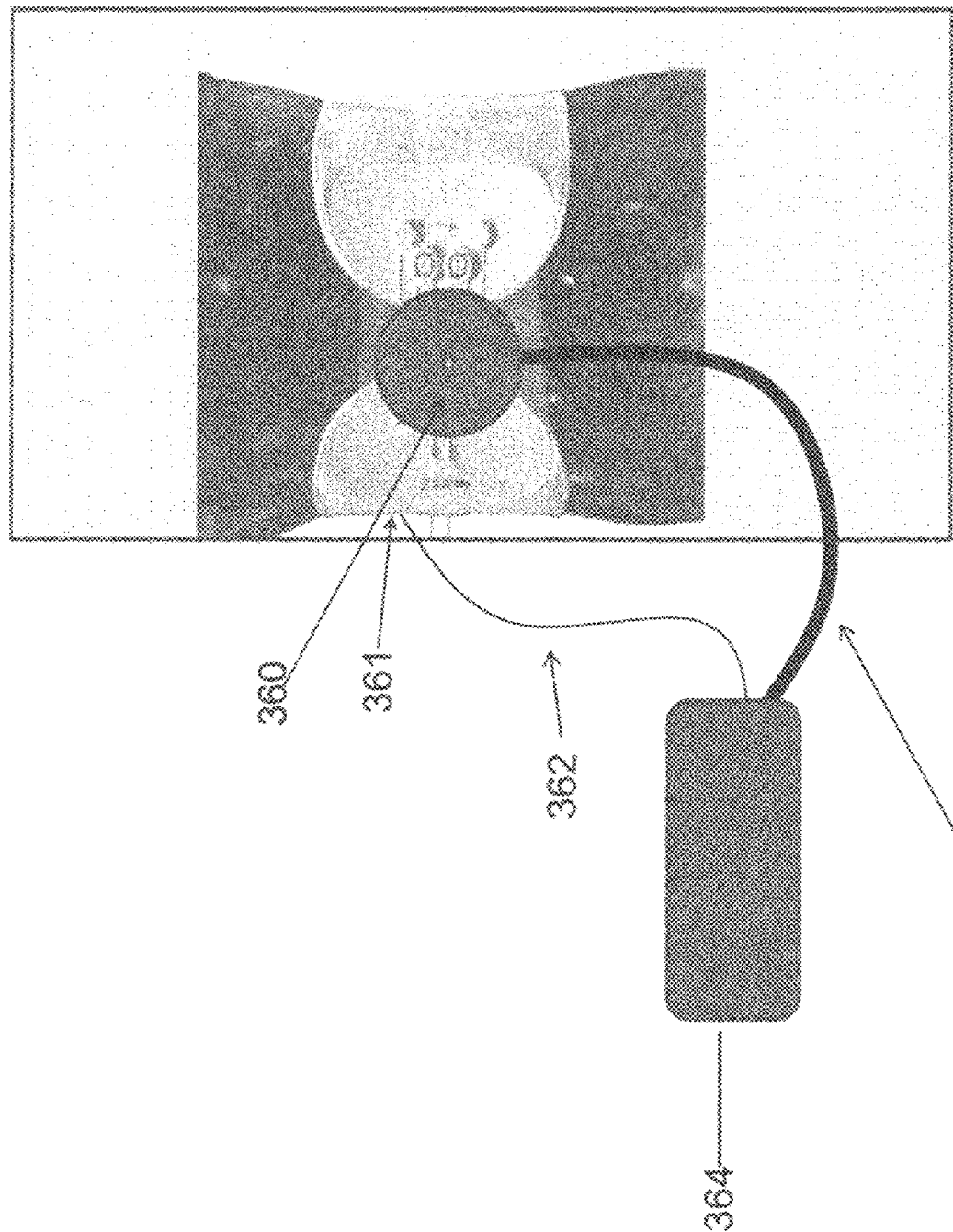
FIG. 35 shows a schematic view of a variation of a system including a back applicator held on a patient's body by an ergonomic positioning element in the form of a belt and a logic controller.

FIG. 35 shows a variation of a back applicator 360 which may be positioned in proximity to or aligned along a spine. The back applicator 360 may have ergonomic features or may be placed in proximity to a spine or a spine may be positioned in proximity to the applicator 360. The applicator 360 may include several coils that are pulsed intermittently. As shown in FIG. 35, the back applicator 360 or focused back applicator may me held on a patient by an ergonomic positioning element 361 (e.g., a belt) and may be fit such the cervical, thoracic, lumbar, sacral and/or lumbosacral curvatures hold the back applicator 360 in the optimal position. The applicator 360 may be located anywhere along the positioning element 361 depending on the individual and area to be stimulated. Optionally, a sensor lead 362 may be placed over musculature or along a nerve excited by activation of the applicator 360. In one variation, a coil power line 365 for supplying power or current from the logic controller 364 to coils positioned in the applicator 360 may include fluid cooling, e.g., air or liquid cooling.

Figure 36:
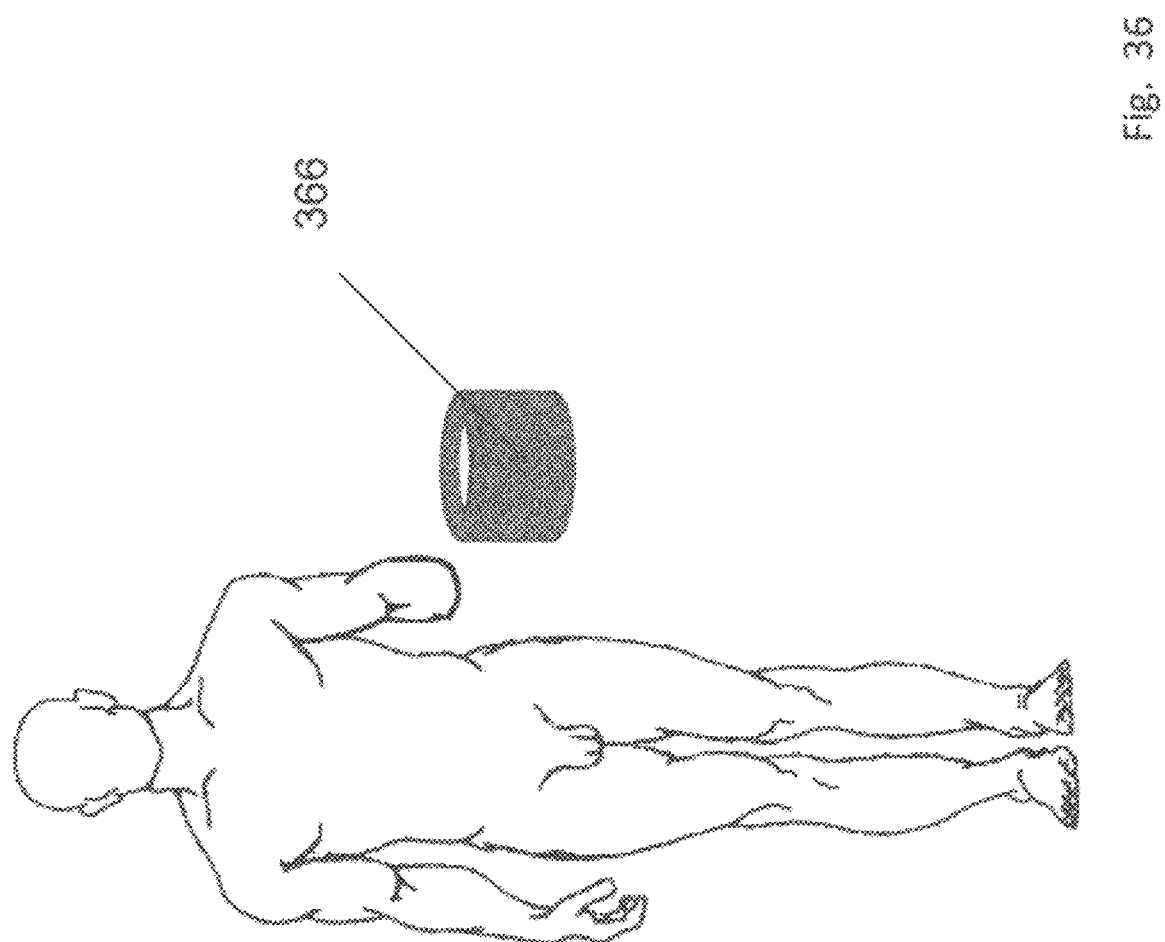
FIG. 36 shows a schematic view of a variation of an applicator designed to stimulate a nerve responsible for phantom or neuropathic pain.

FIG. 36 shows an applicator 366 designed or configured to generate a magnetic field focused on a target nerve responsible for phantom or neuropathic pain. The applicator 366 or phantom pain therapeutic stimulator unit may be utilized to treat phantom pain or neuropathic pain, to provide phantom pain or neuropathic pain therapy. The applicator 366 may be ergonomic or contoured to be positioned relative to or in proximity to a nerve responsible for phantom or neuropathic pain.

Figure 37:
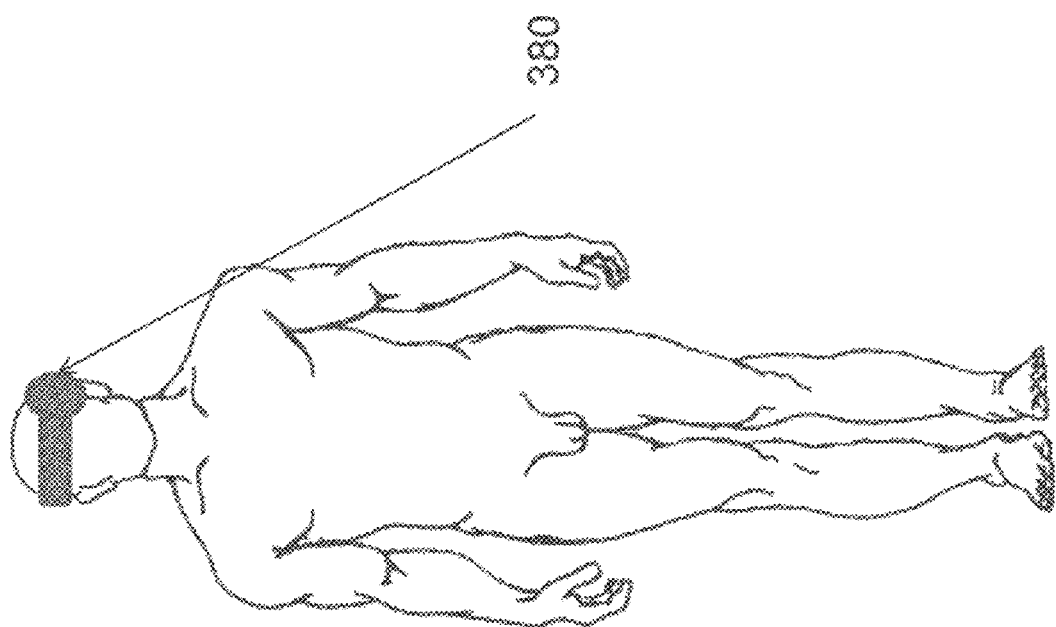
FIG. 37 shows a schematic view of a variation of a facial neuralgia applicator.

FIG. 37 shows a facial neuralgia applicator 380. Facial neuralgia applicator 380 may be may be ergonomic or contoured to a face or head to be positioned relative to a face or head to stimulate a nerve responsible for facial neuralgias. The applicator 380 may be designed or configured to be positioned relative to, in proximity to or on a patient's face or head and to generate a magnetic field focused on nerves responsible for facial neuralgias, e.g., the trigeminal nerve, to treat facial neuralgia. Optionally, a sensor may be positioned along a facial nerve to ensure adequate therapy and to provide feedback, e.g., to a logic controller, regarding nerve conduction or body stimulation.

In certain variations, an applicator may be designed to ergonomically target common nerves responsible for common neuralgias in order to treat such neuralgias. In other variations, an applicator may be used for treating neuralgias virtually anywhere on a patient's body, including in deep nerves due to the ability of magnetic fields generated by the applicator to penetrate painlessly. In certain variations, an applicator may be designed to generate a magnetic field focused on a target nerve to treat central or peripheral neuralgias.

FIG. 38 shows a depression applicator 386 which is designed or configured to be positioned relative to, in proximity to or over a frontal cortex. The applicator 386 may be ergonomic or contoured to a head to be positioned relative to a head to stimulate the frontal cortex. The applicator 386 may generate an electromagnetic or magnetic field focused on the frontal cortex to treat depression. A sensor may be positioned in the offshoots of the motor cortex. The sensor may provide feedback to ensure appropriate placement of the applicator 386 or coil. In one variation, the applicator 386 may include a therapeutic coil and a targeting coil (e.g., a small non-treatment coil), which may be positioned a certain distance behind the therapeutic coil, e.g., about 5 cm behind the therapeutic coil. When firing of the targeting coil is sensed by the sensor (or user-feedback), the therapeutic coil may be positioned in the correct or optimal position over the frontal cortex for depressive therapy.

FIG. 39 shows a migraine applicator 390 which is designed or configured to be positioned relative to, in proximity to or over an occipital nerve. The applicator 390 may be ergonomic or contoured to a face or head to be positioned relative to a face or head to stimulate the occipital nerve. The applicator 390 may generate an electromagnetic or magnetic field focused on the occipital nerve to halt, prevent or treat migraines. The applicator 390 may have an ergonomic design to ensure appropriate placement over the occipital nerve. In one variation, the applicator 390 may be a single (or few) pulse device. The applicator 390 may be in a portable format. The applicator 390 may also be without any significant cooling features. Optionally, the applicator 390 may have cooling features. In another variation, an applicator may be a multiple pulse, higher frequency device. Such an applicator may include cooling features, where cooling is provided by utilizing liquids or airflow, such as rapid airflow to cool the coils or applicator.

FIG. 40 shows a variation of an applicator 396 in the form of a stimulator coil platform which may be ergonomic and contoured to a knee. The applicator 396 is configured to be positioned relative to or in proximity to a knee or the applicator 396 is configured such that a knee may be positioned relative to or in proximity to the applicator 396. The applicator 396 may be configured to generate an electromagnetic or magnetic field focused on the popliteal nerve for peripheral nerve stimulation to treat various conditions, e.g., overactive bladder, neuropathic pain or restless legs. In one variation, a stimulator coil may target an area behind a patient's knee or the popliteal fossa, and the knee may be rested on a stimulator coil platform applicator in any position.

In certain variations, an applicator may include one or two (bilateral) magnetic field generating coils, which may be positioned around the knee when the patient is in a sitting, standing or prostrate position. In certain variations, a pulse generator or logic controller 397 may send energy through one or more coils to create an electromagnetic or magnetic field. The applicator or coils may generate stimulator or non-stimulator fields. Sensor or user feedback may provide feedback to logic controller to optimize therapy, e.g., with the stimulator fields. An applicator may be utilized for generating magnetic fields focused on an area of a patient's body, e.g., the knee, to treat various orthopedic indications, e.g., knee pain or osteoarthritis. An applicator may be utilized for generating magnetic fields focused on a area of a patient's body to treat various non-orthopedic indications, via, e.g., peripheral nerve stimulation.

FIGS. 30A-30B, show a variation of an applicator 400 which may be utilized for popliteal nerve stimulation and/or treatment of the knee. The applicator may be designed or configured to generate an electromagnetic or magnetic field focused on the popliteal nerve for popliteal nerve stimulation or on the knee for treating osteoarthritis. The applicator is configured to be positioned relative to or in proximity to a knee or the applicator is configured such that a knee may be positioned relative to or in proximity to the applicator. A leg may rest on the applicator coil or be positioned above it. Optionally, as shown in FIG. 30B, a foot rest 104 may be provided for holding up a foot.

FIG. 41 shows a system including a variation of an ergonomic back applicator 410 held on a patient's body by an ergonomic positioning element 411 in the form of a shoulder harness. A sensor 412, and a logic controller 414 are also provided. The applicator 410 may include various positioning elements 411, e.g., a shoulder harness, an upper torso garment, or an ergonomic back-countered plate. The applicator 410 may be stimulator or non-stimulator. In another variation, an applicator may be rested on a seat or chair such that a stimulator coil reliably overlies the area of the patient's body requiring stimulation. In certain variations, one or more coils may be fixed on the applicator (requiring prior targeting by a healthcare provider or patient) or one or more coils may move freely within or along the applicator and may be locked into position when the desired or optimal position is located. Coils may also move automatically in order to optimize targeting of the coil based on sensor or user feedback. The system may be incorporated into a single unit or, as illustrated, have at least two components including a separate logic controller.

For any of the applicators described herein, such applicators may include one or more of the following features. The applicators may be ergonomic or contoured to the specific region of the body or anatomy to which the applicator will be delivering stimulation. The applicators may be configured or designed to be positioned relative to, on, around, or in proximity to a specific region of the body or the applicators may be configured or designed such that the targeted region of the body may be positioned relative to, on, around or in proximity to the applicator. The applicators may be openable or adjustable to allow for insertion or entrance of the targeted body part or anatomy into the applicator or to allow for placement of the applicator onto or around the targeted body part or anatomy. The applicators may be flexible or ergonomic to accommodate nearly any type of body habitus. In certain variations, a solenoid-type coil may be incorporated into an applicator for delivering PEMF stimulation directly to the targeted areas or regions of a body. In certain variations, any of the applicators described herein may approximate the respective targeted body area or anatomy or the applicators may be designed such that the body region or targeted anatomy may approximate the applicator.

In certain variations, any of the applicators or systems described herein may be used to provide electromagnetic or magnetic induction therapy with or without a sensor.

In certain variations, electromagnetic stimulating devices or applicators for providing stimulation to tissues of the human body, including nerves, muscles (including superficial and deep muscles), and/or other body tissues for the treatment of various conditions, including, e.g., chronic and acute pain, are provided.

The devices may utilize an inductive coil encased within an ergonomic, body-contoured applicator to target specific regions of the body. The coils may be designed to target peripheral nerves throughout the body that have been implicated or involved in pain syndromes.

The various designs and configuration of the devices described herein allow for easier application, more consistent therapy and home use while targeting anatomic regions with therapeutic pulsed electromagnetic fields. The fields may also be delivered or applied in an intermittent manner to allow for convenience and ease of use while providing a durable benefit. With intermittent external stimulation by pulsed electromagnetic or magnetic fields, a nerve or other tissues may be stimulated in manner that provides a continued and lasting effect on nerve, muscle or tissue function, without habituation.

The electromagnetic or magnetic induction stimulation devices described herein substantially improve the state of the art electromagnetic stimulation technology and may incorporate the delivery of PEMF therapy into a user friendly, body contoured applicator. In certain variations, a delivery system for PEMF therapy may include elements such as, e.g., (1) an ergonomic, body contoured applicator which provides for repetitive application and consistent therapy onto the same body area. The applicator may be coded with clear markings to facilitate repetitive and consistent therapy onto the same body area; (2) the use of a sensor to provide feedback that stimulation is occurring effectively; and/or (3) the use of intermittent stimulation to effectively treat various conditions, e.g., chronic pain, without habituation. These elements individually or the various combinations of these elements have provided for an easy to use, ergonomically designed system that has applications within a host of clinical and home ease of use health applications.

In certain variations, an electromagnetic or magnetic induction stimulation device able to provide stimulation to tissues of the human body, including nerves, muscles (including superficial and deep muscles), and/or other body tissues without significant discomfort to the patient is provided. Conductive stimulating coils may be encased in an ergonomic, body-contoured applicator that is coded with clear markings to provide for repetitive application and consistent therapy onto the same body area. The design of the applicator allows for ease of use and also for the targeting of anatomic regions to be exposed to the impulses of the PEMFs. The electromagnetic stimulating device may provide PEMF in a manner that is patient user friendly and the device may be portable. The device may be utilized in a hospital, an outpatient clinic, a therapist's office, or at a patient's home.

In certain variations, an electromagnetic or magnetic induction stimulation device may stimulate regions of the body to treat conditions requiring both maximal stimulation (i.e., sufficient to cause contraction of muscle fibers and firing of nerves) as well as submaximal stimulation (which will be sufficient to provide therapy but not to cause contraction of muscle fibers).

The electromagnetic or magnetic induction or stimulating devices described herein may be utilized for various indications. The indications may be divided into maximal and submaximal categories, in which the former requires significantly higher levels of inducting current than the latter. The maximal applications of the device include, but are not limited to: Non-invasive stimulation (intermittent or continuous) of the peripheral nervous system for treating chronic pain; stimulation of a nerve for the up- or down-regulation of hormones or cellular proliferation; treatment and/or prevention of atrophy, which would be therapeutic during recovery after an individual sustains a fracture, experiences paralysis of a limb or other body part, or undergoes surgery, such as ACL repair in the knee; treatment of neurogenic or overactive bladder and bowel; and stimulation of the central nervous system to alter neural pathways or up/down-regulate the aforementioned factors.

Additional applications of the devices include but are not limited to: treatment of neuropathic pain (e.g., phantom pain in limbs or other neurologic pain) or orthopedic pain (back and neck pain or skeletal related pain); treatment of overactive bladder and bowel; and treatment of arthritis and/or orthopedic conditions.

In certain variations, a device is provided for delivering PEMF stimulation to selective anatomic regions of the body, utilizing an ergonomic applicator designed to facilitate accurate and targeted delivery of therapy. The applicator may be coded with clear or solid markings to provide for repetitive application and consistent therapy onto the same body area of the body. This design may facilitate the placement of the device for the stimulation of key nerves, muscles, and/or body tissues.

In certain variations, a device is provided which may be utilized to electromagnetically stimulate selective nerves, muscles, and/or body tissues, where the device is user friendly and capable of being used even by an unskilled patient in a home healthcare setting.

In certain variations, a device is provided to electromagnetically stimulate selective nerves, muscles, and body tissues to provide consistent therapy, with an ergonomic applicator targeting key nerves and eliminating the requirement for a highly trained operator to manipulate the device.

In certain variations, an electromagnetic or magnetic induction system or device may be configured or designed to provide intermittently applied pulsed magnetic fields in the treatment of chronic conditions, such as pain. For example, a device as described herein may provide shorter, intermittent stimulation to treat chronic pain or other chronic conditions. The delivery of pulsed magnetic fields may have a continued and lasting effect on nerve function in treating conditions, such as, overactive bladder as well as other chronic neurological and orthopedic conditions such as neuropathic pain, restless legs and orthopedic pain (e.g., spinal pain, back pain, etc.)

In certain variations, intermittent pulsed magnetic fields may be utilized for the treatment of chronic and acute non-orthopedic conditions such as neuropathic pain, phantom pain and chronic neuralgias, as well chronic and acute orthopedic conditions, such as back pain and neck pain. The therapeutic magnetic fields may be applied frequently (e.g., several times a day) or less frequently (e.g., once a week or once a month) depending on the durability of the effect for the individual patient. Treatment involving the use of magnetic fields does not require surgery or needles to stimulate a nerve. Also, the deliver of intermittent pulsed magnetic fields prevents the nerve from becoming habituated to the stimulator signal by ensuring that there are periods during which the nerve is not subjected to the stimulator signal. Accordingly, the electromagnetic or magnetic induction systems or devices described herein may provide unparalleled ease of use, non-invasiveness, reliability of therapy based on sensor feedback and/or ergonomic targeting, and/or a lack of habituation due to intermittent stimulation provided by certain systems and devices.

In certain variations, the electromagnetic or magnetic induction systems or devices described herein may incorporate an air-cooled coil wherein the air coolant, e.g., liquid or air, is drawn through and/or in between the turns of the inductive coil, in direct contact with conductive surfaces of the coil. Drawing air or other fluid through the coil prevents the coil from heating up to the degree that could damage the coil and the electronics of a device, or expose the patient to excessive temperatures.

In certain variations, the systems and devices described therein may be utilized to stimulate nerves for a variety of conditions, including, e.g., atrophy prevention, nerve repair/regeneration, neuromodulation, chronic pain, up or down regulation of hormones, restless legs, phantom pain, etc. The systems and devices may also be used to stimulate muscles and/or other body tissues to accelerate tissue healing, regeneration and/or growth.

In certain variations, the electromagnetic or magnetic induction systems or devices described herein and other implantable or extracorporeal devices may allow for the automatic adjusting of nerve stimulation based on feedback.

In one variation, an extracorporeal or implantable device, e.g., any of the electromagnetic or magnetic induction devices described herein, a pacemaker, defibrillator, or nerve stimulator, may include a feature that allows for automatic adjustment of nerve stimulation based on feedback provided by a sensor or user. This feature may minimize pain and power usage while ensuring optimal therapy delivery. A device may include a stimulator and a sensing component. The stimulator may be automatically adjustable based on feedback from the sensor up to a maximal (safe) threshold. Each therapy may start with lower powered pulses, followed by increasing power pulses until the sensor detects stimulation. The algorithm allows for the minimal amount of power to be used and allows for automatic adjustment of power settings as conditions change. 102411 In one variation, an implantable device may include a sensor, such that the device can stimulate tissue or nerves and sense stimulation at the same site. For example, the sensor may provide feedback to the implantable device regarding nerve conduction at the site of stimulation. As fibroses develops around an implant, at the site of stimulation, the feedback will indicate whether a target nerve is no longer being effectively stimulated due to the fibroses, which will cause the power or level of stimulation to increase or decrease, as is necessary, to effectively stimulate the target site and overcome any obstruction due to fibroses. As fibroses occurs around an implant, a patient need not report back to a physician or other operator for adjustment of the stimulator power of the device. The device will automatically adjust the stimulator power or level based on sensing stimulation of the target nerve or tissue. This eliminate the guesswork involved in the user in monitoring their therapy one day at a time on their own, as they notice the effect of the therapy wear off. This also eliminates the risk of the user being exposed to unnecessarily high power levels that might otherwise by set in order to minimize frequent return visits to a physician or operator for adjustments.

Figure 42A:
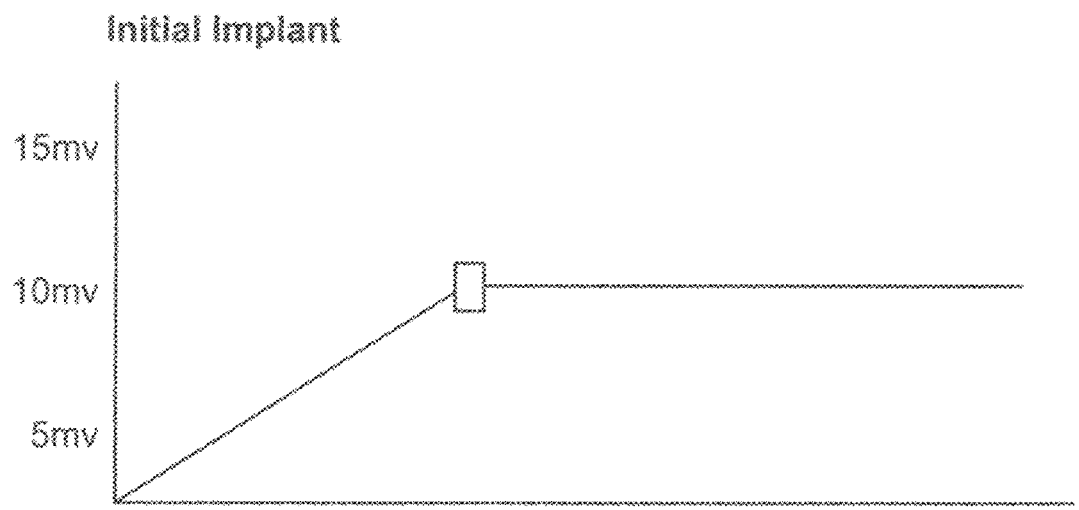
FIGS. 42A and 42B show an example of how the amount of stimulator power required to achieve a desired stimulus may be automatically adjusted as a result of fibroses.
Figure 42B:
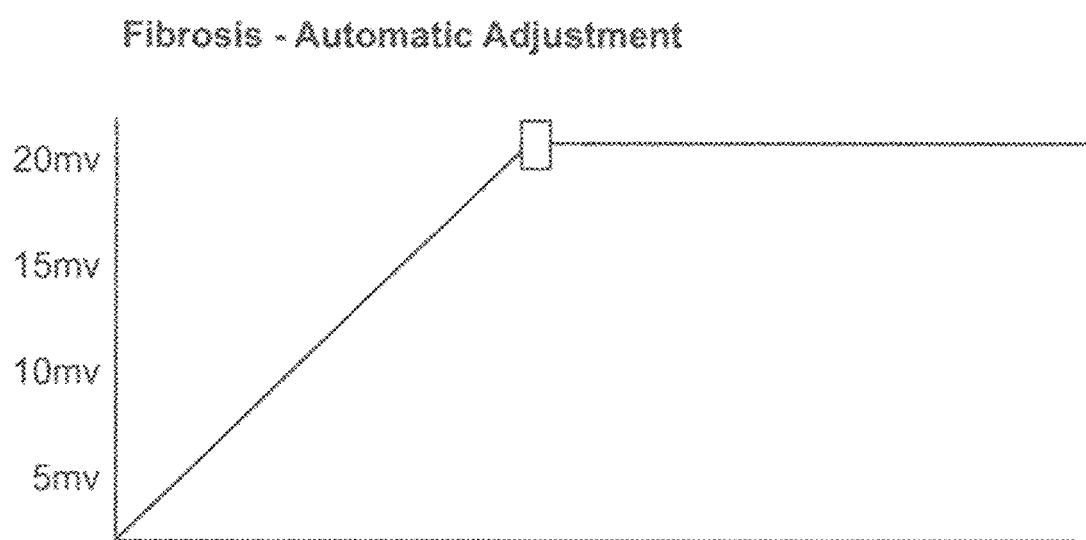

FIGS. 42A and 42 show an example of how the amount of stimulator power required to achieve a desired stimulus may be automatically adjusted as a result of fibroses, according to the above described feature. According to FIG. 42A, after the initial implant of the device, the level of stimulator power is increased until stimulation of the target nerve or tissue is sensed (indicated by square box at, e.g., about 10 mV). An effective stimulator therapy may then be delivered. According to FIG. 42B, after fibroses sets in, in order to maintain the desired level of stimulation to provide an effective stimulator therapy, the level of stimulator power is increased until stimulation of the target nerve or tissue is sensed (indicated by square box, e.g., at 20 mV). According to the example in FIG. 42B, the presence of fibroses required an increase in the stimulator power level to deliver an effective stimulator therapy.

The automatic adjustment feature based on sensor feedback may be utilized in any stimulator or non-stimulator implant or extracorporeal device, where the device incorporates a sensor capable of detecting the desired stimulus and a feedback loop capable of automatically adjusting parameters (e.g., power, frequency, etc.) to ensure appropriate stimulation.

In certain variations, the electromagnetic or magnetic induction systems or devices described herein and other implantable or extracorporeal devices may include a feature that allows for automatic targeting of coils.

A device may include multiple inductive coils or one or more movable inductive coils. The device may also include a sensor based feedback algorithm. In one variation, the device includes a targeting or movable coil which may be positioned over or in proximity to a patient's body at a site that elicits a response that can be sensed automatically or detected by a user. Once this response is detected, the coil may either move to its stimulation position, or in the event that a small targeting coil is used, the therapeutic coil may already overlie the treatment area. Once the response is detected, the therapy may automatically begin.

In one example, relating to the treatment of depression, the motor cortex is stimulated until the thumb is seen to move. The coil may then be advanced, e.g., about 5 cm. to about 5 inches, forward to a position over the frontal cortex. This feature eliminates the guesswork that may otherwise be involved in moving or positioning a coil, and automates therapy based on user feedback or EMG sensor or other sensor feedback, e.g., over a thumb.

Figure 43A:
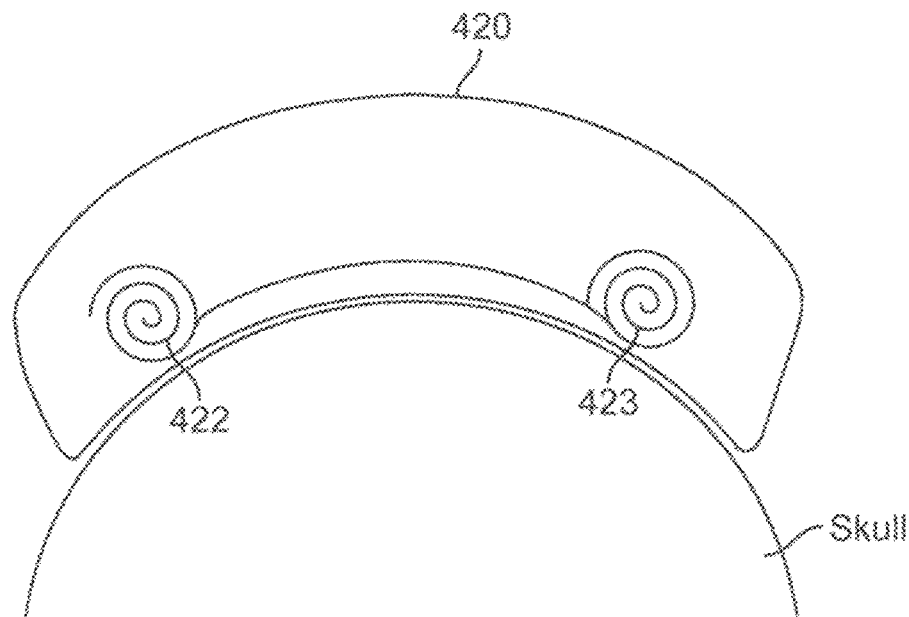
FIGS. 43A and 43B show variations of a coil device positioned on a skull.

FIG. 43A shows an example of a device 420 positioned on a skull. The device includes a treatment coil 422 and a targeting coil 423. The treatment coil 422 may be positioned by EMG detection with targeting coil 423 stimulation, where the targeting coil may not move.

Figure 43B:
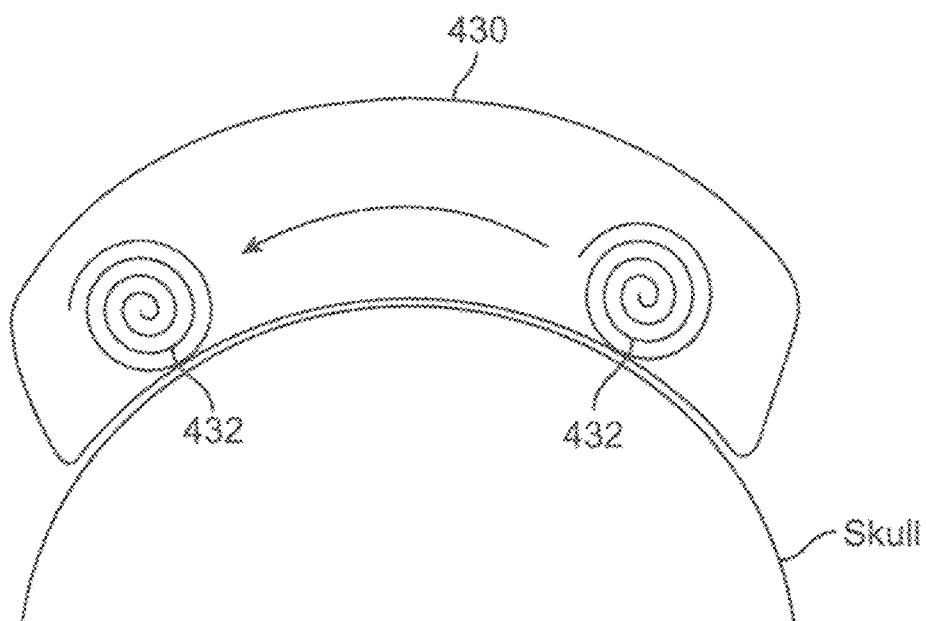

In another variation shown in FIG. 43B, an ergonomic fixture or applicator 430 (e.g., a helmet) may be worn and a coil 432 positioned on the applicator may slide or move from its targeting position to its therapeutic position automatically or by user intervention.

The feature that allows for automatic targeting of coils may be utilized in any device designed to stimulate nerve, body or other tissues with stimulator or sub-stimulator fields in which the device may be targeted based on a detectable signal or response.

Other conditions that may be treated utilizing the various electromagnetic or magnetic induction stimulation systems and methods described herein include but are not limited to:

pelvic pain, interstitial cystitis, fibromyalgia, chronic fatigue and preterm labor, pain syndromes, Irritable Bowel Syndrome, Vulvodynia, Herpetiuc neuralgia, trigeminal neuralgia and Myofascial pain.

EXAMPLES

The following Examples are provided for illustration, not limitation. One with skill in the art would be able to use these examples as guidelines for making and using comparable devices.

In each example, intermittent therapy should be applied and symptoms/scores tracked for a minimum of 6 weeks in order to determine the full extent of the therapies effect.

Example 1

Empirical Testing of Efficacy in the Treatment of Neuropathic Pain: The optimal stimulus intensity for neuropathic pain treatment; the optimal application parameters, i.e. frequency of stimulation, duration of treatment, location of stimulator coils in each disposable array of coils; and the optimal coil diameter/placement within the strays can be determined using the following experimental protocol: Before, during and after treatment, patients will report scores of neuropathic pain after weekly stimulation over a minimum of 6 weeks.

Example 2

Empirical Testing of Efficacy in the Treatment of Neuromuscular Pain: The efficacy of neuromuscular pain treatment can be tested by monitoring patient reported pain scores. A standardized scale may be utilized and, when feasible, local biopsy and blood tests can be useful in determining the impact of the therapeutic fields on circulating factors and local mediators. The optimal pulse amplitude, duration, site of stimulation will be assessed based on reported pain scores and diagnostic tests.

Example 3

Empirical Testing of Efficacy in the Treatment of Orthopedic conditions (i.e., Arthritis, Back pain and neck pain): The efficacy of arthritis treatment can be tested by monitoring patient reported functionality scores. A standardized subjective functionality scale may be utilized and, when feasible, local biopsy may be useful in determining the impact of the therapeutic fields on the cartilage and arthritic regions treated. As cartilage destruction is a well-studied side-effect of arthritis, reduction of this degeneration will be a valuable marker for efficacy of therapeutic treatments. The optimal pulse amplitude, duration, site of stimulation will be assessed based on reported functionality scores and diagnostic tests. Pain scores may also be measured to determine the device's impact on orthopedic conditions such as back pain, neck pain, etc. A standardized pain scale may be used before and after treatment to determine potential benefit.

It is also contemplated that any of the energy emitting systems or devices described herein can be used with or without a sensor for detecting conduction of a stimulated nerve or muscle of tissue stimulation resulting from the electromagnetic or magnetic field generated by the conductive coil and delivered to a patient or an electrical stimulus delivered to a patient. Also, in any of the above variations, a controller may optionally be connected, coupled, integral to or otherwise in communication with the conductive coils and/or the sensor. Optionally, the sensor may be connected, coupled, integral to or otherwise in communication with the conductive coil.

In certain variations, transdermal electrical stimulation therapy may be provided to a patient or subject. One or more stimulator electrodes may be positioned over a glabrous skin surface overlying a target nerve of the patient. Electrical stimulation or an electrical stimulus may then be delivered via the stimulator electrode through or across the glabrous skin surface to the target nerve in the patient, to stimulate the target nerve. The electrical stimulation may be delivered at a level and in a manner sufficient to generate motor and/or sensory nerve conduction. For example, the electrical stimulation may be delivered at a frequency of about 5 Hz to about 80 Hz or about 20 HZ or 30 Hz to about 60 Hz or greater than 30 Hz, while remaining safe and tolerable to the patient. The stimulation may be delivered in a non-invasive manner.

The stimulator electrode may be positioned over or on various regions of the body. In certain variations, the stimulator electrode may be positioned over a palm or plantar skin surface. For example, the stimulator electrode may be positioned over a glabrous skin surface overlying a plantar nerve of the foot, where the electrical stimulation may stimulate the plantar nerve. Stimulation of the plantar nerve may result in stimulation of the tibial nerve to treat various conditions, such as urinary incontinence or overactive bladder.

Various types of electrodes may be utilized as a stimulator electrode, e.g., a surface electrode, microneedle electrode, a TENS (transcutaneous electrical nerve stimulation) patch or other electrode that may be positioned over or on the skin surface. Optionally, a conductive substance may be injected or implanted near the target nerve to improve electrical conductivity to the target nerve from the stimulatory electrode. Electrical stimulation may be delivered intermittently or on a chronic basis and may include one or more electrical signals designed to be constructive and/or destructive in order to improve tissue penetration and/or signal tolerance.

In certain variations, nerve stimulation resulting from the electrical stimulation therapy may be detected via at least one sensor positioned on or near the subject. The sensor may provide a signal indicative of the detected electrical stimulation thereby providing feedback about the efficacy of the applied electrical stimulation therapy such that the therapy may be adjusted or optimized. The feedback loop may be queried such that the electrical stimulation therapy may be adjusted to ensure that the minimum amount of energy is being applied to stimulate the target nerve while reducing the risk of burns or intolerance. Optionally, the feedback loop may be queried such that the positioning of the stimulator electrode may be adjusted to optimize the electrical stimulation therapy. Various sensors may be utilized, including but not limited to a surface electrode, a microneedle electrode, or motion sensor. In certain variations, the sensor may detect conduction of motor and/or sensory nerves. For example, a sensor may detect afferent or efferent nerve stimulation of the target nerve or other nerve or related nerve.

In certain variations, a ground electrode may be utilized. For example, the ground electrode may be positioned on the subject to facilitate penetration of an electrical current from the stimulatory electrode through the glabrous surface to stimulate the target nerve.

In certain variations, a stimulator electrode may be positioned over or attached to a glabrous skin surface with an adhesive or other form of attachment or fastener. In other variations, a stimulator electrode may be positioned over or held in contact with a glabrous skin surface with an ergonomic applicator.

Various applicators for positioning electrodes over various regions of the body to deliver electrical stimulation, e.g., transdermal electrical stimulation, may be utilized. For example, an applicator may be in the form of an insole configured to be positioned against, over, or in contact with the plantar surface or a glabrous surface of the foot such that an electrode positioned on the insole may deliver electrical stimulation through or across the glabrous skin surface, to a target nerve or other tissue within the foot. The insole may be configured to be positioned in an orthotic or a shoe such that electrical stimulation may be delivered to the subject while the subject is walking. In other variations, an applicator may be a foot plate or foot rest or cradle on which a foot or other portion of the leg or body may be positioned to receive electrical stimulation through or across a glabrous skin surface, from the plate, rest or cradle or from electrodes of the plate, rest or cradle.

In another variation, an applicator may be a glove, brace or other hand wrap which is configured to be positioned against, in contact with, or over the palmar surface or a glabrous surface of a hand. An electrode of the glove, brace or wrap may deliver electrical stimulation through or across the glabrous skin surface to a target nerve or tissue within the hand.

Various applicators or ergonomic applicators may be utilized to provide transdermal electrical stimulation therapy to a subject. In certain variations, an applicator may include one or more stimulator electrodes and one or more electrical pulse generators or controllers. The electrical pulse generator may be coupled to the stimulator electrode. The electrical pulse generator may be incorporated into the applicator. Optionally, the electrical pulse generator may be separate from the applicator or located remotely from the applicator or stimulator electrode. An applicator may include one or more sensor electrodes configured to detect nerve stimulation and/or provide feedback about the efficacy of the applied electrical stimulation therapy. Such feedback may allow the therapy to be adjusted, modulated and/or optimized. A sensor may detect motor and/or sensory nerve stimulation. For example, a sensor may detect afferent or efferent nerve stimulation. In certain variations, the positioning of the stimulator electrode may be adjusted based on feedback from the sensor in order to optimize the electrical stimulation therapy.

The applicator may also include one or more ground or ground electrodes. The ground electrode may be a component of the applicator or may be attached to the subject separately via a strap or other attachment. The ground electrode may be positioned on the subject at a location that facilitates penetration of an electrical current through a glabrous surface to stimulate the target nerve, e.g., on the opposite surface of a body portion relative to the stimulator electrode.

As stated supra, an applicator may be designed for various portions of the body. An ergonomic applicator may be in the form of an insole which can be positioned against or over the plantar surface or a glabrous surface of the foot such that an electrode of the insole may deliver electrical stimulation through or across a glabrous surface to a target nerve within the foot. The insole may be positioned in an orthotic or a shoe. An applicator may also be in the form of a foot plate, cradle or foot rest. In other variations, the applicator may be designed to stimulate a portion of a hand or upper extremity. For example, an ergonomic applicator in the form of a glove or brace may be configured to be positioned against or over the palmar surface of a hand such that the electrode of the glove or brace may deliver electrical stimulation across a glabrous surface to a target nerve within the hand.

Any of the various applicators or ergonomic applicators described herein may be designed or configured to position or locate one or more stimulator electrodes over or on a glabrous skin surface of a patient to deliver transdermal electrical stimulation through or across the glabrous skin surface to an underlying target nerve or other tissue to stimulate the target nerve or tissue. In certain variations, an electrical stimulation or stimulus may be delivered at various frequencies, e.g., at a frequency of about 5 Hz to about 60 Hz, or greater than 30 Hz, while remaining safe and tolerable to the subject.

In other variations, one or more stimulatory electrodes may be otherwise attached to a skin surface, e.g., as a wired or wireless patch, adhesive or microneedle electrode in the absence of an ergonomic applicator, to deliver electrical stimulation across or through a glabrous skin surface to stimulate an underlying target nerve or tissue. Such electrodes may be used in combination with one or more ground or sensor electrodes. Such stimulatory electrodes may deliver electrical stimulation or an electrical stimulus at various frequencies, e.g., at a frequency of about 5 Hz to about 60 Hz, or greater than 30 Hz, while remaining safe and tolerable to the subject.

In certain variations an applicator may include two or more stimulator electrodes or two more stimulator electrodes may be utilized without an applicator.

In certain variations, methods, systems and/or applicators for providing an energy based stimulation therapy to a subject are provided. An energy emitting device may be positioned in proximity to a glabrous surface overlying a target tissue. Energy may be delivered from the energy emitting device through or across the glabrous skin surface to the target tissue to stimulate the target tissue, such as a target nerve. Various energy sources or forms of energy may be delivered by the energy emitting device, including but not limited to, an electric current, an electromagnetic or magnetic field or electromagnetic or magnetic induction stimulation, ultrasound, or RF fields. Energy may be delivered at various frequencies. For example, the energy may be delivered at a frequency of about 5 Hz to about 60 Hz, or greater than 30 Hz, while remaining safe and tolerable to the subject.

The energy based stimulation therapy may be utilized to treat various conditions, including but not limited to, overactive bladder, urinary incontinence, fecal incontinence, chronic pain, depression, migraine, epilepsy, obesity, restless leg syndrome, or foot drop. Energy may be delivered through a glabrous skin surface to provide neuromodulation to stimulate other tissue. Tissues that may be stimulated include but are not limited a central nerve, peripheral nerve, muscle, skin, or vasculature. Optionally, conductive substance may be implanted or injected near a target tissue to improve conductivity to the target tissue.

In one variation, a method for treating urinary incontinence or overactive bladder in a subject may include one or more of the following steps, a stimulator electrode, (e.g., in an applicator or as an adhesive or attachment electrode as described above) may be positioned over a glabrous skin surface overlying a plantar nerve or other nerve in the foot. An electrical stimulation may then be delivered through or across the glabrous skin surface to the plantar nerve to stimulate the plantar nerve which results in stimulation of the tibial nerve to treat urinary incontinence or overactive bladder, e.g., via stimulation of the sacral plexus or pudendal nerve.

In other variations, any of the various electrical stimulation methods and electrical stimulator applicators or electrodes may be utilized to treat any of the conditions described herein.

In certain variations, methods, systems and/or applicators for providing an energy based stimulation therapy to a subject are provided. An energy emitting device may be positioned in proximity to or over a skin surface overlying a target nerve or tissue. The energy emitting device may include any of the devices, systems or applicators described herein and/or illustrated in any of the various FIGS. 1-49, e.g., an electrode or applicator for delivering electrical stimulation or an applicator for providing electromagnetic or magnetic stimulation or induction therapy. Energy may be delivered at a frequency of about 1 Hz to about 30 Hz through or across a skin surface (e.g., a glabrous skin surface or any other skin surface or non-glabrous skin surface) to the a target nerve to generate motor and/or sensory nerve conduction while remaining safe and tolerable to the subject. In certain variations, energy may be delivered at a frequency of less than 10 Hz to generate motor and/or sensory nerve conduction.

Energy delivered transdermally, through, or across a patient's skin at a frequency from about 1 Hz to about 30 Hz, or at a frequency of less than 10 Hz has unexpectedly been found to stimulate or generate motor and/or sensory conduction in a target nerve. For example, energy delivered transdermally, through, or across a patients skin at about 1 Hz to about 30 Hz, or at less than 10 Hz has unexpectedly been found to stimulate or generate motor and/or sensory nerve conduction of a tibial nerve, where such level of stimulation may be sufficient to treat a patient suffering from urinary incontinence, overactive bladder, fecal incontinence or other conditions. The energy may be delivered through or across a glabrous skin surface or non-glabrous skin surface or any other skin surface (e.g., any skin surface overlying a tibial nerve).

Various energy sources or forms of energy may be delivered by the energy emitting device, including but not limited to, an electric current, an electromagnetic or magnetic field, ultrasound, or RF fields. The energy based stimulation therapy may be utilized to treat various conditions, including but not limited to, overactive bladder, urinary incontinence, fecal incontinence, chronic pain, depression, migraine, epilepsy, obesity, restless leg syndrome, or foot drop. Energy may be delivered through a glabrous skin surface or any other skin surface to provide neuromodulation to stimulate other tissue. Tissues that may be stimulated include but are not limited a central nerve, peripheral nerve, muscle, skin, or vasculature. Optionally, conductive substance may implanted or injected near a target tissue to improve conductivity to the target tissue.

FIG. 44 shows the anatomy of a foot, providing a view of the underside, sole or plantar or glabrous surface of the foot. The medial and lateral plantar nerves innervate the sole of the foot and arise from the posterior branch of the tibial nerve. Various stimulator sites for stimulating the plantar nerves or branches thereof may be located near, in proximity to or along the plantar nerves. FIG. 44 shows one example of a stimulator site 510 located over the glabrous surface of the foot, over the plantar nerves. A second exemplary stimulator site 512 is also depicted at a location over the glabrous surface of the foot, over the plantar nerves, distal to the first stimulator site 510. An energy based stimulus, e.g., an electrical or electromagnetic stimulus, may be delivered transdermally, through or across a glabrous surface of the foot at one or more of the stimulator sites to stimulate the plantar nerves or other nerves in the foot.

In certain variations, electrical stimulation may be delivered transdermally, through or across a glabrous surface on a subject, e.g., through or across a glabrous surface of the foot or hand. The electrical stimulation may be sufficient to generate conduction of motor and/or sensory nerves. An electrical stimulation may be delivered by placing one or more electrodes anywhere over or on a glabrous skin surface overlying one or more target nerves or other target tissue. Stimulator and/or ground electrodes may be utilized. Exemplary electrodes may include but are not limited to surface electrodes, dry electrodes, gel electrodes, microneedle electrodes or any other suitable electrode for delivering an electrical stimulus. An electrode may be adhered or otherwise attached to a glabrous surface. Optionally, an electrode may be held or positioned in contact with, in proximity to, or over a glabrous surface with a wearable garment, cradle, applicator or body portion rest or support (as described in further detail herein).

In one variation, electrical stimulation may be delivered to one or more of the stimulator sites or similar sites depicted in FIG. 44, by positioning one or more electrodes over a glabrous surface of the foot, over an underlying plantar nerve or other target nerve. A ground electrode (not shown) may be positioned anywhere on the foot. For example, the ground electrode may be positioned over a posterior or upper surface of the foot to encourage or facilitate deeper penetration of the electrical current or stimulation, through the glabrous surface of the foot, to a plantar nerve or other target nerve within the foot.

Delivery of electrical stimulation through or across a glabrous surface of the body via an electrode positioned over a glabrous surface, e.g., a glabrous surface on a palmar or plantar surface, unexpectedly allows for the use of a higher frequency and/or higher amplitude electrical pulsation or electrical stimulus to deliver the electrical stimulation than would otherwise be safe and/or tolerable to deliver electrical stimulation through a non-glabrous surface of the body. For example, an electrical stimulus having a frequency of about 5 Hz to about 60 Hz (a range found to be effective for generating motor and/or sensory nerve conduction of the posterior tibial nerve) may be utilized to stimulate a target nerve (to generate motor and/or sensory nerve conduction therein) or tissue through or across a glabrous skin surface (via an electrode positioned over the glabrous skin surface) in a manner that remains safe and tolerable to the patient and avoids burns or injury. Optionally, an electrical stimulus having a frequency of about 5 Hz to about 60 Hz, or greater than 30 Hz, may be utilized.

In contrast, utilizing an electrical stimulus having a frequency of about 5 Hz to about 60 Hz or greater to stimulate a target nerve or tissue through a non-glabrous skin surface (via an electrode positioned over the non-glabrous skin surface) is intolerable and painful, resulting in burns or injury, and thus making such a procedure impractical and not feasible.

For example, delivering electrical stimulation through a non-glabrous surface of the body, for example, by stimulating a site overlying a nerve near the medial malleolus to elicit a motor response of the abductor hallucis longus, generates a painful shock to the patient. While at a single pulse, such as in the use for EMG diagnostics, such electrical stimulation may be tolerable, as the frequency increases, the shocking sensation builds and quickly becomes painful and intolerable.

It is contemplated that other energy sources, for example, an electromagnetic or magnetic stimulus having a frequency of about 5 Hz to about 60 Hz, or greater than 30 Hz, may be utilized to simulate a target nerve or tissue through a glabrous surface in a manner that remains safe and tolerable to the patient.

Various electrodes and/or applicators for applying an electrical or other energy based stimulation to a patient are described herein.

Figure 45:
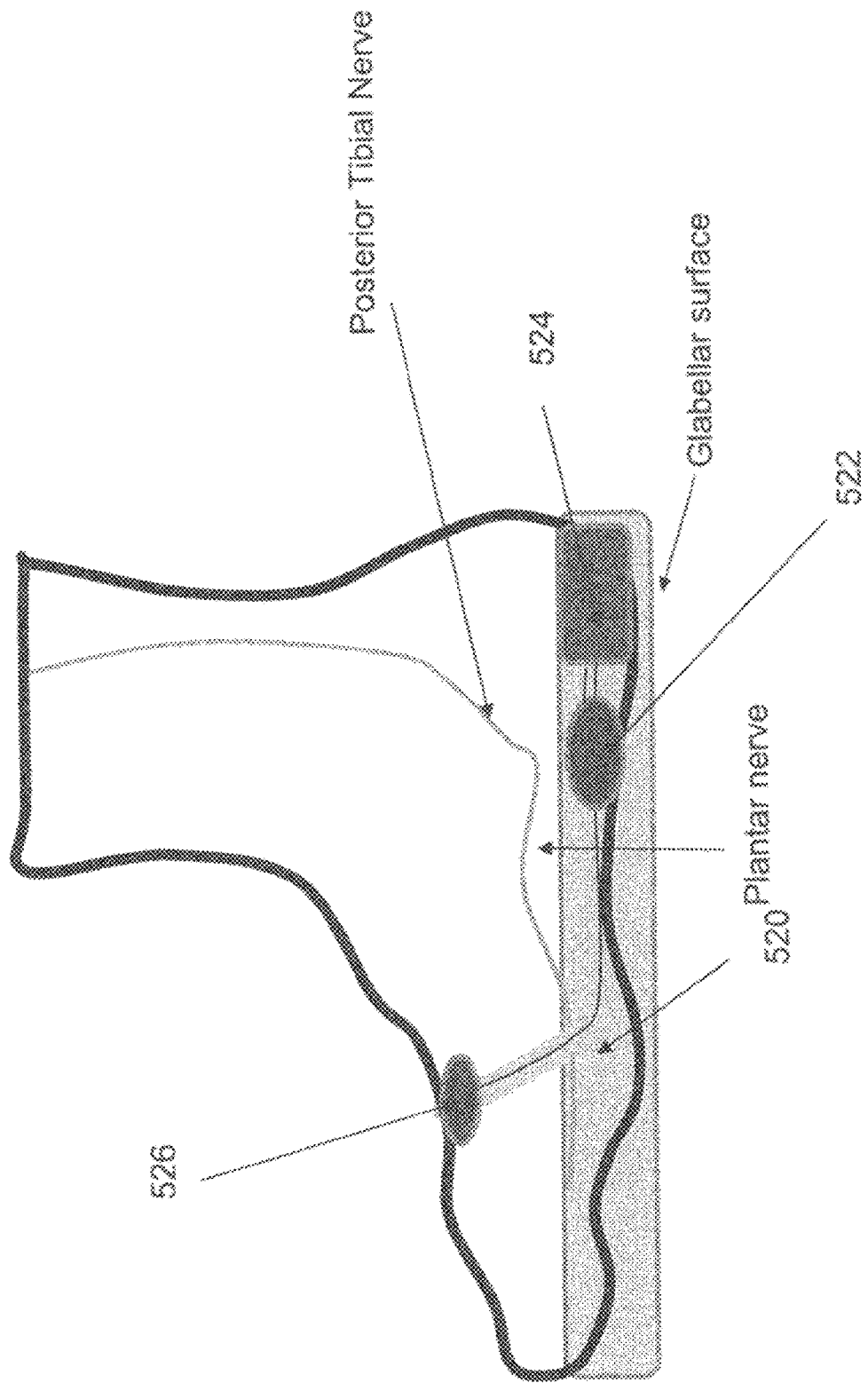
FIG. 45 shows a perspective view of one variation of an insole for delivering electrical stimulation over a glabrous surface of the foot.

FIG. 45 shows one variation of an ergonomic insole or shoe applicator for delivering electrical stimulation over the glabrous surface of a foot. The ergonomic insole 520 may include one or more stimulator electrodes 522 for delivering electrical stimulation to a user. The electrode 522 may be attached to or positioned in the ergonomic insole 520. The ergonomic insole 520 may hold or position the stimulator electrode 522 against, in contact with, or in proximity to a glabrous surface of the foot, to deliver the electrical stimulation through the glabrous surface to an underlying target nerve or tissue. Optionally, the electrodes may be utilized for providing stimulation, sensing and/or grounding. In certain variations, the electrode may be attached to one or more wires or may be wireless and/or coupled to an electrical pulse generator or other generator or controller and/or may not be attached to or positioned in an ergonomic insole. Any of the electrodes described herein may be durable, reusable, and/or disposable.

An electrical pulse generator 524 or other generator or controller may be coupled to the stimulator electrode 522. The electrical pulse generator 524 may be incorporated into or attached to the ergonomic insole 520. A ground electrode 526 or other ground may also be provided. The ground electrode 526 may be attached to a strap or band extending from or attached to the ergonomic insole, an orthotic, shoe, or shoe applicator or elsewhere on the user's body. The ground electrode may be attached to one or more wires or may be wireless and/or may be coupled to the stimulator electrode 522 and/or the pulse generator or controller. The ground electrode 526 may be positioned anywhere on the foot. For example, the ground electrode 526 may be positioned over a posterior or upper surface of the foot to encourage or facilitate deeper penetration of the electrical current or stimulation, through the glabrous surface of the foot, to a plantar nerve or other target nerve within the foot.

In certain variations, the electrical pulse generator or controller may be located distant or remotely from an ergonomic insole and the electrode positioned therein. For example, the electrical pulse generator may attached elsewhere on the body, e.g., attached to a belt, inside a pocket or strapped to the calf or other region of the body. The pulse generator may communicate with or be coupled to the stimulator electrode or other electrodes via a wire or wirelessly.

In certain variations, the ergonomic insole may be custom built into an orthotic, shoe applicator or other support for the foot. For example, the ergonomic insole may be built into an orthotic or shoe applicator providing the user with the freedom to walk around while receiving electrical stimulation therapy.

Figure 48:
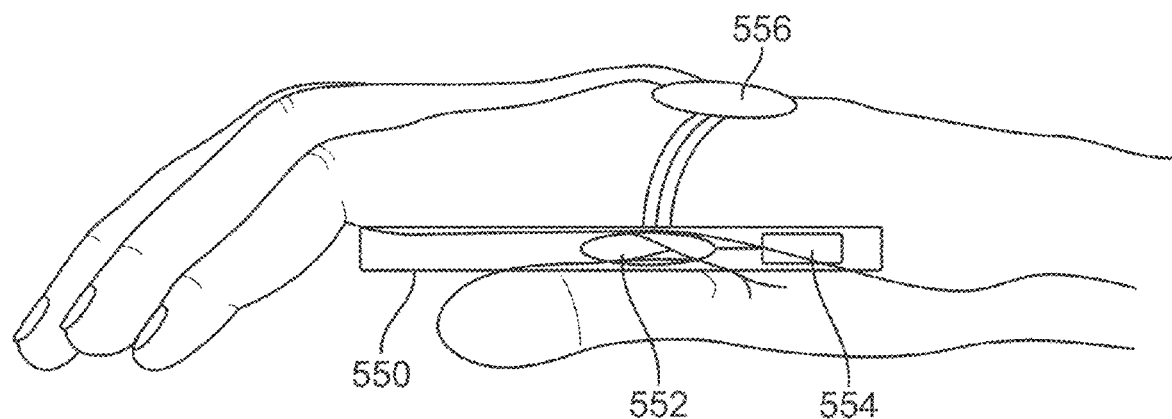
FIG. 48 shows a perspective view of one variation of a hand applicator for delivering electrical stimulation over a glabrous surface of a hand.

Other ergonomic applicators, designed for other regions of the body, may be utilized for delivering electrical stimulation over various regions of the body. For example, FIG. 48 shows a glove, brace or other hand wrap or glove like applicator 550. The applicator 550 may include one or more stimulator electrodes 552, such that the applicator 550 may hold or position an electrode 552 over or in contact with a glabrous surface of the hand or palmar region of the hand to deliver electrical stimulation through or across the glabrous surface, to an underlying target nerve or tissue within the hand. A ground electrode 556 or other ground may be attached to the hand at another location and/or may be attached to a strap of the applicator. The stimulator and/or ground electrodes 552, 556 may be coupled to an electrical pulse generator 554, which may be positioned in the applicator 550 or at various locations on or away from the patient. Optionally, a sensor electrode (not shown) may be attached to the patient to detect nerve or other tissue stimulation and to provide feedback regarding the efficacy of the therapy in order to optimize the therapy. The sensor may be coupled to the electrical pulse generator 554.

In other variations, an applicator may be in the form of a foot or hand plate, cradle or support. For example, a user may rest or position their bare foot on a foot plate to receive electrical stimulation therapy from the plate or from one or more electrodes attached to the plate. In another variation, a user may rest or position the palm of their hand on a hand plate or support to receive electrical stimulation therapy from the plate or from one or more electrodes attached to the plate to provide upper extremity stimulation.

Figure 46:
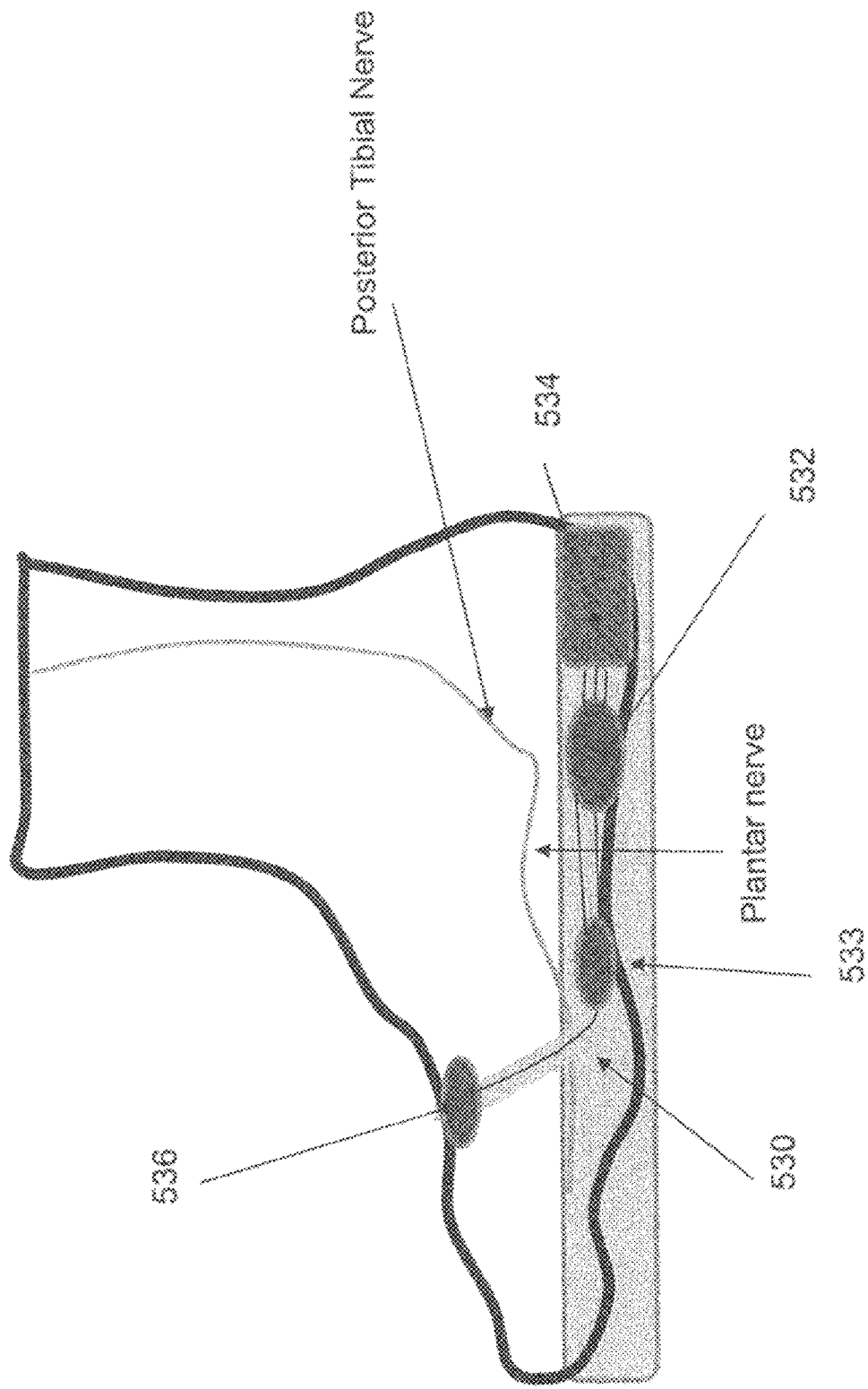
FIG. 46 shows a perspective view of a variation of an insole for delivering electrical stimulation over a glabrous surface of the foot, including a sensor feedback feature.

FIG. 46 shows another variation of an ergonomic insole or shoe applicator for delivering electrical stimulation over the glabrous surface of a foot. The ergonomic insole 530 may include one or more electrodes 532 for delivering electrical stimulation to a user. The electrode 532 may be attached to or positioned in the ergonomic insole 530. The ergonomic insole 20 may hold or position the electrode 532 against, in contact with, or in proximity to or over a glabrous surface or plantar surface of the foot, to deliver the electrical stimulation through the glabrous surface to an underlying target nerve or tissue. In certain variations, the electrode may be attached to one or more wires or may be wireless and/or may be coupled to an electrical pulse generator or other generator or controller and/or may not be attached to or positioned in an ergonomic insole.

An electrical pulse generator 534 or other generator or controller may be coupled to the stimulator electrode 532. The electrical pulse generator 534 may be incorporated into or attached to the ergonomic insole 530. A ground electrode 536 or other ground may also be provided. The ground electrode 536 may be attached to a strap or band extending from or attached to the ergonomic insole, an orthotic, shoe, or shoe applicator or elsewhere on the user's body. The ground electrode may be attached to one or more wires or may be wireless and/or may be coupled to the stimulator electrode 532 and/or the pulse generator or controller. The ground electrode 536 may be positioned anywhere on the foot. For example, the ground electrode 534 may be positioned over a posterior or upper surface of the foot to encourage or facilitate deeper penetration of the electrical current or stimulation, through the glabrous surface of the foot, to a plantar nerve or other target nerve within the foot.

In certain variations, the electrical pulse generator or controller may be located distant or remotely from an ergonomic insole and the electrode positioned therein. For example, the electrical pulse generator may attached elsewhere on the body, e.g., attached to a belt, inside a pocket or strapped to the calf or other region of the body. The pulse generator may communicate with or be coupled to the stimulator electrode or other electrodes via a wire or wirelessly.

The ergonomic insole 530 may include one or more sensor electrodes. For example, in one variation, as shown in FIG. 46, the stimulator electrode 532 may also act as a sensor electrode. The electrode 532 may detect stimulation of the underlying target nerve, to provide feedback regarding the efficacy of the applied electrical stimulation therapy. For example, the electrode 532 may detect motor and/or sensory nerve conduction. Detection of and feedback regarding nerve stimulation via the electrode 532 may provide for automatic adjustment of the treatment parameters or may guide or allow for manual adjustment of the treatment parameters in order to optimize stimulation therapy. Optionally, an additional sensor electrode 533 may be provided as well.

In certain variations, one or more separate or dedicated sensor electrodes may be attached to or positioned in the ergonomic insole to continuously and/or intermittently sense the stimulation of a nerve. The ergonomic insole 530 may hold or position the sensor electrode against, in contact with, or in proximity to a glabrous surface of the foot, to detect stimulation of the underlying target nerve, to provide feedback regarding the efficacy of the applied electrical stimulation therapy. For example, the sensor electrode may detect motor and/or sensory nerve conduction. Detection of and feedback regarding nerve stimulation via the sensor electrode may provide for automatic adjustment of the treatment parameters or may guide or allow for manual adjustment of the treatment parameters in order to optimize stimulation therapy. The sensor electrode may be coupled or connected to the electrical pulse generator. In certain variations, the sensor electrode may be attached to one or more wires, may be wireless and/or may be coupled to a pulse generator and/or may not be attached to or positioned in an ergonomic insole.

A sensor or applicator with a sensor may be capable of sensing stimulation of a nerve underlying a glabrous surface allowing for manual or automatic feedback to adjust the parameters of the stimulation or the position of the area being stimulated in order to optimize the stimulator therapy.

In certain variation, as sensor electrode may be positioned or placed along the path of the nerve conduction or motor or sensory impulse. Optionally, the sensor electrode may be positioned proximal to a stimulator electrode, along the nerve conduction path In certain variations, the electrodes may be attached to one or more wires, may be wireless and/or may be coupled to an electrical pulse generator or other generator or controller and/or may not be positioned in an applicator or support. For example, one or more stimulator electrodes may be adhered to or otherwise attached to a glabrous skin surface of a patient. One or more ground electrodes and/or one or more sensor electrodes may also be adhered to or otherwise attached to the patient. The stimulator electrode, sensor electrode and/or ground may be coupled to an electrical pulse generator and/or each other using wires or wirelessly. The electrical pulse generator may positioned in various locations or located anywhere on a patient. For example, the electrical pulse generator or controller may be held by a patient, located on a belt or strap worn by the patient, or positioned in a pocket or pouch on the patient.

Figure 47:
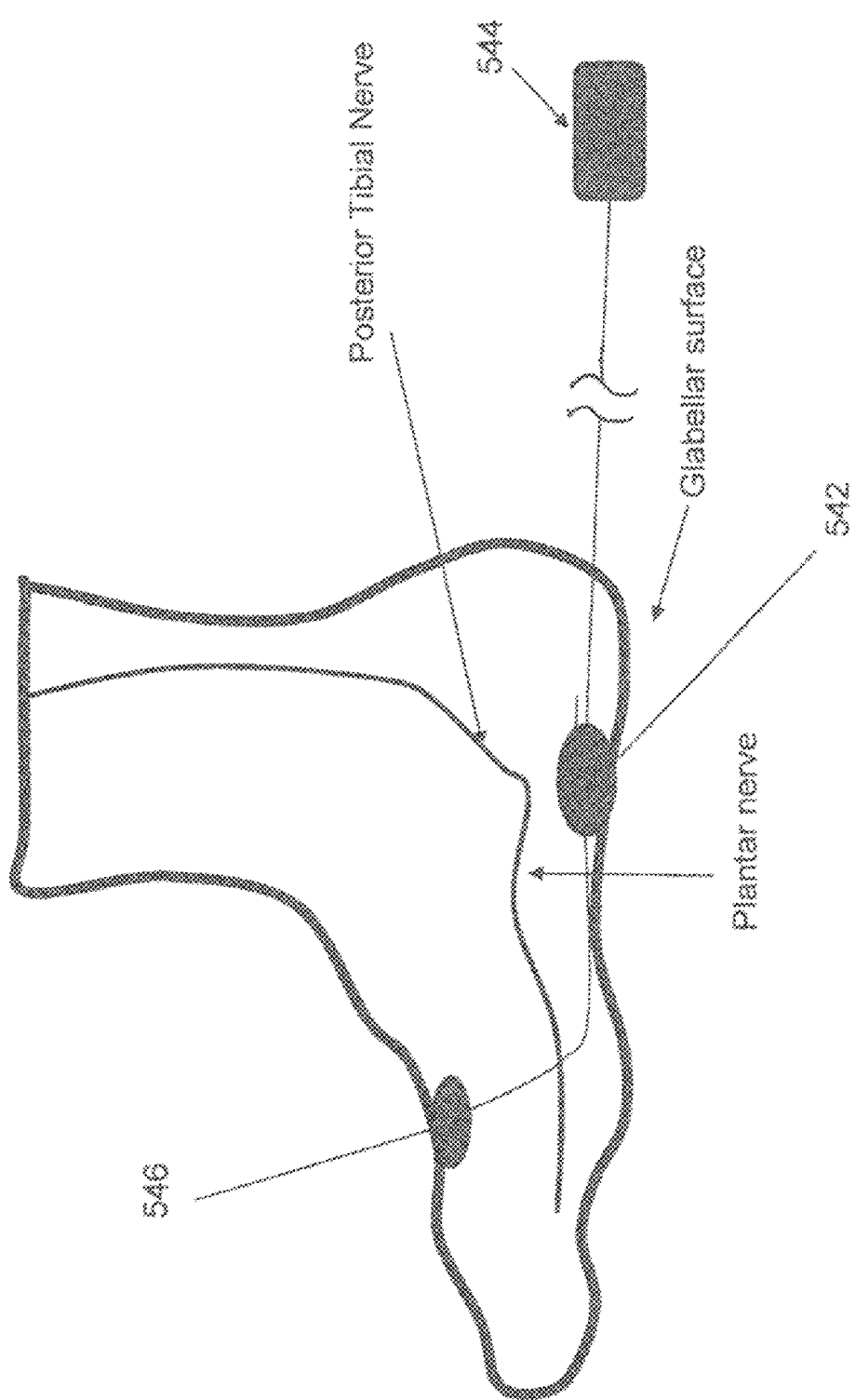
FIG. 47 shows a perspective view of one variation of electrodes for delivering electrical stimulation over a glabrous surface of a foot.

For example, FIG. 47 shows one variation of a stimulator electrode 542 attached to a glabrous skin surface of the foot or sole of the foot. A ground electrode 546 may be attached to the foot at another location. The stimulator and/or ground electrodes 542, 546 may be coupled to an electrical pulse generator 544, which may be positioned at various locations on or away from the patient. Optionally, a sensor electrode (not shown) may be attached to the patient to detect nerve or other tissue stimulation and to provide feedback regarding the efficacy of the therapy to optimize the therapy. The sensor may be coupled to the electrical pulse generator 544.

Figure 49:
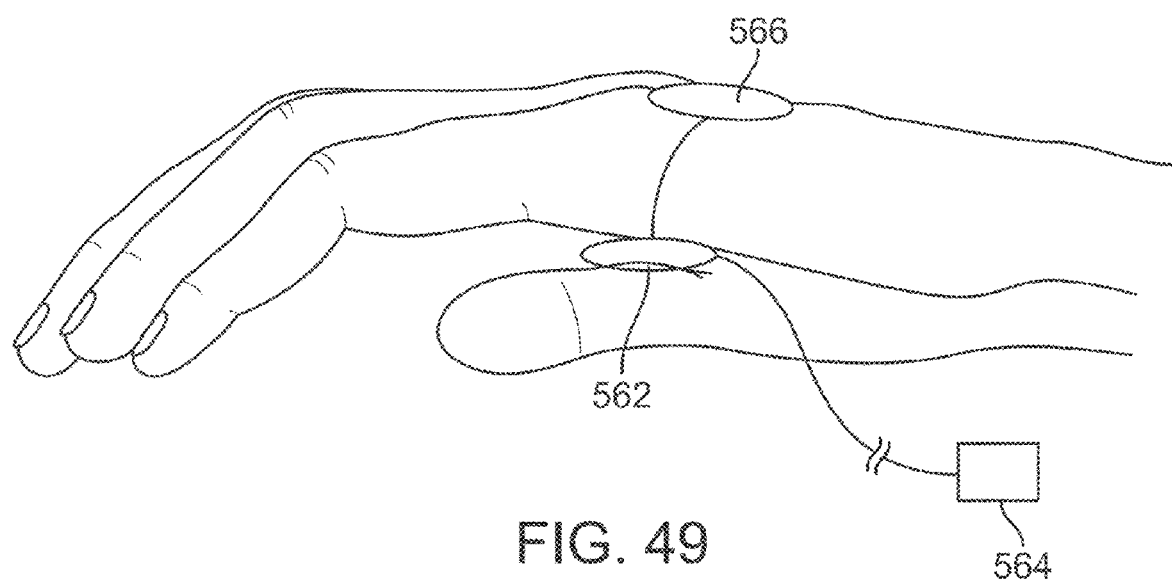
FIG. 49 shows a perspective view of one variation of electrodes for delivering electrical stimulation over a glabrous surface of a hand.

FIG. 49 shows another variation of a stimulator electrode 562 attached to a glabrous skin surface of the hand or palm of the hand. A ground electrode 566 may be attached to the hand at another location. The stimulator and/or ground electrodes 562, 566 may be coupled to an electrical pulse generator 564, which may be positioned at various locations on or away from the patient. Optionally, a sensor electrode (not shown) may be attached to the patient to detect nerve or other tissue stimulation and to provide feedback regarding the efficacy of the therapy to optimize the therapy. The sensor may be coupled to the electrical pulse generator 564.

In certain variations, systems and methods for providing electrostimulation (ES) of the posterior tibial nerve in individuals with OAB and UI, via transdermal electrical fields, are provided. Various electrodes for delivering the electrical stimulation may be utilized, including but not limited to surface electrodes with and without gel, microneedle electrodes, and electrodes under strong pressure.

Electrical stimulation may be directed to nerves underlying glabrous skin surfaces of the body (e.g., the palms and soles). Higher levels of power (than what would be utilized and tolerated on non-glabrous skin surfaces) may be utilized when delivering electrical stimulation transdermally, through or across a glabrous skin surface, while remaining safe and tolerable. For example, stimulation of the plantar nerves or other nerves of the foot via a surface electrode positioned over the glabrous surface of the plantar surface is highly tolerable and results in sensation similar to that found with needle-based, invasive stimulation of the posterior tibial nerve, but in a non-invasive manner.

Various devices or applicators may be applied to the feet and/or hand or other body portions in order to stimulate nerves underlying glabrous surfaces on an intermittent or continuous basis. Electrical stimulation may be delivered via surface or microneedle electrodes. Various devices may be used in conjunction with implantable or injectable substances in order to improve electrical conductivity to a target nerve. As described supra, the various methods and devices for providing transdermal electrical stimulation over a glabrous skin surface may be used to treat any disorder that is impacted by neuromodulation including, but not limited to: overactive bladder, urinary incontinence, fecal incontinence, chronic pain, depression, migraine, epilepsy, obesity, restless leg, or foot drop. The methods may be applied either intermittently or, if necessary, on a chronic basis. A stimulator electrode surface may be held in contact with a glabrous surface via an adhesive or an ergonomic applicator.

Feedback may be provided to the stimulator to indicate that stimulation is occurring as intended. This may involve an eMG type measurement device, a motion sensor or other sensing device. This feedback loop may be intermittently queried so that the stimulation may be adjusted to ensure that the minimum amount of energy is being used to stimulate to reduce the risk of burns or intolerance.

In certain variations, the device may include an ergonomic wrap or cradle. The sensor feedback may allow for optimization of the positioning of electrodes based on sensor feedback further reducing the risk of burns or intolerance while increasing the efficacy of the neuromodulation.

The methods and devices described herein may be utilized to stimulate various body tissues, including nerve, muscle, skin, vasculature, or any other organ or tissue within the human body. The methods and devices may be used to treat any suitable condition or perform any suitable function via neuromodulation regardless of whether the stimulation source is electromagnetic fields, direct electric current, ultrasound, or RF fields.

In certain variations, methods, systems and/or devices for performing neuromodulation and/or low frequency induction therapy through glabrous skin surfaces, e.g., through palmar or plantar surfaces, are provided. The methods and system may be utilized for treating or preventing various conditions, such as urinary incontinence (UI) and/or overactive bladder (OAB).

For example, a patient suffering from UI or OAB may place the glabrous surface of their foot over an insole, foot rest or foot plate applicator to provide contact between the glabrous surface of their foot and a stimulator electrode of the insole, foot rest, or foot plate applicator. Alternatively, a tethered or wired electrode may be used without an applicator or separate from an applicator. The electrode may be attached to or held in contact with the glabrous surface with an adhesive or as a cutaneous patch.

The stimulator electrode may be positioned over the glabrous surface along the course of a target nerve. The stimulator electrode may be positioned proximal to a stimulation site to ensure that afferent nerve stimulation occurs. A ground electrode may be placed on the body as well. One or more sensing electrodes may be placed along the path of the nerve conduction or motor or sensory impulse. Stimulator and/or sensing electrodes may be connected or coupled to a pulse generator. The pulse generator and electrodes may be incorporated or integrated into an insole, foot plate or other applicator. Alternatively, the electrodes may be connected or coupled to a pulse generator where the electrodes are not incorporated or integrated into the insole, foot plate or applicator.

Electrical stimulation via the stimulator electrodes may begin at a low amplitude and may slowly be ramped up or increased until nerve conduction is detected by the sensor electrode and/or detected by the patient who may signal that motor conduction has occurred, e.g., by pressing a button or other indicator.

Once stimulation is detected, the electrical pulses or electrical stimulation may continue for the directed duration of use or therapy. Electrical stimulation may be delivered intermittently to provide intermittent therapy. For example, electrical stimulation may be delivered for 15-30 minute intervals. In another example, electrical stimulation may be delivered continuously to provide continuous therapy.

A sensor may remain in place for the duration of the electrical stimulation therapy to ensure that stimulation occurs the entire time or substantially the entire time, and to allow for correction or adjustment if the signal deteriorates. A controller for operating a pulse generator or sensor may be powered by a portable power source (e.g., a battery) or a fixed power source (e.g., a traditional wall outlet).

In certain variations, the electrical stimulation may have of a square wave electric signal at a frequency of about 5 Hz to about 60 Hz at the targeted tissue depth. The square wave configuration of the signal may be generated via Fourier transformation or may be a ramped current generated in any manner.

The insole, foot rest, or foot plate may be removed from the body when therapeutic stimulation is not being delivered. The insole, foot rest, or foot plate may be reapplied along with a sensor patch (which may be disposable) as indicated. For example, the electrical stimulation therapy my be administered on a daily basis, where one or more of the above steps are repeated.

Electrical stimulation may be delivered according to any of the variations described herein, in a manner such that the stimulation provides motor, sensory and/or subthreshold stimulation. Any of the various energy based stimulation systems described herein may be utilized to provide therapy in various settings, e.g., in home use or to provide ambulatory type therapies.

In certain variations, as described supra, a device, applicator, pad, bracelet, ring or garment e.g., a gel pad or gel pad electrode, may include one or more electrodes, or have one or more electrodes coupled thereto. The device applicator, pad, bracelet, ring, garment and/or electrodes may deliver or provide energy, e.g., electrical, magnetic or electromagnetic, stimulation through or across a glabrous skin surface, e.g., a plantar or palmar skin surface. Pain receptors may be located deep under glabrous skin surfaces (e.g., located on the foot or on the palm) allowing the patient to have a higher tolerance to pain resulting from stimulation of these surfaces, than they might have at another area of their body. Applying stimulation over these surfaces allows for stimulation to be delivered at a higher frequency or power or at a greater strength or for a longer duration because of the higher tolerance to pain that a patient exhibits at these surfaces or areas.

In addition, the device, applicator, bracelet, ring, pad and/or electrode may include, carry or be coated with one or more drugs, agents or therapeutic substances. For example, the applicator or pad 520 or electrode 522, as shown in FIG. 45, or the applicator or pad 550 or electrode 552, as shown in FIG. 48, may be coated with or otherwise include a drug or other therapeutic substance. Optionally, one or more electrodes may be utilized without a pad or applicator and the electrodes may have a drug or agent coating on a surface of the electrode. In certain variations, the applicator, pad and/or electrode may be coated with a pain relief drug, anesthetic or numbing agent. The pain relief drug, anesthetic or numbing agent may provide the patient with an increased or improved pain tolerance or may reduce or eliminate the sensation of pain, such that the energy, e.g., electrical stimulation, may be applied or delivered at a higher frequency, higher power, greater strength and/or longer duration. The drug or agent may coat a surface of the applicator, pad and/or electrode such that the drug or agent is located between the applicator, pad and/or electrode and the glabrous skin surface of the patient when the applicator, pad or electrode is applied to the skin, thereby applying the drug to the skin. The drug or agent may be provided in a slow release form or as a slow release drug or agent, such that the coating provides a slow release of the drug, agent or active ingredient into the patient. Any of the applicators, pads, insoles, gloves, wraps, braces, plates, platforms, electrodes and/or other energy delivery devices described herein for delivering stimulation, e.g., through or across a glabrous surface, may be coated with or include a drug as described above.

In certain variations, stimulation e.g., energy stimulation such as electrical, magnetic or electromagnetic stimulation, may be provided through a glabrous skin surface at parameters that overcome or avoid habituation of the targeted tissue to the stimulation. For example, stimulation may be provided, e.g., continuously, for 10 minutes, where the stimulation is automatically paused or stopped for about a 30 second interval every 10 minutes. This intermittent pausing or interruption of stimulation may prevent or overcome habituation of the target tissue, e.g., nerve, muscle or other tissue, to the delivered stimulation.

In one variation, the treatment parameters for stimulating a target nerve or other tissue through a glabrous skin surface, e.g., a plantar or palmar skin surface, may include the following: Apply electrical or magnetic stimulation for a duration of 30 minutes, pausing for about a 30 second interval after 10 minutes of stimulation and then again after another 10 minutes of stimulation. In other variations, the treatment parameters may vary, e.g., stimulation may be applied for an interval ranging from 0 to 100 minutes or greater or as necessary to treat symptoms. In certain variations, for example, stimulation may be applied or provided for 20, 40, 50 or 60 minutes. In certain variations, for example, the pause in stimulation may be for an interval ranging from 0 to 100 seconds, or 5 to 60 seconds or 20 to 40 seconds.

In other variations, stimulation at varying frequency may be applied or provided for varying times with total stimulation of 20, 40, 50 or 60 minutes. In certain variations, for example, the change in stimulation frequency may be for an interval ranging from 0 to 100 seconds, or 5 to 60 seconds or 20 to 40 seconds.

In another variation, a sensor (e.g., EMG sensor) may be utilized, which may detect signs of habituation, e.g., decreased stimulation or excitation of a target nerve, muscle or other tissue (or lack of any resulting stimulation) or a reduced response to stimulation. Through a feedback loop, detection of habituation or stimulation levels by the sensor, may automatically cause the stimulator to pause or stop delivery of stimulation to the target nerve or tissue for a predetermined interval or duration or until habituation is no longer detected. In any of the variations described herein, the stimulation may be paused automatically, manually or via other controls or via an electrical pulse generator or controller in a predetermined or preset manner and/or based on feedback provided by a sensor.

In certain variations, electrical energy or stimulation may be applied to glabrous skin surfaces through electrodes, e.g., conductive microneedle patches, needles, or other electrodes, or by utilizing any of the devices or applicators described herein. Various electrodes, devices and/or applicators for providing stimulation may be applied to plantar or palmar surfaces of a patient. For example, if applied to plantar surfaces, electrodes may be applied to one foot or both feet. In cases where the stimulation is applied to one foot, the other foot may be used as ground, i.e., stimulation may be delivered into one foot and out the other foot. Various conditions may be treated using the devices, applicators and/or electrodes and/or the various methods, therapies and treatment parameters described herein, e.g., urinary incontinence, overactive bladder, epilepsy, migraines, and depression, etc.

In certain variations, treatment of a patient using electrical stimulation may be monitored and/or adjusted based on the detection of feedback signals using primarily F-wave detection or based on the detection of F-waves or M-waves, e.g., in a foot or hand. For example, detection of an F-wave or F-wave feedback (e.g., via a sensor or electrode sensor) may be used in monitoring and/or to adjust the applied stimulation therapy. Optionally, stimulation may be ramped up until an F-wave is detected and then adjusted as necessary. F-wave detection measures nerve conduction velocity. F-wave detection may be used as opposed to H-reflex detection, which measures reflectory reaction from muscles. In other variations, optionally both F-wave and H-reflex detection may be used or solely H-reflex detection may be used. Stimulating to a sub-motor stimulation may be performed. In certain variations, F-waves, M-waves and/or H-reflex may be detected in the foot, hand or other body part.

Electrical energy may be applied or delivered using any of the devices, applicators or electrodes described herein at specified frequencies and/or parameters or using various duty cycles. In one example, electrical energy may be applied at a frequency of 5 Hz to 20 Hz (e.g., to provide supermaximal stimulation) in a train of 5 pulses followed by a ¼ second break, and then another train of 5 pulses. Up to 10 pulses per treatment cycle may be provided. The train of 10 pulses can be repeated as needed. In another example, a train of 10 pulses followed by a break and then another 10 pulses may applied, e.g., at a frequency of 5 Hz to 20 Hz or at about 20 Hz. The ¼ second break time may be varied as well as the number of pulses applied and the number of cycles. This pulsed treatment may be applied through one or more or several cycles. The pulsed treatment or stimulation may produce F-waves which may be detected. In certain variations, any of the treatment parameters as described herein may be applied where only half of the pulses are stimulatory, e.g., one or more cycles of pulses may be provided at 20 Hz, where only half of the pulses are stimulatory.

In other variations, the treatment parameters may vary, e.g., stimulation frequency may be applied for an interval ranging from 0 to 100 minutes or greater or as necessary to treat symptoms followed by a varying frequency for a time interval. In certain variations, for example, stimulation at certain frequency may be applied or provided for varying times with total stimulation of 20, 40, 50 or 60 minutes. In certain variations, for example, the change in stimulation frequency may be for an interval ranging from 0 to 100 seconds, or 5 to 60 seconds or 20 to 40 seconds.

Figure 50:
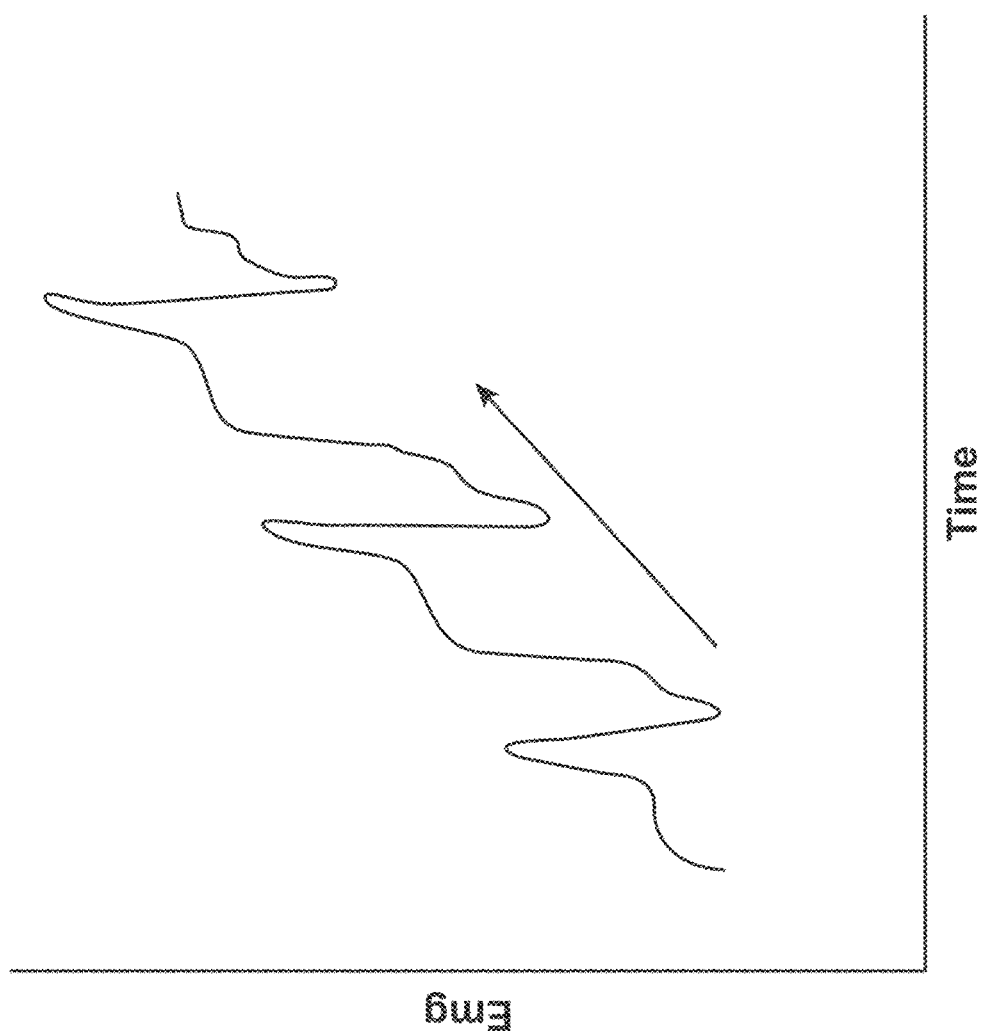
FIG. 50 shows an example of an EMG reading.

Certain frequencies, e.g., frequencies applied at greater than 20 Hz, may lead to a painful condition called tetany (i.e., painful, involuntary muscle cramping), which is an indication that the upper level for frequency has been reached in the patient. Tetany may be monitored using a sensor, e.g., an EMG sensor or Electromyography, to provide feedback regarding tetany. Tetany may be distinguished by EMG. FIG. 50 shows an example of an EMG reading showing a gradual increase in the detected level of stimulation or electrical activity, up to a level where tetany is likely experienced. Once the system detects the beginning of tetany or provides tetany feedback, the treatment frequency or power (of the stimulation delivered by an electrode or device) may be reduced, adjusted or halted automatically or manually. The frequency at which tetany is experienced may vary in different individuals.

In one variation, a treatment device or applicator for delivering energy, e.g., electrical energy, may include a platform with one or more microneedles, microneedle electrode, or other electrodes positioned upon the platform. Microneedles may vary in length to penetrate different layers of the skin, e.g., to penetrate a callus on the skin. A patient may place their foot upon the platform to receive treatment. Optionally, a separate strap having a feedback/monitoring electrode or electrode sensor may be wrapped over the foot to place or position a feedback/monitoring electrode on the patient. The strap and feedback electrode or electrode sensor may be coupled to the platform or be separate. In another variation, the stimulatory electrode may be positioned in a shoe, sock or glove of a patient. In certain variations, a TENS electrode or stimulator may be utilized.

Detection of stimulation, excitation, or conduction using a sensor may provide information to optimize or adjust the applied therapy. If no or reduced stimulation, excitation, electrical activity, response, F-waves, and/or EMG is detected during treatment, this may be indicative of a mis-positioned foot, palm or other body part relative to the one or more electrodes or the device or applicator.

Various conditions may be treated using the devices, applicators and/or electrodes and/or the various methods, therapies and treatment parameters for providing stimulation as described above, e.g., urinary incontinence, overactive bladder, epilepsy, migraines, and depression, etc.

In certain variations, electrical, electromagnetic, magnetic energy and/or other energy may be utilized to provide stimulation according to any of the systems and/or methods described above.

The present invention may use electrical stimulation of one or more of the Ulnar nerve, the Median nerve, the tibial nerve, or other nerves, either alone or simultaneously, separately or with other types of therapy to treat various neurological conditions, including neuropathies, migraine, pain, headaches, depression, epilepsy, post-traumatic stress disorder, overactive bladder, incontinence, subcutaneous fat, effects of stroke, memory enhancement, etc. In some embodiments, treatment can be combined with certain drugs to increase treatment effectiveness.

Devices used to stimulate one or more of the Ulnar, Median or Tibial nerves can be a completely external device, a fully implantable device or a device that comprises both external and internal components. The devices typically comprise a pulse generating component that provides an electrical wave form as output. The electrical pulse comprises certain typical parameters, such as pulse width, frequency, number of pulses and amplitude among other parameters. The choice of parameters may depend on the nerve, the location of the electrodes, the desired effect sought and the amount of time the therapy treatment occurs.

Figures 51A, 51B, 51C:
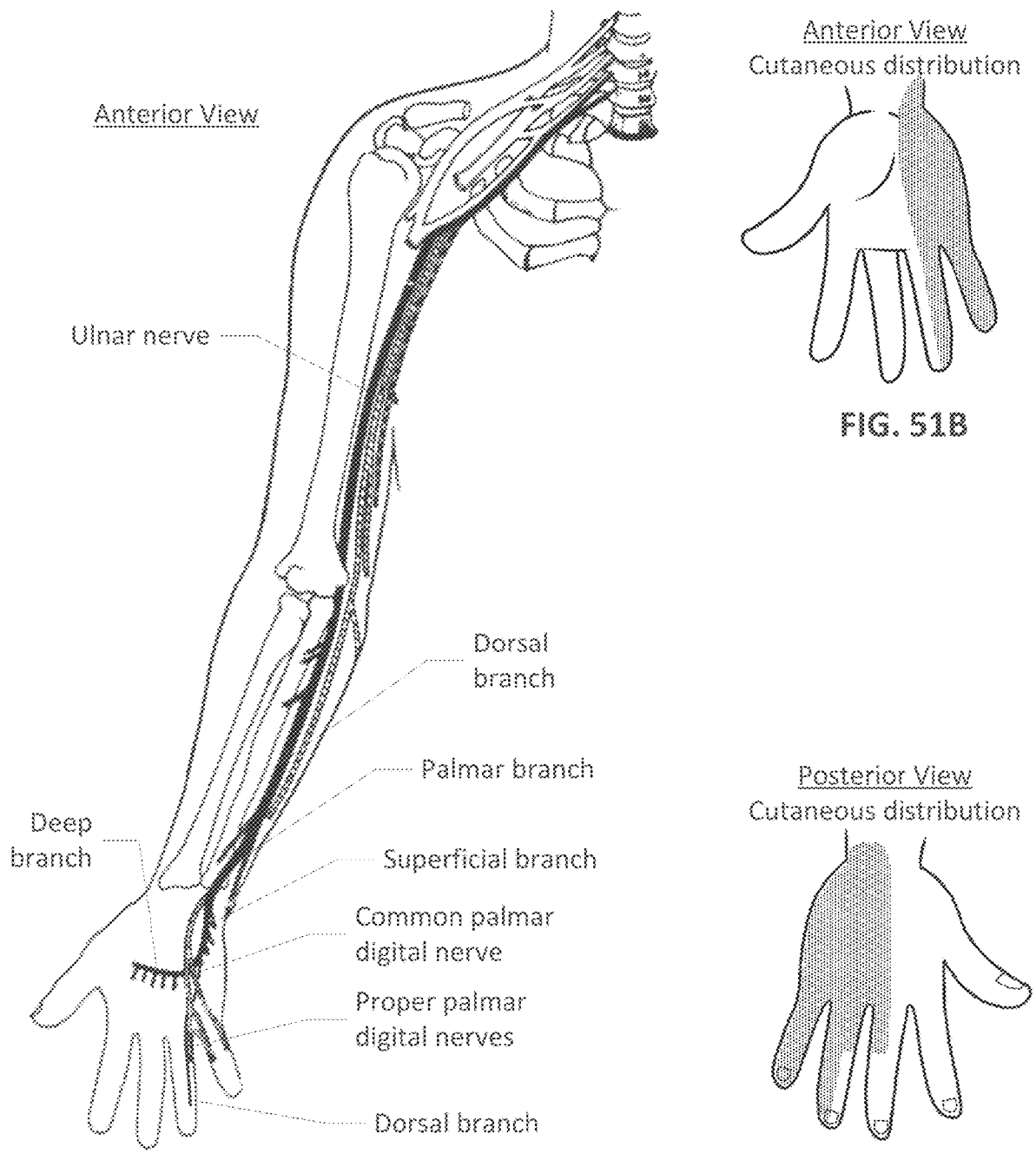
FIG. 51A shows the anterior or palmar view of the forearm and the Ulnar nerve.
FIG. 51B shows the anterior view of the cutaneous distribution of the Ulnar nerve.
FIG. 51C shows the posterior view of the cutaneous distribution of the Ulnar nerve.
Figure 52:
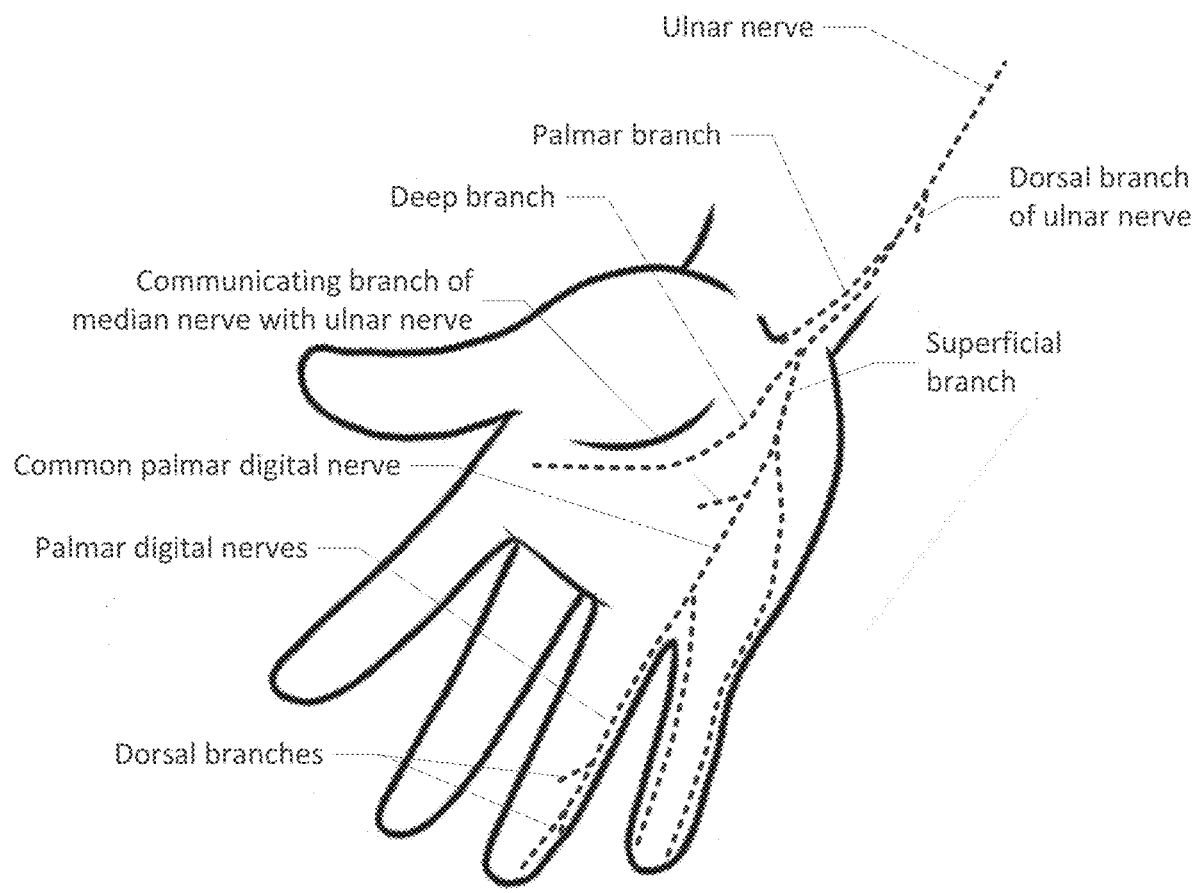
FIG. 52 shows a close up view of the Ulnar nerve and its branches including the palmar branch.
Figure 53:
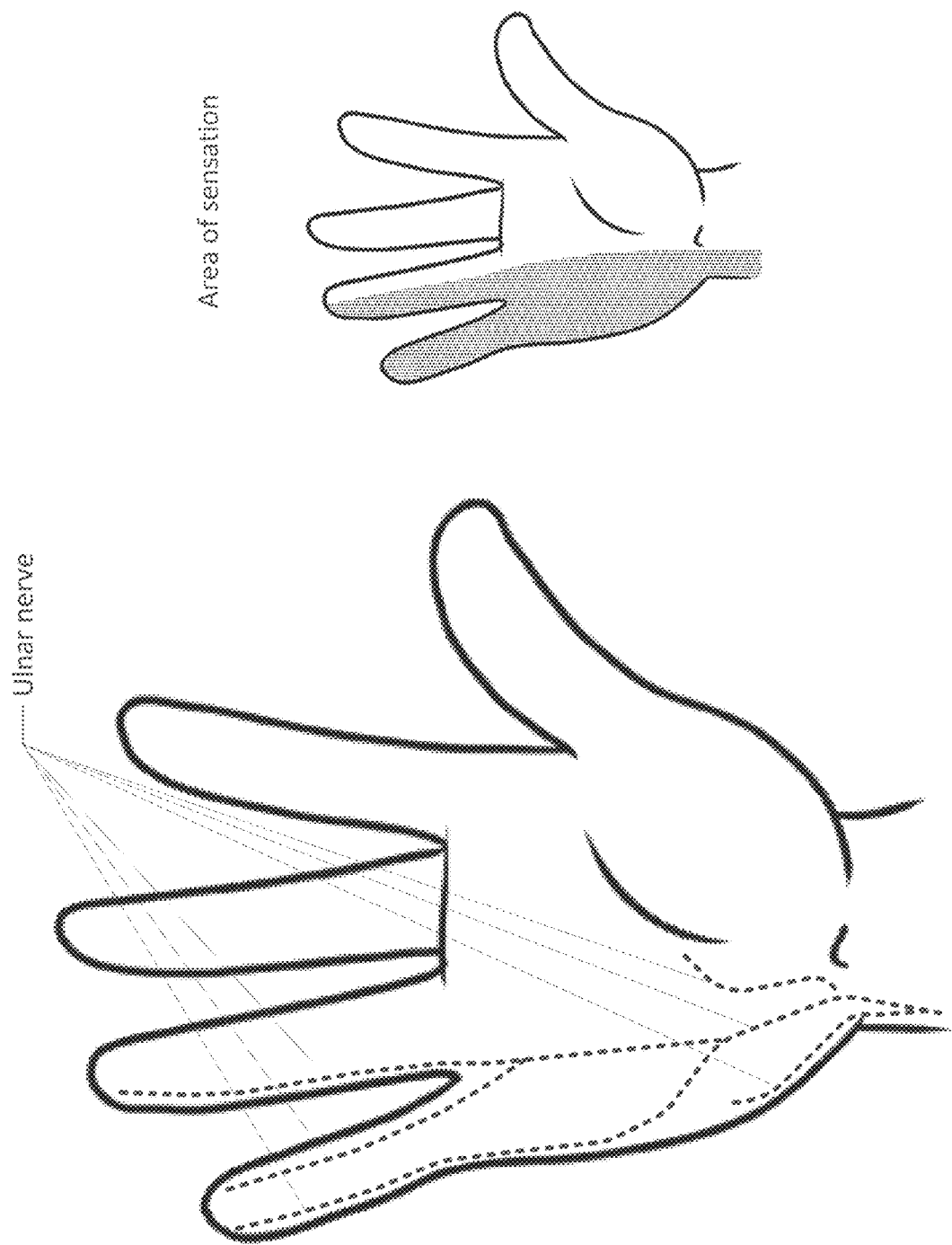
FIG. 53 shows a close up palmar view of the palmar branch of the Ulnar nerve including the area of sensation.

One method of using the present invention is to stimulate one or both of the Ulnar and Median nerves to treat migraine. The Ulnar and Median nerves innervate portions of the arm and hands. FIG. 51A shows the anterior or palmar view of the forearm and the Ulnar nerve. FIG. 51B shows the anterior view of the cutaneous distribution of the Ulnar nerve. FIG. 51C shows the posterior view of the cutaneous distribution of the Ulnar nerve. FIG. 52 shows a close up view of the Ulnar nerve and its branches including the palmar branch. FIG. 53 shows a close up palmar view of the palmar branch of the Ulnar nerve including the area of sensation.

Figure 54A:
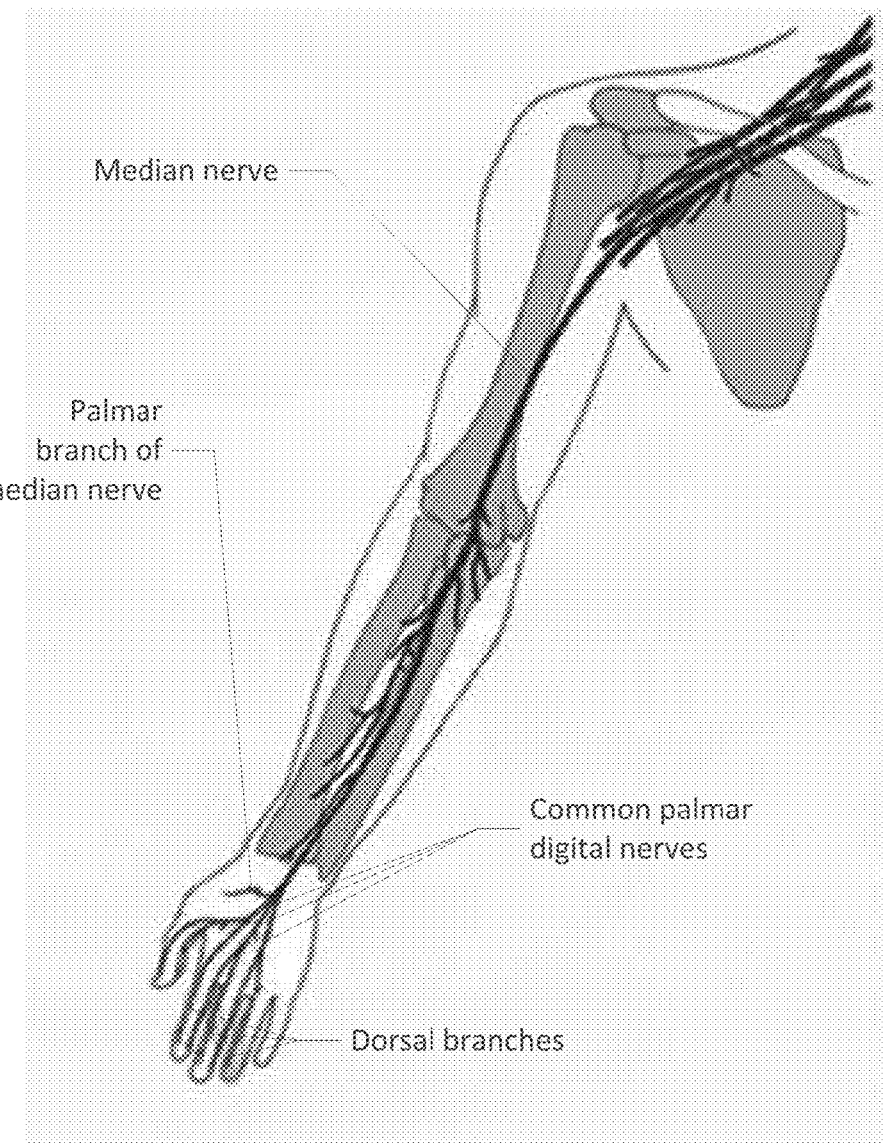
FIG. 54A shows an anterior view of the Median nerve of the forearm including the Median nerve's palmar branch.
Figure 54B:
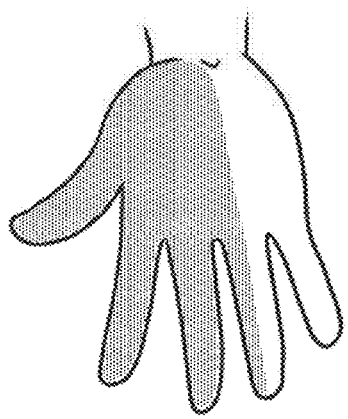
FIG. 54B shows the anterior or palmar view of the Median nerve's cutaneous innervation.
Figure 54C:
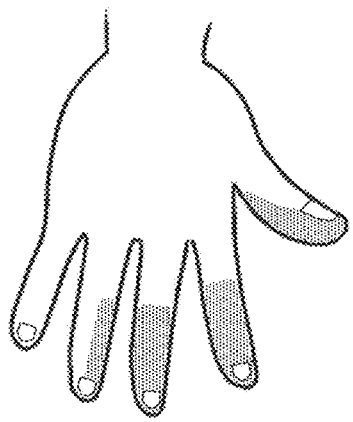
FIG. 54C shows the posterior or dorsal view of the Median nerve's cutaneous innervation.

FIG. 54A shows an anterior view of the Median nerve of the forearm including the Median nerve's palmar branch. FIG. 54B shows the anterior or palmar view of the Median nerve's cutaneous innervation. FIG. 54C shows the posterior or dorsal view of the Median nerve's cutaneous innervation. FIG. 55 shows a close up anterior or palmar view of the Median nerve's palmar branch in the hand and its area of sensation.

Figure 56A:
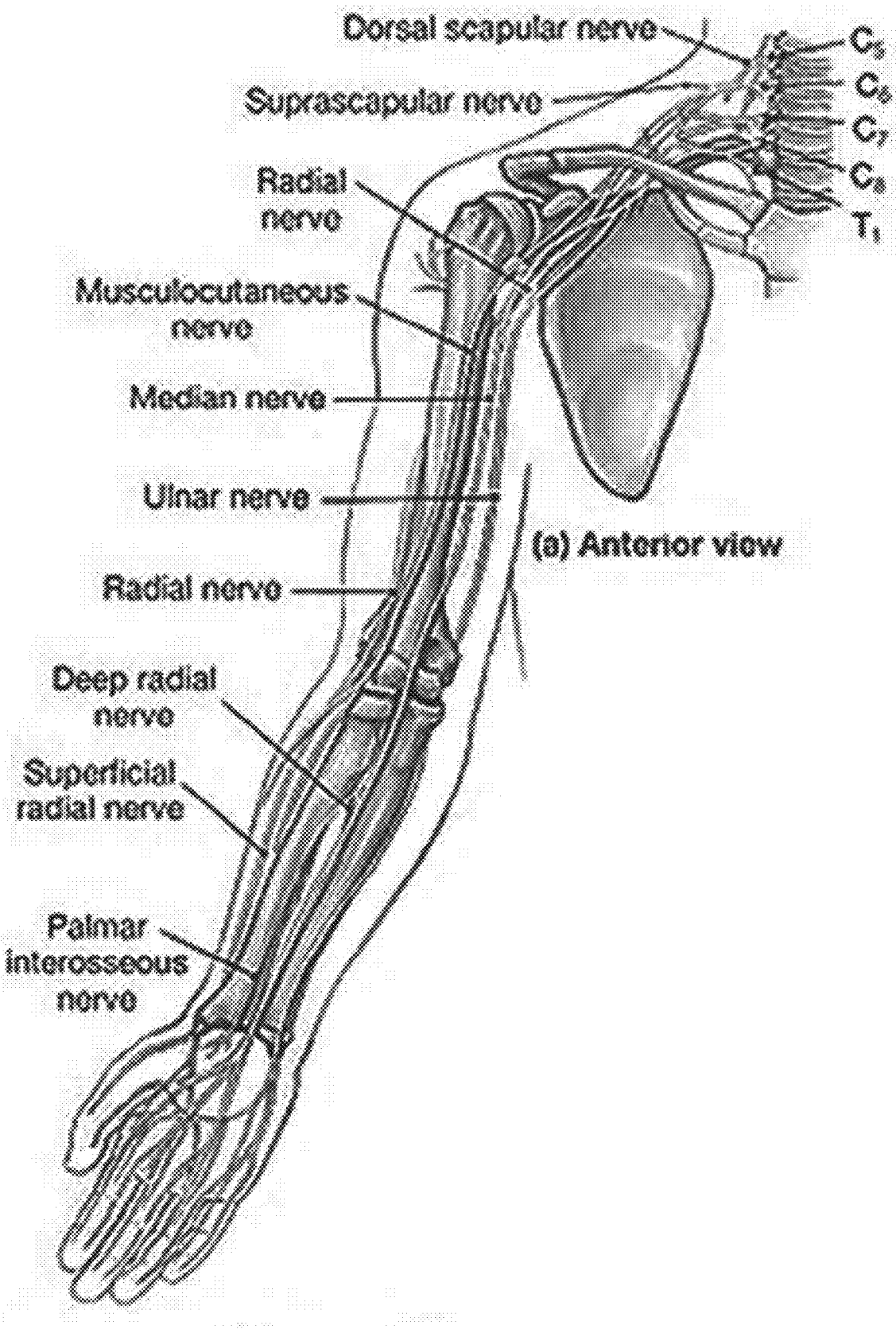
FIG. 56A shows the anterior view of the forearm including the Median and Ulnar and their respective palmar branches.
Figure 56B:
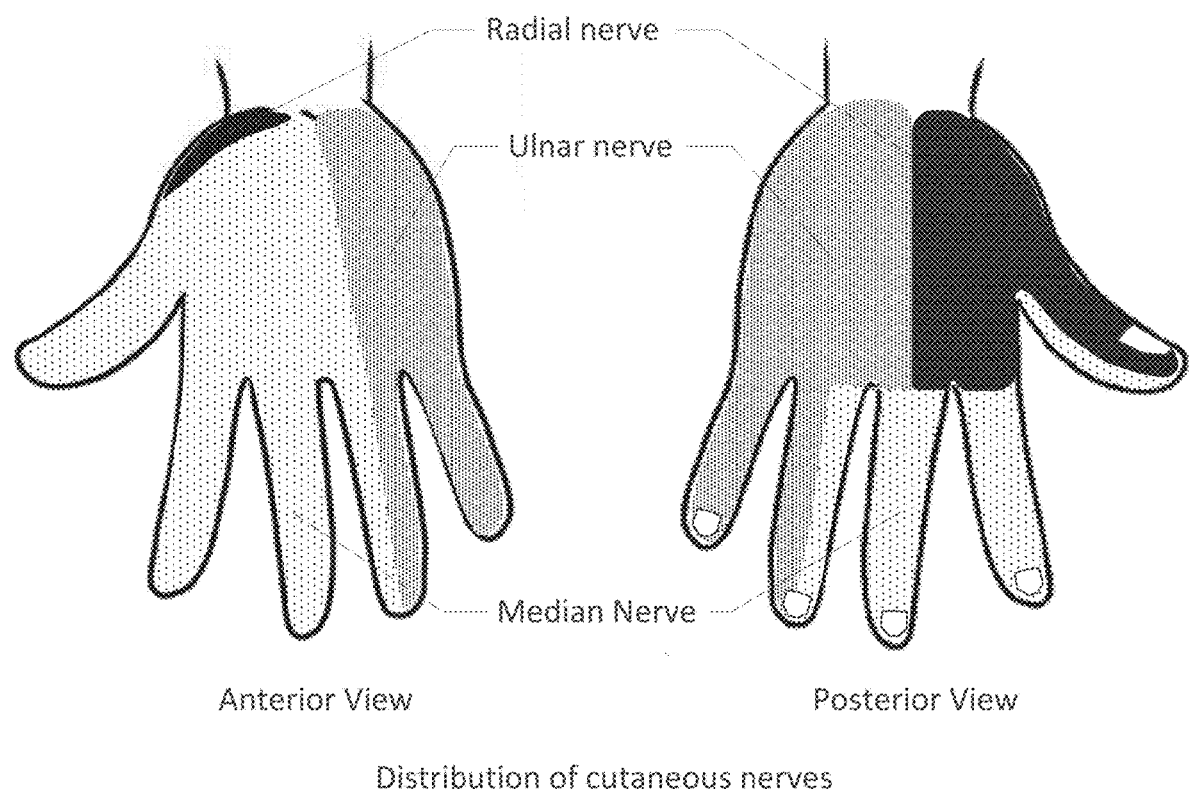
FIG. 56B shows the anterior or palmar view and the posterior or dorsal view of the distribution of the cutaneous nerves.

FIG. 56A shows the anterior view of the forearm including the Median and Ulnar and their respective palmar branches. FIG. 56B shows the anterior or palmar view and the posterior or dorsal view of the distribution of the cutaneous nerves.

Figure 56C:
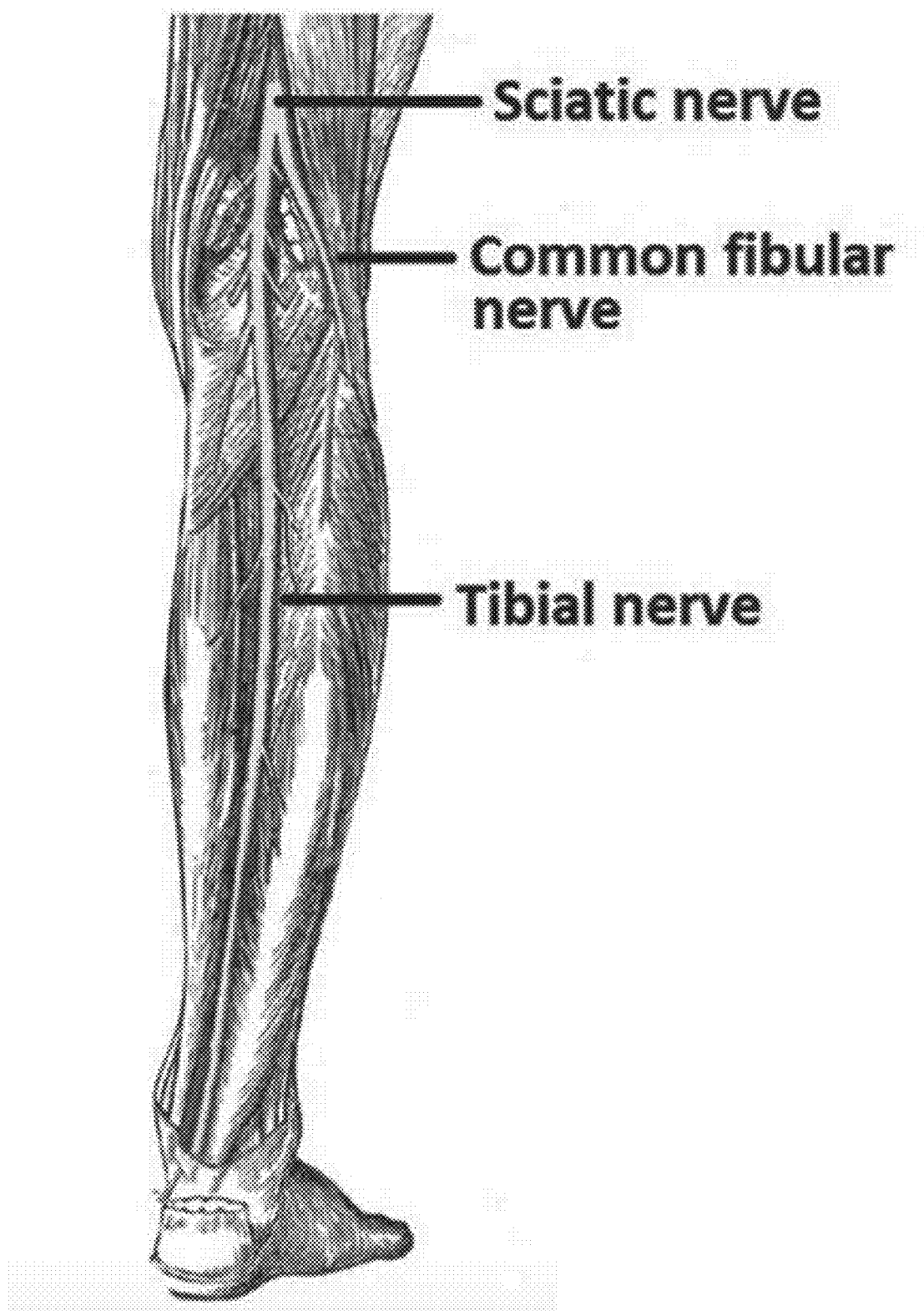
FIGS. 56C-56F show branches of the Tibial nerve, electrode placement and innervation of the plantar portion of the foot.
Figure 56E:
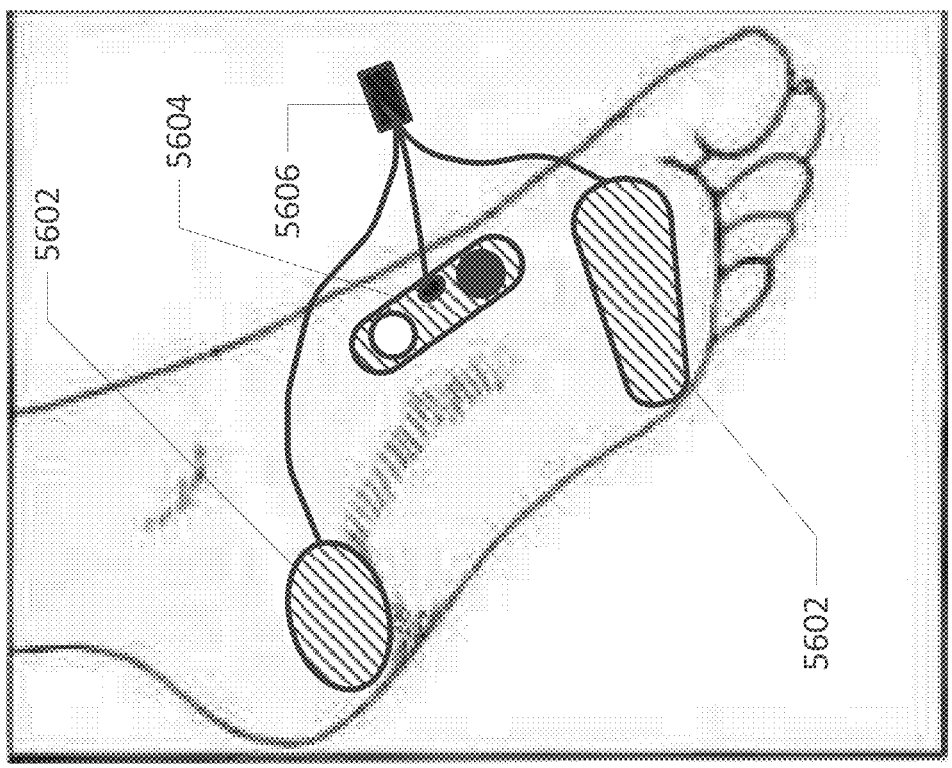
Figure 56D:
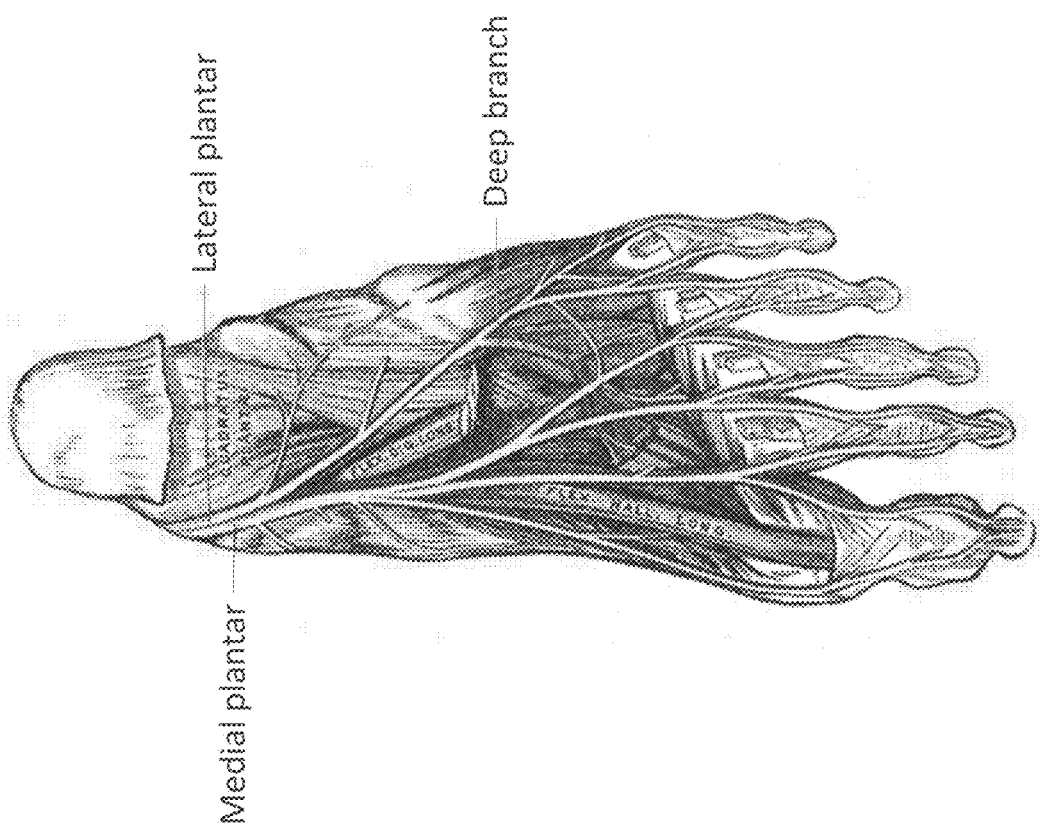
Figure 56F:
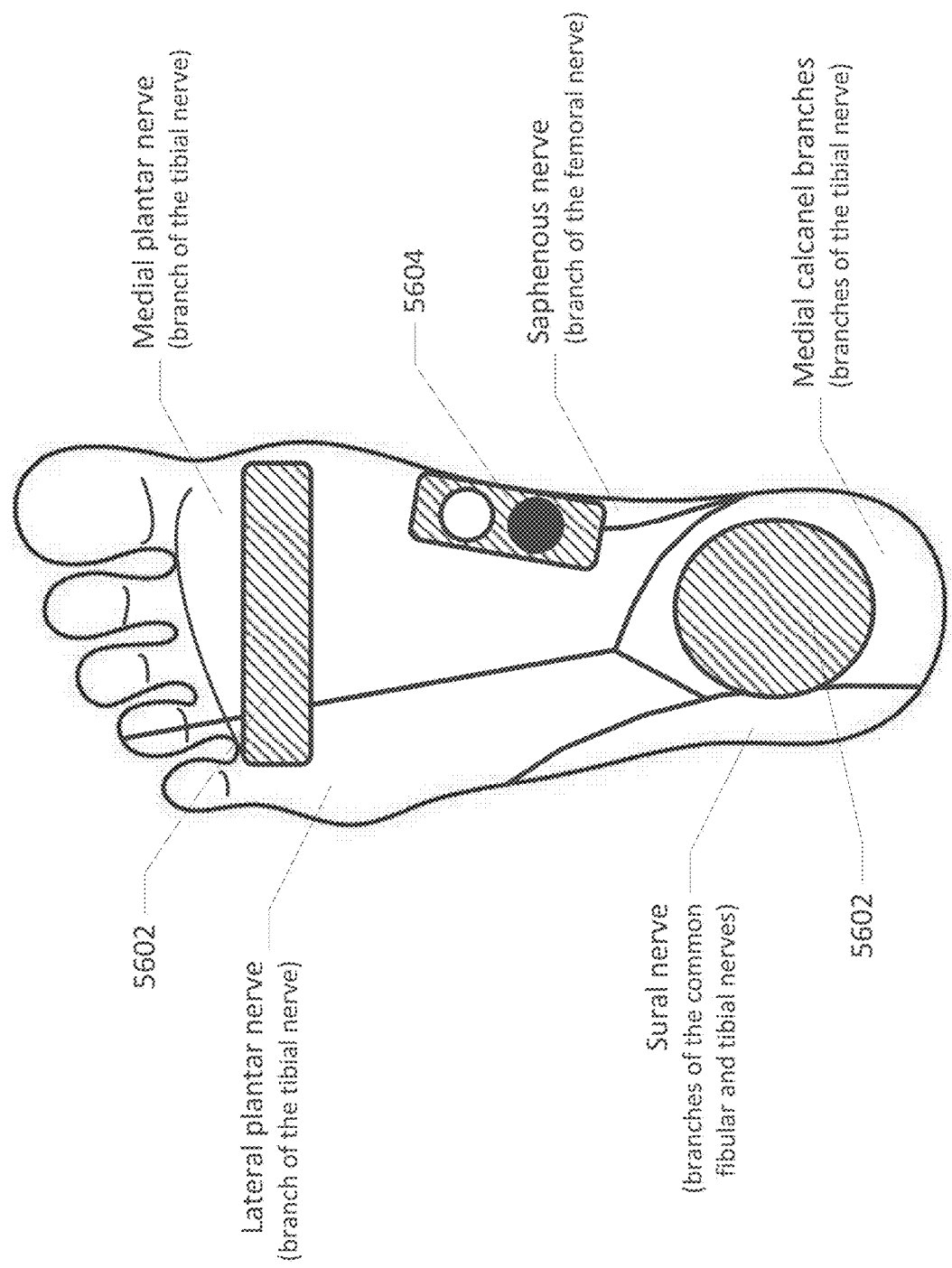

FIGS. 56C-56F show branches of the Tibial nerve, electrode placement and innervation of the plantar portion of the foot. In FIG. 56C, the Tibial nerve and its branches are shown extending from the Sciatic nerve. The Tibial nerve continues to the bottom of the foot as show in FIG. 56D. FIG. 56E shows possible placement of electrodes 5602 and EMG pad 5604 containing multi electrodes, all of which are connected to controller 5604. Both electrodes 5602 may be microneedles or both may be patch or surface electrodes or one may be a microneedle electrode while the other is a patch electrode. FIG. 56F shows how placement of the electrodes correspond to the various cutaneous innervation regions on the bottom of the foot.

Figure 57:
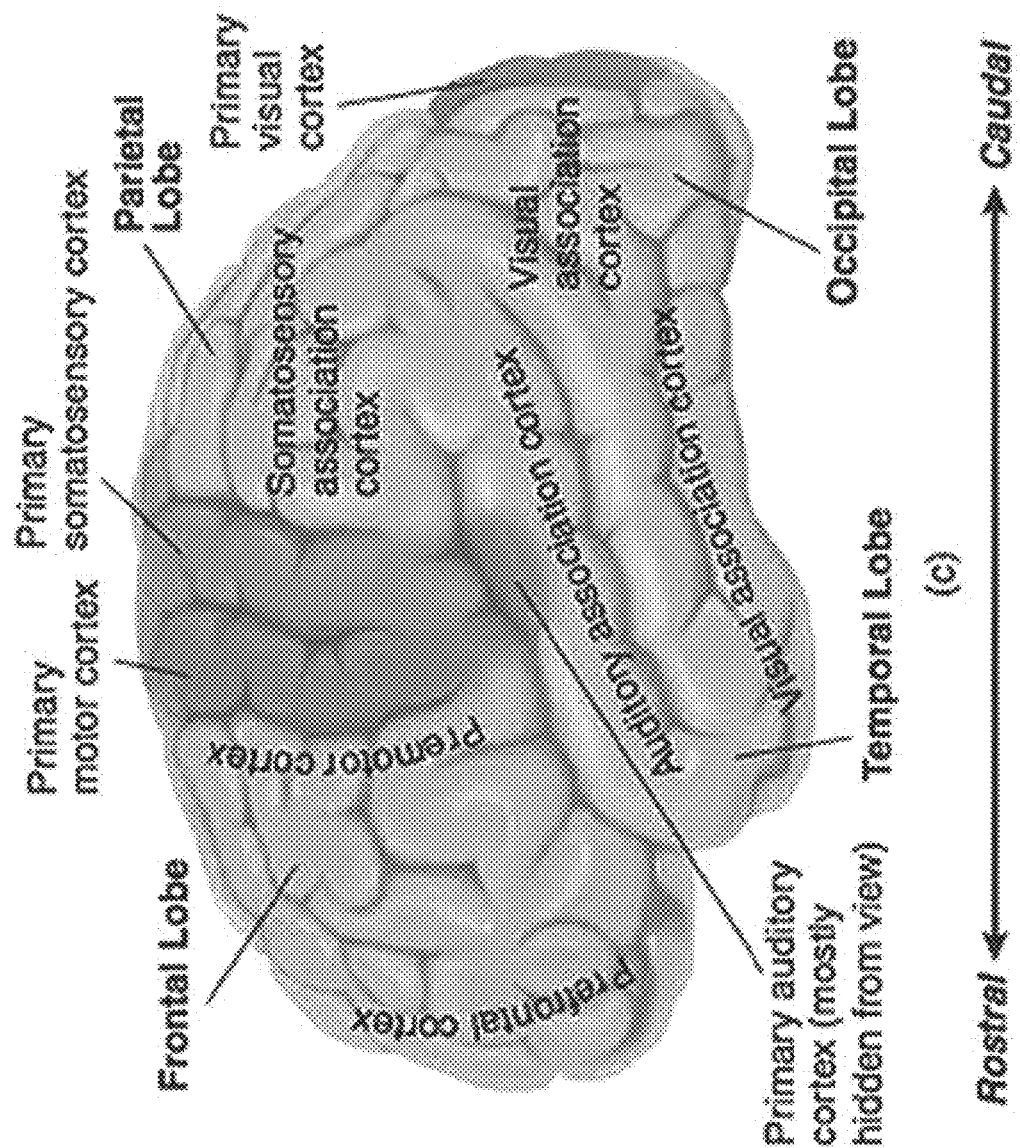
FIG. 57 is a diagram showing a mapping of the human cortex as laid out against the various lobes.

FIG. 57 is a diagram showing a mapping of the human cortex as laid out against the various lobes. An area of possible interest related to the present invention is the primary motor and somatosensory cortex. As is known, sensory inputs and motor outputs are arranged along each of these two cortexes. However, the human body does not scale perfectly proportionally across these cortexes. In order to understand how the various parts of these areas relate to the body, it is helpful to view a cortical homunculus. The cortical homunculus is a physical representation of the human body, located within the brain. A cortical homunculus is a neurological "map" of the anatomical divisions of the body. There are two types of cortical homunculi: sensory and motor.

Figure 58:
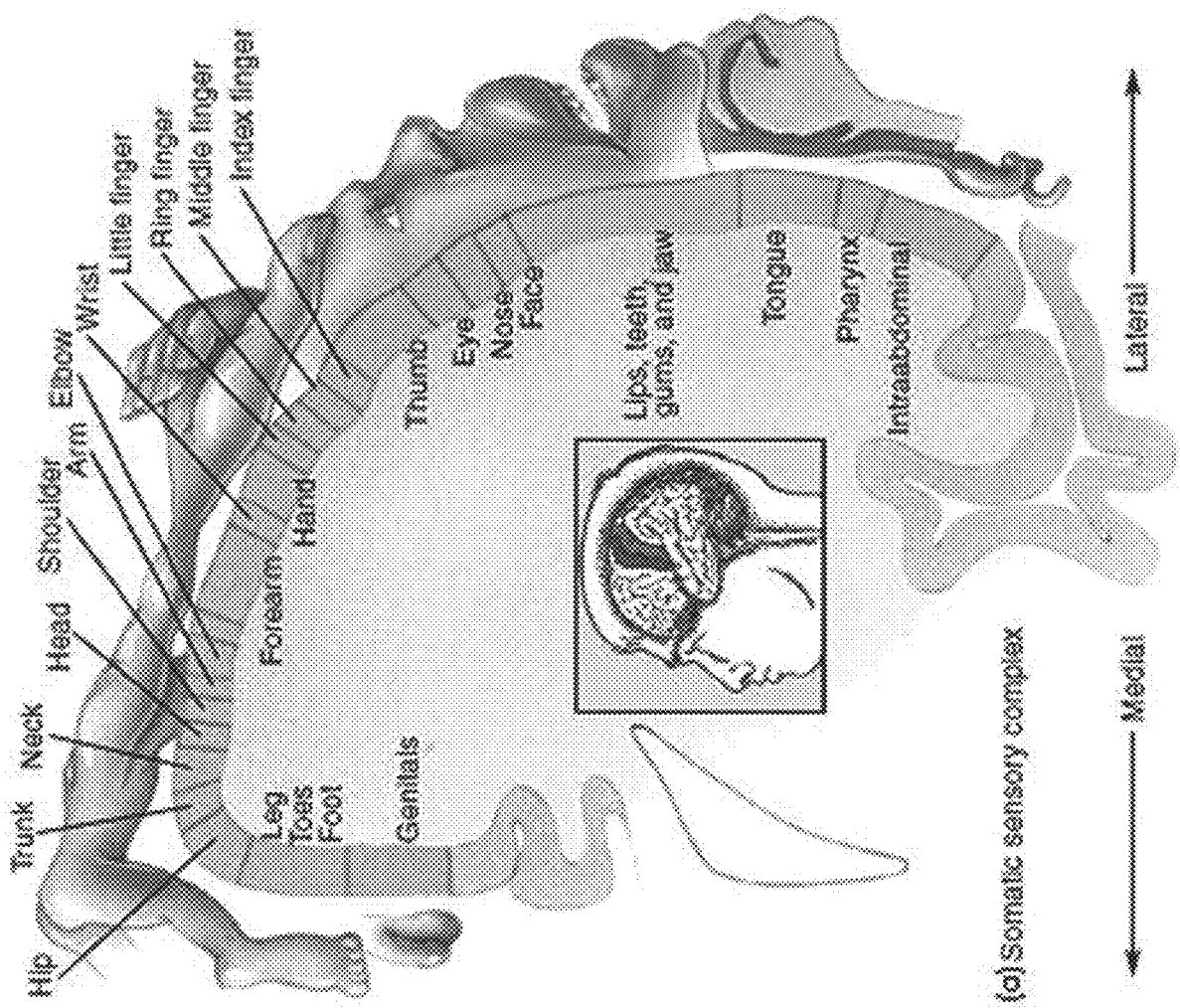
FIGS. 58, 59A and 59B illustrate how different areas of the human body take up different cortical "real estate" of the somatosensory cortex.

For example, as is show in FIG. 58, different areas of the human body take up different cortical "real estate" of the somatosensory cortex. One can see by such mapping, that the hand takes up much more of the somatosensory cortex than, for example, the head, neck or trunk, even though physically, the head, neck and trunk take up more physical space on the body.

Figure 59A:
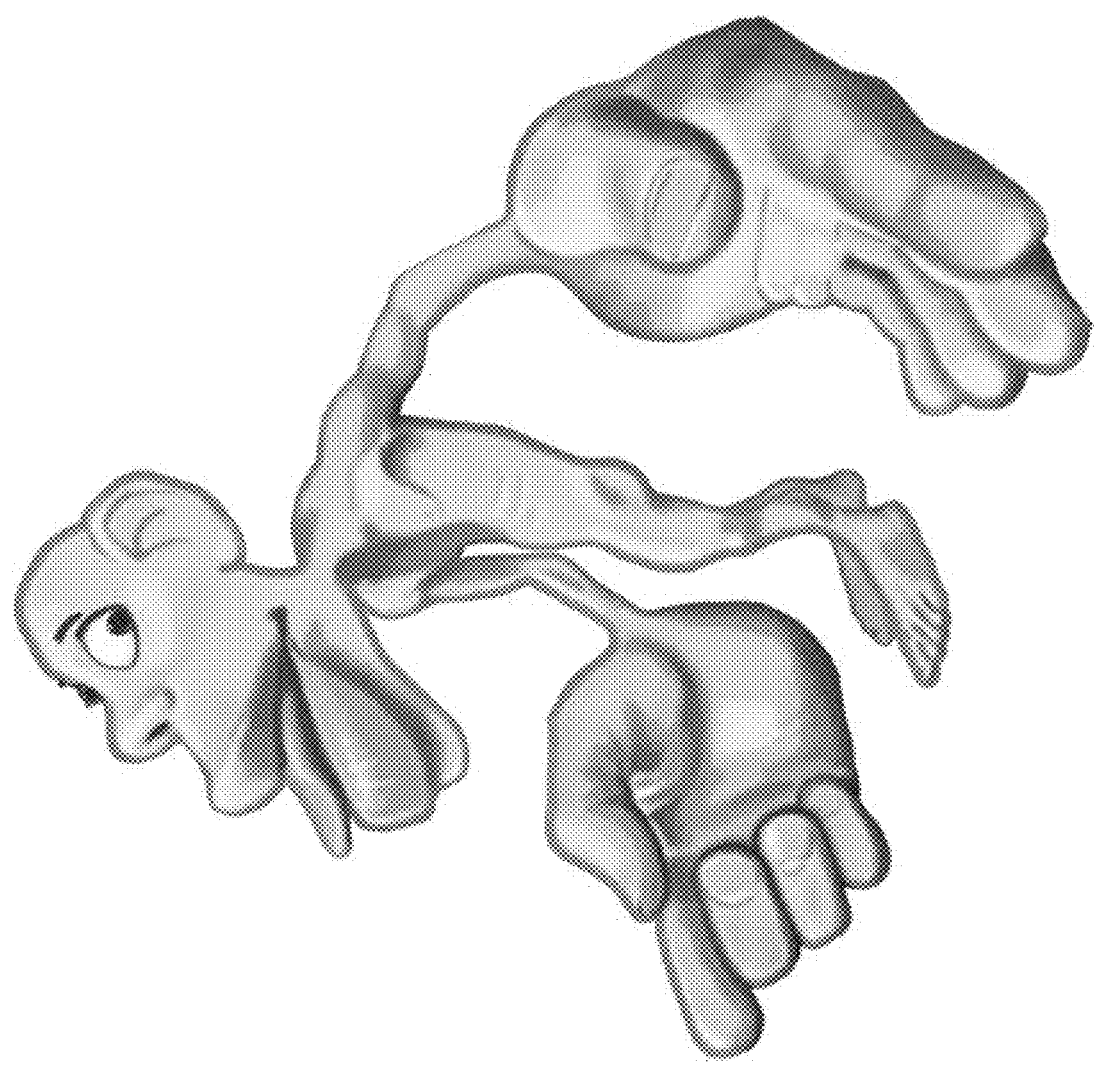
Figure 59B:
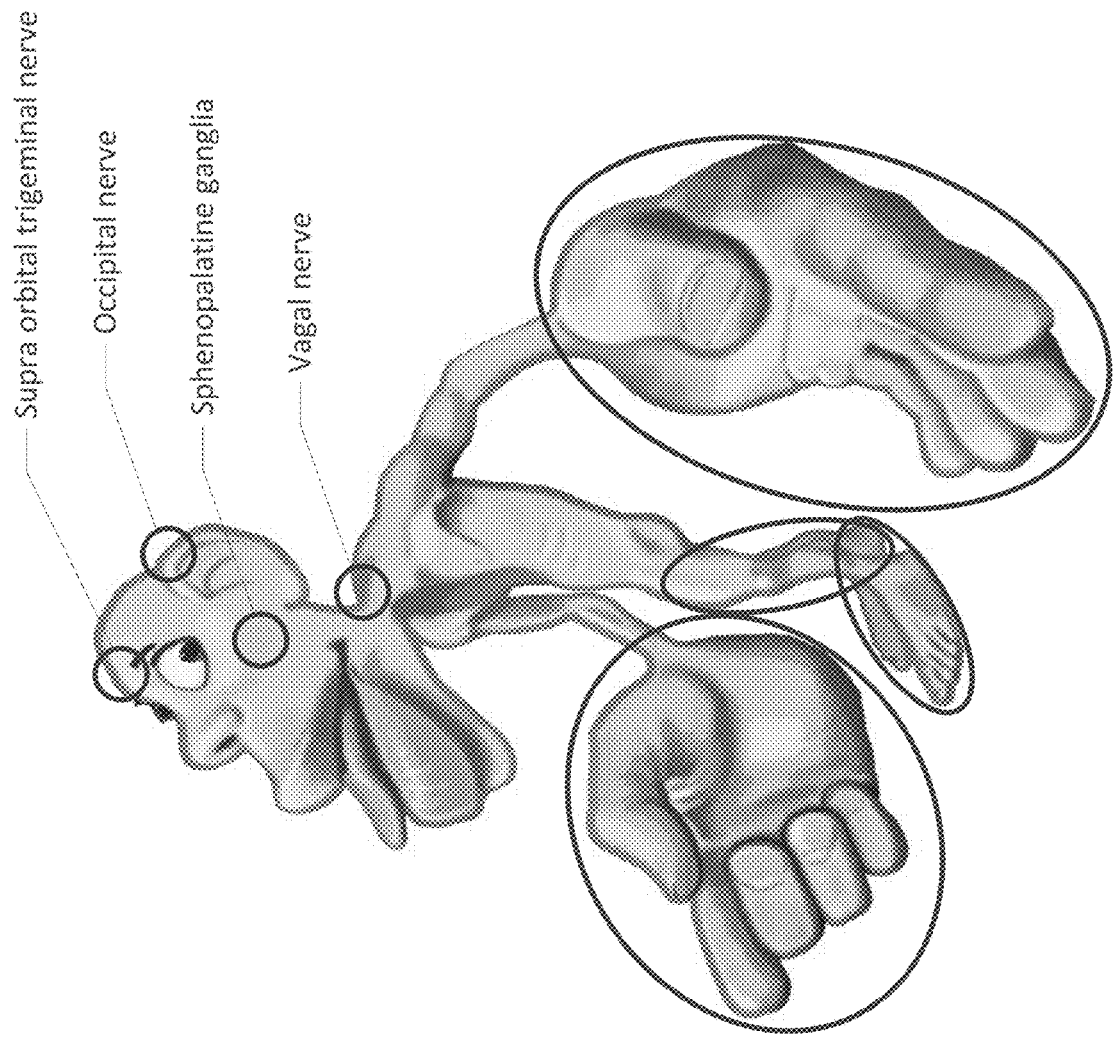

A different way of visualizing the cortical homunculus in FIG. 58 is shown in FIGS. 59A and 59B. As shown in FIG. 59A, that the human hands and face, including the lips and tongue, take up a larger part of the cortexes than is proportional to their size relative to the rest of the human body.

Figure 60A:
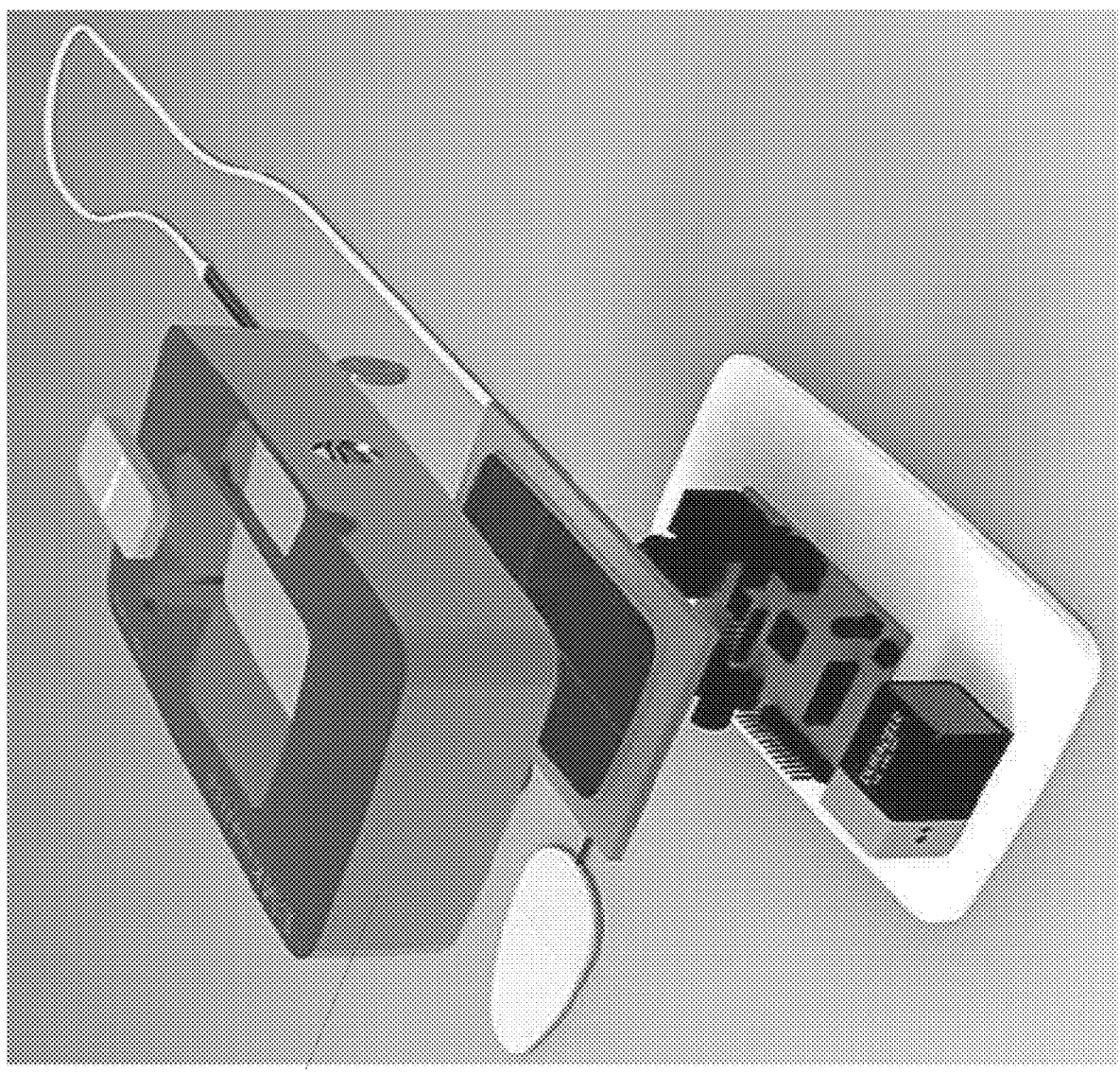
FIG. 60A shows an exploded view of the external generator or controller that can be used in some embodiments of the present invention.

FIG. 60A shows an exploded view of the external generator or controller that can be used in some embodiments of the present invention. The external generator/controller has housing 6002 which contains internal components. The internal components may include a microprocessor, memory, a battery, on/off switches and various other electronic components for storing various operational and functional programs and executing those programs in accordance with a desired instruction set for the relevant indication or neurological malady. Such programs will include but not be limited to instructions related to the parameters for electronic pulses which emit from the electrodes. They typical instruction set will include the desired pulse width, frequency, amplitude and the desired time intervals, and possibly, time length, for the therapy. The instructions may include more or less information as desired, such as burst modes, high frequency sequencing, coordinated reset functions and the like. In addition to delivering pulses, the generator/controller may also contain electronics for sensing F and M waves, and the ability to display, interpret and/or act on such sensed F and M waves. "Acting on" may mean that the controller analyzes and determines whether the parameter instruction set requires adjustments in order to maximize therapy effectiveness. If an adjustment is required, the instruction set will either make an automatic adjustment or send an alert or other information to the display to prompt a manual adjustment.

Figure 60B:
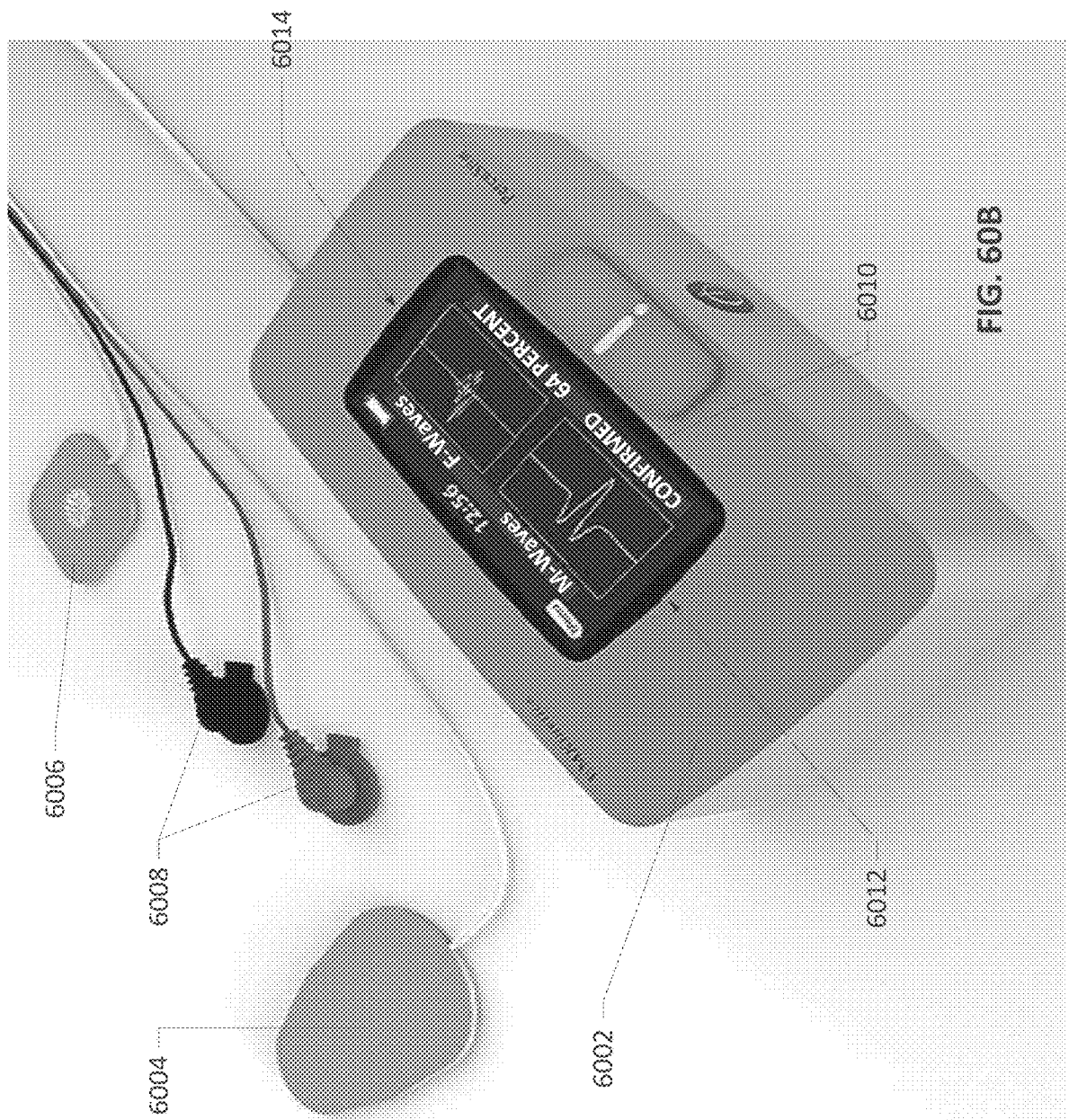
FIG. 60B shows the external generator/controller in FIG. 60A in a non-exploded view.

FIG. 60B shows the external generator/controller in FIG. 60A in a non-exploded view with electrodes 6004 and 6006 and F/M wave sensors 6008 all connected via insulated wires. The display 6010 shown in this example displays an M-wave confirmation result 6012 and an F-wave display 6014 that shows the F-wave percent. The display may show other information such as the pulse parameters described above. In some embodiments, the external generator/controller provides a manual mode switch for determining which mode the system will be set to. It also contains an on/off switch and a display for displaying various information relating to the therapy and/or pulse parameters. The system may include two electrodes, one of which can be a percutaneous microneedle electrode and one a return electrode. It should be understood, though, that any of the systems may contain two surface, or skin, electrodes or two percutaneous microneedle electrodes or one microneedle electrode and one surface electrode. The microneedle electrodes may be similar to those disclosed herein, or to those already known in the art and currently sold on the market. This embodiment may also have one or more EMG sensing electrodes to sense F-Wave and M-Wave electrodes. All the electrodes may be connected to a generator/controller via a connection cable or wireless connection.

Figure 60C:
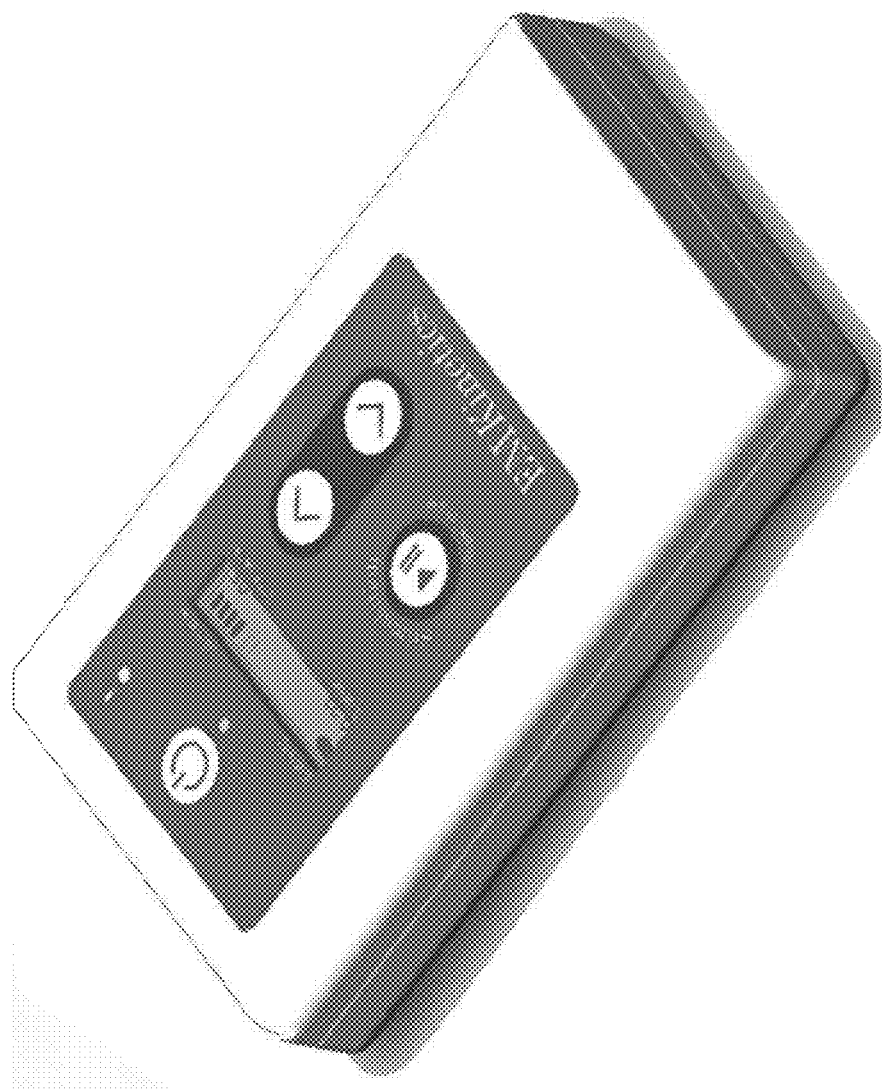
FIG. 60C shows another embodiment of a generator/controller.

FIG. 60C shows another embodiment of a generator/controller. This generator/controller can have all, some of, or additional attributes as those generator/controllers disclosed herein. FIG. 60C has the components in a compact, portable case. It may have advanced features, such as wireless communication, such as Bluetooth®, or other wireless technology, and the ability to communicate with current smartphones or other computers via different applications. For example, any of the embodiments disclosed herein may include a controller which sends, and possible receives, data to/from a centralized server wirelessly. The connection may be via wi-fi, Bluetooth®, cellular connection etc. The controller may be a smartphone, tablet, or other computer and/or may communicate with a smartphone, tablet, or other computer. The data sent from the controller and/or received by the controller may be anonymous or patient specific data. The data sent/received may be specific to one person or may be aggregate data of more than one user.

Alternatively, all or some of the functions of the generator/controller may be incorporated into a mobile computing device, such as a smart phone, tablet, mobile phone etc. The mobile computing device may include an "app" or application installed on the mobile device, which controls the functions of the electrodes, display and/or mobile device. The electrodes may be incorporated into the casing of the generator/controller, for example in a ball or handheld format. The electrodes may be incorporated into a casing which is physically attached to a mobile computing device. The casing may be powered by the mobile computing device or may be powered separately. Electrodes may be dry and built into the case for stimulation and EMG so that the user is in contact with the electrodes when the case is gripped. Electrodes may alternatively be wet and replaceable with attachments, such as snaps, which attach to, or connect to, the case. The app may use an EMG incorporated into the case, or may use accelerometers in the mobile device itself to measure intensity of stimulation. Since the gripping of the case may cause the fingers of the user to lay on the touchscreen display, the touchscreen may sense contraction of the fingers/hand and give an indication of stimulation presence/intensity. The touchscreen may sense the manner in which the fingers move (distance, direction, number of fingers etc.) or with 3D touch, the pressure on the screen may be measured.

The generator/controller and/or electrodes may also be incorporated into a glove.

Figure 60D:
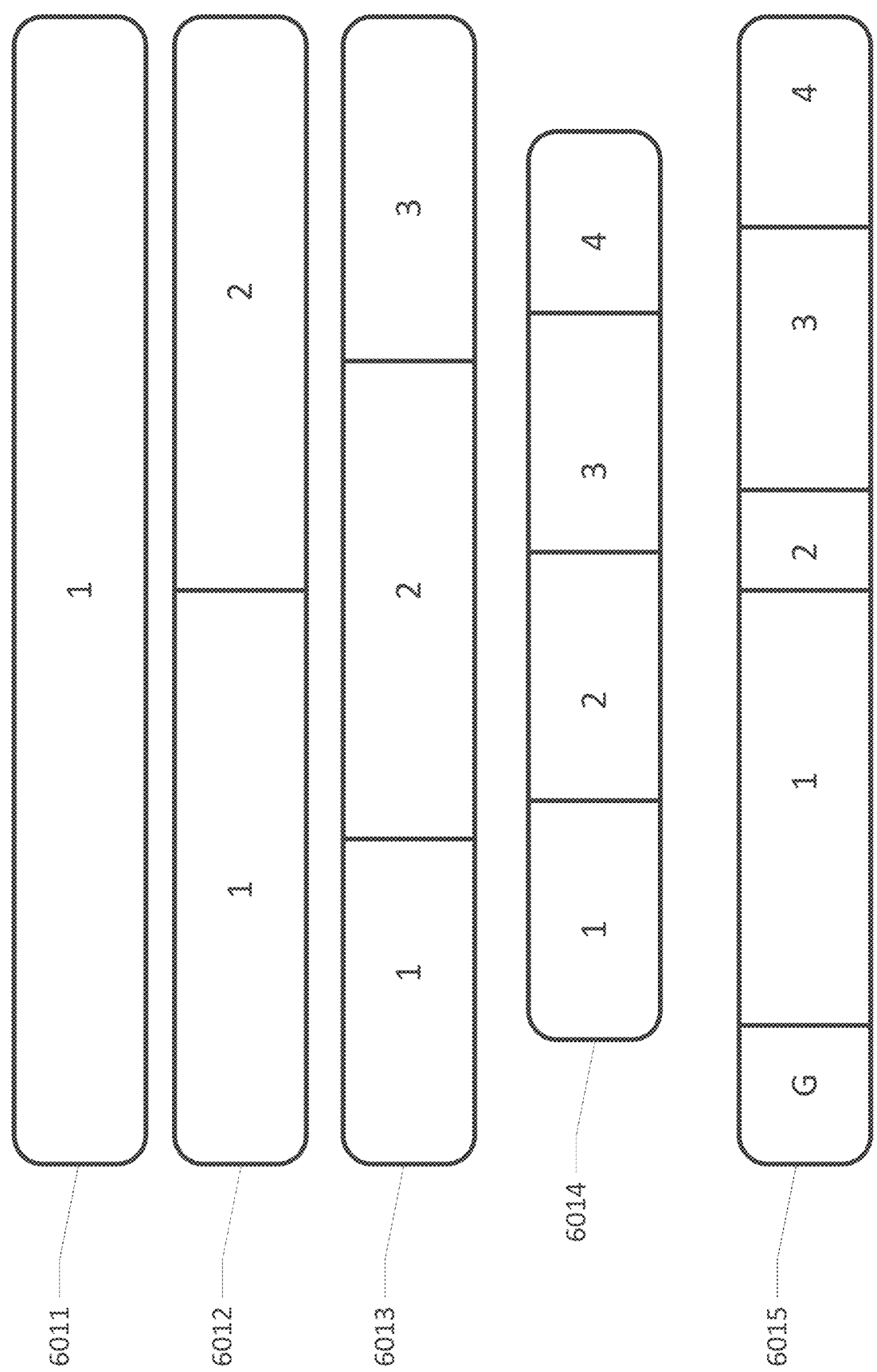
FIG. 60D shows four exemplary patch electrodes that are suitable to use with the present invention.

FIG. 60D shows four exemplary patch electrodes that are suitable to use with the present invention. Patch 6011 is a patch electrode with only one surface electrode contact area, 1. Patch 6012 is a patch electrode configuration where the patch contains 2 electrode contact areas, 1 and 2. Likewise, patch 6013 includes 3 electrode contact areas, 1, 2 and 3. Patch 6014 includes 4 contact areas, 1, 2, 3 and 4. Patch 6015 includes 5 electrode contact areas, with one contact area, G, being configured to serve as a possible ground for the other electrodes.

FIG. 60D shows a few of the different configurations of electrodes. These contact areas can be equally spaced or spaced according to the anatomy of the desired stimulation area. For example, in patch 6014, contact area 4 may be the same size or smaller or larger than contact area 3 depending on the stimulation area desired. Additionally, FIG. 60D show patch electrodes, but it should be understood that the descriptions here are translatable to microneedle electrodes used alone or in conjunction with patch electrodes or fully implantable electrodes or both.

Figure 61A:
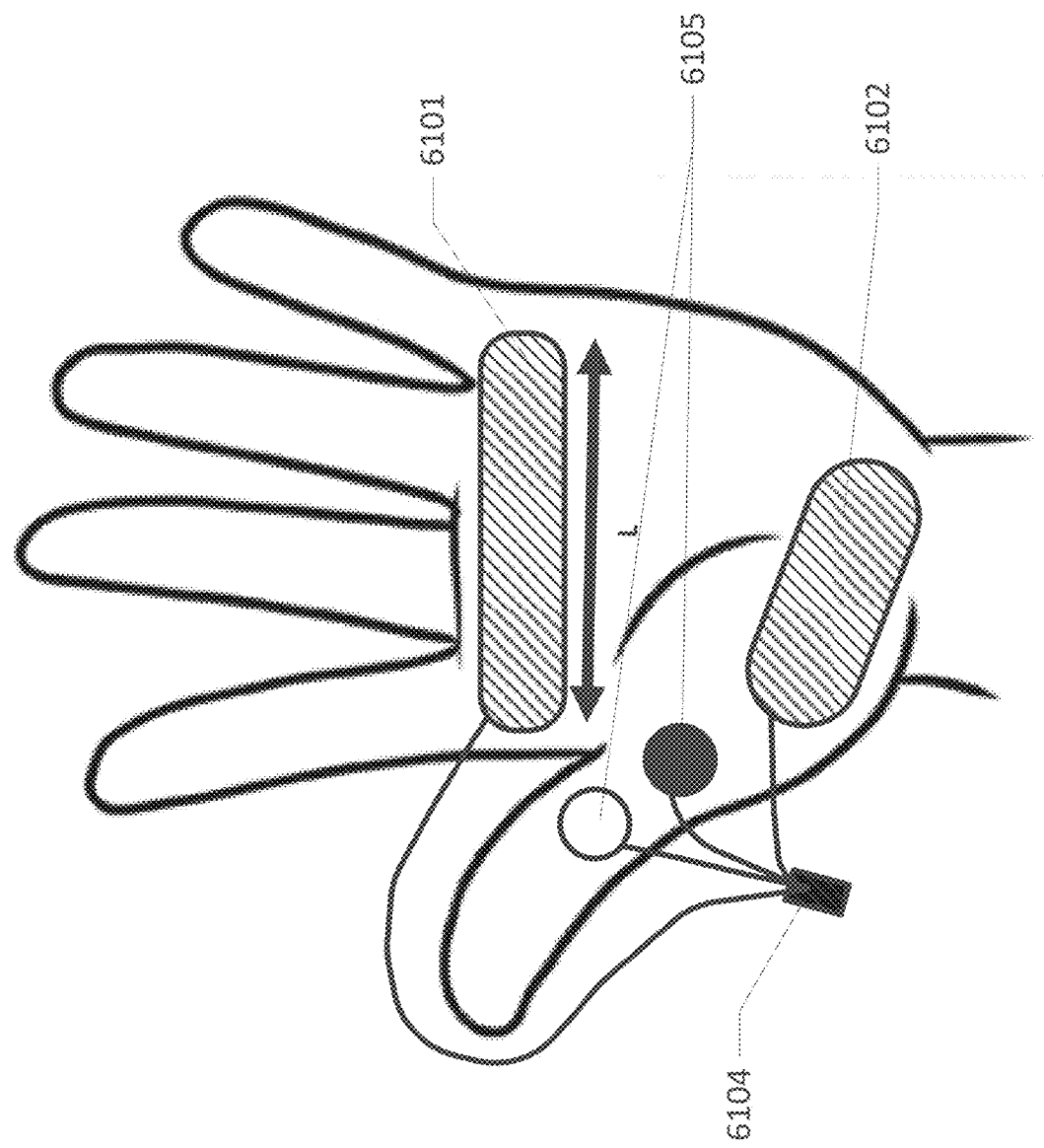
FIG. 61A shows electrodes designed for the palmar surface of the hands along with F/M wave detecting electrodes.

FIG. 61A shows electrodes designed for the palmar surface of the hands along with F/M wave detecting electrodes 6105. In FIG. 61A, contact electrode(s) 6101 are placed across the upper palm portion of the hand and second electrode 6102 is place across towards, near or on the heel of the hand. The electrodes are connected to generator/controller 6104 and electrical pulses are delivered to the hand per the instructions on the controller. Depending on the length "L" and placement of electrode 6101, electrical stimulation of the hand will stimulate the Median or the Ulnar nerve or both. It should be understood that depending on the therapy and other considerations, the desired stimulation may be either one or both the Ulnar or Median nerve.

Figure 61B:
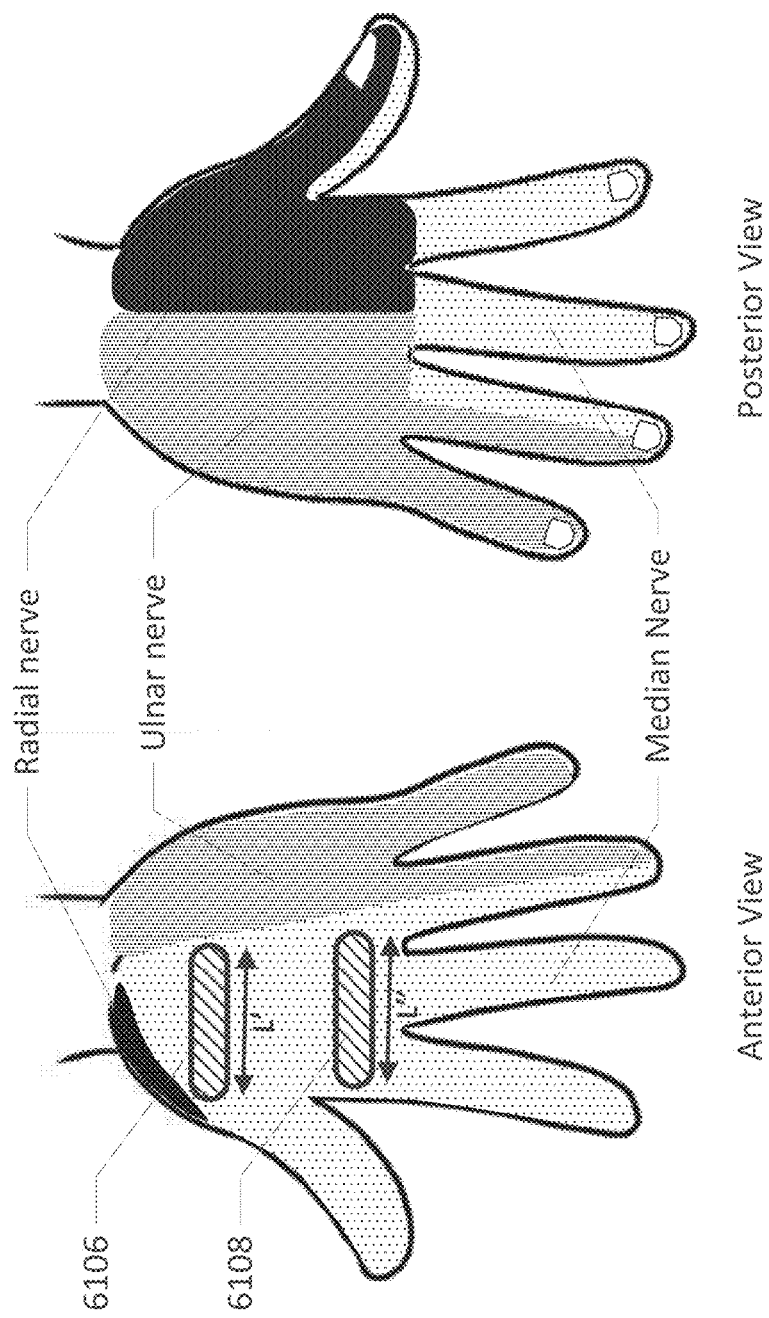
FIGS. 61B-61G show electrodes with different types for stimulating different nerves.
Figure 61C:
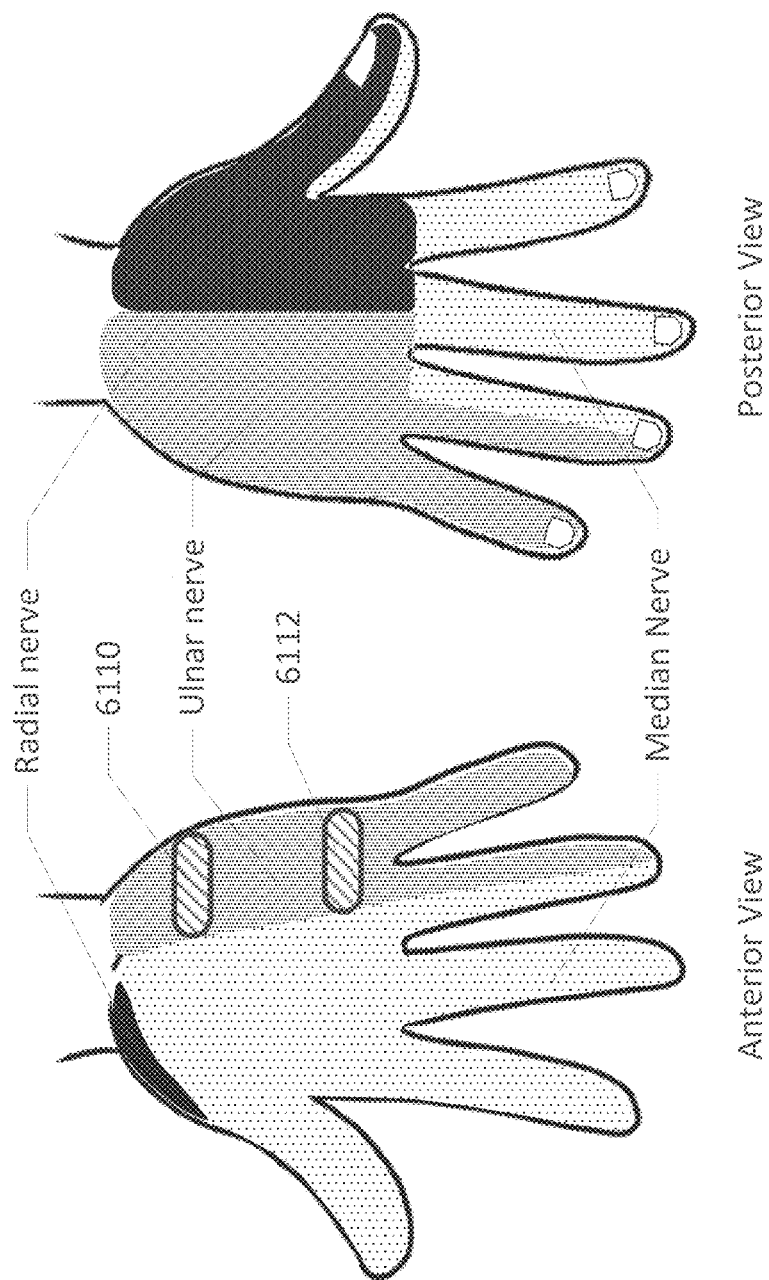
Figure 61D:
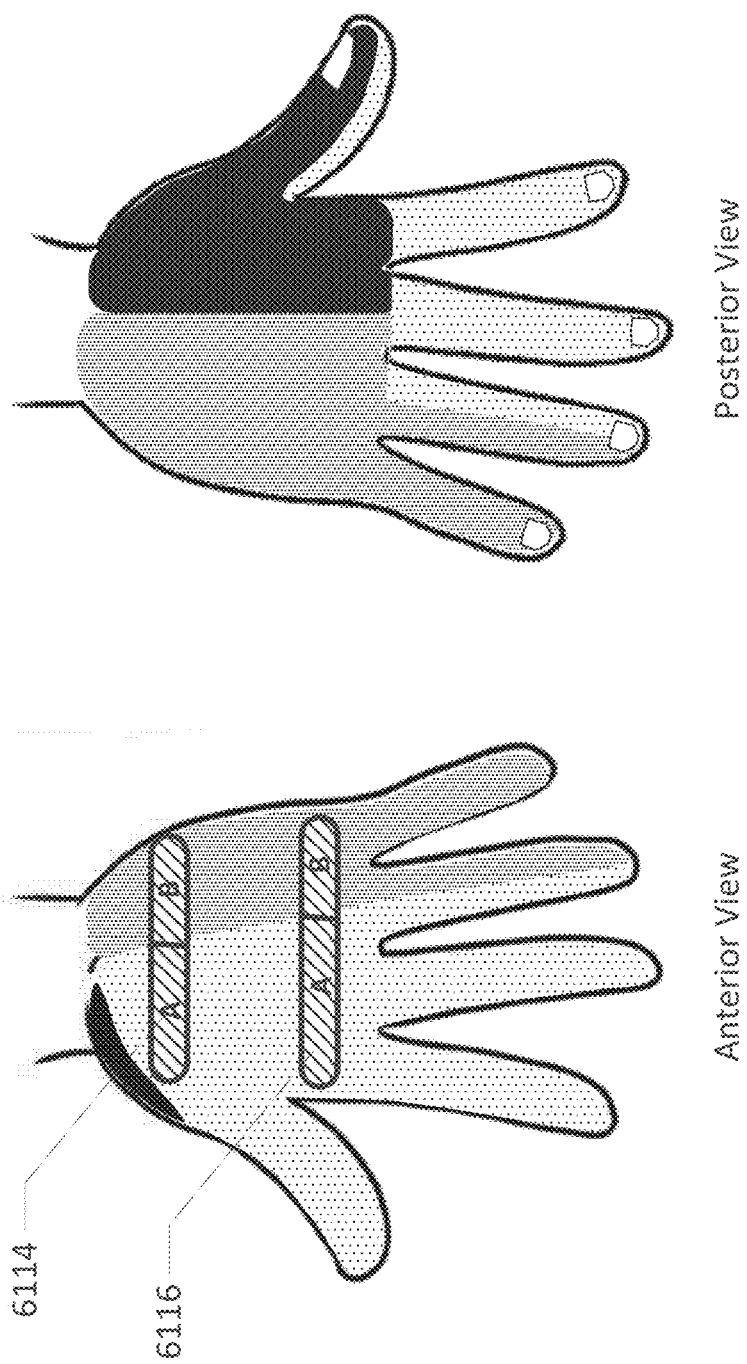
Figure 61E:
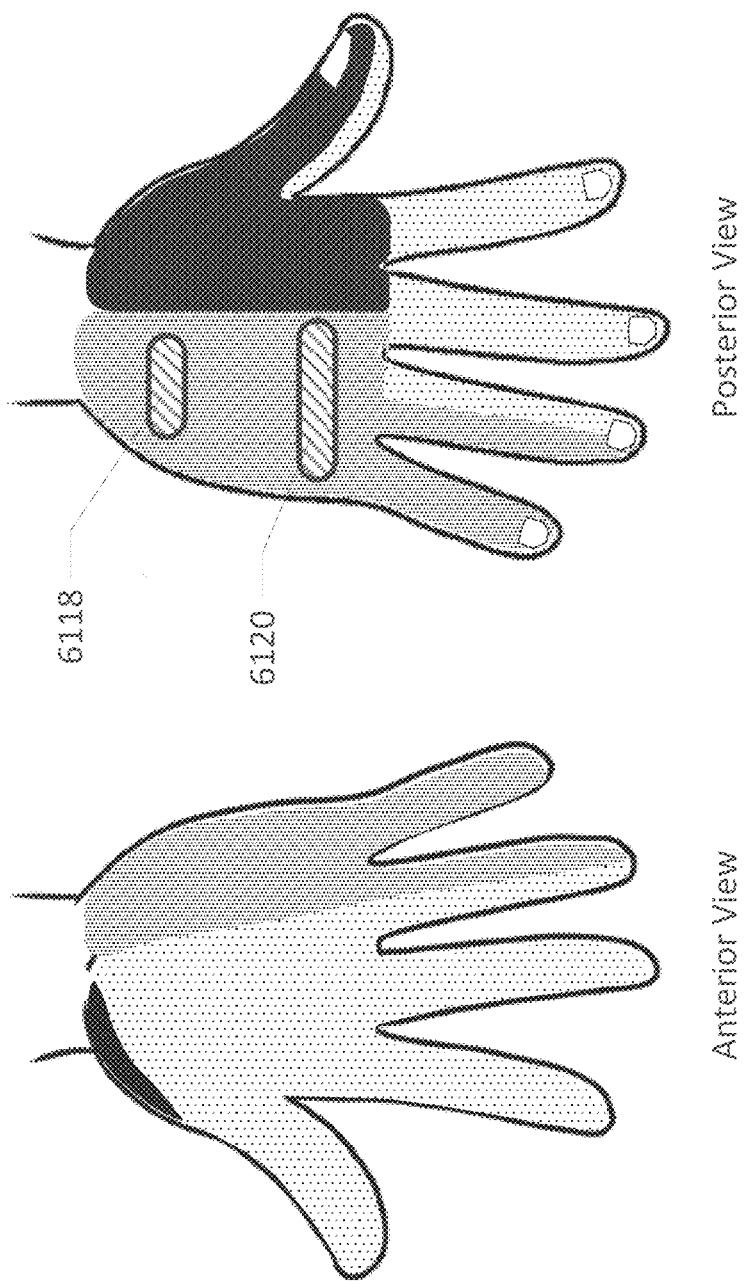
Figure 61F:
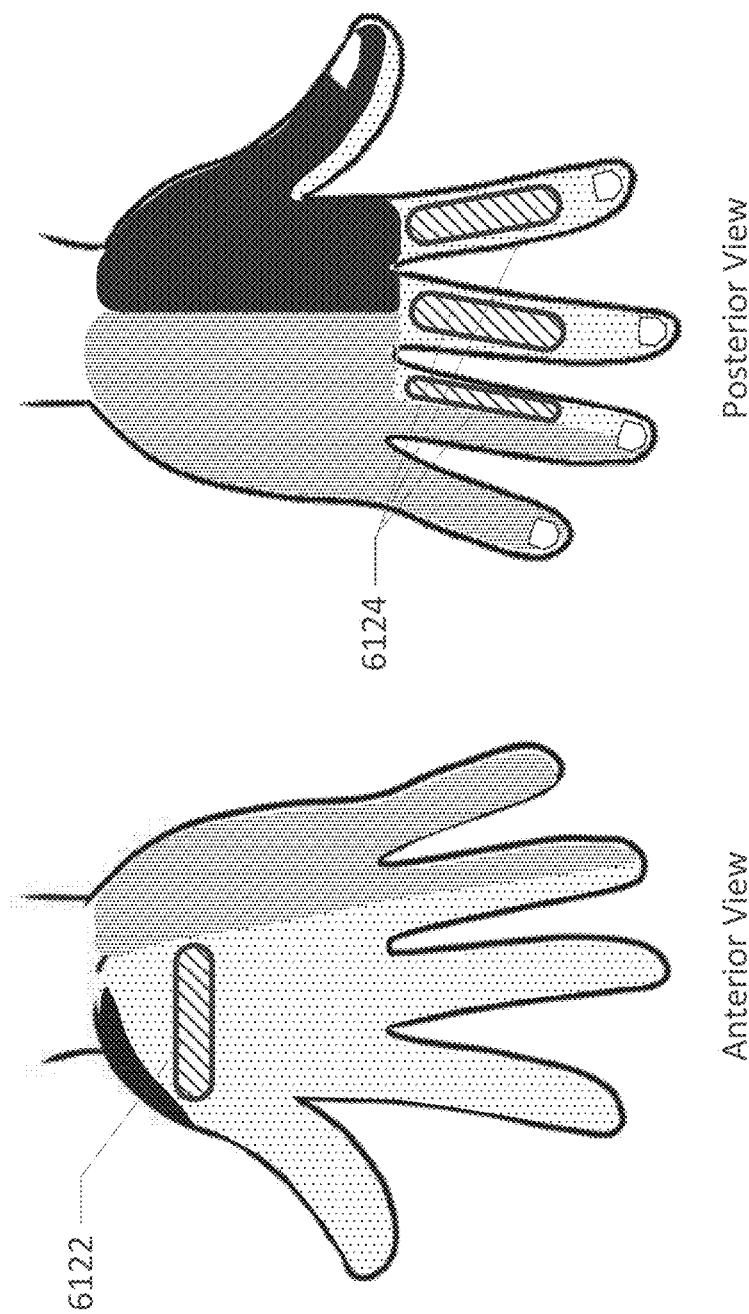
Figure 61G:
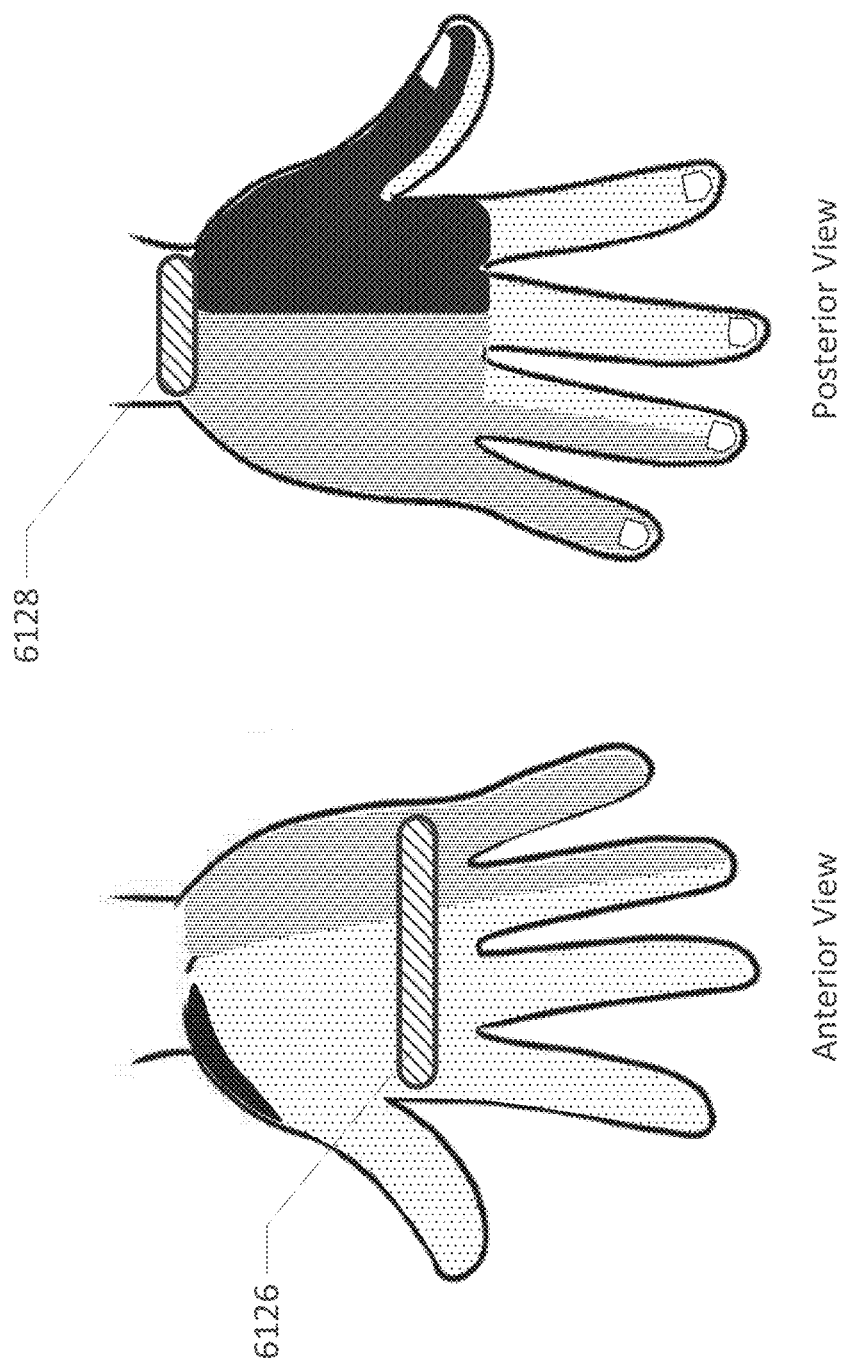

FIGS. 61B-61G shows electrodes with a length L' and L" (L" may be the same or different size from L') that are placed in a manner that will increase the likelihood that only the Median or Ulnar nerve will be stimulated, if that is the desired stimulation result. For example, FIG. 61B shows electrodes 6106 and 6108 placed in a manner that will either preferentially or only stimulate (depending on the parameters and desired therapy) the Median nerve. FIG. 61C likewise shows placement of electrodes 6110 and 6112 to preferentially or only stimulate the Ulnar nerves. FIG. 61D shows an exemplary external stimulating pair of patches 6114 and 6116, each containing two electrodes (A and B) that can be used to alternatively stimulation the Ulnar and Median nerve if that is the desired stimulation therapy. FIG. 61E shows electrodes 6118 and 6120 on the posterior portion of the hand to stimulate the Ulnar nerve. FIG. 61F shows electrode(s) 6122 on the anterior portion of the hand and electrodes 6124 on the posterior portion of certain fingers to stimulate the Median nerve. It is important to note that in FIG. 61F, one, two or all three fingers could be stimulated depending on the desired stimulation result sought. FIG. 61G shows electrode 6126 placed on the anterior and electrode 6128 placed on the posterior portion of the hand to stimulate both Ulnar and Median nerve simultaneously.

FIGS. 61A-61G are exemplary only. The present invention contemplates placing the electrode patches in one or more of the combinations listed above, or in other combinations, as required to achieve the desired stimulation therapy. Also, the present invention contemplates using single patch electrodes or one or more patches with two or more electrodes each that may stimulate with a more refined or focused field. For example, it is known in the art to use "anodal guarding" to localize the electric field to stimulate the desired areas while electrical "guarding" or reducing the field to not stimulate those other areas surrounding the particular focus of the stimulation therapy. Additionally, while not shown in FIGS. 61B-61G, the invention contemplates that sensing electrode(s) (as shown in FIG. 61A) may be used in these combinations. FIGS. 61A-61G show patch electrodes, but it should be understood that the descriptions here are translatable to microneedle electrodes used alone or in conjunction with patch electrodes or fully implantable electrodes (such as those disclosed below) or both.

The type of energy delivered to the nerve or nerves during stimulation by the device may depend on the pulse parameters. For example, in one therapy type, the pulse parameters have a frequency of somewhere between about 1-20 hz, a pulse width between about 0-500 microseconds and an amplitude of between about 0 and 90 mA. In another therapy, high frequency stimulation can be used, namely frequencies from about 20 hz up to about 10,000 hz. Such high frequencies can be effective using either external electrodes, or fully implantable electrodes, or both. The electrodes are placed in a location to stimulate the Ulnar nerve, the Median nerve or both nerves.

The energy pulse amplitude may also vary during the treatment. This modulation can increase both comfort and efficacy. For example, the pulse energy applied to the electrodes may be at 100% amplitude for X pulses (for example, 5 pulses) and then at a lower amplitude (for example, 50% amplitude) for Y pulses (for example, 5 pulses). The pulse amplitude and length may vary, for example, there may be two amplitude levels, or 3 or more. The different amplitude durations may be the same, or they may be different. The amplitude variations may be preset, or may be reset during the use of the device.

Figure 62:
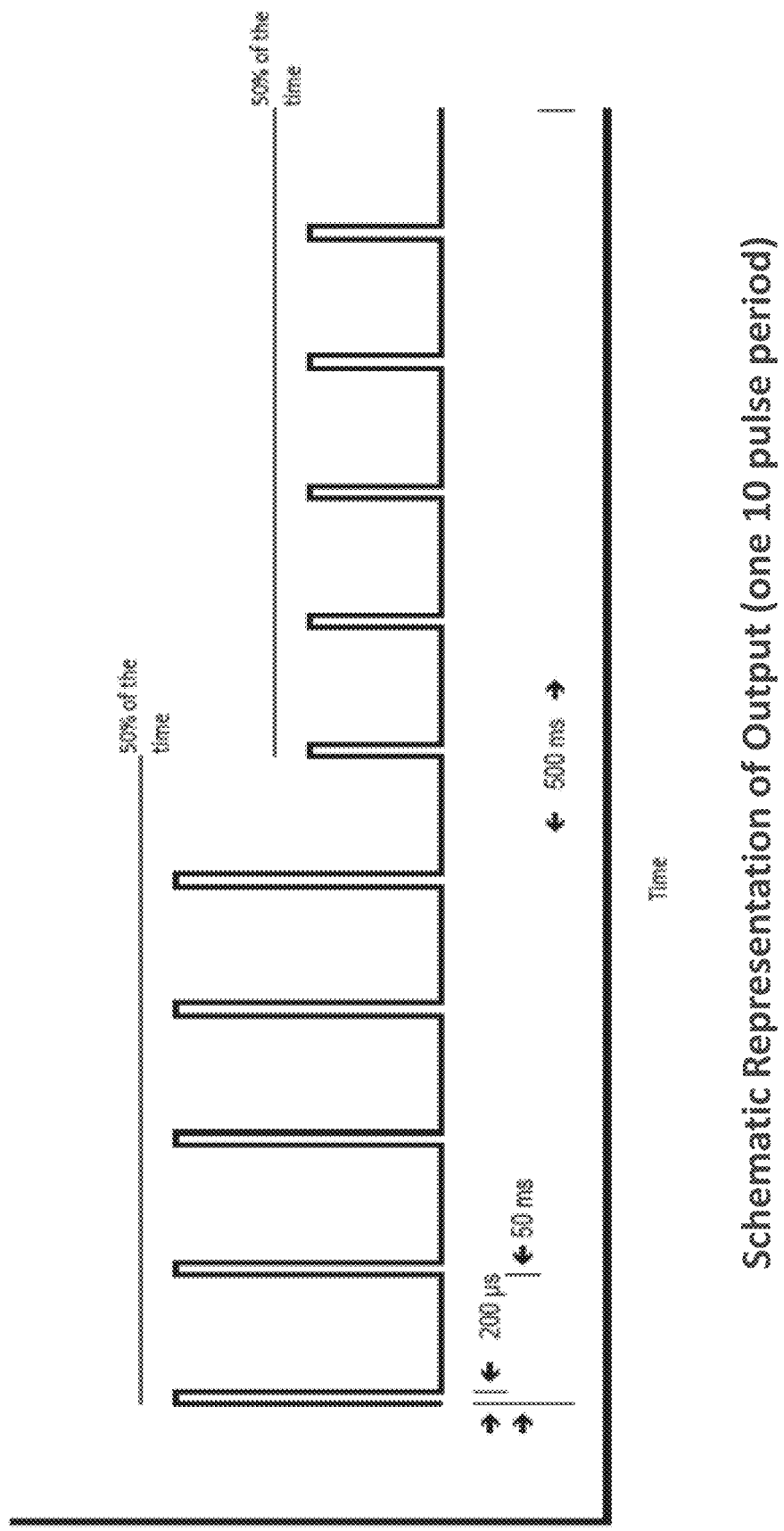
FIG. 62 shows a pulse train of one embodiment.

FIG. 62 shows one example of varying amplitudes where the amplitude magnitude is 100% and 50%, each for 5 pulses, alternating between 100% and 50% amplitude. More complicated variations are also envisioned. For example, the amplitude may vary in a sine function, or a multiple level function with the different amplitude lengths varying per amplitude. The amplitude variations may be the same across users or custom to each user, or even each user experience.

The parameters of the amplitude function include amplitude as a percent of maximum, amplitude time length, amplitude number of pulses, number of different amplitudes, order of different amplitudes, etc. These parameters may be communicated to a remote server for analysis to optimize treatment of individual users in the future. The data may also be aggregated (preferably anonymously) to develop treatment algorithms for different patient populations. Effectiveness input from the individual users may also be incorporated into the algorithms, for example pain level over time, comfort level, medication taken etc.

Similarly, pulse frequency parameters can also be modulated. Similarly, pulse width parameters an also be modulated.

In some embodiments of the device, an amplitude (and/or frequency) modulator adapter may be added to a commercially available TENS (Transcutaneous Electrical Nerve Stimulation) device. This adapter would modulate the amplitude and/or frequency of the signal produced by the TENS device so that the signal delivered to the user via the electrodes can be optimized for comfort and efficacy.

Some embodiments allow the user to use the device inconspicuously, for example at work, or in a meeting. The electrodes may be part of a phone case so that the user's hand is in contact with the electrodes while holding the phone. The electrodes may be part of a beverage mug, computer mouse, steering wheel, etc.

Feasibility Study.

A feasibility study was conducted stimulating the Ulnar and Median nerve of the hand, and the Tibial nerve of the foot. The following paragraphs are the steps taken during the study. One should note that it is recognized that these steps are not exclusive and more or fewer steps may be taken. Additional, while the feasibility study occurred under a controlled setting, such limitations are not required for the invention in practice. Therefore, these steps, the parameters, etc., are to show the one implementation of the invention, but do not restrict the invention in any way.

A study was performed to assess the non-invasive peripheral nerve stimulation device to treat triggered migraine attacks. Stimulation was introduced to the palmar surface of each hand (distal branches of median and ulnar nerves) and plantar surface of each foot (distal branches of posterior tibial nerve).

Methods

Volunteer participants who met ICHD-III beta criteria for episodic migraine without aura were given an intravenous infusion of glyceryl trinitrate to trigger an attack. Triggered attacks were then treated with the peripheral nerve stimulation device: 15 minutes at each extremity, in random order. The primary outcome measure was pain relief (i.e. mild or no pain) at two hours.

Results

Figure 64:
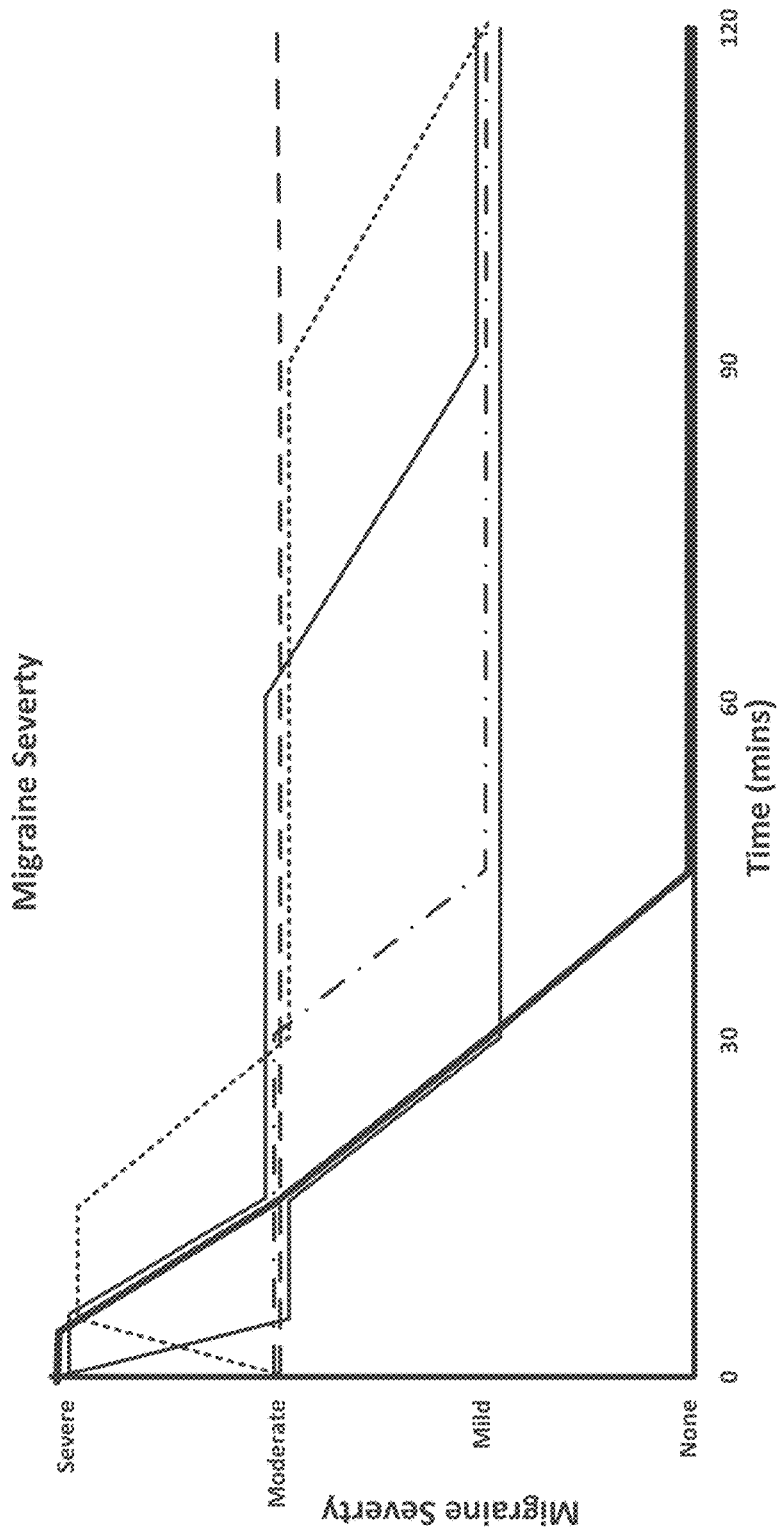
FIG. 64 shows results from a migraine study.

See FIG. 64 for the following discussion. Seven patients were enrolled: 5 women, 2 men; mean age 33.7 years (SD 11.5). Mean headache frequency was 7.1 (SD 2.8) days/month. Five successfully had a migraine attack triggered. The mean time to trigger was 110 minutes (SD 65). Of the five, 4 (80%) had mild/no headache at two hours. One needed headache rescue medication at 2 hours. Of four with follow-up data, none had recurrent headache within 24 hours.

The details of the use of the device to treat a migraine follows. This is an example of using the system, but is not the only way to stimulate the Ulnar, Median or Tibial nerves.

The operator (physician, physician's representative, company representative or patient) connects the stimulator, electrode patches, and EMG electrodes to the generator/controller at their appropriate connectors. The operator then places the electrode patches on the palmar surfaces of the patient at the correct locations per the instructions for use (see FIGS. 61A-61G for examples of the placement locations). Additionally, two or more small, self-adhering EMG foam/hydrogel patches were placed over the Ulnar muscle during palmar stimulation to provide real-time electromyographic evaluation of nerve stimulation. It should be noted that the whether the patches and F/M wave electrodes are placed on the hand prior to connecting to the generator/controller or after is not important. The patient is typically seated comfortably and each hand is stimulated. The stimulation can be for each hand at the same time, one at a time or just one hand alone. In a recent study of 7 patients, each hand was stimulated one at a time for 15 minutes each.

Once the electrodes are connected, the generator/controller is turned on to the lowest setting in pretreatment confirmation mode. The operator increases the setting of the power until the patient experiences maximal stimulation as demonstrated by finger-curl or until the limit of patient tolerability is reached or the maximum power setting is reached. During confirmation mode, the system displays the power setting, captured M- and F-waves, and the battery power status indicator.

Once the power setting has been determined, the power setting is set by the operator via the current control knob, if necessary. The operator actuates the mode button to start the treatment mode. The embedded software of the generator/controller then automatically completes a 15-minute session of treatment at the pre-determined output cycle. In this configuration, the operator does not adjust the settings of the output of the generator/controller during the treatment. The output screen displays the captured electromyographical waves during treatment, a timer, and a battery power status indicator.

After the 15-minute treatment is complete, as determined by the internal software timer, the generator/controller returns to non-treatment mode (no output to the treatment leads and no EMG capture/display). The operator turns the generator/controller off and removes the electrodes from the patient's hand and optionally repeats the treatment protocol on the second hand.

An Example of a Set Up Procedure:

Check the Battery Level.

Place the electrode on the palm (FIGS. 61A-G). Locate the placement site for the electrode. The median and Ulnar nerve access sites are located on the upper and base of the palm. To prepare the electrode placement site, use an alcohol pad to clean the skin area surrounding the identified placement site. Place the patient in a comfortable position, supine or sitting, for easy access to the placement site. Open the electrode package, remove the electrode then remove the backing to expose the patient contacting side. Place the electrodes patient contacting side over the identified and cleaned placement site. Hold the electrode pads parallel to the placement site and place the electrode pads. Connect the electrode electrical wire lead to the signal generator/controller. If one desires to use the F/M Wave electrodes to confirm therapy, then add two or more small, self-adhering foam/hydrogel patches to the hand. Cable leads will connect the electrodes to the device to monitor and record M-Wave and F-Wave appearance.

Determine Current Setting for Therapy. Turn on the signal generator/controller. In order to determine stimulation of afferent pathways, intermittent pulses are masked to confirm and record M-waves and F-waves. By default, the current when the signal generator/controller is powered on is 0 mA. Slowly increase the current amplitude (90 mA maximum level in the particular generator/controller used) to the patient's maximum tolerability while observing the patient's hand for a response. Patient response is generally a finger curl, flex or fan, or an extension of the entire hand. The patient may also report a tingling sensation across the palm or heal of the hand. Once the patient's maximum tolerability is reached, reduce current amplitude setting by one level. By observation, confirm M-wave appearance and confirm active neurostimulation of the Median and Ulnar nerves via F-Wave appearance on the feedback monitor. If the incremental adjustment of current amplitude fails to elicit finger curl, flex or fan, inactivate the current (0 mA) and reposition the electrode slightly. Resume therapy using the preceding instructions. If repositioning the electrode and repeating the current step-up procedure fails to elicit patient response, discard the electrode. Open another electrode, and repeat the procedure on the other hand.

Conduct therapy. After the current level is established, the operator will initiate 15-minutes of ongoing electric stimulation. Begin therapy at the current amplitude determined above. The current can be adjusted to increase or decrease the current level at any time during therapy. In order to determine stimulation of afferent pathways, intermittent pulses are masked to confirm and record M-waves and F-waves. When the therapy time has elapsed, inactivate the current (0 mA).

Repeat Treatment Session. Repeat the steps above on the opposite hand then complete treatment session.

Complete Treatment Session. Turn off the signal generator/controller. Remove the cable leads from the electrodes. The treatment session is now complete. Remove electrodes from the patient. The skin may be cleaned with wipes to remove gel residue on the skin from the electrodes.

In the study conducted, the stimulation system that comprised an electrode that connected by an electrical cable to a battery-powered pulse source (electrical signal generator/controller). The signal generator/controller produced an adjustable electrical pulse that traveled to the brachial nerve plexus via the Median and Ulnar nerves when applied to the palmar surface of the hand.

Study Device Details:

The electrode was placed onto the hand and used to stimulate the Median and Ulnar nerves on the hands. The system consists of a 9 volt battery powered electrical signal generator/controller with electromyographical capture, display, and patient contact leads and electrodes.

The generator/controller housing is a plastic enclosure with an on/off switch, adjustable current control, mode switch button, and LCD screen facing the operator. The generator/controller has connections for a stimulation electrode (output), return electrode (input) and two electromyographic (EMG) capture electrodes (input). The generator/controller housing has a removable door for replacement of the 9 volt battery. The housing encloses the printed circuit board assembly and prevents contact by the user with the internal electronics.

Physical Principles to External Generate Output:

The generator/controller is a 9-volt battery powered, microprocessor controlled, electrical-neural stimulator with embedded software that delivers pulses of DC energy to the patient via the stimulation and return electrodes. The device simultaneously reads electromyographical signals from the patient via the EMG electrodes and displays them on a display screen. The goal is to stimulate the Median and Ulnar nerves of the treated hand.

Electrical Current Settings

There is an adjustable dial to increase/decrease current setting levels with a current range of 0 mA to approximately 90 mA. The signal generator/controller display has a current setting readout. At level 0, the device produces 0 mA current.

Pulse characteristics:

Used a fixed pulse frequency of 20 Hz, but can be 0-1000 hz

Used a pulse width of 200 microseconds but range can be 0-500 microseconds

Used a generator/controller with max amplitude of 90 mA, but range can be up to 200 mA Square waveform, but can use other shaped waveforms Stimulation Signal Program See FIG. 62, which shows the pulse train used in this study for the following discussion. The generator/controller used embedded software to output patterns of monophasic square wave DC energy at a 20 Hertz frequency. The amplitude of the square waves of the system is adjusted by the current controller on the generator/controller in order to achieve complete stimulation. The output program used in this study consisted of patterns of 5 pulses of maximum stimulation followed by 5 pulses of half-maximum stimulation for a 15 minute long preprogrammed treatment time. But other paradigms can be used.

During initial testing of the system, the 100%/50% duty cycle enabled neurostimulation of the peripheral nerves without inducing tetany (muscle pain). The maximum length of maximal neurostimulation without tetany using a 20 Hz pulse train was found to be 0.5 seconds (10 pulses at 20 Hz). Trains of pulses at this frequency were also found to be tolerable as long as there was at least 0.25 seconds of non-maximal, or resting, stimulation between trains.

The stimulation of the peripheral nerves with the system is intended to be tolerable for the patient while generating neural stimulation. In this study, the duty cycle, frequency, shape, length of each pulse, and length of the treatment program were fixed, and the amplitude of the square waves was adjustable by the operator.

Principles of Electromyography

Figure 63:
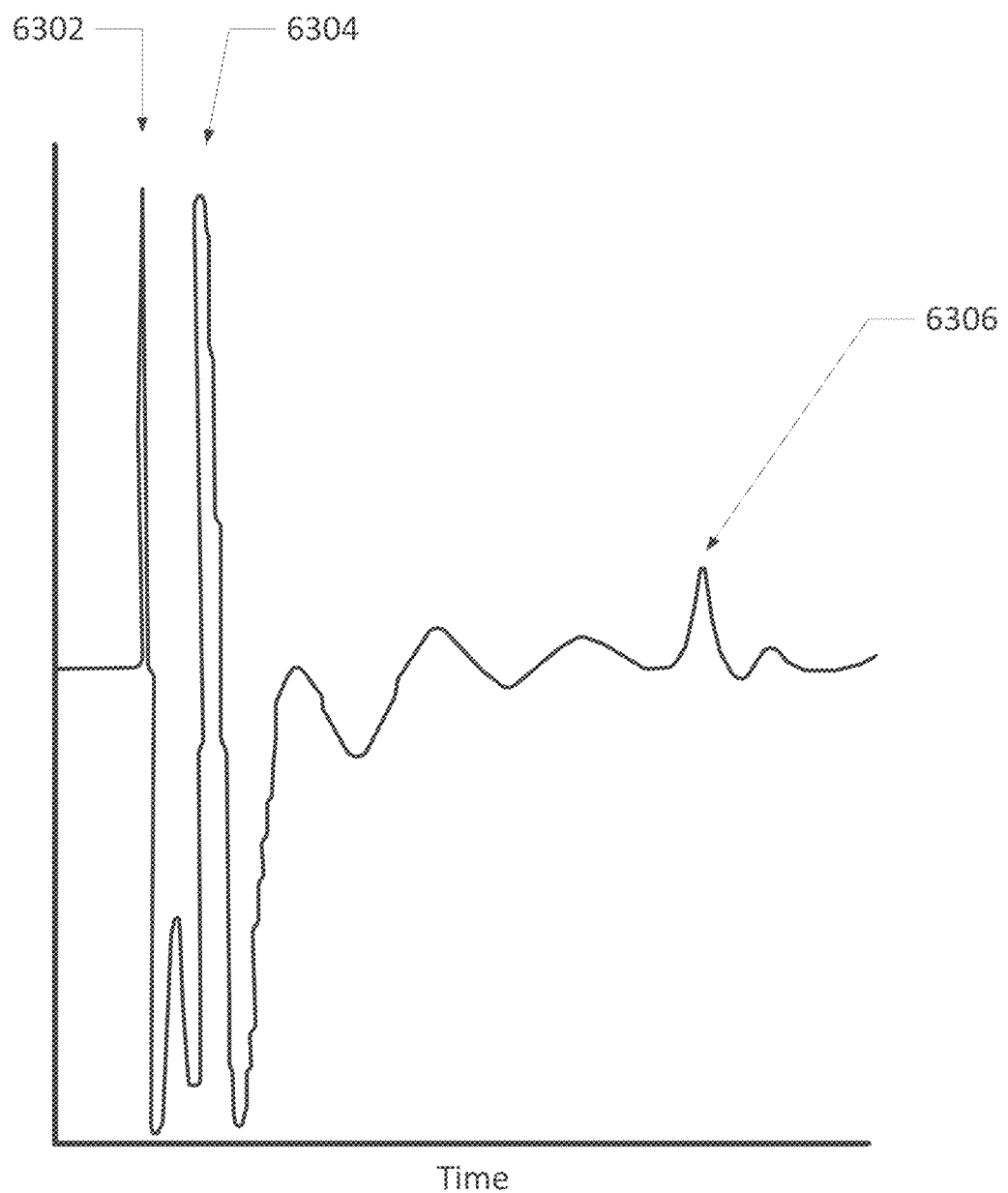
FIG. 63 shows an M-Wave and F-Wave display.

See FIG. 63 for the following discussion. The system also captures and displays electromyographic information during the treatment. Electromyography is the study of the electrical signals in the muscles for analysis of the behavior of the muscle or nervous systems in a body. During electrical neural muscle stimulation, signals called M-waves and F-waves are created by the body in the stimulated muscles and nerves in response to the electrical stimulation. In neuroscience, the M-Wave is the first, and the F-wave is the second, voltage change observed after electrical stimulation is applied to the distal region of a nerve. F-waves are often used to measure nerve conduction velocity, and are particularly useful for evaluating conduction problems in the proximal region of nerves (i.e., portions of nerves near the spinal cord). The signal is called the F-wave because it was initially recorded in the foot muscles.

In a typical F-wave study, a strong electrical stimulus (above maximal muscle stimulation levels) is applied to the skin surface above (proximally to) the distal portion of a nerve so that the impulse travels both distally (towards the muscle fiber) and proximally (back to the motor neurons of the spinal cord; these directions are also known as orthodromic and antidromic, respectively). When the orthodromic stimulus reaches the muscle fiber, it elicits a strong M-response indicative of muscle contraction (M-wave). When the antidromic stimulus reaches the motor neuron cell bodies, a small portion of the motor neurons fire in the other direction and an orthodromic wave travels back down the nerve towards the muscle. This reflected stimulus evokes a small proportion of the muscle fibers causing a small, second compound muscle action potential (CMAP) called the F-wave.

FIG. 63 shows a graph of detected voltage vs. time and shows M-wave 6304 and F-wave 6306 following stimulation 6302. This type of graph may be displayed by the controller to the end user. Alternatively, a different parameter of an M-wave and/or an F-wave may be displayed to the user, such as whether or not the wave exists, the amplitude of the wave, the travel time of the wave, etc.

The generator/controller may capture and display both the M-wave and F-wave on the display screen during confirmation and treatment modes. Being able to view the M-waves and F-waves during treatments allows the operator to confirm maximal stimulation of the nerve in question (Ulnar, Median or Tibial) and its branches in the feet; and the median and Ulnar nerves in the hand.

Example of Data Processing System

FIG. 65 is a block diagram of a data processing system, which may be used with any embodiment of the invention. For example, the system 6500 may be used as part of a controller, server, mobile device, hand piece, computer, tablet, etc. Note that while FIG. 65 illustrates various components of a computer system, it is not intended to represent any particular architecture or manner of interconnecting the components; as such details are not germane to the present invention. It will also be appreciated that network computers, handheld computers, mobile devices, tablets, cell phones and other data processing systems which have fewer components or perhaps more components may also be used with the present invention.

As shown in FIG. 65, the computer system 6500, which is a form of a data processing system, includes a bus or interconnect 6502 which is coupled to one or more microprocessors 6503 and a ROM 6507, a volatile RAM 6505, and a non-volatile memory 6506. The microprocessor 6503 is coupled to cache memory 6504. The bus 6502 interconnects these various components together and also interconnects these components 6503, 6507, 6505, and 6506 to a display controller and display device 6508, as well as to input/output (I/O) devices 6510, which may be mice, keyboards, modems, network interfaces, printers, and other devices which are well-known in the art.

Typically, the input/output devices 6510 are coupled to the system through input/output controllers 6509. The volatile RAM 6505 is typically implemented as dynamic RAM (DRAM) which requires power continuously in order to refresh or maintain the data in the memory. The non-volatile memory 6506 is typically a magnetic hard drive, a magnetic optical drive, an optical drive, or a DVD RAM or other type of memory system which maintains data even after power is removed from the system. Typically, the non-volatile memory will also be a random access memory, although this is not required.

While FIG. 65 shows that the non-volatile memory is a local device coupled directly to the rest of the components in the data processing system, the present invention may utilize a non-volatile memory which is remote from the system; such as, a network storage device which is coupled to the data processing system through a network interface such as a modem or Ethernet interface. The bus 6502 may include one or more buses connected to each other through various bridges, controllers, and/or adapters, as is well-known in the art. In one embodiment, the I/O controller 6509 includes a USB (Universal Serial Bus) adapter for controlling USB peripherals. Alternatively, I/O controller 6509 may include an IEEE-1394 adapter, also known as FireWire adapter, for controlling FireWire devices.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as those set forth in the claims below, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The techniques shown in the FIGS. can be implemented using code and data stored and executed on one or more electronic devices. Such electronic devices store and communicate (internally and/or with other electronic devices over a network) code and data using computer-readable media, such as non-transitory computer-readable storage media (e.g., magnetic disks; optical disks; random access memory; read only memory; flash memory devices; phase-change memory) and transitory computer-readable transmission media (e.g., electrical, optical, acoustical or other form of propagated signals—such as carrier waves, infrared signals, digital signals).

The processes or methods depicted in the FIGS. herein may be performed by processing logic that comprises hardware (e.g. circuitry, dedicated logic, etc.), firmware, software (e.g., embodied on a non-transitory computer readable medium), or a combination of both. Although the processes or methods are described above in terms of some sequential operations, it should be appreciated that some of the operations described may be performed in a different order. Moreover, some operations may be performed in parallel rather than sequentially.

Each of the individual variations described and illustrated herein has discrete components and features which may be readily separated from or combined with the features of any of the other variations. Modifications may be made to adapt a particular situation, material, composition of matter, process, process act(s) or step(s) to the objective(s), spirit or scope of the present invention.

Methods recited herein may be carried out in any order of the recited events which is logically possible, as well as the recited order of events. Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, and equivalents of the variations described herein. Further, the scope of the disclosure fully encompasses other variations that may become obvious to those skilled in the art in view of this disclosure. The scope of the present invention is limited only by the appended claims.

What is claimed is:

1. An apparatus for treating tremor in a subject, comprising:
    an applicator configured for application to a hand or arm of the subject;
    an electrode located along the applicator so as to contact a skin surface of the subject when the applicator is worn by the subject;
    an electrical pulse generator in communication with the electrode; and
    a sensor positionable on the subject and in communication with the electrical pulse generator,
    wherein the electrical pulse generator provides an electrical stimulation through the electrode and into a target nerve underlying the skin surface such that the sensor detects a motion of the subject and provides a feedback signal to the electrical pulse generator so as to mitigate the tremor by adjusting or optimizing the electrical stimulation.

2. The apparatus of claim 1 wherein the electrode is located along the applicator in proximity to the target nerve which extends through a hand of the subject.

3. The apparatus of claim 1 wherein the applicator comprises a strap or band.

4. The apparatus of claim 3 wherein the electrode is attached to the strap or band so as to contact the skin surface of the subject.

5. The apparatus of claim 1 further comprising an additional electrode separate from the electrode.

6. The apparatus of claim 1 wherein a parameter of the electrical stimulation comprises a frequency which is adjustable.

7. An apparatus for treating tremor in a subject, comprising:
    an applicator configured for application to a region of the subject;
    an electrode located along the applicator so as to contact a skin surface of the subject when the applicator is worn by the subject;
    a controller in communication with the electrode; and
    a sensor positionable on the subject and in communication with the controller, wherein the controller transmits via the electrode an electrical stimulation having an adjustable frequency through the skin surface and into a target nerve underlying the skin surface,
    wherein the sensor detects a motion of the subject and provides a feedback signal to the controller so as to mitigate the tremor by adjusting or optimizing the electrical stimulation.

8. The apparatus of claim 7 wherein the electrode is located along the applicator in proximity to the target nerve which extends through a hand of the subject.

9. The apparatus of claim 7 wherein the applicator comprises a strap or band.

10. The apparatus of claim 9 wherein the electrode is attached to the strap or band so as to contact the skin surface of the subject.

11. The apparatus of claim 7 further comprising an additional electrode separate from the electrode.

12. A method for treating tremors in a subject, comprising:
    transmitting an electrical stimulation from an electrical pulse generator and through an electrode located along an applicator and contacted against a skin surface of a hand or arm of the subject such that the electrical stimulation targets a nerve underlying the skin surface;

monitoring for a motion of the subject via a sensor positionable on the subject and in communication with the electrical pulse generator;

receiving a feedback signal via the sensor; and adjusting or optimizing the electrical stimulation from the electrical pulse stimulation in response to the feedback signal until the tremors are mitigated.

13. The method of claim 12 wherein the electrode is located along the applicator in proximity to the target nerve which extends through a hand of the subject.

14. The method of claim 12 wherein transmitting the electrical stimulation comprises transmitting through the electrode located along an applicator comprising a strap or band.

15. The method of claim 14 wherein the electrode is attached to the strap or band so as to contact the skin surface of the subject.

16. The method of claim 12 further comprising transmitting the electrical stimulation via an additional electrode separate from the electrode.

17. The method of claim 12 further comprising adjusting a frequency of the electrical stimulation in response to the feedback signal.

* * * * *